(12) United States Patent
Crowley et al.

(10) Patent No.: US 11,152,100 B2
(45) Date of Patent: Oct. 19, 2021

(54) HEALTH APPLICATION USER INTERFACES

(71) Applicant: Apple Inc., Cupertino, CA (US)

(72) Inventors: Matthew W. Crowley, San Francisco, CA (US); Pablo F. Caro, San Francisco, CA (US); Dmitri Cavander, San Francisco, CA (US); Heather E. Daniel, San Jose, CA (US); Nicholas Felton, Sunnyvale, CA (US); Ruchi Goswami, Sunnyvale, CA (US); Charmian Bondoc Naguit, Woodside, CA (US); Evan R. Doll, Palo Alto, CA (US); Kevin Lynch, Woodside, CA (US); Aroon Pahwa, Palo Alto, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/880,714

(22) Filed: May 21, 2020

(65) Prior Publication Data
US 2020/0381099 A1 Dec. 3, 2020

Related U.S. Application Data

(60) Provisional application No. 62/856,061, filed on Jun. 1, 2019.

(51) Int. Cl.
*G06F 3/0484* (2013.01)
*G16H 20/30* (2018.01)

(52) U.S. Cl.
CPC .......... *G16H 20/30* (2018.01); *G06F 3/0484* (2013.01)

(58) Field of Classification Search
CPC combination set(s) only.
See application file for complete search history.

(56) References Cited

U.S. PATENT DOCUMENTS

| 5,475,653 | A  | 12/1995 | Yamada et al.   |
|-----------|----|---------|-----------------|
| 5,515,344 | A  | 5/1996  | Ng              |
| 5,642,731 | A  | 7/1997  | Kehr            |
| 5,655,094 | A  | 8/1997  | Cline et al.    |
| 6,253,075 | B1 | 6/2001  | Beghtol et al.  |
| 6,416,471 | B1 | 7/2002  | Kumar et al.    |
| 6,597,378 | B1 | 7/2003  | Shiraishi et al.|

(Continued)

FOREIGN PATENT DOCUMENTS

| AU | 2016102028 B4 | 7/2017 |
|----|---------------|--------|
| CA | 2815518 A1    | 5/2012 |

(Continued)

OTHER PUBLICATIONS

International Preliminary Report on Patentability received for PCT Patent Application No. PCT/US2019/019694, dated Sep. 24, 2020, 12 pages.

(Continued)

*Primary Examiner* — Hien L Duong
(74) *Attorney, Agent, or Firm* — Dentons US LLP

(57) ABSTRACT

The present disclosure generally relates to health-related user interfaces. In some embodiments, user interfaces for managing health-related data are described. In some embodiments, user interfaces for viewing health data are described. In some embodiments, user interfaces related to sharing health data are described.

30 Claims, 85 Drawing Sheets

(56) References Cited

U.S. PATENT DOCUMENTS

| | | |
|---|---|---|
| 6,600,696 B1 | 7/2003 | Lynn |
| 6,603,477 B1 | 8/2003 | Tittle |
| 6,661,438 B1 | 12/2003 | Shiraishi et al. |
| 6,705,972 B1 | 3/2004 | Takano et al. |
| 6,941,345 B1 | 9/2005 | Kapil et al. |
| 6,950,839 B1 | 9/2005 | Green et al. |
| 7,128,693 B2 | 10/2006 | Brown et al. |
| 7,166,078 B2 | 1/2007 | Saini et al. |
| 7,739,148 B2 | 6/2010 | Suzuki et al. |
| 7,953,393 B2 | 5/2011 | Chin et al. |
| 8,144,136 B2 | 3/2012 | Minakuchi et al. |
| 8,150,930 B2 | 4/2012 | Satterfield et al. |
| 8,285,258 B2 | 10/2012 | Schultz et al. |
| 8,321,006 B1 | 11/2012 | Snyder et al. |
| 8,475,339 B2 | 7/2013 | Hwang et al. |
| 8,676,170 B2 | 3/2014 | Porrati et al. |
| 8,725,527 B1 | 5/2014 | Kahn et al. |
| 8,758,262 B2 | 6/2014 | Rhee et al. |
| 8,784,115 B1 | 7/2014 | Chuang |
| 9,026,927 B2 | 5/2015 | Brumback et al. |
| 9,224,291 B2 | 12/2015 | Moll-Carrillo et al. |
| 9,575,591 B2 | 2/2017 | Yang et al. |
| 9,579,060 B1 | 2/2017 | Lisy et al. |
| 9,589,445 B2 | 3/2017 | White et al. |
| 9,672,715 B2 | 6/2017 | Roberts et al. |
| 9,712,629 B2 | 7/2017 | Molettiere et al. |
| 9,721,066 B1 | 8/2017 | Funaro et al. |
| 9,730,621 B2 | 8/2017 | Cohen et al. |
| 9,801,562 B1 | 10/2017 | Host-Madsen |
| 9,808,206 B1* | 11/2017 | Zhao ............... A61B 5/0295 |
| 9,813,642 B1 | 11/2017 | Chen et al. |
| 9,940,682 B2 | 4/2018 | Hoffman et al. |
| 10,175,781 B2 | 1/2019 | Karagozler et al. |
| 10,254,911 B2 | 4/2019 | Yang |
| 10,339,830 B2 | 7/2019 | Han et al. |
| 10,576,327 B2 | 3/2020 | Kim et al. |
| 10,602,964 B2 | 3/2020 | Kerber |
| 10,635,267 B2 | 4/2020 | Williams |
| 10,674,942 B2 | 6/2020 | Williams et al. |
| 10,762,990 B1 | 9/2020 | Schilling et al. |
| 10,764,700 B1 | 9/2020 | Felton |
| 10,777,314 B1 | 9/2020 | Williams et al. |
| 10,796,549 B2 | 10/2020 | Roberts et al. |
| 2001/0039503 A1 | 11/2001 | Chan et al. |
| 2002/0037715 A1 | 3/2002 | Mauney et al. |
| 2002/0095292 A1 | 7/2002 | Mittal et al. |
| 2003/0098871 A1 | 5/2003 | Kawano et al. |
| 2003/0126114 A1 | 7/2003 | Tedesco |
| 2003/0181291 A1 | 9/2003 | Ogawa |
| 2003/0191609 A1 | 10/2003 | Bernardi et al. |
| 2003/0200483 A1 | 10/2003 | Sutton |
| 2003/0216971 A1 | 11/2003 | Sick et al. |
| 2003/0226695 A1 | 12/2003 | Mault |
| 2004/0017300 A1 | 1/2004 | Kotzin et al. |
| 2004/0034288 A1 | 2/2004 | Hennessy et al. |
| 2004/0041841 A1 | 3/2004 | Lemogne et al. |
| 2004/0077958 A1 | 4/2004 | Kato et al. |
| 2004/0190729 A1 | 9/2004 | Yonovitz et al. |
| 2004/0193069 A1 | 9/2004 | Takehara |
| 2004/0236189 A1 | 11/2004 | Hawthorne et al. |
| 2005/0010117 A1 | 1/2005 | Agutter et al. |
| 2005/0027208 A1 | 2/2005 | Shiraishi et al. |
| 2005/0075214 A1 | 4/2005 | Brown et al. |
| 2005/0079905 A1 | 4/2005 | Martens |
| 2005/0149362 A1 | 7/2005 | Peterson et al. |
| 2005/0187794 A1 | 8/2005 | Kimak |
| 2005/0228735 A1 | 10/2005 | Duquette |
| 2005/0244013 A1 | 11/2005 | Battenberg et al. |
| 2005/0268237 A1 | 12/2005 | Crane et al. |
| 2005/0272564 A1 | 12/2005 | Pyles et al. |
| 2006/0026245 A1 | 2/2006 | Cunningham et al. |
| 2006/0092177 A1 | 5/2006 | Blasko et al. |
| 2006/0094969 A1 | 5/2006 | Nissila |
| 2006/0098109 A1 | 5/2006 | Ooki |
| 2006/0106741 A1 | 5/2006 | Janarthanan |
| 2006/0123427 A1 | 6/2006 | Harold et al. |
| 2006/0136173 A1 | 6/2006 | Case, Jr. et al. |
| 2006/0149144 A1 | 7/2006 | Lynn et al. |
| 2006/0152372 A1 | 7/2006 | Stout |
| 2006/0182287 A1 | 8/2006 | Schulein et al. |
| 2006/0205564 A1 | 9/2006 | Peterson |
| 2006/0229014 A1 | 10/2006 | Harada et al. |
| 2006/0235319 A1 | 10/2006 | Belohlavek et al. |
| 2006/0294452 A1 | 12/2006 | Matsumoto |
| 2007/0016440 A1 | 1/2007 | Stroup |
| 2007/0036300 A1 | 2/2007 | Brown et al. |
| 2007/0056727 A1 | 3/2007 | Newman |
| 2007/0061786 A1 | 3/2007 | Zhou et al. |
| 2007/0288932 A1 | 12/2007 | Horvitz et al. |
| 2008/0005106 A1 | 1/2008 | Schumacher et al. |
| 2008/0012701 A1* | 1/2008 | Kass ............... A61B 5/165 340/539.11 |
| 2008/0021884 A1 | 1/2008 | Jones et al. |
| 2008/0058626 A1 | 3/2008 | Miyata et al. |
| 2008/0091166 A1 | 4/2008 | Fitzgerald et al. |
| 2008/0119176 A1 | 5/2008 | Chen et al. |
| 2008/0146892 A1 | 6/2008 | Leboeuf et al. |
| 2008/0159547 A1 | 7/2008 | Schuler et al. |
| 2008/0180408 A1 | 7/2008 | Forstall et al. |
| 2008/0200312 A1 | 8/2008 | Tagliabue |
| 2008/0205660 A1 | 8/2008 | Goldstein |
| 2008/0228045 A1 | 9/2008 | Gao et al. |
| 2008/0240519 A1 | 10/2008 | Nagamitsu |
| 2008/0243885 A1 | 10/2008 | Harger et al. |
| 2008/0300110 A1 | 12/2008 | Smith et al. |
| 2008/0320391 A1 | 12/2008 | Lemay et al. |
| 2009/0007596 A1 | 1/2009 | Goldstein et al. |
| 2009/0052677 A1 | 2/2009 | Smith |
| 2009/0055494 A1 | 2/2009 | Fukumoto et al. |
| 2009/0105552 A1 | 4/2009 | Nishiyama et al. |
| 2009/0118100 A1 | 5/2009 | Oliver et al. |
| 2009/0138815 A1 | 5/2009 | Mercer |
| 2009/0172773 A1 | 7/2009 | Moore |
| 2009/0180631 A1 | 7/2009 | Michael et al. |
| 2009/0181726 A1 | 7/2009 | Vargas et al. |
| 2009/0192823 A1 | 7/2009 | Hawkins et al. |
| 2009/0210078 A1 | 8/2009 | Crowley |
| 2009/0216556 A1 | 8/2009 | Martin et al. |
| 2009/0240521 A1 | 9/2009 | Simons et al. |
| 2009/0245537 A1 | 10/2009 | Morin |
| 2009/0248247 A1 | 10/2009 | Furuichi et al. |
| 2009/0249247 A1 | 10/2009 | Tseng et al. |
| 2009/0259134 A1 | 10/2009 | Levine |
| 2009/0262088 A1 | 10/2009 | Moll-Carrillo et al. |
| 2009/0287103 A1 | 11/2009 | Pillai |
| 2009/0287327 A1 | 11/2009 | Hsu et al. |
| 2009/0290721 A1 | 11/2009 | Goldstein et al. |
| 2009/0298444 A1 | 12/2009 | Shigeta |
| 2009/0307715 A1 | 12/2009 | Santamaria et al. |
| 2009/0319243 A1 | 12/2009 | Suarez-Rivera et al. |
| 2010/0003951 A1 | 1/2010 | Ray et al. |
| 2010/0010832 A1 | 1/2010 | Boute et al. |
| 2010/0017489 A1 | 1/2010 | Birnbaum et al. |
| 2010/0027807 A1 | 2/2010 | Jeon |
| 2010/0042949 A1 | 2/2010 | Chen |
| 2010/0046767 A1 | 2/2010 | Bayley et al. |
| 2010/0058231 A1 | 3/2010 | Duarte et al. |
| 2010/0062905 A1 | 3/2010 | Rottler et al. |
| 2010/0076331 A1 | 3/2010 | Chan et al. |
| 2010/0094658 A1 | 4/2010 | Mok et al. |
| 2010/0099539 A1 | 4/2010 | Haataja |
| 2010/0119093 A1 | 5/2010 | Uzuanis et al. |
| 2010/0121700 A1 | 5/2010 | Wigder et al. |
| 2010/0144368 A1 | 6/2010 | Sullivan et al. |
| 2010/0150378 A1 | 6/2010 | Lee et al. |
| 2010/0171759 A1 | 7/2010 | Nickolov et al. |
| 2010/0179832 A1 | 7/2010 | Van et al. |
| 2010/0191818 A1 | 7/2010 | Satterfield et al. |
| 2010/0222645 A1 | 9/2010 | Nadler et al. |
| 2010/0281409 A1 | 11/2010 | Rainisto et al. |
| 2010/0292600 A1* | 11/2010 | DiBenedetto ........ A61B 5/024 600/520 |
| 2010/0305965 A1 | 12/2010 | Benjamin et al. |
| 2010/0312138 A1 | 12/2010 | Regas |

(56) References Cited

U.S. PATENT DOCUMENTS

| | | |
|---|---|---|
| 2010/0332518 A1 | 12/2010 | Song et al. |
| 2011/0010195 A1 | 1/2011 | Cohn |
| 2011/0066051 A1 | 3/2011 | Moon et al. |
| 2011/0093481 A1 | 4/2011 | Hussam |
| 2011/0096011 A1 | 4/2011 | Suzuki |
| 2011/0098928 A1 | 4/2011 | Hoffman et al. |
| 2011/0106553 A1 | 5/2011 | Tanaka et al. |
| 2011/0111728 A1 | 5/2011 | Ferguson et al. |
| 2011/0119088 A1 | 5/2011 | Gunn et al. |
| 2011/0137678 A1 | 6/2011 | Williams |
| 2011/0151418 A1 | 6/2011 | Delespaul et al. |
| 2011/0152656 A1 | 6/2011 | Weinert et al. |
| 2011/0166631 A1 | 7/2011 | Breining |
| 2011/0167383 A1 | 7/2011 | Schuller et al. |
| 2011/0183650 A1 | 7/2011 | Mckee |
| 2011/0201911 A1 | 8/2011 | Johnson et al. |
| 2011/0214162 A1 | 9/2011 | Brakensiek et al. |
| 2011/0225547 A1 | 9/2011 | Fong et al. |
| 2011/0239158 A1 | 9/2011 | Barraclough et al. |
| 2011/0245623 A1 | 10/2011 | Chutani et al. |
| 2011/0254684 A1 | 10/2011 | Antoci et al. |
| 2011/0265041 A1 | 10/2011 | Ganetakos et al. |
| 2011/0306389 A1 | 12/2011 | Nagayama |
| 2011/0307821 A1 | 12/2011 | Martens |
| 2012/0002510 A1 | 1/2012 | Berman, Jr. |
| 2012/0023586 A1 | 1/2012 | Flickner et al. |
| 2012/0029303 A1 | 2/2012 | Shaya |
| 2012/0038651 A1 | 2/2012 | Case et al. |
| 2012/0041767 A1 | 2/2012 | Hoffman et al. |
| 2012/0059664 A1 | 3/2012 | Georgiev et al. |
| 2012/0065480 A1 | 3/2012 | Badilini et al. |
| 2012/0071770 A1 | 3/2012 | Grey et al. |
| 2012/0077463 A1 | 3/2012 | Robbins et al. |
| 2012/0102437 A1 | 4/2012 | Worley et al. |
| 2012/0105358 A1 | 5/2012 | Momeyer et al. |
| 2012/0108215 A1 | 5/2012 | Kameli et al. |
| 2012/0112908 A1 | 5/2012 | Prykaeri et al. |
| 2012/0116550 A1 | 5/2012 | Hoffman et al. |
| 2012/0117507 A1 | 5/2012 | Tseng et al. |
| 2012/0150970 A1 | 6/2012 | Peterson et al. |
| 2012/0154431 A1 | 6/2012 | Fram |
| 2012/0158511 A1 | 6/2012 | Lucero et al. |
| 2012/0172088 A1 | 7/2012 | Kirch et al. |
| 2012/0185267 A1 | 7/2012 | Kamen et al. |
| 2012/0203124 A1 | 8/2012 | Lim |
| 2012/0216127 A1 | 8/2012 | Meyr |
| 2012/0232929 A1 | 9/2012 | Experton |
| 2012/0245447 A1 | 9/2012 | Karan et al. |
| 2012/0283587 A1 | 11/2012 | Gosh et al. |
| 2012/0283855 A1 | 11/2012 | Hoffman et al. |
| 2012/0302840 A1 | 11/2012 | Kubo |
| 2012/0304084 A1 | 11/2012 | Kim et al. |
| 2012/0317167 A1 | 12/2012 | Rahman et al. |
| 2012/0321094 A1 | 12/2012 | Schiller et al. |
| 2013/0002425 A1 | 1/2013 | Hatch et al. |
| 2013/0002580 A1 | 1/2013 | Sudou |
| 2013/0007665 A1 | 1/2013 | Chaudhri et al. |
| 2013/0011819 A1 | 1/2013 | Horseman |
| 2013/0012788 A1 | 1/2013 | Horseman |
| 2013/0013331 A1 | 1/2013 | Horseman |
| 2013/0033376 A1 | 2/2013 | Seyed et al. |
| 2013/0054150 A1 | 2/2013 | Sacks et al. |
| 2013/0063383 A1 | 3/2013 | Anderssonreimer et al. |
| 2013/0065566 A1 | 3/2013 | Gisby et al. |
| 2013/0065569 A1 | 3/2013 | Leipzig et al. |
| 2013/0073960 A1 | 3/2013 | Eppolito et al. |
| 2013/0091298 A1 | 4/2013 | Ozzie et al. |
| 2013/0095459 A1 | 4/2013 | Tran |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0138334 A1 | 5/2013 | Meredith et al. |
| 2013/0141233 A1 | 6/2013 | Jacobs et al. |
| 2013/0144653 A1 | 6/2013 | Poe et al. |
| 2013/0151285 A1 | 6/2013 | Mclaren et al. |
| 2013/0151961 A1 | 6/2013 | Sasaki |
| 2013/0158367 A1 | 6/2013 | Pacione et al. |
| 2013/0158416 A1 | 6/2013 | Hatlestad et al. |
| 2013/0159941 A1 | 6/2013 | Langlois et al. |
| 2013/0187923 A1 | 7/2013 | Yoshimoto et al. |
| 2013/0191647 A1 | 7/2013 | Ferrara, Jr. et al. |
| 2013/0197679 A1 | 8/2013 | Balakrishnan et al. |
| 2013/0202121 A1 | 8/2013 | Georgiou et al. |
| 2013/0215042 A1 | 8/2013 | Messerschmidt et al. |
| 2013/0222236 A1 | 8/2013 | Gardenfors et al. |
| 2013/0231575 A1 | 9/2013 | Erkkila et al. |
| 2013/0231947 A1 | 9/2013 | Shusterman |
| 2013/0262155 A1 | 10/2013 | Hinkamp |
| 2013/0268353 A1 | 10/2013 | Zeto et al. |
| 2013/0268398 A1 | 10/2013 | Agami et al. |
| 2013/0274628 A1 | 10/2013 | Fausti et al. |
| 2013/0304510 A1 | 11/2013 | Chen et al. |
| 2013/0304616 A1 | 11/2013 | Raleigh et al. |
| 2013/0307809 A1 | 11/2013 | Sudou |
| 2013/0317380 A1 | 11/2013 | Liley et al. |
| 2013/0321314 A1 | 12/2013 | Oh et al. |
| 2013/0322634 A1 | 12/2013 | Bennett et al. |
| 2013/0325396 A1 | 12/2013 | Yuen et al. |
| 2013/0325511 A1 | 12/2013 | Neagle et al. |
| 2013/0325951 A1 | 12/2013 | Chakra et al. |
| 2013/0332286 A1 | 12/2013 | Medelius et al. |
| 2013/0332892 A1 | 12/2013 | Matsuki |
| 2013/0339436 A1 | 12/2013 | Gray |
| 2013/0346882 A1 | 12/2013 | Shiplacoff et al. |
| 2013/0347018 A1 | 12/2013 | Limp et al. |
| 2014/0037107 A1 | 2/2014 | Marino et al. |
| 2014/0038781 A1 | 2/2014 | Foley et al. |
| 2014/0046926 A1 | 2/2014 | Walton |
| 2014/0058873 A1 | 2/2014 | Sorensen et al. |
| 2014/0073486 A1 | 3/2014 | Ahmed et al. |
| 2014/0081118 A1 | 3/2014 | Reinhold et al. |
| 2014/0088995 A1 | 3/2014 | Damani |
| 2014/0100885 A1 | 4/2014 | Stern |
| 2014/0118272 A1 | 5/2014 | Gunn |
| 2014/0127996 A1 | 5/2014 | Park et al. |
| 2014/0129007 A1* | 5/2014 | Utter, II ............... G06Q 90/00 700/92 |
| 2014/0129243 A1 | 5/2014 | Utter |
| 2014/0135592 A1 | 5/2014 | Ohnemus et al. |
| 2014/0136633 A1 | 5/2014 | Murillo et al. |
| 2014/0142403 A1 | 5/2014 | Brumback et al. |
| 2014/0143678 A1 | 5/2014 | Mistry et al. |
| 2014/0164611 A1 | 6/2014 | Molettiere et al. |
| 2014/0176335 A1 | 6/2014 | Brumback et al. |
| 2014/0176475 A1 | 6/2014 | Myers et al. |
| 2014/0180595 A1 | 6/2014 | Brumback et al. |
| 2014/0184422 A1 | 7/2014 | Mensinger et al. |
| 2014/0189030 A1 | 7/2014 | Benchenaa et al. |
| 2014/0189510 A1 | 7/2014 | Ozcan |
| 2014/0189533 A1 | 7/2014 | Krack et al. |
| 2014/0197946 A1 | 7/2014 | Park et al. |
| 2014/0200426 A1 | 7/2014 | Taub et al. |
| 2014/0213295 A1 | 7/2014 | Conklin |
| 2014/0223358 A1 | 8/2014 | Park |
| 2014/0240122 A1 | 8/2014 | Roberts et al. |
| 2014/0240349 A1 | 8/2014 | Tuukkanen |
| 2014/0244715 A1 | 8/2014 | Hodges et al. |
| 2014/0258935 A1 | 9/2014 | Nishida et al. |
| 2014/0266776 A1 | 9/2014 | Miller et al. |
| 2014/0275852 A1 | 9/2014 | Hong et al. |
| 2014/0275856 A1 | 9/2014 | Kohlrausch et al. |
| 2014/0278220 A1 | 9/2014 | Yuen |
| 2014/0297217 A1 | 10/2014 | Yuen |
| 2014/0310643 A1 | 10/2014 | Karmanenko et al. |
| 2014/0327527 A1 | 11/2014 | Goldstein et al. |
| 2014/0336796 A1 | 11/2014 | Agnew |
| 2014/0344687 A1 | 11/2014 | Durham et al. |
| 2014/0354494 A1 | 12/2014 | Katz |
| 2014/0358012 A1 | 12/2014 | Richards et al. |
| 2014/0362702 A1 | 12/2014 | Luna |
| 2014/0368333 A1 | 12/2014 | Touloumtzis et al. |
| 2014/0371887 A1 | 12/2014 | Hoffman et al. |

(56) References Cited

U.S. PATENT DOCUMENTS

| | | |
|---|---|---|
| 2015/0007049 A1 | 1/2015 | Langlois |
| 2015/0061862 A1 | 3/2015 | Shin et al. |
| 2015/0081210 A1 | 3/2015 | Yeh et al. |
| 2015/0089536 A1 | 3/2015 | Byerley |
| 2015/0099991 A1 | 4/2015 | Yamaguchi et al. |
| 2015/0100245 A1 | 4/2015 | Huang et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0142689 A1 | 5/2015 | Squires |
| 2015/0181314 A1 | 6/2015 | Swanson |
| 2015/0181373 A1 | 6/2015 | Xie et al. |
| 2015/0182843 A1 | 7/2015 | Esposito et al. |
| 2015/0185967 A1 | 7/2015 | Ly et al. |
| 2015/0196804 A1 | 7/2015 | Koduri et al. |
| 2015/0205930 A1 | 7/2015 | Shaanan et al. |
| 2015/0205947 A1 | 7/2015 | Berman et al. |
| 2015/0216448 A1 | 8/2015 | Lotan et al. |
| 2015/0217163 A1 | 8/2015 | Amis et al. |
| 2015/0220883 A1 | 8/2015 | Bfar et al. |
| 2015/0230717 A1 | 8/2015 | Wan |
| 2015/0248389 A1 | 9/2015 | Kahn et al. |
| 2015/0262499 A1 | 9/2015 | Wicka et al. |
| 2015/0286387 A1 | 10/2015 | Gu et al. |
| 2015/0286391 A1 | 10/2015 | Jacobs et al. |
| 2015/0286800 A1 | 10/2015 | Kanagala et al. |
| 2015/0288944 A1 | 10/2015 | Nistico et al. |
| 2015/0289823 A1 | 10/2015 | Rack-gomer et al. |
| 2015/0297134 A1 | 10/2015 | Albert et al. |
| 2015/0324751 A1 | 11/2015 | Orenstein et al. |
| 2015/0334533 A1 | 11/2015 | Luo et al. |
| 2015/0347711 A1 | 12/2015 | Soli et al. |
| 2015/0350129 A1 | 12/2015 | Cary et al. |
| 2015/0350140 A1 | 12/2015 | Garcia et al. |
| 2015/0350146 A1 | 12/2015 | Cary et al. |
| 2015/0350861 A1 | 12/2015 | Soli et al. |
| 2015/0379476 A1 | 12/2015 | Chaudhri et al. |
| 2016/0019360 A1 | 1/2016 | Pahwa et al. |
| 2016/0027282 A1 | 1/2016 | Lee |
| 2016/0055420 A1 | 2/2016 | Karanam et al. |
| 2016/0058313 A1 | 3/2016 | Sato |
| 2016/0058336 A1 | 3/2016 | Blahnik et al. |
| 2016/0058337 A1 | 3/2016 | Blahnik et al. |
| 2016/0062540 A1 | 3/2016 | Yang et al. |
| 2016/0062570 A1 | 3/2016 | Dascola et al. |
| 2016/0062582 A1 | 3/2016 | Wilson et al. |
| 2016/0063215 A1 | 3/2016 | Zamer |
| 2016/0085937 A1 | 3/2016 | Dettinger et al. |
| 2016/0086500 A1 | 3/2016 | Kaleal, III |
| 2016/0098522 A1 | 4/2016 | Weinstein |
| 2016/0106398 A1 | 4/2016 | Kuppuswami |
| 2016/0107031 A1 | 4/2016 | Palatsi et al. |
| 2016/0109961 A1 | 4/2016 | Parshionikar |
| 2016/0132046 A1 | 5/2016 | Beoughter et al. |
| 2016/0135719 A1 | 5/2016 | Von Kraus et al. |
| 2016/0135731 A1 | 5/2016 | Drennan |
| 2016/0150978 A1 | 6/2016 | Yuen et al. |
| 2016/0157225 A1 | 6/2016 | Joshi et al. |
| 2016/0166181 A1 | 6/2016 | Shennib |
| 2016/0174857 A1 | 6/2016 | Eggers et al. |
| 2016/0196635 A1 | 7/2016 | Cho et al. |
| 2016/0210099 A1 | 7/2016 | Hampapuram et al. |
| 2016/0210434 A1 | 7/2016 | Al-Sharif |
| 2016/0232638 A1 | 8/2016 | Chen |
| 2016/0235325 A1 | 8/2016 | Chou |
| 2016/0235374 A1 | 8/2016 | Miller et al. |
| 2016/0249857 A1 | 9/2016 | Choi et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0270717 A1 * | 9/2016 | Luna ............... A61B 5/743 |
| 2016/0275310 A1 | 9/2016 | Edwards et al. |
| 2016/0275990 A1 | 9/2016 | Vassort |
| 2016/0287177 A1 | 10/2016 | Huppert et al. |
| 2016/0292373 A1 | 10/2016 | Spors et al. |
| 2016/0299526 A1 | 10/2016 | Inagaki et al. |
| 2016/0299769 A1 | 10/2016 | Hunter et al. |
| 2016/0301761 A1 | 10/2016 | Sanchez-Sandoval et al. |
| 2016/0301794 A1 | 10/2016 | Schlakman et al. |
| 2016/0302666 A1 | 10/2016 | Shaya |
| 2016/0314670 A1 * | 10/2016 | Roberts ............... A61B 5/486 |
| 2016/0314683 A1 | 10/2016 | Felch et al. |
| 2016/0317341 A1 | 11/2016 | Galvan |
| 2016/0324457 A1 | 11/2016 | Dagum |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0360100 A1 | 12/2016 | Kim et al. |
| 2016/0379511 A1 | 12/2016 | Dawson et al. |
| 2017/0000348 A1 | 1/2017 | Karsten et al. |
| 2017/0000359 A1 | 1/2017 | Kohli et al. |
| 2017/0007159 A1 | 1/2017 | Dieffenderfer et al. |
| 2017/0007167 A1 | 1/2017 | Kostic et al. |
| 2017/0032168 A1 | 2/2017 | Kim |
| 2017/0039327 A1 | 2/2017 | Bitran et al. |
| 2017/0043214 A1 | 2/2017 | Higashi |
| 2017/0046024 A1 | 2/2017 | Dascola et al. |
| 2017/0053542 A1 | 2/2017 | Wilson et al. |
| 2017/0071551 A1 | 3/2017 | Jain et al. |
| 2017/0075551 A1 | 3/2017 | Robinson et al. |
| 2017/0083202 A1 | 3/2017 | Yang et al. |
| 2017/0086693 A1 | 3/2017 | Peterson et al. |
| 2017/0127997 A1 | 5/2017 | Hyde et al. |
| 2017/0132395 A1 | 5/2017 | Futch |
| 2017/0136297 A1 | 5/2017 | Penie |
| 2017/0147197 A1 | 5/2017 | Yang et al. |
| 2017/0150917 A1 | 6/2017 | Brief et al. |
| 2017/0153795 A1 | 6/2017 | Yang et al. |
| 2017/0156593 A1 | 6/2017 | Ferber et al. |
| 2017/0161014 A1 | 6/2017 | Kikugawa et al. |
| 2017/0172522 A1 | 6/2017 | Insler et al. |
| 2017/0177797 A1 | 6/2017 | Kurniawan et al. |
| 2017/0181645 A1 | 6/2017 | Mahalingam et al. |
| 2017/0188841 A1 | 7/2017 | Ma et al. |
| 2017/0188893 A1 | 7/2017 | Venkatraman et al. |
| 2017/0188979 A1 | 7/2017 | Volpe |
| 2017/0202496 A1 | 7/2017 | Ramanathan |
| 2017/0235443 A1 | 8/2017 | Suzuki |
| 2017/0237694 A1 | 8/2017 | Choudhary et al. |
| 2017/0243508 A1 | 8/2017 | Cheng et al. |
| 2017/0258455 A1 | 9/2017 | Qi |
| 2017/0274149 A1 | 9/2017 | Aeschlimann |
| 2017/0274267 A1 | 9/2017 | Blahnik |
| 2017/0293727 A1 | 10/2017 | Klaassen et al. |
| 2017/0294174 A1 | 10/2017 | Albadawi et al. |
| 2017/0300186 A1 | 10/2017 | Kuhar et al. |
| 2017/0303844 A1 | 10/2017 | Baker et al. |
| 2017/0319184 A1 | 11/2017 | Sano |
| 2017/0330297 A1 | 11/2017 | Cronin et al. |
| 2017/0348562 A1 | 12/2017 | Jung et al. |
| 2017/0353836 A1 | 12/2017 | Gordon et al. |
| 2017/0354845 A1 | 12/2017 | Williams et al. |
| 2017/0357329 A1 | 12/2017 | Park et al. |
| 2017/0357520 A1 | 12/2017 | De Vries et al. |
| 2018/0000426 A1 | 1/2018 | Li |
| 2018/0001184 A1 | 1/2018 | Tran et al. |
| 2018/0011686 A1 | 1/2018 | Zhao et al. |
| 2018/0032234 A1 | 2/2018 | Michalske |
| 2018/0042559 A1 | 2/2018 | Cabrera et al. |
| 2018/0047277 A1 | 2/2018 | Thyroff |
| 2018/0049659 A1 | 2/2018 | Briante et al. |
| 2018/0049696 A1 | 2/2018 | Eom et al. |
| 2018/0055490 A1 | 3/2018 | Lee et al. |
| 2018/0060522 A1 | 3/2018 | Petterson et al. |
| 2018/0064356 A1 | 3/2018 | Mendenhall et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |

(56) References Cited

U.S. PATENT DOCUMENTS

| | | |
|---|---|---|
| 2018/0081918 A1 | 3/2018 | Nites et al. |
| 2018/0096739 A1 | 4/2018 | Sano |
| 2018/0107962 A1 | 4/2018 | Lundin et al. |
| 2018/0117414 A1 | 5/2018 | Miyasaka et al. |
| 2018/0120985 A1 | 5/2018 | Wallace et al. |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140927 A1 | 5/2018 | Kito et al. |
| 2018/0154212 A1 | 6/2018 | Park et al. |
| 2018/0157864 A1 | 6/2018 | Tribble et al. |
| 2018/0189077 A1 | 7/2018 | Gupta et al. |
| 2018/0211020 A1 | 7/2018 | Fukuda |
| 2018/0213354 A1 | 7/2018 | Wang et al. |
| 2018/0239869 A1 | 8/2018 | Laing et al. |
| 2018/0255159 A1 | 9/2018 | Cohen et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263517 A1 | 9/2018 | Kubo |
| 2018/0279885 A1 | 10/2018 | Bulut |
| 2018/0294053 A1 | 10/2018 | Runyon et al. |
| 2018/0336530 A1 | 11/2018 | Johnson et al. |
| 2018/0345078 A1 | 12/2018 | Blahnik et al. |
| 2018/0350451 A1 | 12/2018 | Ohnemus et al. |
| 2018/0368814 A1 | 12/2018 | R. Kudtarkar |
| 2018/0376107 A1 | 12/2018 | Shibaev et al. |
| 2019/0012898 A1 | 1/2019 | Wittrup |
| 2019/0014205 A1 | 1/2019 | Miloseski et al. |
| 2019/0034050 A1 | 1/2019 | Williams et al. |
| 2019/0034494 A1 | 1/2019 | Bradley et al. |
| 2019/0043337 A1 | 2/2019 | Liu et al. |
| 2019/0090800 A1 | 3/2019 | Bosworth et al. |
| 2019/0090816 A1 | 3/2019 | Horseman |
| 2019/0104951 A1 | 4/2019 | Valys et al. |
| 2019/0122523 A1 | 4/2019 | Roberts et al. |
| 2019/0138696 A1 | 5/2019 | Carpenter et al. |
| 2019/0192086 A1 | 6/2019 | Menon et al. |
| 2019/0206538 A1 | 7/2019 | Xing et al. |
| 2019/0223843 A1 | 7/2019 | Vitti |
| 2019/0228179 A1 | 7/2019 | Rakshit et al. |
| 2019/0228847 A1 | 7/2019 | Soli |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0286301 A1 | 9/2019 | Yang et al. |
| 2019/0298230 A1 | 10/2019 | Nicholson et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0365332 A1 | 12/2019 | Fedichev et al. |
| 2020/0000441 A1 | 1/2020 | Lafon et al. |
| 2020/0008010 A1 | 1/2020 | Pai et al. |
| 2020/0126673 A1 | 4/2020 | Tanabe et al. |
| 2020/0186960 A1 | 6/2020 | Nolan |
| 2020/0245928 A1* | 8/2020 | Kang .................. A61B 5/486 |
| 2020/0261011 A1 | 8/2020 | Seppänen et al. |
| 2020/0273566 A1 | 8/2020 | Bhowmik et al. |
| 2020/0297249 A1 | 9/2020 | Williams et al. |
| 2020/0315544 A1 | 10/2020 | Levine |
| 2020/0356687 A1 | 11/2020 | Salzman et al. |
| 2020/0357522 A1 | 11/2020 | Pahwa et al. |
| 2020/0363914 A1 | 11/2020 | Dascola et al. |
| 2020/0374682 A1 | 11/2020 | Newman et al. |
| 2020/0379611 A1 | 12/2020 | Dryer et al. |
| 2020/0381100 A1 | 12/2020 | Williams et al. |
| 2020/0381123 A1 | 12/2020 | Dryer et al. |
| 2020/0382866 A1 | 12/2020 | Felton |
| 2020/0382867 A1 | 12/2020 | Felton |
| 2020/0382908 A1 | 12/2020 | Behzadi et al. |
| 2020/0384314 A1 | 12/2020 | Lee et al. |
| 2020/0409537 A1 | 12/2020 | Story et al. |
| 2021/0068714 A1 | 3/2021 | Crowley et al. |
| 2021/0113137 A1 | 4/2021 | Soli et al. |

FOREIGN PATENT DOCUMENTS

| | | |
|---|---|---|
| CN | 1429364 A | 7/2003 |
| CN | 1585943 A | 2/2005 |
| CN | 1852335 A | 10/2006 |
| CN | 1950762 A | 4/2007 |
| CN | 101107619 A | 1/2008 |
| CN | 101150810 A | 3/2008 |
| CN | 101390371 A | 3/2009 |
| CN | 101651870 A | 2/2010 |
| CN | 102111505 A | 6/2011 |
| CN | 102339201 A | 2/2012 |
| CN | 102395128 A | 3/2012 |
| CN | 102404458 A | 4/2012 |
| CN | 102448555 A | 5/2012 |
| CN | 102790761 A | 11/2012 |
| CN | 103370924 A | 10/2013 |
| CN | 103403627 A | 11/2013 |
| CN | 103500079 A | 1/2014 |
| CN | 103581413 A | 2/2014 |
| CN | 103582873 A | 2/2014 |
| CN | 103944811 A | 7/2014 |
| CN | 104720765 A | 6/2015 |
| CN | 106537397 A | 3/2017 |
| CN | 106709235 A | 5/2017 |
| CN | 106725384 A | 5/2017 |
| CN | 107278138 A | 10/2017 |
| CN | 107361755 A | 11/2017 |
| CN | 107591211 A | 1/2018 |
| CN | 107713981 A | 2/2018 |
| EP | 2391004 A1 | 11/2011 |
| EP | 2568409 A1 | 3/2013 |
| EP | 2574026 A1 | 3/2013 |
| EP | 2849042 A1 | 3/2015 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3557590 A1 | 10/2019 |
| JP | 6-187118 A | 7/1994 |
| JP | 11-45117 A | 2/1999 |
| JP | 2001-76078 A | 3/2001 |
| JP | 2002-366485 A | 12/2002 |
| JP | 2003-337863 A | 11/2003 |
| JP | 2004-102609 A | 4/2004 |
| JP | 2004-113466 A | 4/2004 |
| JP | 2005-79814 A | 3/2005 |
| JP | 2006-79427 A | 3/2006 |
| JP | 2006-113637 A | 4/2006 |
| JP | 2006-129429 A | 5/2006 |
| JP | 2006-230679 A | 9/2006 |
| JP | 2008-011865 A | 1/2008 |
| JP | 2008-104068 A | 5/2008 |
| JP | 2008-183339 A | 8/2008 |
| JP | 2010-12335 A | 1/2010 |
| JP | 2010-517725 A | 5/2010 |
| JP | 2010-162297 A | 7/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-259253 A | 12/2011 |
| JP | 2012-59264 A | 3/2012 |
| JP | 2012-198369 A | 10/2012 |
| JP | 2012-524640 A | 10/2012 |
| JP | 2013-48389 A | 3/2013 |
| JP | 2013-117690 A | 6/2013 |
| JP | 2013-544140 A | 12/2013 |
| JP | 2014-57129 A | 3/2014 |
| JP | 2014-519126 A | 8/2014 |
| JP | 2016-502875 A | 2/2016 |
| JP | 2016-528016 A | 9/2016 |
| JP | 2016-177151 A | 10/2016 |
| JP | 2016-202751 A | 12/2016 |
| JP | 2017-134689 A | 8/2017 |

(56) References Cited

FOREIGN PATENT DOCUMENTS

| | | |
|---|---|---|
| JP | 2017-211994 A | 11/2017 |
| JP | 2017-532069 A | 11/2017 |
| KR | 10-2011-0017076 A | 2/2011 |
| KR | 10-2012-0023657 A | 3/2012 |
| KR | 10-2013-0093837 A | 8/2013 |
| KR | 10-2013-0111569 A | 10/2013 |
| KR | 10-2013-0111570 A | 10/2013 |
| KR | 10-2013-0135282 A | 12/2013 |
| KR | 10-1594486 B1 | 2/2016 |
| KR | 10-2016-0028351 A | 3/2016 |
| KR | 10-2017-0003608 A | 1/2017 |
| KR | 10-2019-0094795 A | 8/2019 |
| WO | 1999/41682 A2 | 8/1999 |
| WO | 2001/96986 A2 | 12/2001 |
| WO | 2002/27530 A2 | 4/2002 |
| WO | 2003/067202 A2 | 8/2003 |
| WO | 2006/046648 A1 | 5/2006 |
| WO | 2008/073359 A2 | 6/2008 |
| WO | 2009/082377 A1 | 7/2009 |
| WO | 2010/126825 A1 | 11/2010 |
| WO | 2012/060588 A2 | 5/2012 |
| WO | 2012/061438 A2 | 5/2012 |
| WO | 2012/061440 A2 | 5/2012 |
| WO | 2012/078079 A2 | 6/2012 |
| WO | 2012/128824 A1 | 9/2012 |
| WO | 2012/170446 A2 | 12/2012 |
| WO | 2013/052789 A1 | 4/2013 |
| WO | 2013/093558 A1 | 6/2013 |
| WO | 2013/109916 A1 | 7/2013 |
| WO | 2013/169842 A2 | 11/2013 |
| WO | 2013/169865 A2 | 11/2013 |
| WO | 2013/169870 A1 | 11/2013 |
| WO | 2013/169875 A2 | 11/2013 |
| WO | 2014/015378 A1 | 1/2014 |
| WO | 2014/065846 A1 | 5/2014 |
| WO | 2014/083001 A2 | 6/2014 |
| WO | 2015/027133 A1 | 2/2015 |
| WO | 2015/034163 A1 | 3/2015 |
| WO | 2015/038684 A1 | 3/2015 |
| WO | 2015/120358 A1 | 8/2015 |
| WO | 2015/187799 A1 | 12/2015 |
| WO | 2015/198488 A1 | 12/2015 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2017/003045 A1 | 1/2017 |
| WO | 2017/037242 A1 | 3/2017 |
| WO | 2017/062621 A1 | 4/2017 |
| WO | 2017/087642 A1 | 5/2017 |
| WO | 2017/090810 A1 | 6/2017 |
| WO | 2017/215203 A1 | 12/2017 |
| WO | 2018/148356 A1 | 8/2018 |
| WO | 2018/222313 A1 | 12/2018 |
| WO | 2019/017508 A1 | 1/2019 |
| WO | 2019/020977 A1 | 1/2019 |
| WO | 2019/168956 A1 | 9/2019 |

OTHER PUBLICATIONS

Non-Final Office Action received for U.S. Appl. No. 16/894,309, dated Oct. 15, 2020, 24 pages.
Non-Final Office Action received for U.S. Appl. No. 16/907,261, dated Sep. 30, 2020, 22 pages.
Office Action received for Australian Patent Application No. 2020200028, dated Sep. 24, 2020, 3 pages.
Result of Consultation received for European Patent Application No. 19721883.7, dated Oct. 7, 2020, 3 pages.
Applicant-Initiated Interview Summary received for U.S. Appl. No. 16/584,186, dated Feb. 3, 2020, 4 pages.
Corrected Notice of Allowance received for U.S. Appl. No. 16/584,186, dated Jul. 31, 2020, 2 pages.
Decision to Grant received for Danish Patent Application No. PA201870601, dated Aug. 17, 2020, 2 pages.
Decision to Grant received for Danish Patent Application No. PA201870602, dated Aug. 18, 2020, 2 pages.
Extended European Search Report received for European Patent Application No. 20180592.6, dated Aug. 11, 2020, 10 pages.
Final Office Action received for U.S. Appl. No. 16/138,809, dated Aug. 27, 2020, 24 pages.
International Search Report and written Opinion received for PCT Patent Application No. PCT/US2020/025768, dated Aug. 10, 2020, 11 pages.
Non-Final Office Action received for U.S. Appl. No. 16/584,186, dated Dec. 6, 2019, 13 pages.
Non-Final Office Action received for U.S. Appl. No. 16/880,552, dated Jul. 23, 2020, 19 pages.
Notice of Allowance received for U.S. Appl. No. 16/584,186, dated Mar. 24, 2020, 10 pages.
Office Action received for Chinese Patent Application No. 201380081349.6, dated Jul. 15, 2020, 9 pages (4 pages of English Translation and 5 pages of Official Copy).
Office Action received for Danish Patent Application No. PA201970534, dated Jun. 29, 2020, 2 pages.
Office Action received for Korean Patent Application No. 10-2019-7025538, dated Aug. 15, 2020, 8 pages (4 pages of English Translation and 4 pages of Official Copy).
Search Report and Opinion received for Danish Patent Application No. PA201970534, dated Sep. 23, 2019, 6 pages.
Advisory Action received for U.S. Appl. No. 16/144,864, dated Jul. 6, 2020, 6 pages.
Applicant-Initiated Interview Summary received for U.S. Appl. No. 16/144,864, dated Jun. 22, 2020, 3 pages.
Intention to Grant received for European Patent Application No. 18170262.2, dated Jun. 30, 2020, 8 pages.
Office Action received for European Patent Application No. 19726205.8, dated Jun. 26, 2020, 9 pages.
Applicant Initiated Interview Summary received for U.S. Appl. No. 16/143,997, dated Aug. 13, 2020, 3 pages.
Extended European Search Report received for European Patent Application No. 20180581.9, dated Aug. 12, 2020, 9 pages.
Invitation to Pay Additional Fees received for PCT Patent Application No. PCT/US2020/034155, dated Jul. 27, 2020, 12 pages.
Epstein et al., "Examining Menstrual Tracking to Inform the Design of Personal Informatics Tools", Proceedings of the 2017 CHI Conference on Human Factors in Computing Systems, CHI '17, ACM Press, Denver, CO, USA, May 6-11, 2017, pp. 6876-6888.
Moglia et al., "Evaluation of Smartphone Menstrual Cycle Tracking Applications Using an Adapted APPLICATIONS Scoring System", Obstetrics and Gynecology, vol. 127. No. 6, Jun. 2016, pp. 1153-1160.
Notice of Allowance received for Chinese Patent Application No. 201910972529.2, dated Sep. 14, 2020, 6 pages (3 pages of English Translation and 3 pages of Official Copy).
Notice of Allowance received for U.S. Appl. No. 16/144,864, dated Sep. 29, 2020, 2 pages.
Advisory Action received for U.S. Appl. No. 16/144,864, dated Jul. 29, 2019, 6 pages.
Advisory Action received for U.S. Appl. No. 14/475,446, dated Sep. 20, 2019, 12 pages.
Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/838,263, dated Jul. 12, 2018, 3 pages.
Advisory Action received for U.S. Appl. No. 16/143,909, dated Nov. 7, 2019, 5 pages.
Advisory Action received for U.S. Appl. No. 16/143,997, dated Dec. 26, 2019, 7 pages.
Advisory Action received for U.S. Appl. No. 16/144,849, dated Aug. 12, 2019, 5 pages.
Airize, "Notification & Control Center Problem Issue Solution", Available online at: "https://www.youtube.com/watch?v=K0zCueYlaTA", Dec. 6, 2013, 1 page.

(56) References Cited

OTHER PUBLICATIONS

Applicant Initiated Interview Summary received for U.S. Appl. No. 14/475,471, dated Mar. 18, 2020, 5 pages.
Applicant Initiated Interview Summary received for U.S. Appl. No. 14/475,471, dated Oct. 28, 2019, 5 pages.
Applicant Initiated Interview Summary received for U.S. Appl. No. 14/838,263, dated Jan. 17, 2020, 6 pages.
Applicant Initiated Interview Summary received for U.S. Appl. No. 16/144,849, dated Jan. 21, 2020, 6 pages.
Applicant Initiated Interview Summary received for U.S. Appl. No. 16/144,864, dated Apr. 29, 2020, 4 pages.
Basu, Saikat, "MS Outlook Tip: How to Automatically Organize Incoming Emails", Available online at: http://www.makeuseof.com/tag/ms-outlook-productivity-tip-how-to-move-emails-to-individual-folders-automatically/, Sep. 27, 2009, pp. 1-6.
Casella Cel Casella, "The Casella dBadge2—World's First Truly Wireless Noise Dosimeter and Airwave App!", Online available at: https://www.youtube.com/watch?v=Xvy2fl3cgYo, May 27, 2015, 3 pages.
Certificate of Examination received for Australian Patent Application No. 2019100222, dated Aug. 29, 2019, 2 pages.
Cho H.S., "Satisfactory Innovative Smart-watch (fitbit force) review after seven days of use, such as the amount of sleep and movement (improving sleep is the object of X-Blue", Online Available at: https://x-blueuv.blogspot.com/2013/12/fitbit-force.html, Dec. 3, 2013, 8 pages (2 pages of English Translation and 6 pages of Official Copy).
CNET, "Google Fit's automatic activity tracking is getting smarter on Android Wear", Available online at: https://www.youtube.com/watch?v=IttzlCid_d8, May 18, 2016, 1 page.
Corrected Notice of Allowance received for U.S. Appl. No. 14/732,773, dated Feb. 10, 2020, 3 pages.
Corrected Notice of Allowance received for U.S. Appl. No. 14/732,773, dated Mar. 24, 2020, 3 pages.
Corrected Notice of Allowance received for U.S. Appl. No. 16/143,909, dated Feb. 20, 2020, 3 pages.
Corrected Notice of Allowance received for U.S. Appl. No. 16/143,909, dated Mar. 18, 2020, 3 pages.
Corrected Notice of Allowance received for U.S. Appl. No. 16/143,959, dated Dec. 13, 2019, 2 pages.
Decision to Grant received for Danish Patent Application No. PA201770126, dated Mar. 27, 2018, 2 pages.
Decision to Grant received for Danish Patent Application No. PA201870379, dated Jul. 5, 2019, 2 pages.
Decision to Grant received for Danish Patent Application No. PA201870600, dated Oct. 17, 2019, 2 pages.
Decision to Grant received for European Patent Application No. 15759981.2, dated Jan. 8, 2020, 2 pages.
Decision to Refuse received for European Application No. 13811085.3, dated Sep. 11, 2018, 21 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 18170262.2, dated Jul. 25, 2018, 8 pages.
Final Office Action received for U.S. Appl. No. 14/475,446, dated Apr. 18, 2019, 28 pages.
Final Office Action received for U.S. Appl. No. 14/475,446, dated Jul. 14, 2017, 20 pages.
Final Office Action received for U.S. Appl. No. 14/475,471, dated Jul. 11, 2019, 18 pages.
Final Office Action received for U.S. Appl. No. 14/475,471, dated Jun. 28, 2017, 16 pages.
Final Office Action received for U.S. Appl. No. 14/475,471, dated May 15, 2020, 19 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/838,235, dated Jun. 15, 2016, 18 pages.
Final Office Action received for U.S. Appl. No. 14/838,263, dated Feb. 21, 2019, 31 pages.
Final Office Action received for U.S. Appl. No. 14/838,263, dated Mar. 22, 2018, 33 pages.
Final Office Action received for U.S. Appl. No. 15/167,699, dated Jun. 30, 2017, 8 pages.
Final Office Action received for U.S. Appl. No. 16/143,909, dated Aug. 28, 2019, 20 pages.
Final Office Action received for U.S. Appl. No. 16/143,997, dated Sep. 30, 2019, 16 pages.
Final Office Action received for U.S. Appl. No. 16/144,030, dated Feb. 13, 2020, 11 pages.
Final Office Action received for U.S. Appl. No. 16/144,030, dated Oct. 1, 2019, 13 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Final Office Action received for U.S. Appl. No. 16/144,864, dated May 28, 2020, 29 pages.
"Fitbit App", Available online at: http://web.archive.org/web/20180114083150/https://www.fitbit.com/au/app, Jan. 14, 2018, 8 pages.
Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.
"Graphs and Charts", Online available at: https://www.teachervision.com/lesson-planning/graph-chart-teacher-resources, retrieved on Dec. 12, 2018, 4 pages.
"How to Move Mail to Different Folders in Gmail", Available online at https://web.archive.org/web/20140731230338/http://www.wikihow.com/Move-Mail-to-Different-Folders-in-Gmail, Jul. 31, 2014, pp. 1-4.
Intention to Grant received for Danish Patent Application No. PA201570550, dated Dec. 22, 2016, 2 pages.
Intention to Grant received for Danish Patent Application No. PA201870379, dated May 2, 2019, 2 pages.
Intention to Grant received for Danish Patent Application No. PA201870600, dated Jul. 10, 2019, 2 pages.
Intention to Grant received for Danish Patent Application No. PA201870601, dated Apr. 24, 2020, 2 pages.
Intention to Grant received for Danish Patent Application No. PA201870602, dated Apr. 24, 2020, 2 pages.
Intention to Grant received for Denmark Patent Application No. PA201770126, dated Jan. 19, 2018, 2 pages.
Intention to Grant received for European Patent Application No. 15759981.2, dated Aug. 12, 2019, 8 pages.
Intention to Grant received for European Patent Application No. 15759981.2, dated Mar. 21, 2019, 8 pages.
International Preliminary Report on Patentability received for PCT Patent Application No. PCT/US2013/073188, dated Jun. 16, 2016, 6 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/030591, dated Dec. 8, 2016, 10 pages.
International Preliminary Report on Patentability received for PCT Patent Application No. PCT/US2015/044083, dated Mar. 16, 2017, 24 pages.
International Preliminary Report on Patentability received for PCT Patent Application No. PCT/US2015/046805, dated Mar. 16, 2017, 8 pages.
International Preliminary Report on Patentability received for PCT Patent Application No. PCT/US2015/046807, dated Mar. 16, 2017, 13 pages.
International Search Report and Written Opinion received for PCT Application No. PCT/US2015/030591, dated Jul. 21, 2015, 11 pages.

(56) References Cited

OTHER PUBLICATIONS

International Search Report and Written Opinion received for PCT Application No. PCT/US2015/046807, dated Apr. 1, 2016, 17 pages.
International Search Report and Written Opinion received for PCT Patent Application No. PCT/US2013/073188 dated Feb. 24, 2014, 8 pages.
International Search Report and Written Opinion received for PCT Patent Application No. PCT/US2015/044083, dated Feb. 4, 2016, 33 pages.
International Search Report and Written Opinion received for PCT Patent Application No. PCT/US2015/046805, dated Dec. 10, 2015, 11 pages.
International Search Report and Written Opinion received for PCT Patent Application No. PCT/US2019/019694, dated Sep. 2, 2019, 17 pages.
International Search Report and Written Opinion received for PCT Patent Application No. PCT/US2019/024570, dated Aug. 8, 2019, 18 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Additional Fees received for PCT Application No. PCT/US2015/046807, dated Dec. 15, 2015, 7 pages.
Invitation to Pay Additional Fees received for PCT Patent Application No. PCT/US2015/044083, dated Nov. 4, 2015, 11 pages.
Invitation to Pay Additional Fees received for PCT Patent Application No. PCT/US2019/019694, dated Jul. 10, 2019, 12 pages.
Invitation to Pay Search Fees received for European Patent Application No. 19726205.8, dated Feb. 14, 2020, 5 pages.
Iosvlog Daily, "iOS 7 Notification Center Complete Walkthrough", Available online at: "https://www.youtube.com/watch?v=gATXt-o42LA", Jun. 10, 2013, 1 page.
Jenbsjourney, "Wondering About a Fitbit?", Available online at: https://jenbsjourney.blogspot.kr/2013/08/wondering-about-fitbit.html, Aug. 6, 2013, 12 pages.
Jonathan Ho, Leonard, "How to dismiss banner notifications or toast notifications on ios7", Available online at: "https://www.youtube.com/watch?v=vSjHnBFIW_M", Dec. 17, 2013, 1 page.
Lewis, Jeffery, "iOS Notification Banner Pull Down to Notification Center in iOS 7 Beta 5", Available online at: "https://www.youtube.com/watch?v=nP0s6ETPxDg", Aug. 6, 2013, 1 page.
Megadepot, "Casella dBadge2 Noise Dosimeter", Available online at: https://www.youtube.com/watch?v=pHiHLiYCD08, Jun. 12, 2018, 3 pages.
Minutes of Oral Proceedings received for European Patent Application No. 13811085.3, mailed on Sep. 11, 2018, 3 pages.
Multi-Set Bar Chart, The Data Visualization Catalogue, Available Online at: https://datavizcatalogue.com/methods/multiset_barchart.html, Feb. 8, 2014, 3 pages.
Myflo App, "Functional Medicine Period Tracker and Hormone Balancing App", Available online at: https://web.archive.org/web/20170127104125/https://myflotracker.com/, Jan. 2017, 14 pages.
Myflo Tutorial, "How to change the start date of your current period", Available online at: https://www.youtube.com/watch?v=uQQ-odlBJB4, Jan. 23, 2017, 3 pages.
Myflo Tutorial, "Setting and changing the end date of your period", Available online at: https://www.youtube.com/watch?v=UvAA4OgqL3E, Jan. 23, 2017, 3 pages.
Non-Final Office Action received for U.S. Appl. No. 14/838,263, dated Jul. 14, 2017, 34 pages.
Non-Final Office Action received for U.S. Appl. No. 14/838,263, dated Sep. 21, 2018, 33 pages.
Non-Final Office Action received for U.S. Appl. No. 14/475,446, dated Jun. 28, 2018, 21 pages.
Non-Final Office Action received for U.S. Appl. No. 14/475,446, dated Mar. 18, 2020, 20 pages.
Non-Final Office Action received for U.S. Appl. No. 14/475,446, dated Nov. 18, 2016, 24 pages.
Non-Final Office Action received for U.S. Appl. No. 14/475,471, dated Dec. 19, 2019, 20 pages.
Non-Final Office Action received for U.S. Appl. No. 14/475,471, dated Nov. 18, 2016, 19 pages.
Non-Final Office Action received for U.S. Appl. No. 14/475,471, dated Sep. 18, 2018, 25 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018, 45 pages.
Non-Final Office Action received for U.S. Appl. No. 14/838,263, dated Aug. 16, 2019, 33 pages.
Non-Final Office Action received for U.S. Appl. No. 15/167,699, dated Oct. 21, 2016, 13 pages.
Non-Final Office Action received for U.S. Appl. No. 15/425,273, dated Oct. 3, 2018, 10 pages.
Non-Final Office Action received for U.S. Appl. No. 15/431,435, dated Jun. 8, 2017, 13 pages.
Non-Final Office Action received for U.S. Appl. No. 15/885,448, dated Apr. 16, 2020, 9 pages.
Non-Final Office Action received for U.S. Appl. No. 16/138,809, dated Feb. 28, 2020, 22 pages.
Non-Final Office Action received for U.S. Appl. No. 16/143,909, dated Apr. 19, 2019, 16 pages.
Non-Final Office Action received for U.S. Appl. No. 16/143,959, dated Apr. 17, 2019, 15 pages.
Non-Final Office Action received for U.S. Appl. No. 16/143,997, dated May 21, 2019, 15 pages.
Non-Final Office Action received for U.S. Appl. No. 16/144,030, dated Apr. 12, 2019, 8 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action Received for U.S. Appl. No. 16/144,864, dated Dec. 18, 2018, 19 pages.
Non-Final Office Action received for U.S. Appl. No. 16/144,864, dated Jan. 31, 2020, 29 pages.
Non-Final Office Action received for U.S. Appl. No. 14/838,235, dated Jan. 5, 2016, 3 pages.
Notice from the European Patent Office dated Oct. 1, 2007 Concerning Business Methods, Official Journal EPO, Available online at: http://archive.epo.org/epo/pubs/oj007/11_07/11_5927.pdf, Nov. 2007, pp. 592-593.
Notice of Acceptance received for Australian Patent Application No. 2013406817, dated Nov. 21, 2017, 3 pages.
Notice of Acceptance received for Australian Patent Application No. 2018201260, dated Jan. 15, 2020, 3 pages.
Notice of Acceptance received for Australian Patent Application No. 2018204430, dated Jun. 26, 2019, 3 pages.
Notice of Acceptance received for Australian Patent Application No. 2019222943, dated May 5, 2020, 3 pages.
Notice of Acceptance received for Australian Patent Application No. 2019246830, dated Oct. 24, 2019, 3 pages.
Notice of Acceptance received for Australian Patent Application No. 2015312369, dated Mar. 21, 2018, 3 pages.
Notice of Allowance received for Chinese Patent Application No. 201380081315.7, dated Jan. 4, 2019, 2 pages (1 page of English Translation and 1 page of Official Copy).
Notice of Allowance received for Chinese Patent Application No. 201510549056.7, dated Jul. 2, 2019, 2 pages (1 page of English Translation and 1 page of Official Copy).
Notice of Allowance received for Chinese Patent Application No. 201520669842.6, dated May 18, 2016, 4 pages (2 pages of English Translation and 2 pages of Official Copy).
Notice of Allowance received for Chinese Patent Application No. 201580028073.4, dated Oct. 22, 2019, 2 pages (1 page of English Translation and 1 page of Official Copy).
Notice of Allowance received for Chinese Patent Application No. 201620830403.3, dated Sep. 8, 2017, 2 pages (1 page of English Translation and 1 page of Official Copy).
Notice of Allowance received for Danish Patent Application No. PA201570550, dated Mar. 20, 2017, 2 pages.

(56) References Cited

OTHER PUBLICATIONS

Notice of Allowance received for Japanese Patent Application No. 2016-535045, dated Mar. 2, 2018, 4 pages (1 page of English Translation and 3 pages of Official Copy).
Notice of Allowance received for Japanese Patent Application No. 2017-510297, dated May 7, 2018, 4 pages (1 page of English Translation and 3 pages of Official Copy).
Notice of Allowance received for Japanese Patent Application No. 2018-068846, dated Dec. 9, 2019, 4 pages (1 page of English Translation and 3 pages of Official Copy).
Notice of Allowance received for Japanese Patent Application No. 2018-072632, dated Dec. 7, 2018, 4 pages (1 page of English Translation and 3 pages of Official Copy).
Notice of Allowance received for Korean Patent Application No. 10-2016-7014353, dated Aug. 2, 2018, 3 pages (Official Copy Only) (See Communication under 37 CFR § 1.98(a) (3)).
Notice of Allowance received for Korean Patent Application No. 10-2016-7014577, dated May 30, 2019, 5 pages (2 pages of English Translation and 3 pages of Official Copy).
Notice of Allowance received for Korean Patent Application No. 10-2017-7005628, dated Jun. 18, 2018, 5 pages (2 page of English Translation and 3 pages of Official Copy).
Notice of Allowance Received for Korean Patent Application No. 10-2018-7027006, dated May 23, 2019, 4 pages (1 pages of English Translation and 3 pages of Official Copy).
Notice of Allowance received for Korean Patent Application No. 10-2018-7032096, dated Dec. 12, 2018, 4 pages (1 page of English Translation and 3 pages of Official copy).
Notice of Allowance received for Korean Patent Application No. 10-2019-7024901, dated May 12, 2020, 5 pages (2 pages of English Translation and 3 pages of Official Copy).
Notice of Allowance received for Taiwanese Patent Application No. 104128702, dated Oct. 25, 2017, 3 pages (Official Copy Only) (See Communication under 37 CFR § 1.98(a) (3)).
Notice of Allowance received for Taiwanese Patent Application No. 104128704, dated Feb. 21, 2018, 5 pages (2 pages of English Translation and 3 pages of Official copy).
Notice of Allowance received for U.S. Appl. No. 14/732,773, dated Dec. 18, 2019, 21 pages.
Notice of Allowance received for U.S. Appl. No. 14/838,235, dated Dec. 29, 2016, 4 pages.
Notice of Allowance Received for U.S. Appl. No. 14/838,235, dated Oct. 4, 2016, 7 pages.
Notice of Allowance received for U.S. Appl. No. 14/838,263, dated Mar. 24, 2020, 9 pages.
Notice of Allowance received for U.S. Appl. No. 15/167,699, dated Oct. 27, 2017, 8 pages.
Notice of Allowance received for U.S. Appl. No. 15/425,273, dated Mar. 7, 2019, 8 pages.
Notice of Allowance received for U.S. Appl. No. 15/431,435, dated Jan. 23, 2018, 8 pages.
Notice of Allowance received for U.S. Appl. No. 16/143,909, dated Jan. 21, 2020, 9 pages.
Notice of Allowance received for U.S. Appl. No. 16/143,959, dated Oct. 31, 2019, 10 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Office Action received for Australian Patent Application No. 2013406817, dated Aug. 1, 2017, 3 pages.
Office Action received for Australian Patent Application No. 2013406817, dated Nov. 14, 2016, 4 pages.
Office Action received for Australian Patent Application No. 2015101188, dated Apr. 14, 2016, 3 pages.
Office Action received for Australian Patent Application No. 2015267514 dated May 25, 2017, 3 pages.
Office Action received for Australian Patent Application No. 2015267514, dated May 22, 2018, 3 pages.
Office Action received for Australian Patent Application No. 2015312369, dated Mar. 29, 2017, 3 pages.
Office Action received for Australian Patent Application No. 2017100197, dated Apr. 28, 2017, 4 pages.
Office Action received for Australian Patent Application No. 2017100198, dated Apr. 20, 2017, 4 pages.
Office Action received for Australian Patent Application No. 2018201260, dated Feb. 12, 2019, 6 pages.
Office Action received for Australian Patent Application No. 2018201260, dated Jul. 17, 2019, 3 pages.
Office Action received for Australian Patent Application No. 2018201260, dated Sep. 5, 2019, 5 pages.
Office Action received for Australian Patent Application No. 2018203708, dated Aug. 15, 2019, 5 pages.
Office Action received for Australian Patent Application No. 2018203708, dated Jan. 3, 2019, 4 pages.
Office Action received for Australian Patent Application No. 2018204430, dated Aug. 15, 2018, 5 pages.
Office Action received for Australian Patent Application No. 2019100222, dated May 24, 2019, 6 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Chinese Patent Application No. 201380081315.7, dated Aug. 16, 2018, 6 pages (3 pages of English Translation and 3 pages of Official Copy).
Office Action received for Chinese Patent Application No. 201380081315.7, dated Mar. 2, 2018, 12 pages (5 pages of English Translation and 7 pages of Official Copy).
Office Action received for Chinese Patent Application No. 201380081349.6, dated Feb. 26, 2019, 12 pages (6 pages of English Translation and 6 pages of Official Copy).
Office Action received for Chinese Patent Application No. 201380081349.6, dated Jan. 16, 2020, 11 pages (6 pages of English Translation and 5 pages of Official Copy).
Office Action received for Chinese Patent Application No. 201380081349.6, dated Jul. 15, 2019, 10 pages (5 pages of English Translation and 5 pages of Official Copy).
Office Action received for Chinese Patent Application No. 201510549056.7, dated Aug. 7, 2018, 7 pages (2 pages of English Translation and 5 pages of Official Copy).
Office Action received for Chinese Patent Application No. 201510549056.7, dated Mar. 15, 2019, 7 pages (3 pages of English Translation and 4 pages of Official Copy).
Office Action received for Chinese Patent Application No. 2015105490567, dated Nov. 24, 2017, 15 pages (6 pages of English Translation and 9 pages of Official Copy).
Office Action received for Chinese Patent Application No. 201520669842.6, dated Dec. 4, 2015, 7 pages (4 pages of English Translation and 3 pages of Official Copy).
Office Action received for Chinese Patent Application No. 201580028073.4, dated Feb. 2, 2019, 18 pages (10 pages of English Translation and 8 pages of Official Copy).
Office Action Received for Chinese Patent Application No. 201620830403.3, dated Jun. 7, 2017, 2 pages (1 page of English Translation and 1 page of Official Copy).
Office Action Received for Chinese Patent Application No. 201620830403.3, dated Mar. 7, 2017, 3 pages (2 pages of English Translation and 1 page of Official Copy).
Office Action received for Danish Patent Application No. PA201570550, dated Dec. 7, 2015, 6 pages.
Office Action received for Danish Patent Application No. PA201570550, dated Jan. 19, 2016, 2 pages.
Office Action received for Danish Patent Application No. PA201570550, dated Oct. 19, 2016, 3 pages.
Office Action received for Danish Patent Application No. PA201770125, dated Jan. 26, 2018, 5 pages.

(56) References Cited

OTHER PUBLICATIONS

Office Action received for Danish Patent Application No. PA201770125, dated Jul. 20, 2018, 2 pages.
Office Action received for Danish Patent Application No. PA201770126, dated Oct. 18, 2017, 3 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201870599, dated Dec. 20, 2019, 5 pages.
Office Action received for Danish Patent Application No. PA201870600, dated May 8, 2019, 3 pages.
Office Action received for Danish Patent Application No. PA201870601, dated Dec. 13, 2018, 8 pages.
Office Action received for Danish Patent Application No. PA201870601, dated Jan. 14, 2020, 3 pages.
Office Action received for Danish Patent Application No. PA201870601, dated Jun. 25, 2019, 3 pages.
Office Action received for Danish Patent Application No. PA201870602, dated Feb. 5, 2020, 3 pages.
Office Action received for Danish Patent Application No. PA201870602, dated Jun. 26, 2019, 3 pages.
Office Action received for European Patent Application No. 13811085.3, dated Apr. 20, 2018, 15 pages.
Office Action received for European Patent Application No. 13812320.3, dated Mar. 28, 2018, 7 pages.
Office Action received for European Patent Application No. 15727130.5, dated Feb. 14, 2020, 4 pages.
Office Action received for European Patent Application No. 15727130.5, dated Jun. 8, 2018, 5 pages.
Office Action received for European Patent Application No. 15727130.5, dated Mar. 13, 2019, 4 pages.
Office Action received for European Patent Application No. 15759981.2, dated Apr. 19, 2018, 6 pages.
Office Action received for European Patent Application No. 15759981.2, dated Aug. 6, 2018, 10 pages.
Office Action received for European Patent Application No. 15759981.2, dated May 16, 2018, 6 pages.
Office Action received for European Patent Application No. 18170262.2, dated Dec. 9, 2019, 3 pages.
Office Action received for European Patent Application No. 18170262.2, dated May 16, 2019, 6 pages.
Office Action received for European Patent Application No. 18170262.2, dated May 27, 2019, 6 pages.
Office Action received for European Patent Application No. 19721883.7, dated Jan. 10, 2020, 4 pages.
Office Action received for Indian Patent Application No. 201617016494, dated Apr. 27, 2020, 7 pages.
Office Action received for Japanese Patent Application No. 2016-535045, dated May 12, 2017, 10 pages (5 pages of English Translation and 5 pages of Official Copy).
Office Action received for Japanese Patent Application No. 2017-510297, dated Dec. 4, 2017, 5 pages (2 page of English Translation and 3 pages of Official Copy).
Office Action received for Japanese Patent Application No. 2017-510297, dated Jul. 2017, 10 pages (5 pages of English Translation and 5 pages of Official Copy).
Office Action received for Japanese Patent Application No. 2018-068846, dated Jan. 8, 2019, 6 pages (3 pages of English Translation and 3 pages of Official Copy).
Office Action received for Japanese Patent Application No. 2018-072632, dated Jul. 9, 2018, 5 Pages (2 Pages of English Translation and 3 pages of Official Copy).
Office Action received for Japanese Patent Application No. 2019-000698, dated Mar. 9, 2020, 8 pages (4 pages of English Translation and 4 pages of Official Copy).
Office Action received for Japanese Patent Application No. 2019-162293, dated Jan. 31, 2020, 8 pages (4 pages of English Translation and 4 pages of Official Copy).
Office Action received for Korean Patent Application No. 10-2016-7014353, dated Mar. 21, 2018, 11 pages (5 pages of English Translation and 6 pages of Official Copy).
Office Action received for Korean Patent Application No. 10-2016-7014577, dated Dec. 26, 2017, 14 pages (6 pages of English Translation and 8 pages of Official Copy).
Office Action received for Korean Patent Application No. 10-2016-7014577, dated Oct. 31, 2018, 11 pages (5 pages of English Translation and 6 pages of Official Copy).
Office Action received for Korean Patent Application No. 10-2017-7005628, dated Jan. 30, 2018, 6 pages (2 pages of English Translation and 4 pages of Official Copy).
Office Action received for Korean Patent Application No. 10-2017-7005628, dated May 10, 2017, 12 pages (5 pages of English Translation and 7 pages of Official Copy).
Office Action Received for Korean Patent Application No. 10-2018-7027006, dated Jan. 14, 2019, 6 pages (2 pages of English Translation and 4 pages of Official Copy).
Office Action received for Korean Patent Application No. 10-2019-7024901, dated Sep. 26, 2019, 6 pages (2 pages of English Translation and 4 pages of Official Copy).
Office Action received for Korean Patent Application No. 10-2019-7025538, dated Feb. 17, 2020, 12 pages (6 pages of English Translation and 6 pages of Official Copy).
Office Action received for Korean Patent Application No. 10-2019-7025781, dated Nov. 26, 2019, 10 pages (4 pages of English Translation and 6 pages of Official Copy).
Office Action received for Taiwanese Patent Application No. 104128702, dated Feb. 7, 2017, 12 pages (5 pages of English Translation and 7 pages of Official Copy).
Office Action received for Taiwanese Patent Application No. 104128704, dated Jul. 31, 2017, 7 pages (3 pages of English Translation and 4 pages of Official Copy).
Office Action received for Taiwanese Patent Application No. 104128704, dated Nov. 2, 2016, 12 pages (5 pages of English Translation and 7 pages of Official Copy).
Patterson, Ben, "iOS 7 tip: Alerts, banners, and badgesâwhats the difference?", Available online at: https://web.archive.org/web/20140128072440/http://heresthethingblog.com/2014/01/22/ios-7-tip-whats-difference-alert/, Jan. 22, 2014, 5 pages.
Rainmaker, "Garmin Fenix3 New Auto Climb Functionality", Available online at: https://www.youtube.com/watch?v=iuavOSNpVRc, Feb. 19, 2015, 1 page.
Rizknows, "TomTom Multisport Cardio Review", Online available at: https://www.youtube.com/watch?v=WoVCzLrSN9A, Sep. 4, 2015, 1 page.
"Samsung User Manual", SM-R380_UM_EU_Eng_D13_140411.pdf, Apr. 2014, 78 pages.
Samsung, "Samsung Gear 2 User manual", Online Available at: https://data2.manualslib.com/pdf3/76/7550/754923samsung/gear_2.pdf?7eb313a9f65b1566bcf9ff58661c6b3a&take=binary>, XP055464984, retrieved on Apr. 5, 2018, Apr. 9, 2014, pp. 1-97.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201870599, dated Dec. 21, 2018, 9 pages.
Search Report and Opinion received for Danish Patent Application No. PA201870600, dated Jan. 31, 2019, 8 pages.
Search Report and Opinion received for Danish Patent Application No. PA201870602, dated Dec. 19, 2018, 8 pages.

(56) References Cited

OTHER PUBLICATIONS

Search Report and Opinion received for Netherlands Patent Application No. 2015354, completed on Jun. 22, 2017, 24 pages (10 pages of English Translation and 14 pages of Official Copy).
Search Report and Opinion received for Netherlands Patent Application No. 2019878, dated Apr. 6, 2018, 24 pages (12 pages of English Translation and 12 pages of Official Copy).
Search Report received for Danish Patent Application No. PA201770125, dated May 5, 2017, 10 pages.
Search Report received for Danish Patent Application No. PA201770126, dated Apr. 26, 2017, 8 pages.
Smith, "Garmin Fenix 5 Activity/Smart Watch Review", Online Available at: https://www.youtube.com/watch?v=6PkQxXQxpoU, Sep. 2, 2017, 1 page.
Sportstechguides, "Garmin Fenix 5: How to Add Power Data Fields", Online available at: https://www.youtube.com/watch?v=ZkPptnnXEiQ, Apr. 29, 2017, 2 pages.
Sportstechguides, "Garmin Fenix 5: How to Set Up Run Alerts", Online available at: https://www.youtube.com/watch?v=gSMwv8vIhB4, May 13, 2017, 2 pages.
Studiosixdigital,"Dosimeter", Online available at: https://studiosixdigital.com/audiotools-modules-2/spl-modules/dosimeter.html, Mar. 3, 2017, 6 pages.
Summons to attend oral proceedings received for European Patent Application No. 13811085.3, mailed on Jan. 26, 2018, 14 pages.
Supplemental Notice of Allowance received for U.S. Appl. No. 16/144,849, dated Mar. 31, 2020, 2 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at: https://www.youtube.com/watch?v=aixfoCnS0OU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
User Manual, Available online at: http://www.manualslib.com/download/754923/Samsung-Gear-2.html, 2014, pp. 1-97.
Utilization of Galaxy S4—S Health, ChatOn and Samsung Hub, Available at: http://seeit.kr/1263, Jun. 12, 2013, 25 pages (Official Copy Only) (See Communication under 37 CFR § 1.98(a) (3)).
"Visual Pace Alarm app", Available Online at: https://apps.garmin.com/en-US/apps/3940f3a2-4847-4078-a911-d77422966c82, Oct. 19, 2016, 1 page.
Weiyu et al., "A Multi-identities Authentication and Authorization Schema in Cloud Computing", Aug. 20, 2012, pp. 7-10 (English Abstract Submitted).
Wesley, "Apple Watch Series 1", Online available at: http://toolbox.info/blog/archives/1737-unknown.html, May 28, 2015, 5 pages (Official Copy Only) (See Communication under 37 CFR § 1.98(a) (3)).
Youtube, "Apple Watch Series 3", Online available at: https://www.youtube.com/watch?v=iBPr9gEfkK8, Nov. 21, 2017, 15 pages (Official Copy Only) (See Communication under 37 CFR § 1.98(a) (3)).
Zlelik, "Garmin Fenix 5 Open Water Swimming Activity Demo", Online Available at: https://www.youtube.com/watch?v=iSVhdvw2dcs, Jun. 9, 2017, 1 page.
Chatrzarrin Hanieh, "Feature Extraction for the Differentiation of Dry and Wet Cough Sounds", Carleton University, Sep. 2011, 144 pages.
Haslam Oliver, "Stop Coronavirus in its Tracks by Using This Apple Watch App to Time Hand Washes", Available Online at: <https://www.imore.com/stop-coronavirus-its-tracks-using-apple-watch-app-time-hand-washes>, Mar. 12, 2020, 12 pages.
International Preliminary Report on Patentability received for PCT Patent Application No. PCT/US2019/014215, dated Aug. 6, 2020, 14 pages.
International Search Report and Written Opinion received for PCT Patent Application No. PCT/US2019/014215, dated Jun. 4, 2019, 17 pages.
International Search Report and written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Invitation to Pay Addition Fees and Partial International Search Report received for PCT Patent Application No. PCT/US2019/014215, dated Apr. 12, 2019, 13 pages.
Liaqat et al., "Challenges with Real-World Smartwatch based Audio Monitoring", WearSys'18, Munich, Germany, Available Online at: <https://doi.org/10.1145/3211960.3211977>, Jun. 10, 2018, 6 pages.
Lyles Taylor, "Wear OS Smartwatches are Now Sending Reminders to Wash Your Hands", Available Online at: <https://www.theverge.com/2020/4/14/21221294/google-wear-os-smartwatches-reminders-wash-your-hands>, Apr. 14, 2020, 2 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2019-162293, dated Jul. 27, 2020, 9 pages (5 pages of English Translation and 4 pages of Official Copy).
Peters Jay, "Samsung's Smartwatches Get a Hand-Washing Reminder and Timer App", Available Online at: <https://www.theverge.com/2020/4/17/21225205/samsung-smartwatch-galaxy-active-hand-washing-timer-reminder-app>, Apr. 17, 2020, 2 pages.
Schoon Ben, "Wear OS Now Sends a Reminder to Wash Your Hands Every Few Hours", Available Online at: <https://9to5google.com/2020/04/14/wear-os-wash-hands-reminder-coronavirus/>, Apr. 14, 2020, 7 pages.
Search Report and Opinion received for Danish Patent Application No. PA201970532, dated Nov. 8, 2019, 9 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Office Action received for Chinese Patent Application No. 201910972529.2, dated Jun. 28, 2020, 8 pages (1 page of English Translation and 7 pages of Official Copy).
Applicant-Initiated Interview Summary received for U.S. Appl. No. 16/138,809, dated Jun. 9, 2020, 4 pages.
Notice of Allowance received for U.S. Appl. No. 15/885,448, dated Jun. 16, 2020, 5 pages.
Office Action received for European Patent Application No. 19721883.7, dated May 28, 2020, 11 pages.
Non-Final Office Action received for U.S. Appl. No. 16/143,997, dated Jul. 27, 2020, 15 pages.
Notice of Acceptance received for Australian Patent Application No. 2020204153, dated Jul. 6, 2020, 3 pages.

(56) References Cited

OTHER PUBLICATIONS

Notice of Allowance received for U.S. Appl. No. 16/144,864, dated Jul. 28, 2020, 27 pages.
Final Office Action received for U.S. Appl. No. 16/894,309, dated Feb. 24, 2021, 30 pages.
International Search Report and Written Opinion received for PCT Patent Application No. PCT/US2020/035164, dated Feb. 8, 2021, 26 pages.
International Search Report and Written Opinion received for PCT Patent Application No. PCT/US2020/052041, dated Feb. 8, 2021, 18 pages.
Non-Final Office Action received for U.S. Appl. No. 16/880,552, dated Feb. 19, 2021, 11 pages.
Office Action received for Chinese Patent Application No. 201380081349.6, dated Jan. 5, 2021, 16 pages (7 pages of English Translation and 9 pages of Official Copy).
Office Action received for Danish Patent Application No. PA201970534, dated Feb. 16, 2021, 2 pages.
Office Action received for Korean Patent Application No. 10-2020-7026035, dated Feb. 19, 2021, 13 pages (6 pages of English Translation and 7 pages of Official Copy).
Applicant Initiated Interview Summary received for U.S. Appl. No. 16/586,154, dated Mar. 11, 2020, 4 pages.
Applicant-Initiated Interview Summary received for U.S. Appl. No. 16/669,187, dated Nov. 23, 2020, 3 pages.
Final Office Action received for U.S. Appl. No. 16/586,154, dated Jul. 6, 2020, 27 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/034155, dated Sep. 17, 2020, 19 pages.
International Search Report and Written Opinion received for PCT Patent Application No. PCT/US2020/035462, dated Sep. 11, 2020, 17 pages.
Non-Final Office Action received for U.S. Appl. No. 16/586,154, dated Dec. 9, 2019, 23 pages.
Non-Final Office Action received for U.S. Appl. No. 16/669,187, dated Sep. 25, 2020, 40 pages.
Notice of Acceptance received for Australian Patent Application No. 2020200028, dated Nov. 10, 2020, 3 pages.
Notice of Allowance received for U.S. Appl. No. 16/880,552, dated Dec. 1, 2020, 7 pages.
Office Action received for European Patent Application No. 15727130.5, dated Nov. 19, 2020, 5 pages.
Office Action received for Japanese Patent Application No. 2019000698, dated Oct. 23, 2020, 4 pages (2 pages of English Translation and 2 pages of Official Copy).
Applicant Initiated Interview Summary received for U.S. Appl. No. 16/894,309, dated Jan. 26, 2021, 3 pages.
Extended European Search Report received for European Patent Application No. 20203526.7, dated Jan. 29, 2021, 13 pages.
International Search Report and Written Opinion received for PCT Patent Application No. PCT/US2020/042439, dated Oct. 9, 2020, 14 pages.
Office Action received for Japanese Patent Application No. 2020-000492, dated Dec. 11, 2020, 6 pages (3 pages English Translation and 3 pages of Official Copy).
Result of Consultation received for European Patent Application No. 18170262.2, dated Jan. 18, 2021, 3 pages.
Lovejoy Ben, "Apple Watch blood sugar measurement coming in Series 7, claims report", Available Online at: https://9to5mac.com/2021/01/25/apple-watch-blood-sugar-measurement/, Jan. 25, 2021, 6 pages.
Final Office Action received for U.S. Appl. No. 16/143,997, dated Feb. 9, 2021, 16 pages.
Notice of Allowance received for Japanese Patent Application No. 2019-000698, dated Feb. 8, 2021, 4 pages (1 page of English Translation and 3 pages of Official Copy).

Notice of Allowance received for U.S. Appl. No. 16/144,864, dated Feb. 9, 2021, 13 pages.
Office Action received for Korean Patent Application No. 10-2020-7026391, dated Jan. 27, 2021, 5 pages (2 pages of English Translation and 3 pages of Official Copy).
Office Action received for Korean Patent Application No. 10-2020-7026453, dated Jan. 27, 2021, 5 pages (2 pages of English Translation and 3 pages of Official Copy).
Applicant-Initiated Interview Summary received for U.S. Appl. No. 16/138,809, dated Dec. 16, 2020, 7 pages.
Applicant-Initiated Interview Summary received for U.S. Appl. No. 16/586,154, dated Dec. 11, 2020, 5 pages.
Applicant-Initiated Interview Summary received for U.S. Appl. No. 16/880,552, dated Dec. 16, 2020, 6 pages.
Applicant-Initiated Interview Summary received for U.S. Appl. No. 16/907,261, dated Dec. 16, 2020, 6 pages.
Board Decision received for Chinese Patent Application No. 201380081349.6, dated Nov. 23, 2020, 2 pages (1 page of English Translation and 1 page of Official Copy).
International Search Report and Written Opinion received for PCT Patent Application No. PCT/US2020/035474, dated Nov. 26, 2020, 16 pages.
Non-Final Office Action received for U.S. Appl. No. 16/820,383, dated Dec. 14, 2020, 11 pages.
Search Report and Opinion received for Danish Patent Application No. PA202070335, dated Nov. 27, 2020, 10 pages.
Search Report and Opinion received for Danish Patent Application No. PA202070395, dated Nov. 24, 2020, 10 pages.
Gupta Rajat, "Disable High Volume Warning (no root) in Samsung S7, S8 / Android 7.0" Online available at: <https://www.youtube.com/watch?v=9fKwRBtk-x8>, Retrieved on Nov. 26, 2020; esp. 2:04, Aug. 6, 2017, 1 page.
Tech, Kalyani,"I See Some problems in Honor Band 5", Retrieved from: https://www.youtube.com/watch?v=5XPnYJFqajl, May 19, 2020, 1 page.
Ticks, Smartwatch,"SENBONO S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
Notice of Allowance received for Japanese Patent Application No. 2020-104679, dated Jan. 4, 2021, 4 pages (1 page of English Translation and 3 pages of Official Copy).
Bagala et al., "Evaluation of Accelerometer-Based Fall Detection Algorithms on Real-World Falls", PloS ONE, vol. 7, No. 5, May 16, 2012, 9 pages.
Invitation to Pay Additional Fees and Partial International Search Report received for PCT Patent Application No. PCT/US2020/035164, dated Oct. 16, 2020, 14 pages.
Non-Final Office Action received for U.S. Appl. No. 16/144,030, dated Nov. 5, 2020, 5 pages.
Office Action received for Australian Patent Application No. 2019234289, dated Nov. 2, 2020, 6 pages.
Office Action received for Australian Patent Application No. 2020230340, dated Nov. 2, 2020, 5 pages.
Office Action received for European Patent Application No. 20182116.2, dated Nov. 6, 2020, 9 pages.
Office Action received for Korean Patent Application No. 10-2019-7025781, dated Oct. 30, 2020, 10 pages (4 pages of English Translation and 6 pages of Official Copy).
Summons to Attend Oral Proceedings received for European Patent Application No. 19726205.8, mailed on Oct. 29, 2020, 13 pages.
Corrected Notice of Allowance received for U.S. Appl. No. 16/880,552, dated Dec. 23, 2020, 2 pages.
Non-Final Office Action received for U.S. Appl. No. 16/586,154, dated Dec. 28, 2020, 26 pages.
Search Report and Opinion received for Danish Patent Application No. PA202070620, dated Dec. 11, 2020, 9 pages.
Summons to Attend Oral Proceedings received for European Patent Application No. 18170262.2, mailed on Dec. 15, 2020, 5 pages.
Applicant-Initiated Interview Summary received for U.S. Appl. No. 16/880,552, dated Oct. 20, 2020, 6 pages.
European Search Report received for European Patent Application No. 20182116.2, dated Oct. 21, 2020, 4 pages.

(56) References Cited

OTHER PUBLICATIONS

Invitation to Pay Addition Fees received for PCT Patent Application No. PCT/US2020/035474, dated Oct. 2, 2020, 11 pages.
Office Action received for Japanese Patent Application No. 2020-104679, dated Sep. 18, 2020, 13 pages (7 pages of English Translation and 6 pages of Official Copy).
Applicant-Initiated Interview Summary received for U.S. Appl. No. 16/249,627, dated Jun. 2, 2021, 5 pages.
Cook James, "German Period Tracking App Clue Has Over 2.5 Million Active Users—But It's Still Not Sure How It's Going to Make Money", Available online at https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.
FAQ|SleepScore, Available Online at: https://www.sleepscore.com/sleepscore-app/faq/, Retreived on May 26, 2021, 31 pages.
Final Office Action received for U.S. Appl. No. 16/586,154, dated May 24, 2021, 29 pages.
Notice of Allowance received for Korean Patent Application No. 10-2020-7026391, dated May 11, 2021, 3 pages (1 page of English Translation and 2 pages of Official Copy).
Notice of Allowance received for Korean Patent Application No. 10-2020-7026453, dated May 11, 2021, 3 pages (1 page of English Translation and 2 pages of Official Copy).
Office Action received for Australian Patent Application No. 2019210192, dated May 25, 2021, 4 pages.
Office Action received for European Patent Application No. 20182116.2, dated May 25, 2021, 9 pages.
Applicant-Initiated Interview Summary received for U.S. Appl. No. 14/475,446, dated May 3, 2021, 3 pages.
Applicant-Initiated Interview Summary received for U.S. Appl. No. 16/143,997, dated May 3, 2021, 4 pages.
Applicant-Initiated Interview Summary received for U.S. Appl. No. 16/586,154, dated Apr. 14, 2021, 4 pages.
Applicant-Initiated Interview Summary received for U.S. Appl. No. 16/820,383, dated Mar. 11, 2021, 2 pages.
Applicant-Initiated Interview Summary received for U.S. Appl. No. 16/880,552, dated Apr. 21, 2021, 3 pages.
Applicant-Initiated Interview Summary received for U.S. Appl. No. 16/907,261, dated Mar. 25, 2021, 2 pages.
Decision on Appeal received for Korean Patent Application No. 10-2019-7025538, dated Feb. 24, 2021, 20 pages (4 pages of English Translation and 16 pages of Official Copy).
Examiner's Answer to Appeal Brief received for U.S. Appl. No. 14/475,471, dated Apr. 23, 2021, 12 pages.
Final Office Action received for U.S. Appl. No. 16/669,187, dated Mar. 31, 2021, 46 pages.
Final Office Action received for U.S. Appl. No. 16/907,261, dated Mar. 18, 2021, 20 pages.
International Search Report and Written Opinion received for PCT Patent Application No. PCT/US2020/070280, dated Nov. 30, 2020, 20 pages.
Invitation to Pay Additional Fees received for PCT Patent Application No. PCT/US2020/070280, dated Oct. 7, 2020, 12 pages.
Non-Final Office Action received for U.S. Appl. No. 14/475,446, dated Mar. 9, 2021, 22 pages.
Non-Final Office Action received for U.S. Appl. No. 16/249,627, dated Mar. 11, 2021, 21 pages.
Non-Final Office Action received for U.S. Appl. No. 16/990,846, dated May 10, 2021, 16 pages.
Notice of Allowance received for Japanese Patent Application No. 2019-162293, dated Apr. 9, 2021, 4 pages (1 page of English Translation and 3 pages of Official Copy).
Notice of Allowance received for Korean Patent Application No. 10-2019-7025538, dated Mar. 10, 2021, 5 pages (2 pages of English Translation and 3 pages of Official Copy).
Notice of Allowance received for U.S. Appl. No. 16/138,809, dated Apr. 16, 2021, 11 pages.
Notice of Allowance received for U.S. Appl. No. 16/143,997, dated May 13, 2021, 10 pages.
Notice of Allowance received for U.S. Appl. No. 16/144,030, dated Apr. 5, 2021, 8 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/820,383, dated Mar. 31, 2021, 11 pages.
Notice of Allowance received for U.S. Appl. No. 16/880,552, dated May 12, 2021, 7 pages.
Office Action received for Australian Patent Application No. 2019234289, dated Mar. 16, 2021, 8 pages.
Office Action received for Australian Patent Application No. 2020230340, dated Mar. 2, 2021, 6 pages.
Office Action received for Chinese Patent Application No. 201810654707.2, dated Mar. 1, 2021, 23 pages (8 pages of English translation and 15 pages of official copy).
Office Action received for Chinese Patent Application No. 202010606407.4, dated Jan. 27, 2021, 16 pages (7 pages of English Translation and 9 pages of Official Copy).
Office Action received for Chinese Patent Application No. 202010618240.3, dated Mar. 29, 2021, 21 pages (11 pages of English Translation and 10 pages of Official Copy).
Office Action received for Chinese Patent Application No. 202010618569.X, dated Mar. 12, 2021, 14 pages (7 pages of English Translation and 7 pages of Official Copy).
Office Action received for Danish Patent Application No. PA202070620, dated May 10, 2021, 5 pages.
Office Action received for European Patent Application No. 20180581.9, dated Apr. 1, 2021, 11 pages.
Office Action received for European Patent Application No. 20180592.6, dated Apr. 1, 2021, 11 pages.
Office Action received for Japanese Patent Application No. 2018-184532, dated Mar. 1, 2021, 11 pages (6 pages of English Translation and 5 pages of Official Copy).
Office Action received for Japanese Patent Application No. 2020-547369, dated Apr. 9, 2021, 4 pages (2 pages of English Translation and 2 pages of Official Copy).
Result of Consultation received for European Patent Application No. 19726205.8, dated Mar. 15, 2021, 19 pages.
Search Report and Opinion received for Danish Patent Application No. PA202070815, dated Mar. 16, 2021, 8 pages.
Summons to Attend Oral Proceedings received for European Patent Application No. 13812320.3, dated Mar. 12, 2021, 9 pages.
Office Action received for Australian Patent Application No. 2020239692, dated Jul. 20, 2021, 5 pages.

* cited by examiner

700

702
Display, via the display device, a first instance of a first user interface including a first notification that, when selected, causes display of the first set of data.

704
The first notification includes a visual property:

706
In accordance with a determination that the first set of data corresponds to a first application, the first visual property has a first value.

708
In accordance with a determination that the first set of data corresponds to a second application, the first visual property has a second value different from the first value.

812
In accordance with a determination that a type of data corresponding to the first health data has been identified by user input, including a first representation of the first health data

814
In accordance with a determination that a type of data corresponding to the first health data has not been identified by user input, not including a first representation of the first health data

B

816
In accordance with a determination that a first set of highlight criteria are met, including a second representation of the first health data different from the first representation

818
In accordance with a determination that the first set of highlight criteria are not met, not including the second representation of the first health data

912
In accordance with a determination that a first clinical health record of the first type of clinical health record fails to meet a first set of graphing criteria, a first textual representation for the first clinical health record based on the clinical health record data, where the first user interface does not include a graphical representation for the first clinical health record

914
In accordance with a determination that the first clinical health meets the first set of graphing criteria, a first graphical representation for the first clinical health record based on the clinical health record data (B)

916
In accordance with a determination that a second clinical health record of the second type of clinical health record fails to meet the first set of graphing criteria, a second textual representation for the second clinical health record based on the clinical health record data, where the user interface does not include a graphical representation for the second clinical health record

918
In accordance with a determination that the second clinical health record meets the first set of graphing criteria, a second graphical representation for the second clinical health record based on the clinical health record data

*FIG. 9B*

1010
In response to receiving the first user input, display, via the display device, a second user interface, including:

1012
A second representation, based on the first clinical health record data, for the first clinical health record of the first type of clinical health record, where the second representation is different from the first representation

1014
A third representation, based on the first clinical health record data, for a second clinical health record of the first type of clinical health record, where the third representation is different from the second representation and the second clinical health record of the first type is different from the first clinical health record of the first type

1016
While displaying the second user interface, receive second user input corresponding to selection of the third representation.

1018
In response to receiving the second user input, display, via the display device, a third user interface, including a fourth representation, based on the first clinical health record data, for the first clinical health record of the first type of clinical health record, where the fourth representation is different from the first representation, and where the fourth representation is different from the second representation.

1102
Receive a request to display a first user interface.

1104
In response to receiving the first request, display, via the display device, the first user interface, including:

1106
A first portion, including a first category affordance

1108
A second portion including a first shared affordance corresponding to a second user account (A)

*FIG. 11A*

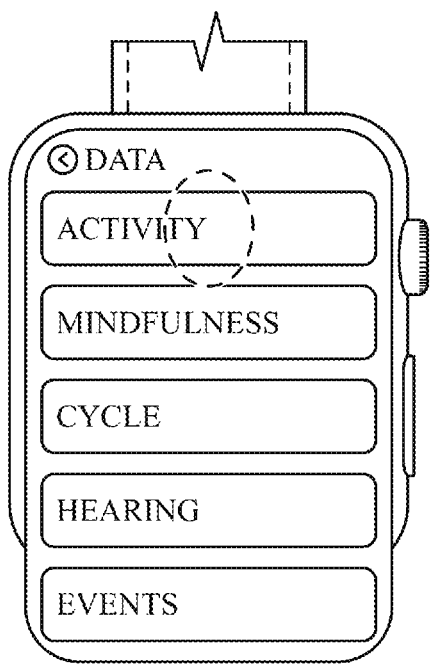 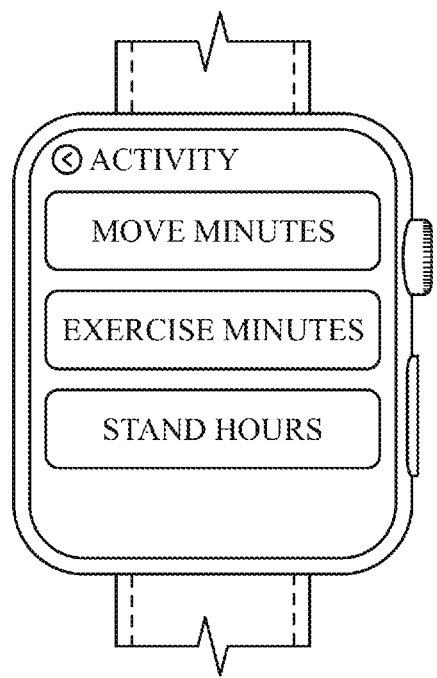
*FIG. 15C*  *FIG. 15D*

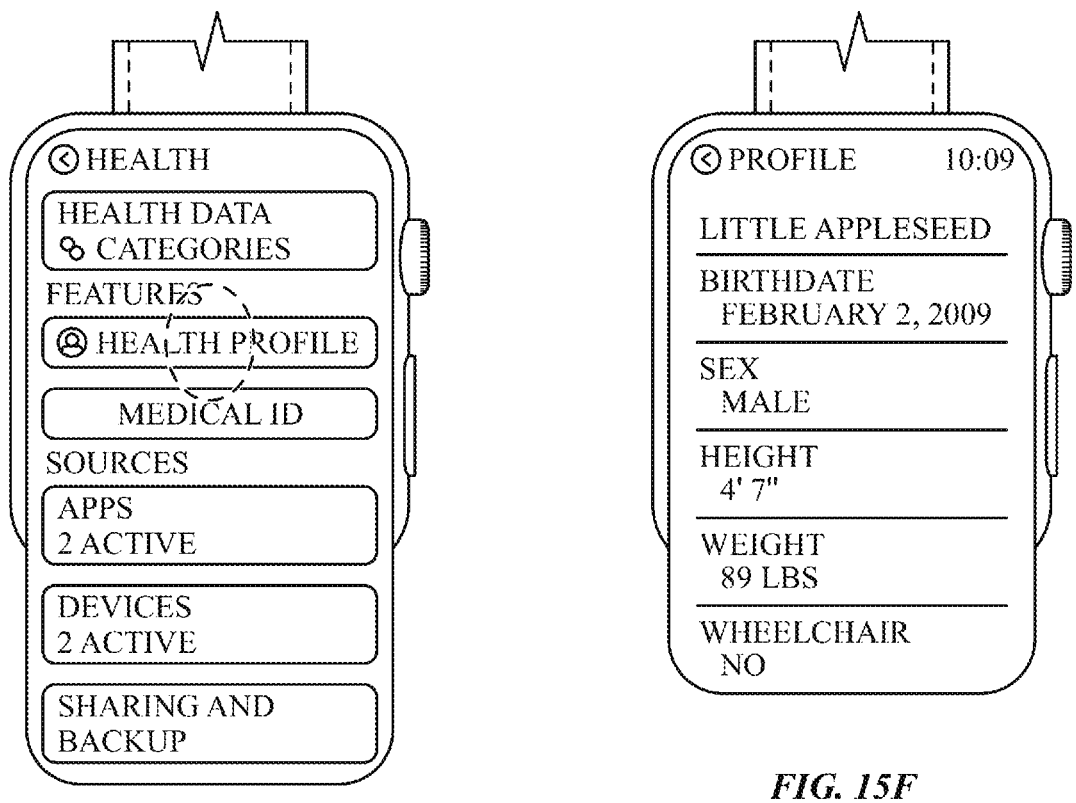

HEALTH APPLICATION USER INTERFACES

CROSS-REFERENCE TO RELATED APPLICATIONS

This application claims priority to U.S. Provisional Application No. 62/856,061, filed Jun. 1, 2019, entitled "HEALTH APPLICATION USER INTERFACES," the contents of which are hereby incorporated by reference in its entirety.

FIELD

The present disclosure relates generally to computer user interfaces, and more specifically to techniques and user interfaces for managing health information and functions.

BACKGROUND

Electronic devices collect, store, and access health-related information for users. Such devices provide the user with the ability to manage health information and corresponding functions using the electronic device.

BRIEF SUMMARY

Some techniques for managing health information and functions using electronic devices, however, are generally cumbersome and inefficient. For example, some existing techniques use a complex and time-consuming user interface, which can include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for managing health information and functions. Such methods and interfaces optionally complement or replace other methods for managing health information and functions. Such methods and interfaces reduce the cognitive burden on a user and produce a more efficient human-machine interface. For battery-operated computing devices, such methods and interfaces conserve power and increase the time between battery charges.

In accordance with some embodiments, a method is described. In some embodiments, the method is performed at an electronic device with a display device. In some embodiments, the method comprises: displaying, via the display device, a first instance of a first user interface including a first notification that, when selected, causes display of a first set of data; and after displaying the first instance of the first user interface, displaying a second instance of the first user interface, where: in accordance with a determination that a set of interaction criteria are met, the set of interaction criteria including a criterion that is met when the first set of data has been displayed, and in accordance with a determination that a first set of removal criteria are not met, the first set of removal criteria including a first criterion that is based on a first period of time, the second instance of the first user interface includes the first notification; in accordance with a determination that the set of interaction criteria are met and in accordance with a determination that the first set of removal criteria are met, the second instance of the first user interface does not include the first notification; in accordance with a determination that the set of interaction criteria are not met and in accordance with a determination that a second set of removal criteria are not met, the second set of removal criteria including a second criterion that is based on a second period of time that is greater than the first period of time, the second instance of the first user interface includes the first notification; and in accordance with a determination that the set of interaction criteria are not met and in accordance with a determination that the second set of removal criteria are met, the second instance of the first user interface does not include the first notification.

In accordance with some embodiments, a non-transitory computer-readable storage medium storing one or more programs configured to be executed by one or more processors of an electronic device with a display device is described. In some embodiments, the one or more programs include instructions for: displaying, via the display device, a first instance of a first user interface including a first notification that, when selected, causes display of a first set of data; and after displaying the first instance of the first user interface, displaying a second instance of the first user interface, where: in accordance with a determination that a set of interaction criteria are met, the set of interaction criteria including a criterion that is met when the first set of data has been displayed, and in accordance with a determination that a first set of removal criteria are not met, the first set of removal criteria including a first criterion that is based on a first period of time, the second instance of the first user interface includes the first notification; in accordance with a determination that the set of interaction criteria are met and in accordance with a determination that the first set of removal criteria are met, the second instance of the first user interface does not include the first notification; in accordance with a determination that the set of interaction criteria are not met and in accordance with a determination that a second set of removal criteria are not met, the second set of removal criteria including a second criterion that is based on a second period of time that is greater than the first period of time, the second instance of the first user interface includes the first notification; and in accordance with a determination that the set of interaction criteria are not met and in accordance with a determination that the second set of removal criteria are met, the second instance of the first user interface does not include the first notification.

In accordance with some embodiments, a transitory computer-readable storage medium storing one or more programs configured to be executed by one or more processors of an electronic device with a display device is described. In some embodiments, the one or more programs include instructions for: displaying, via the display device, a first instance of a first user interface including a first notification that, when selected, causes display of a first set of data; and after displaying the first instance of the first user interface, displaying a second instance of the first user interface, where: in accordance with a determination that a set of interaction criteria are met, the set of interaction criteria including a criterion that is met when the first set of data has been displayed, and in accordance with a determination that a first set of removal criteria are not met, the first set of removal criteria including a first criterion that is based on a first period of time, the second instance of the first user interface includes the first notification; in accordance with a determination that the set of interaction criteria are met and in accordance with a determination that the first set of removal criteria are met, the second instance of the first user interface does not include the first notification; in accordance with a determination that the set of interaction criteria are not met and in accordance with a determination that a second set of removal criteria are not met, the second set of removal criteria including a second criterion that is based on a second period of time that is greater than the first period of time, the second instance of the first user interface includes the first notification; and in accordance with a determination that the set of interaction criteria are not met and in accordance with a determination that the second set of removal criteria are met, the second instance of the first user interface does not include the first notification.

In accordance with some embodiments, an electronic device is described. In some embodiments, the electronic device includes: a display device; one or more processors; and memory storing one or more programs configured to be executed by the one or more processors, the one or more programs including instructions for: displaying, via the display device, a first instance of a first user interface including a first notification that, when selected, causes display of a first set of data; and after displaying the first instance of the first user interface, displaying a second instance of the first user interface, where: in accordance with a determination that a set of interaction criteria are met, the set of interaction criteria including a criterion that is met when the first set of data has been displayed, and in accordance with a determination that a first set of removal criteria are not met, the first set of removal criteria including a first criterion that is based on a first period of time, the second instance of the first user interface includes the first notification; in accordance with a determination that the set of interaction criteria are met and in accordance with a determination that the first set of removal criteria are met, the second instance of the first user interface does not include the first notification; in accordance with a determination that the set of interaction criteria are not met and in accordance with a determination that a second set of removal criteria are not met, the second set of removal criteria including a second criterion that is based on a second period of time that is greater than the first period of time, the second instance of the first user interface includes the first notification; and in accordance with a determination that the set of interaction criteria are not met and in accordance with a determination that the second set of removal criteria are met, the second instance of the first user interface does not include the first notification.

In accordance with some embodiments, an electronic device is described. In some embodiments, the electronic device includes: a display device; means for displaying, via the display device, a first instance of a first user interface including a first notification that, when selected, causes display of a first set of data; and means, after displaying the first instance of the first user interface, for displaying a second instance of the first user interface, where: in accordance with a determination that a set of interaction criteria are met, the set of interaction criteria including a criterion that is met when the first set of data has been displayed, and in accordance with a determination that a first set of removal criteria are not met, the first set of removal criteria including a first criterion that is based on a first period of time, the second instance of the first user interface includes the first notification; in accordance with a determination that the set of interaction criteria are met and in accordance with a determination that the first set of removal criteria are met, the second instance of the first user interface does not include the first notification; in accordance with a determination that the set of interaction criteria are not met and in accordance with a determination that a second set of removal criteria are not met, the second set of removal criteria including a second criterion that is based on a second period of time that is greater than the first period of time, the second instance of the first user interface includes the first notification; and in accordance with a determination that the set of interaction criteria are not met and in accordance with a determination that the second set of removal criteria are met, the second instance of the first user interface does not include the first notification.

In accordance with some embodiments, a method is described. In some embodiments, the method is performed at an electronic device with a display device. In some embodiments, the method comprises: receiving first health data; receiving a request to display a first user interface; in response to receiving the request, displaying, via the display device, the first user interface including: a first region: in accordance with a determination that a type of data corresponding to the first health data has been identified by user input, including a first representation of the first health data; and in accordance with a determination that the type of data corresponding to the first health data has not been identified by user input, not including the representation of the first health data; and a second region: in accordance with a determination that a first set of highlight criteria are met, including a second representation of the first health data different from the first representation; and in accordance with a determination that the first set of highlight criteria are not met, not including the second representation of the first health data.

In accordance with some embodiments, a non-transitory computer-readable storage medium storing one or more programs configured to be executed by one or more processors of an electronic device with a display device is described. In some embodiments, the one or more programs include instructions for: receiving first health data; receiving a request to display a first user interface; in response to receiving the request, displaying, via the display device, the first user interface including: a first region: in accordance with a determination that a type of data corresponding to the first health data has been identified by user input, including a first representation of the first health data; and in accordance with a determination that the type of data corresponding to the first health data has not been identified by user input, not including the representation of the first health data; and a second region: in accordance with a determination that a first set of highlight criteria are met, including a second representation of the first health data different from the first representation; and in accordance with a determination that the first set of highlight criteria are not met, not including the second representation of the first health data.

In accordance with some embodiments, a transitory computer-readable storage medium storing one or more programs configured to be executed by one or more processors of an electronic device with a display device is described. In some embodiments, the one or more programs include instructions for: receiving first health data; receiving a request to display a first user interface; in response to receiving the request, displaying, via the display device, the first user interface including: a first region: in accordance with a determination that a type of data corresponding to the first health data has been identified by user input, including a first representation of the first health data; and in accordance with a determination that the type of data corresponding to the first health data has not been identified by user input, not including the representation of the first health data; and a second region: in accordance with a determination that a first set of highlight criteria are met, including a second representation of the first health data different from the first representation; and in accordance with a determination that the first set of highlight criteria are not met, not including the second representation of the first health data.

In accordance with some embodiments, an electronic device is described. In some embodiments, the electronic device includes: a display device; one or more processors; and memory storing one or more programs configured to be executed by the one or more processors, the one or more programs including instructions for: receiving first health data; receiving a request to display a first user interface; in response to receiving the request, displaying, via the display device, the first user interface including: first region: in accordance with a determination that a type of data corresponding to the first health data has been identified by user input, including a first representation of the first health data; and in accordance with a determination that the type of data corresponding to the first health data has not been identified by user input, not including the representation of the first health data; and a second region: in accordance with a determination that a first set of highlight criteria are met, including a second representation of the first health data different from the first representation; and in accordance with a determination that the first set of highlight criteria are not met, not including the second representation of the first health data.

In accordance with some embodiments, an electronic device is described. In some embodiments, the electronic device includes: a display device; means for receiving first health data; means for receiving a request to display a first user interface; and means, responsive to receiving the request, for displaying, via the display device, the first user interface including: a first region: in accordance with a determination that a type of data corresponding to the first health data has been identified by user input, including a first representation of the first health data; and in accordance with a determination that the type of data corresponding to the first health data has not been identified by user input, not including the representation of the first health data; and a second region: in accordance with a determination that a first set of highlight criteria are met, including a second representation of the first health data different from the first representation; and in accordance with a determination that the first set of highlight criteria are not met, not including the second representation of the first health data.

In accordance with some embodiments, a method is described. In some embodiments, the method is performed at an electronic device with a display device. In some embodiments, the method comprises: receiving clinical health record data corresponding to a particular health institution; receiving a request to display a first user interface; and in response to receiving the request, displaying, via the display device, the first user interface including: a first region corresponding to a first type of clinical health record, where the first region includes: in accordance with a determination that a first clinical health record of the first type of clinical health record fails to meet a first set of graphing criteria, a first textual representation for the first clinical health record based on the clinical health record data, where the first user interface does not include a graphical representation for the first clinical health record; and in accordance with a determination that the first clinical health meets the first set of graphing criteria, a first graphical representation for the first clinical health record based on the clinical health record data; and a second region corresponding to a second type of clinical health record, where the second region includes: in accordance with a determination that a second clinical health record of the second type of clinical health record fails to meet the first set of graphing criteria, a second textual representation for the second clinical health record based on the clinical health record data, where the user interface does not include a graphical representation for the second clinical health record; and in accordance with a determination that the second clinical health record meets the first set of graphing criteria, a second graphical representation for the second clinical health record based on the clinical health record data.

In accordance with some embodiments, a non-transitory computer-readable storage medium storing one or more programs configured to be executed by one or more processors of an electronic device with a display device is described. In some embodiments, the one or more programs include instructions for: receiving clinical health record data corresponding to a particular health institution; receiving a request to display a first user interface; and in response to receiving the request, displaying, via the display device, the first user interface including: a first region corresponding to a first type of clinical health record, where the first region includes: in accordance with a determination that a first clinical health record of the first type of clinical health record fails to meet a first set of graphing criteria, a first textual representation for the first clinical health record based on the clinical health record data, where the first user interface does not include a graphical representation for the first clinical health record; and in accordance with a determination that the first clinical health meets the first set of graphing criteria, a first graphical representation for the first clinical health record based on the clinical health record data; and a second region corresponding to a second type of clinical health record, where the second region includes: in accordance with a determination that a second clinical health record of the second type of clinical health record fails to meet the first set of graphing criteria, a second textual representation for the second clinical health record based on the clinical health record data, where the user interface does not include a graphical representation for the second clinical health record; and in accordance with a determination that the second clinical health record meets the first set of graphing criteria, a second graphical representation for the second clinical health record based on the clinical health record data.

In accordance with some embodiments, a transitory computer-readable storage medium storing one or more programs configured to be executed by one or more processors of an electronic device with a display device is described. In some embodiments, the one or more programs include instructions for: receiving clinical health record data corresponding to a particular health institution; receiving a request to display a first user interface; and in response to receiving the request, displaying, via the display device, the first user interface including: a first region corresponding to a first type of clinical health record, where the first region includes: in accordance with a determination that a first clinical health record of the first type of clinical health record fails to meet a first set of graphing criteria, a first textual representation for the first clinical health record based on the clinical health record data, where the first user interface does not include a graphical representation for the first clinical health record; and in accordance with a determination that the first clinical health meets the first set of graphing criteria, a first graphical representation for the first clinical health record based on the clinical health record data; and a second region corresponding to a second type of clinical health record, where the second region includes: in accordance with a determination that a second clinical health record of the second type of clinical health record fails to meet the first set of graphing criteria, a second textual representation for the second clinical health record based on the clinical health record data, where the user interface does not include a graphical representation for the second clinical health record; and in accordance with a determination that the second clinical health record meets the first set of graphing criteria, a second graphical representation for the second clinical health record based on the clinical health record data.

In accordance with some embodiments, an electronic device is described. In some embodiments, the electronic device includes: a display device; one or more processors; and memory storing one or more programs configured to be executed by the one or more processors, the one or more programs including instructions for: receiving clinical health record data corresponding to a particular health institution; receiving a request to display a first user interface; and in response to receiving the request, displaying, via the display device, the first user interface including: a first region corresponding to a first type of clinical health record, where the first region includes: in accordance with a determination that a first clinical health record of the first type of clinical health record fails to meet a first set of graphing criteria, a first textual representation for the first clinical health record based on the clinical health record data, where the first user interface does not include a graphical representation for the first clinical health record; and in accordance with a determination that the first clinical health meets the first set of graphing criteria, a first graphical representation for the first clinical health record based on the clinical health record data; and a second region corresponding to a second type of clinical health record, where the second region includes: in accordance with a determination that a second clinical health record of the second type of clinical health record fails to meet the first set of graphing criteria, a second textual representation for the second clinical health record based on the clinical health record data, where the user interface does not include a graphical representation for the second clinical health record; and in accordance with a determination that the second clinical health record meets the first set of graphing criteria, a second graphical representation for the second clinical health record based on the clinical health record data.

In accordance with some embodiments, an electronic device is described. In some embodiments, the electronic device includes: a display device; means for receiving clinical health record data corresponding to a particular health institution; means for receiving a request to display a first user interface; and means, responsive to receiving the request, for displaying, via the display device, the first user interface including: a first region corresponding to a first type of clinical health record, where the first region includes: in accordance with a determination that a first clinical health record of the first type of clinical health record fails to meet a first set of graphing criteria, a first textual representation for the first clinical health record based on the clinical health record data, where the first user interface does not include a graphical representation for the first clinical health record; and in accordance with a determination that the first clinical health meets the first set of graphing criteria, a first graphical representation for the first clinical health record based on the clinical health record data; and a second region corresponding to a second type of clinical health record, where the second region includes: in accordance with a determination that a second clinical health record of the second type of clinical health record fails to meet the first set of graphing criteria, a second textual representation for the second clinical health record based on the clinical health record data, where the user interface does not include a graphical representation for the second clinical health record; and in accordance with a determination that the second clinical health record meets the first set of graphing criteria, a second graphical representation for the second clinical health record based on the clinical health record data.

In accordance with some embodiments, a method is described. In some embodiments, the method is performed at an electronic device with a display device. In some embodiments, the method comprises: receiving clinical health record data, including: first clinical health record data corresponding to a first type of clinical health record; and second clinical health record data corresponding to a second type of clinical health record; receiving a request to display a first user interface; in response to receiving the request, displaying, via the display device, the first user interface, including: a first representation, based on the first clinical health record data, for a first clinical health record of the first type of clinical health record; while displaying the first user interface, receiving first user input corresponding to selection of the first representation; in response to receiving the first user input: displaying, via the display device, a second user interface, including: a second representation, based on the first clinical health record data, for the first clinical health record of the first type of clinical health record, where the second representation is different from the first representation; and a third representation, based on the first clinical health record data, for a second clinical health record of the first type of clinical health record, where the third representation is different from the second representation and the second clinical health record of the first type is different from the first clinical health record of the first type; while displaying the second user interface, receiving second user input corresponding to selection of the third representation; and in response to receiving the second user input: displaying, via the display device, a third user interface, including a fourth representation, based on the first clinical health record data, for the first clinical health record of the first type of clinical health record, where the fourth representation is different from the first representation, and where the fourth representation is different from the second representation.

In accordance with some embodiments, a non-transitory computer-readable storage medium storing one or more programs configured to be executed by one or more processors of an electronic device with a display device is described. In some embodiments, the one or more programs include instructions for: receiving clinical health record data, including: first clinical health record data corresponding to a first type of clinical health record; and second clinical health record data corresponding to a second type of clinical health record; receiving a request to display a first user interface; in response to receiving the request, displaying, via the display device, the first user interface, including: a first representation, based on the first clinical health record data, for a first clinical health record of the first type of clinical health record; while displaying the first user interface, receiving first user input corresponding to selection of the first representation; in response to receiving the first user input: displaying, via the display device, a second user interface, including: a second representation, based on the first clinical health record data, for the first clinical health record of the first type of clinical health record, where the second representation is different from the first representation; and a third representation, based on the first clinical health record data, for a second clinical health record of the first type of clinical health record, where the third representation is different from the second representation and the second clinical health record of the first type is different from the first clinical health record of the first type; while displaying the second user interface, receiving second user input corresponding to selection of the third representation; and in response to receiving the second user input: displaying, via the display device, a third user interface, including a fourth representation, based on the first clinical health record data, for the first clinical health record of the first type of clinical health record, where the fourth representation is different from the first representation, and where the fourth representation is different from the second representation.

In accordance with some embodiments, a transitory computer-readable storage medium storing one or more programs configured to be executed by one or more processors of an electronic device with a display device is described. In some embodiments, the one or more programs include instructions for: receiving clinical health record data, including: first clinical health record data corresponding to a first type of clinical health record; and second clinical health record data corresponding to a second type of clinical health record; receiving a request to display a first user interface; in response to receiving the request, displaying, via the display device, the first user interface, including: a first representation, based on the first clinical health record data, for a first clinical health record of the first type of clinical health record; while displaying the first user interface, receiving first user input corresponding to selection of the first representation; in response to receiving the first user input: displaying, via the display device, a second user interface, including: a second representation, based on the first clinical health record data, for the first clinical health record of the first type of clinical health record, where the second representation is different from the first representation; and a third representation, based on the first clinical health record data, for a second clinical health record of the first type of clinical health record, where the third representation is different from the second representation and the second clinical health record of the first type is different from the first clinical health record of the first type; while displaying the second user interface, receiving second user input corresponding to selection of the third representation; and in response to receiving the second user input: displaying, via the display device, a third user interface, including a fourth representation, based on the first clinical health record data, for the first clinical health record of the first type of clinical health record, where the fourth representation is different from the first representation, and where the fourth representation is different from the second representation.

In accordance with some embodiments, an electronic device is described. In some embodiments, the electronic device includes: a display device; one or more processors; and memory storing one or more programs configured to be executed by the one or more processors, the one or more programs including instructions for: receiving clinical health record data, including: first clinical health record data corresponding to a first type of clinical health record; and second clinical health record data corresponding to a second type of clinical health record; receiving a request to display a first user interface; in response to receiving the request, displaying, via the display device, the first user interface, including: a first representation, based on the first clinical health record data, for a first clinical health record of the first type of clinical health record; while displaying the first user interface, receiving first user input corresponding to selection of the first representation; in response to receiving the first user input: displaying, via the display device, a second user interface, including: a second representation, based on the first clinical health record data, for the first clinical health record of the first type of clinical health record, where the second representation is different from the first representation; and a third representation, based on the first clinical health record data, for a second clinical health record of the first type of clinical health record, where the third representation is different from the second representation and the second clinical health record of the first type is different from the first clinical health record of the first type; while displaying the second user interface, receiving second user input corresponding to selection of the third representation; and in response to receiving the second user input: displaying, via the display device, a third user interface, including a fourth representation, based on the first clinical health record data, for the first clinical health record of the first type of clinical health record, where the fourth representation is different from the first representation, and where the fourth representation is different from the second representation.

In accordance with some embodiments, an electronic device is described. In some embodiments, the electronic device includes: a display device; means for receiving clinical health record data, including: first clinical health record data corresponding to a first type of clinical health record; and second clinical health record data corresponding to a second type of clinical health record; means for receiving a request to display a first user interface; means, responsive to receiving the request, for displaying, via the display device, the first user interface, including: a first representation, based on the first clinical health record data, for a first clinical health record of the first type of clinical health record; means, while displaying the first user interface, for receiving first user input corresponding to selection of the first representation; means, responsive to receiving the first user input, for: displaying, via the display device, a second user interface, including: a second representation, based on the first clinical health record data, for the first clinical health record of the first type of clinical health record, where the second representation is different from the first representation; and a third representation, based on the first clinical health record data, for a second clinical health record of the first type of clinical health record, where the third representation is different from the second representation and the second clinical health record of the first type is different from the first clinical health record of the first type; means, while displaying the second user interface, for receiving second user input corresponding to selection of the third representation; and means, responsive to receiving the second user input, for: displaying, via the display device, a third user interface, including a fourth representation, based on the first clinical health record data, for the first clinical health record of the first type of clinical health record, where the fourth representation is different from the first representation, and where the fourth representation is different from the second representation.

In accordance with some embodiments, a method is described. In some embodiments, the method is performed at an electronic device with a display device, where the electronic device is associated with a first user account. In some embodiments, the method comprises: receiving a request to display a first user interface; in response to receiving the first request, displaying, via the display device, the first user interface, including: a first portion, including a first category affordance; and a second portion including a first shared affordance corresponding to a second user account; while displaying the first user interface: receiving first user input corresponding to selection of the first category affordance; and receiving second user input corresponding to selection of the first shared affordance; in response to receiving the first user input, displaying, via the display device, a second user interface, including a representation of first health data associated with the first user account for the first category; in response to receiving the second user input, displaying, via the display device, a third user interface, including: a first portion, including: a second category affordance corresponding to health data associated with the second user account for the first category; while displaying the third user interface, receiving third user input corresponding to selection of the second category affordance; and in response to receiving the third user input, displaying, via the display device, a fourth user interface, including a representation of health data associated with the second user account for the first category.

In some embodiments, a non-transitory computer-readable storage medium storing one or more programs configured to be executed by one or more processors of an electronic device, associated with a first user account, with a display device is described. In some embodiments, the one or more programs include instructions for: receiving a request to display a first user interface; in response to receiving the first request, displaying, via the display device, the first user interface, including: a first portion, including a first category affordance; and a second portion including a first shared affordance corresponding to a second user account; while displaying the first user interface: receiving first user input corresponding to selection of the first category affordance; and receiving second user input corresponding to selection of the first shared affordance; in response to receiving the first user input, displaying, via the display device, a second user interface, including a representation of first health data associated with the first user account for the first category; in response to receiving the second user input, displaying, via the display device, a third user interface, including: a first portion, including: a second category affordance corresponding to health data associated with the second user account for the first category; while displaying the third user interface, receiving third user input corresponding to selection of the second category affordance; and in response to receiving the third user input, displaying, via the display device, a fourth user interface, including a representation of health data associated with the second user account for the first category.

In some embodiments, a transitory computer-readable storage medium storing one or more programs configured to be executed by one or more processors of an electronic device, associated with a first user account, with a display device is described. In some embodiments, the one or more programs include instructions for: receiving a request to display a first user interface; in response to receiving the first request, displaying, via the display device, the first user interface, including: a first portion, including a first category affordance; and a second portion including a first shared affordance corresponding to a second user account; while displaying the first user interface: receiving first user input corresponding to selection of the first category affordance; and receiving second user input corresponding to selection of the first shared affordance; in response to receiving the first user input, displaying, via the display device, a second user interface, including a representation of first health data associated with the first user account for the first category; in response to receiving the second user input, displaying, via the display device, a third user interface, including: a first portion, including: a second category affordance corresponding to health data associated with the second user account for the first category; while displaying the third user interface, receiving third user input corresponding to selection of the second category affordance; and in response to receiving the third user input, displaying, via the display device, a fourth user interface, including a representation of health data associated with the second user account for the first category.

In accordance with some embodiments, an electronic device associated with a first user account is disclosed. In some embodiments, the electronic device includes: a display device; one or more processors; and memory storing one or more programs configured to be executed by the one or more processors, the one or more programs including instructions for: receiving a request to display a first user interface; in response to receiving the first request, displaying, via the display device, the first user interface, including: a first portion, including a first category affordance; and a second portion including a first shared affordance corresponding to a second user account; while displaying the first user interface: receiving first user input corresponding to selection of the first category affordance; and receiving second user input corresponding to selection of the first shared affordance; in response to receiving the first user input, displaying, via the display device, a second user interface, including a representation of first health data associated with the first user account for the first category; in response to receiving the second user input, displaying, via the display device, a third user interface, including: a first portion, including: a second category affordance corresponding to health data associated with the second user account for the first category; while displaying the third user interface, receiving third user input corresponding to selection of the second category affordance; and in response to receiving the third user input, displaying, via the display device, a fourth user interface, including a representation of health data associated with the second user account for the first category.

In accordance with some embodiments, an electronic device associated with a first user account is disclosed. In some embodiments, the electronic device includes: a display device; means for receiving a request to display a first user interface; means, responsive to receiving the first request, for displaying, via the display device, the first user interface, including: a first portion, including a first category affordance; and a second portion including a first shared affordance corresponding to a second user account; means, while displaying the first user interface, for: receiving first user input corresponding to selection of the first category affordance; and receiving second user input corresponding to selection of the first shared affordance; means, responsive to receiving the first user input, for displaying, via the display device, a second user interface, including a representation of first health data associated with the first user account for the first category; means, responsive to receiving the second user input, for displaying, via the display device, a third user interface, including: a first portion, including: a second category affordance corresponding to health data associated with the second user account for the first category; means, while displaying the third user interface, for receiving third user input corresponding to selection of the second category affordance; and means, in response to receiving the third user input, for displaying, via the display device, a fourth user interface, including a representation of health data associated with the second user account for the first category.

In accordance with some embodiments, a method is described. In some embodiments, the method is performed at a first electronic device with a display device. In some embodiments, the method comprises: receiving a request to share health data associated with the first electronic device; in response to receiving the request, displaying, via the display device at a first time, a first notification, including a first affordance that, when selected, initiates a process for sharing of health data, associated with the first electronic device, with a second electronic device; while displaying the notification, receiving a first user input corresponding to selection of the first affordance; in response to receiving the first user input, initiating a process for sharing of health data, associated with the first electronic device, with the second electronic device; and after receiving the first user input: sharing health data associated with the first electronic device with the second electronic device; and displaying, via the display device at a second time, a second notification corresponding to the sharing of health data, the second notification including a second affordance that, when selected, initiates a process to end sharing of health data, associated with the first electronic device, with the second electronic device.

In accordance with some embodiments, a non-transitory computer-readable storage medium storing one or more programs configured to be executed by one or more processors of a first electronic device with a display device is described. In some embodiments, the one or more programs include instructions for: receiving a request to share health data associated with the first electronic device; in response to receiving the request, displaying, via the display device at a first time, a first notification, including a first affordance that, when selected, initiates a process for sharing of health data, associated with the first electronic device, with a second electronic device; while displaying the notification, receiving a first user input corresponding to selection of the first affordance; in response to receiving the first user input, initiating a process for sharing of health data, associated with the first electronic device, with the second electronic device; and after receiving the first user input: sharing health data associated with the first electronic device with the second electronic device; and displaying, via the display device at a second time, a second notification corresponding to the sharing of health data, the second notification including a second affordance that, when selected, initiates a process to end sharing of health data, associated with the first electronic device, with the second electronic device.

In accordance with some embodiments, a transitory computer-readable storage medium storing one or more programs configured to be executed by one or more processors of a first electronic device with a display device is described. In some embodiments, the one or more programs include instructions for: receiving a request to share health data associated with the first electronic device; in response to receiving the request, displaying, via the display device at a first time, a first notification, including a first affordance that, when selected, initiates a process for sharing of health data, associated with the first electronic device, with a second electronic device; while displaying the notification, receiving a first user input corresponding to selection of the first affordance; in response to receiving the first user input, initiating a process for sharing of health data, associated with the first electronic device, with the second electronic device; and after receiving the first user input: sharing health data associated with the first electronic device with the second electronic device; and displaying, via the display device at a second time, a second notification corresponding to the sharing of health data, the second notification including a second affordance that, when selected, initiates a process to end sharing of health data, associated with the first electronic device, with the second electronic device.

In accordance with some embodiments, a first electronic device is described. In some embodiments, the first electronic device includes: a display device; one or more processors; and memory storing one or more programs configured to be executed by the one or more processors, the one or more programs including instructions for: receiving a request to share health data associated with the first electronic device; in response to receiving the request, displaying, via the display device at a first time, a first notification, including a first affordance that, when selected, initiates a process for sharing of health data, associated with the first electronic device, with a second electronic device; while displaying the notification, receiving a first user input corresponding to selection of the first affordance; in response to receiving the first user input, initiating a process for sharing of health data, associated with the first electronic device, with the second electronic device; and after receiving the first user input: sharing health data associated with the first electronic device with the second electronic device; and displaying, via the display device at a second time, a second notification corresponding to the sharing of health data, the second notification including a second affordance that, when selected, initiates a process to end sharing of health data, associated with the first electronic device, with the second electronic device.

In accordance with some embodiments, a first electronic device is described. In some embodiments, the first electronic device includes: a display device; means for receiving a request to share health data associated with the first electronic device; means, responsive to receiving the request, for displaying, via the display device at a first time, a first notification, including a first affordance that, when selected, initiates a process for sharing of health data, associated with the first electronic device, with a second electronic device; means, while displaying the notification, for receiving a first user input corresponding to selection of the first affordance; means, responsive to receiving the first user input, for initiating a process for sharing of health data, associated with the first electronic device, with the second electronic device; and means, after receiving the first user input, for: sharing health data associated with the first electronic device with the second electronic device; and displaying, via the display device at a second time, a second notification corresponding to the sharing of health data, the second notification including a second affordance that, when selected, initiates a process to end sharing of health data, associated with the first electronic device, with the second electronic device.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for managing health information and functions, thereby increasing the effectiveness, efficiency, and user satisfaction with such devices. Such methods and interfaces can complement or replace other methods for managing health information and functions.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 7A-7B are a flow diagram illustrating a method for managing notifications using an electronic device, in accordance with some embodiments.

FIGS. 8A-8B are a flow diagram illustrating a method for managing display of health-related information using an electronic device, in accordance with some embodiments.

FIGS. 9A-9B are a flow diagram illustrating a method for managing display of clinical health record representations using an electronic device, in accordance with some embodiments.

FIGS. 10A-10B are a flow diagram illustrating a method for managing display of clinical health record representations using an electronic device, in accordance with some embodiments.

FIGS. 11A-11C are a flow diagram illustrating a method for managing display of health-related information for various user accounts using an electronic device, in accordance with some embodiments.

FIGS. 15A-15F illustrate exemplary user interfaces related to viewing health data using an electronic device, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for managing health information and functions. For example, it is advantageous to provide timely health-related notifications and cease to display unhelpful notifications. For another example, it is advantageous to emphasize certain health-related information for the user. Such techniques can reduce the cognitive burden on a user who manage health information and functions, thereby enhancing productivity. Further, such techniques can reduce processor and battery power otherwise wasted on redundant user inputs.

Figures 6A, 6B:
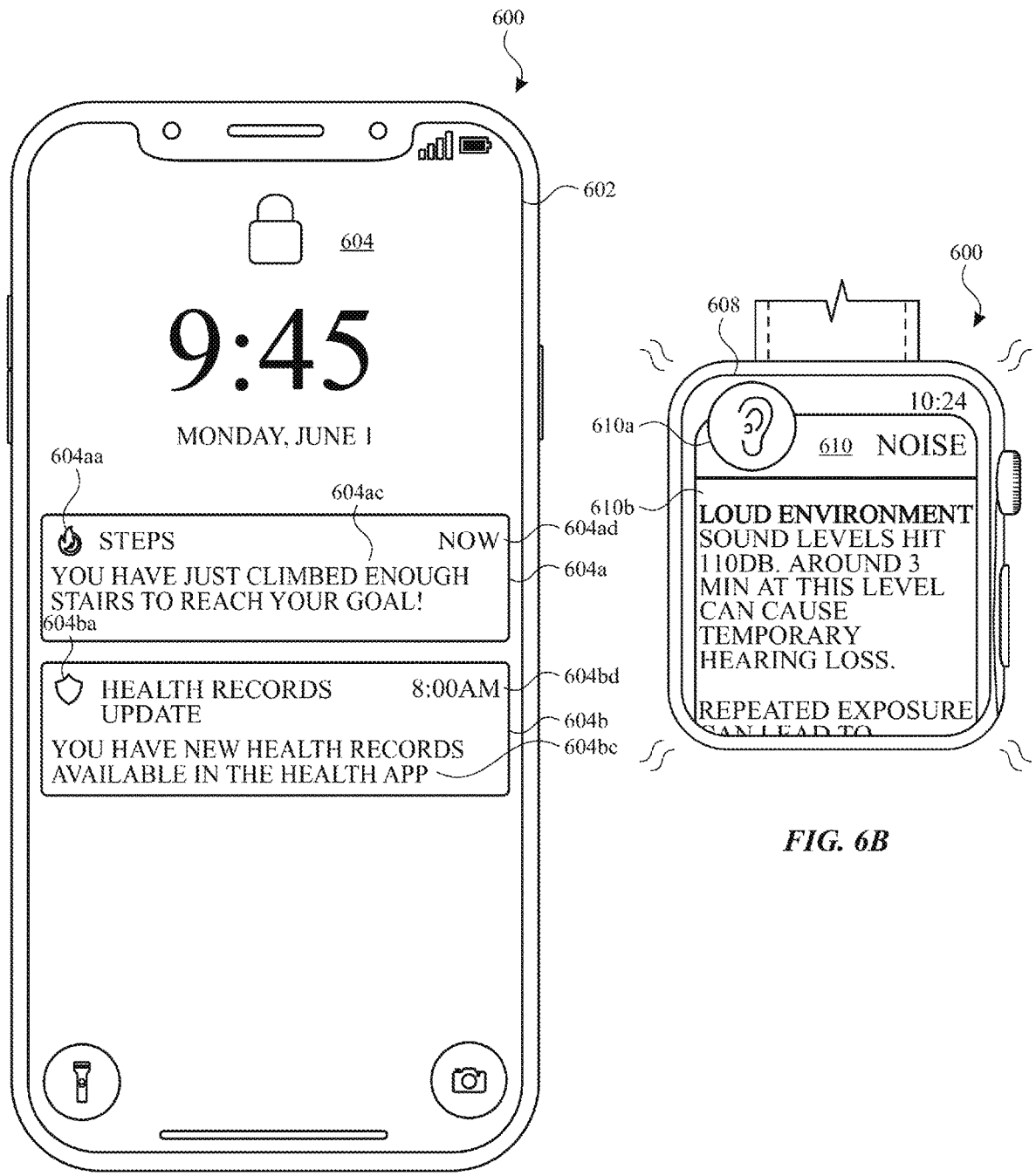
FIGS. 6A-6Z illustrate exemplary user interfaces related to viewing health data using an electronic device, in accordance with some embodiments.
Figure 6Z:
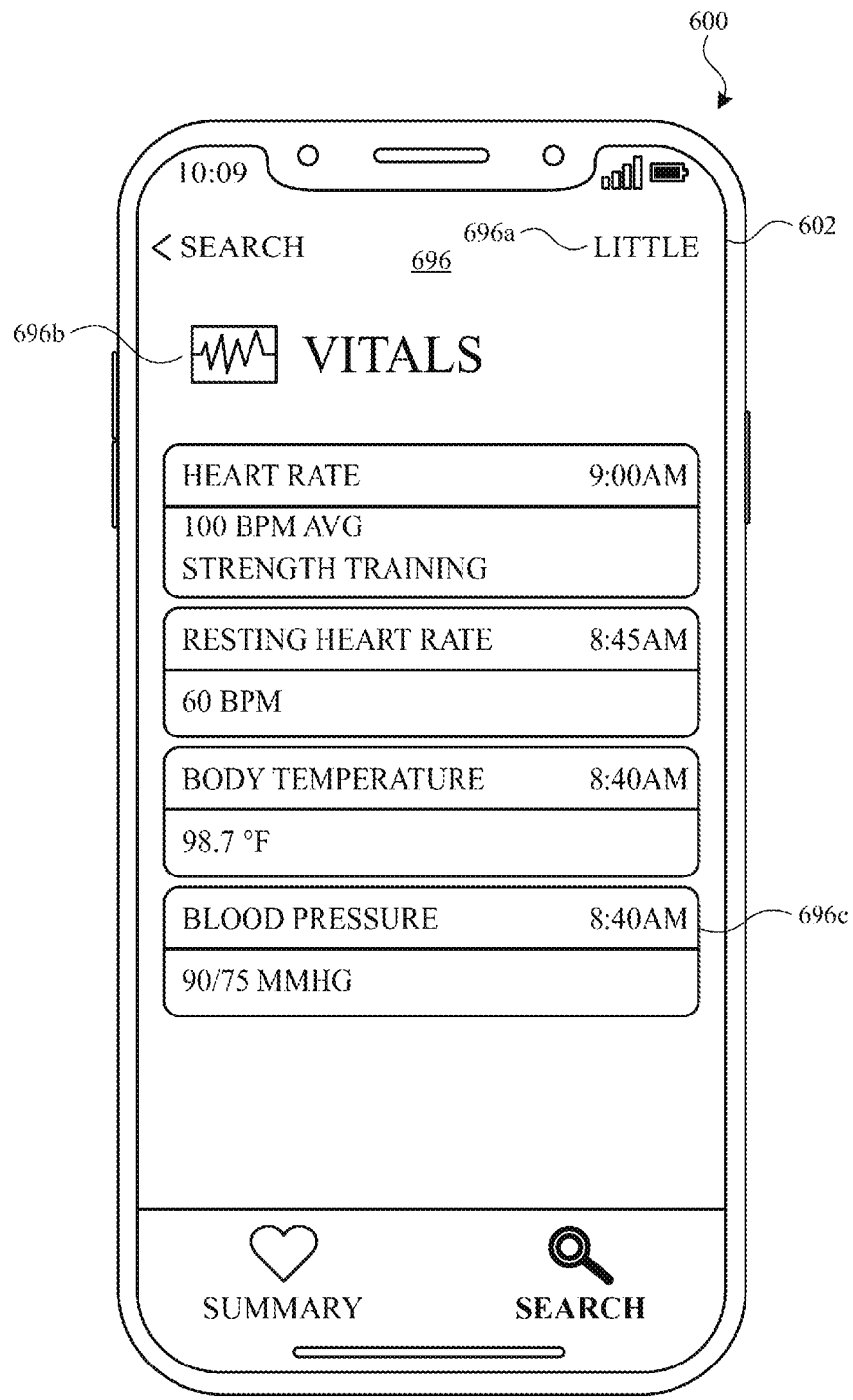
Figure 7B:
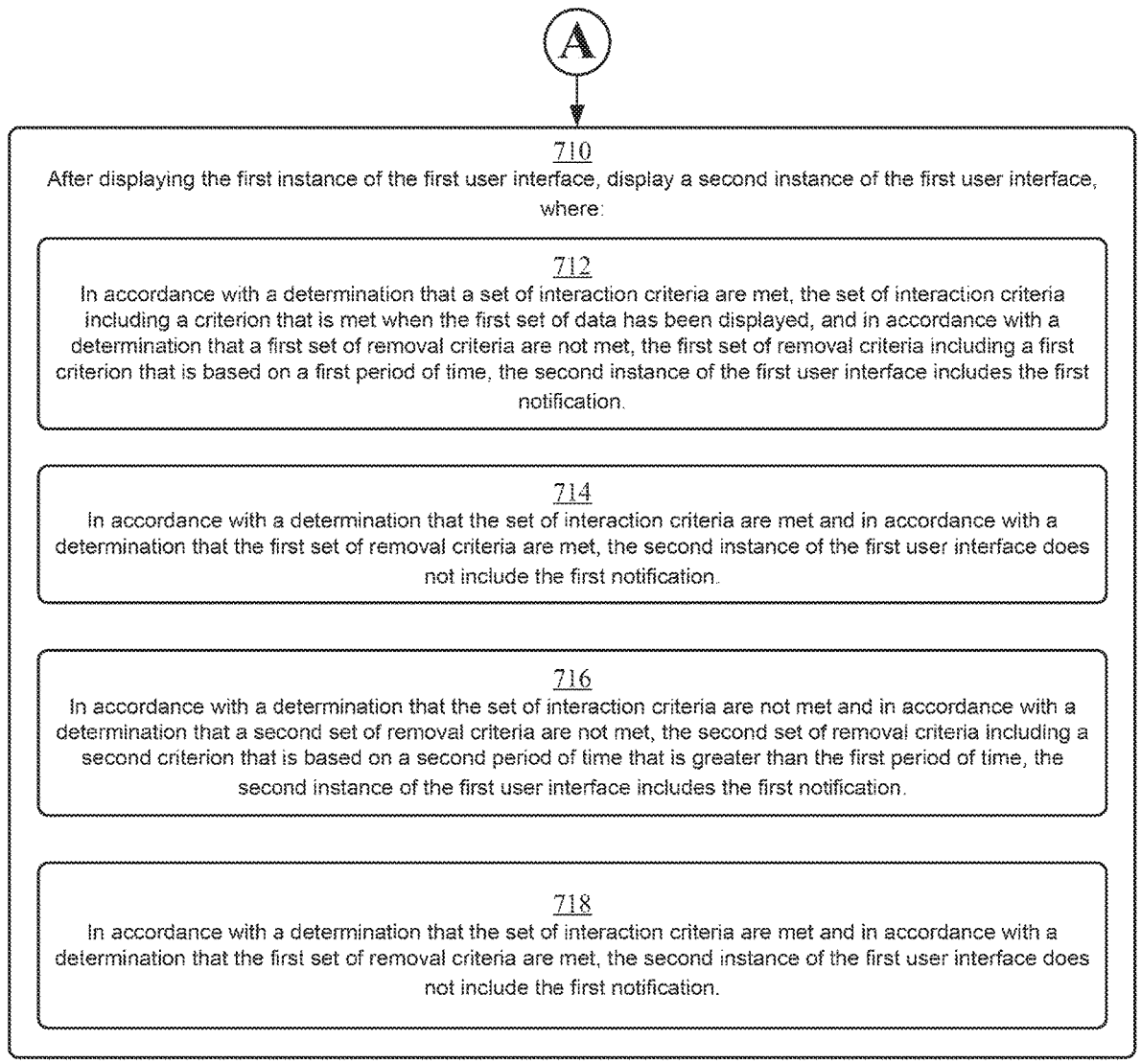
Figure 8A:
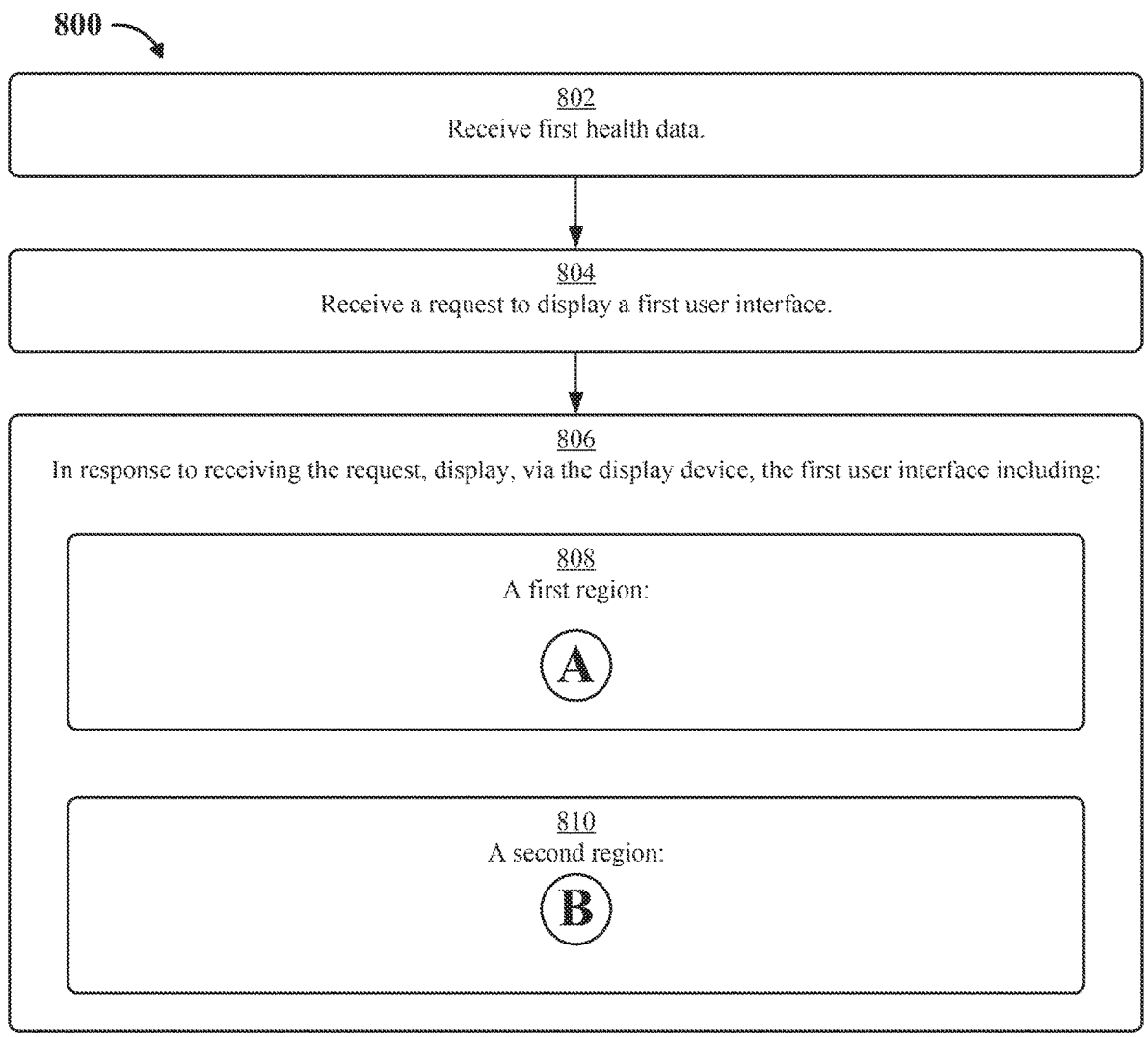
Figure 9A:
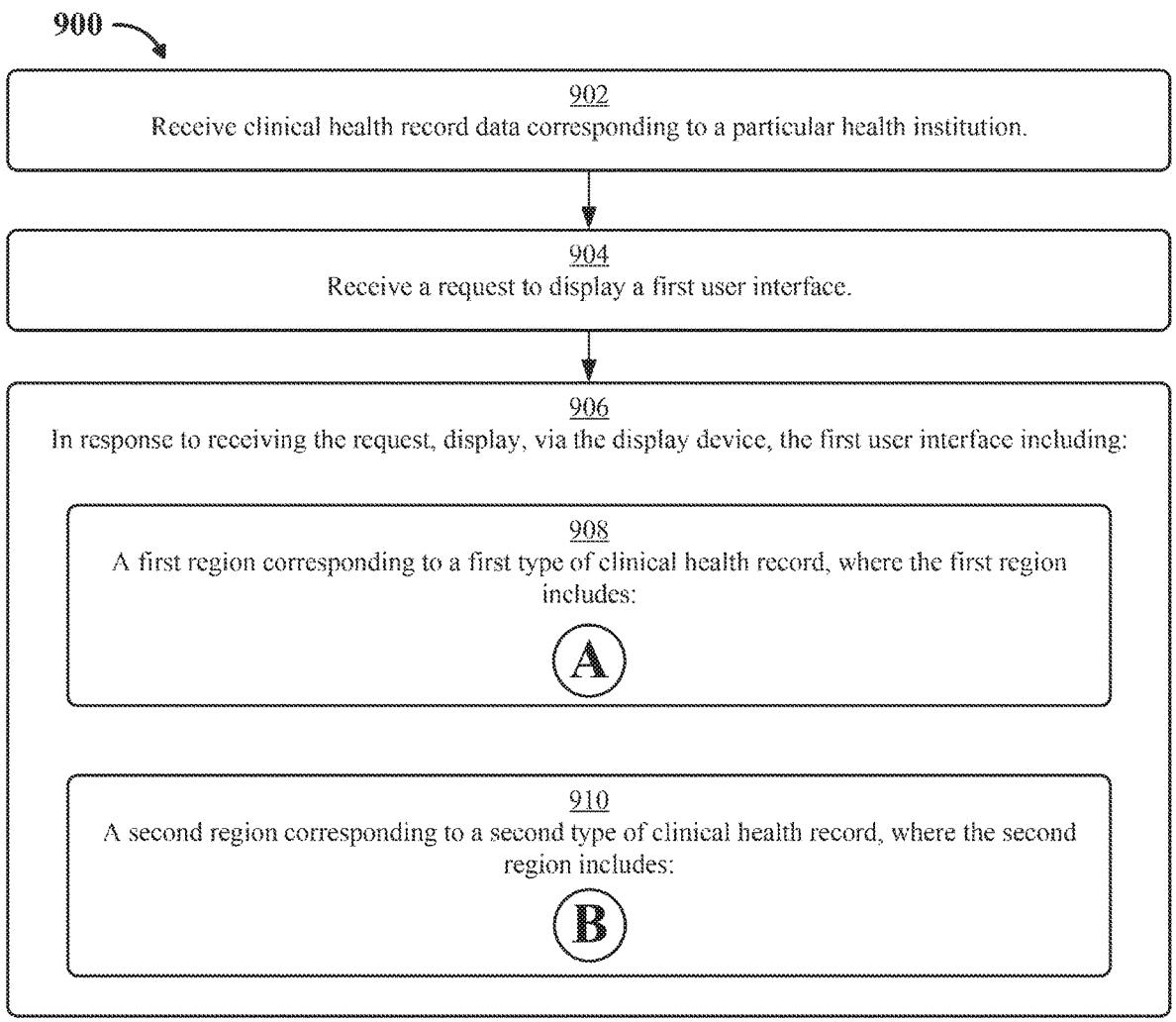
Figure 10A:
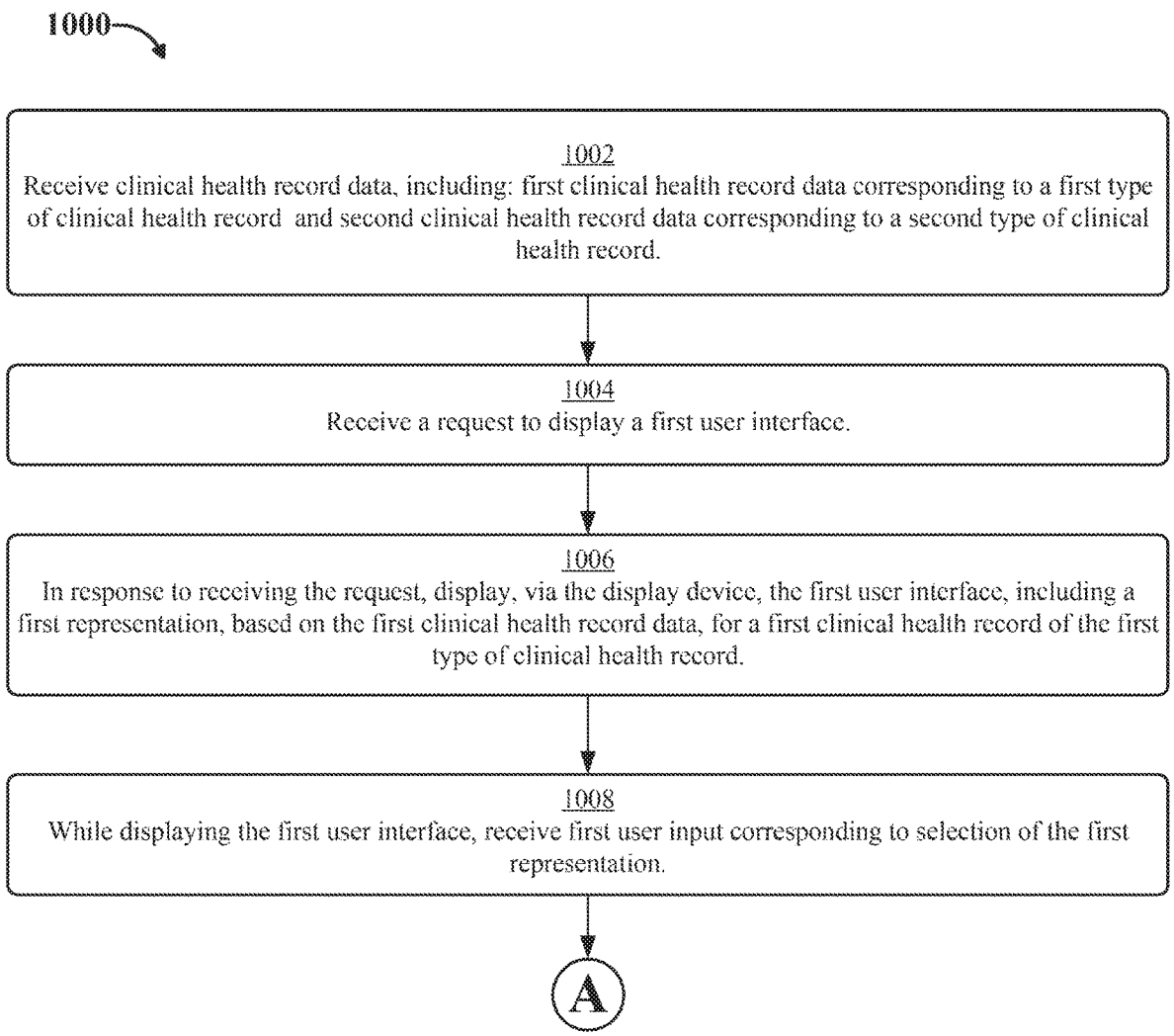
Figure 11B:
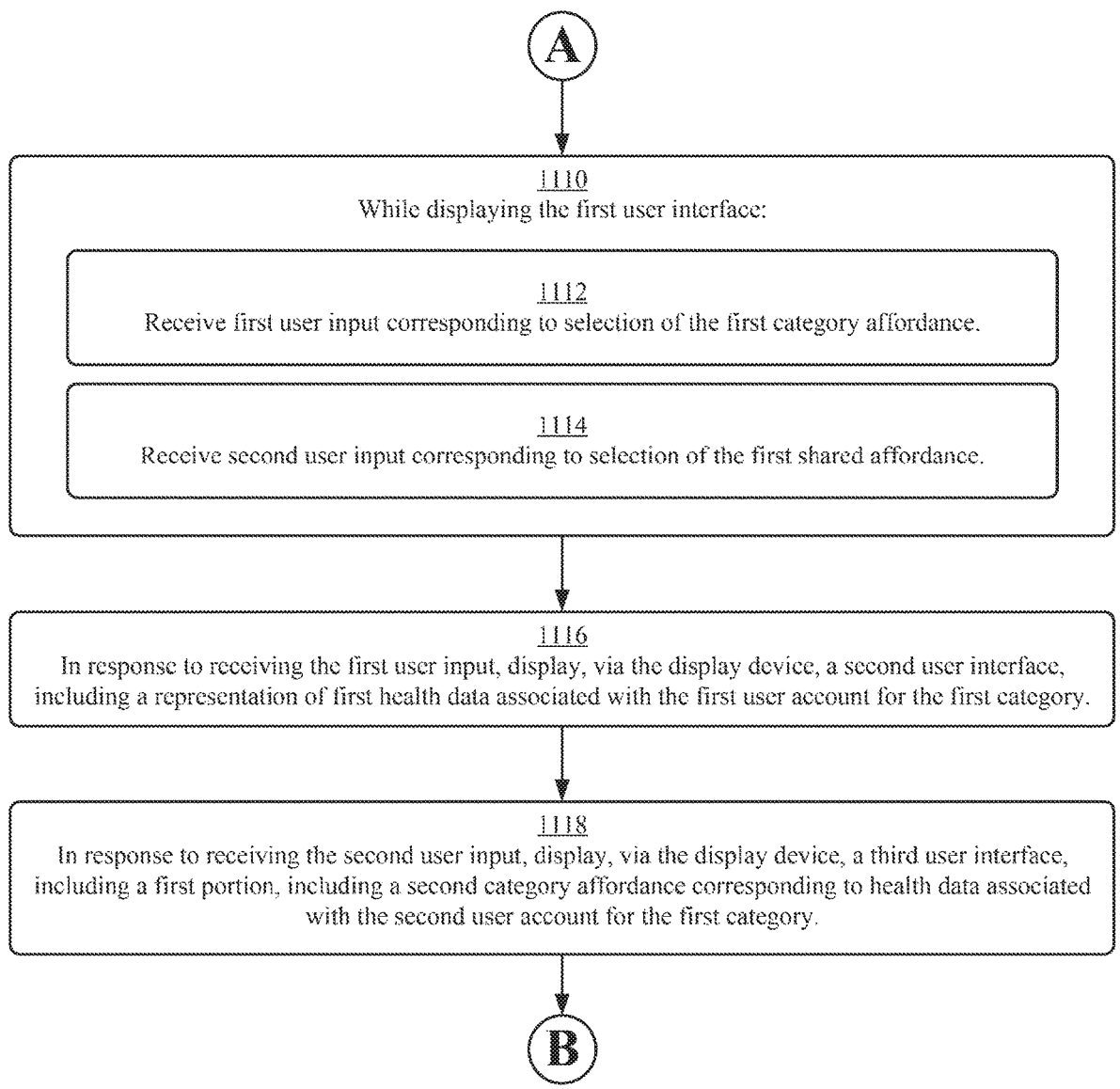
Figure 11C:
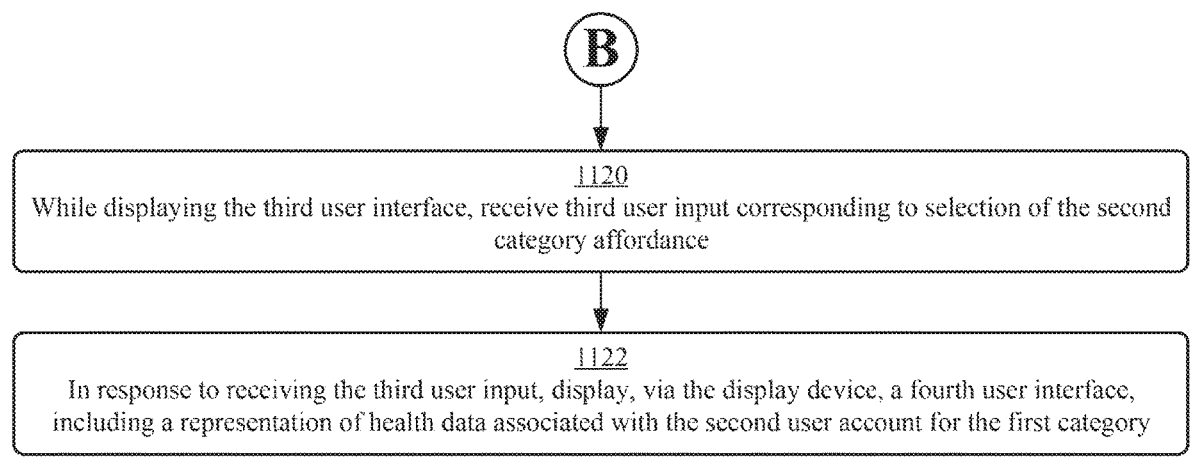

Below, FIGS. 1A-1B, 2, 3, 4A-4B, and 5A-5H provide a description of exemplary devices for performing the techniques for managing event notifications. FIGS. 6A-6Z illustrate exemplary user interfaces related to viewing health data using an electronic device, in accordance with some embodiments. FIGS. 7A-7B are a flow diagram illustrating a method for managing notifications using an electronic device, in accordance with some embodiments. FIGS. 8A-8B are a flow diagram illustrating a method for managing display of health-related information using an electronic device, in accordance with some embodiments. FIGS. 9A-9B are a flow diagram illustrating a method for managing display of clinical health record representations using an electronic device, in accordance with some embodiments. FIGS. 10A-10B are a flow diagram illustrating a method for managing display of clinical health record representations using an electronic device, in accordance with some embodiments. FIGS. 11A-11C are a flow diagram illustrating a method for managing display of health-related information for various user accounts using an electronic device, in accordance with some embodiments. The user interfaces in FIGS. 6A-6Z are used to illustrate the processes described below, including the processes in FIGS. 7A-7B, 8A-8B, 9A-9B, 10A-10B, 11A-11C. FIGS. 12A-12I illustrate exemplary user interfaces related to viewing health data using an electronic device, in accordance with some embodiments. FIGS. 13A-13G illustrate exemplary user interfaces related to sharing health data using an electronic device, in accordance with some embodiments. FIGS. 14A-14B are a flow diagram illustrating methods related to sharing health data, in accordance with some embodiments. The user interfaces in FIGS. 13A-13G are used to illustrate the processes described below, including the processes in FIGS. 14A-14B. FIGS. 15A-15F illustrate exemplary user interfaces related to viewing health data using an electronic device, in accordance with some embodiments.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
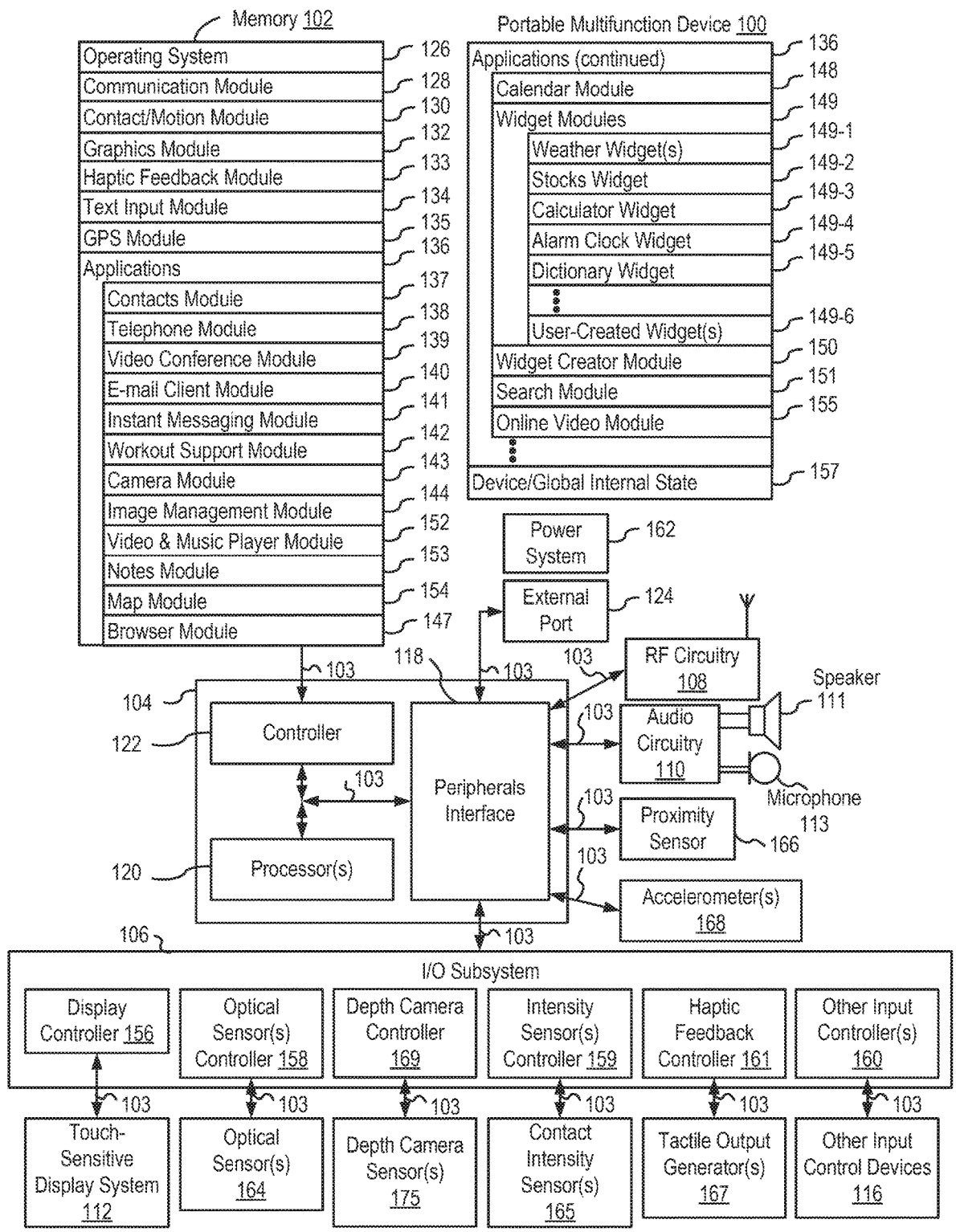
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system."

Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that can otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
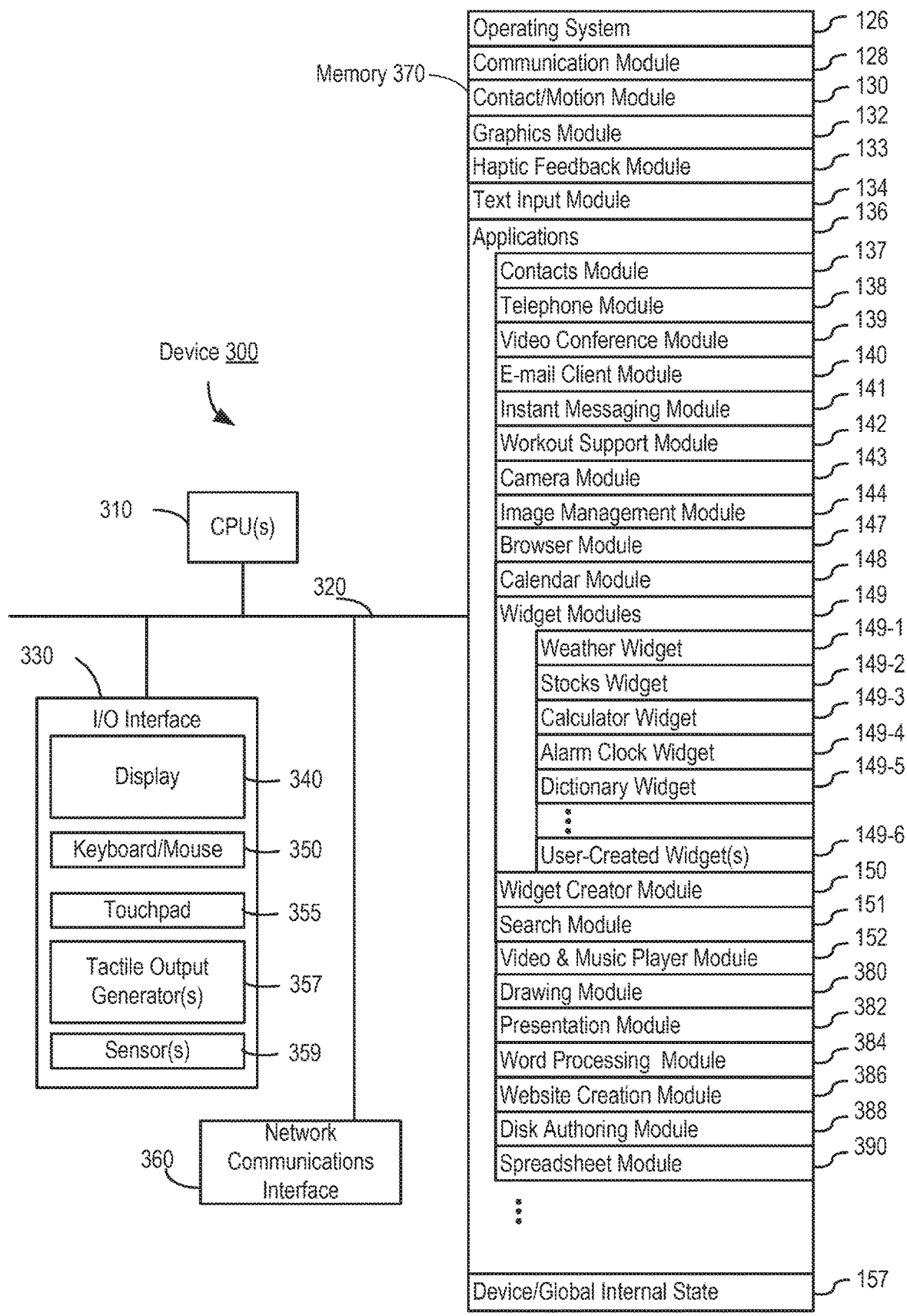
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE- WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:

Contacts module 137 (sometimes called an address book or contact list);
Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module;
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
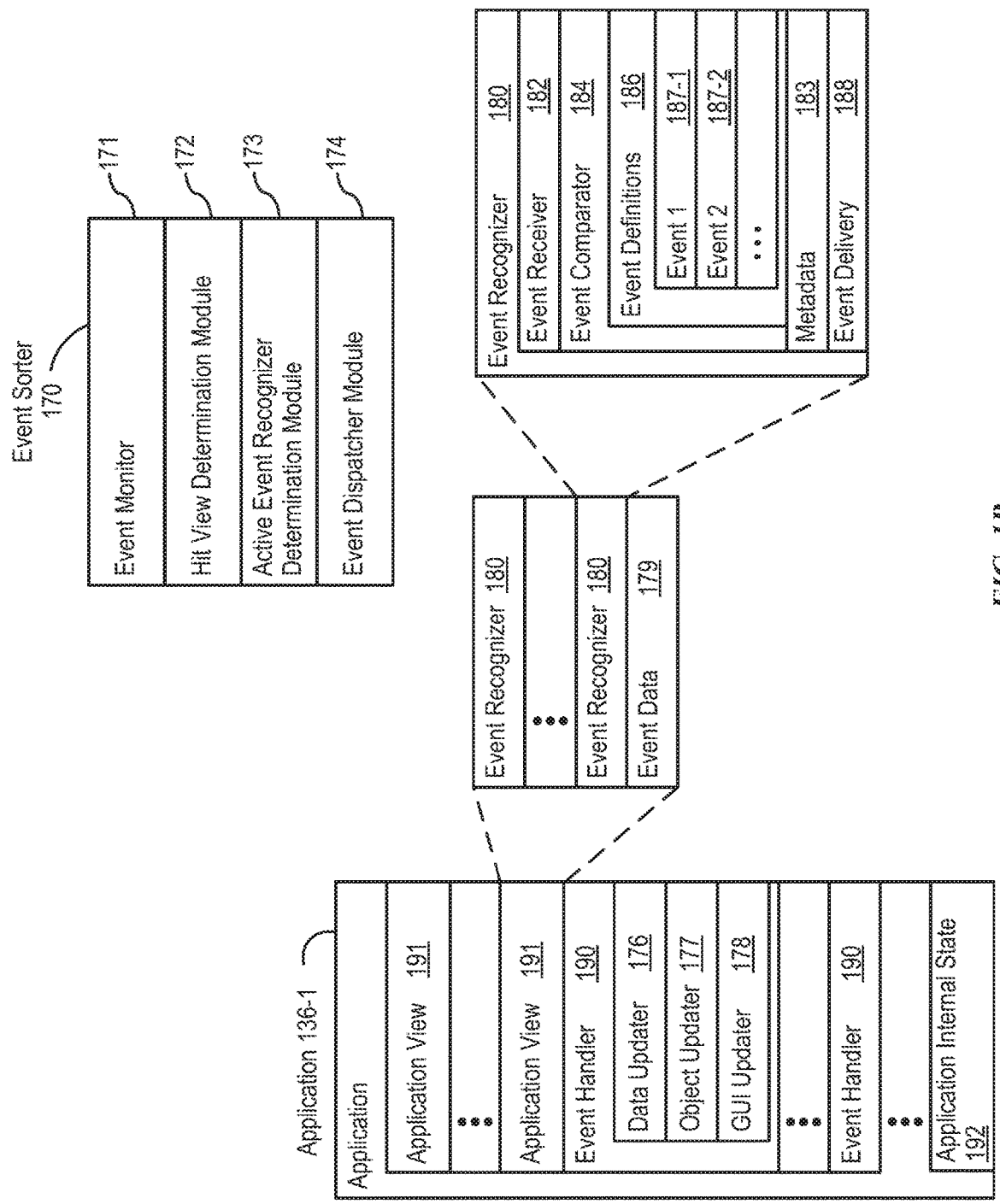
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
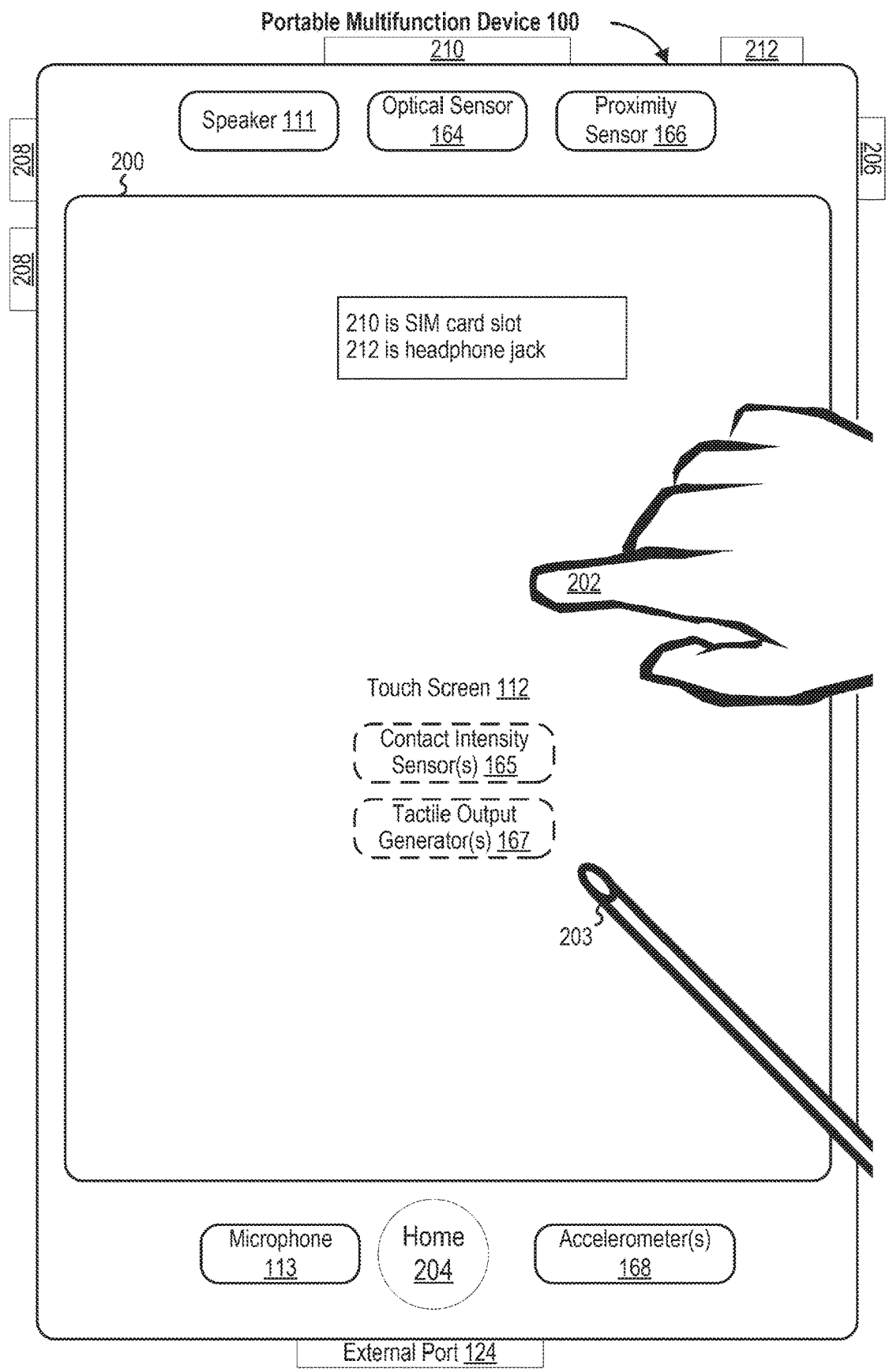
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
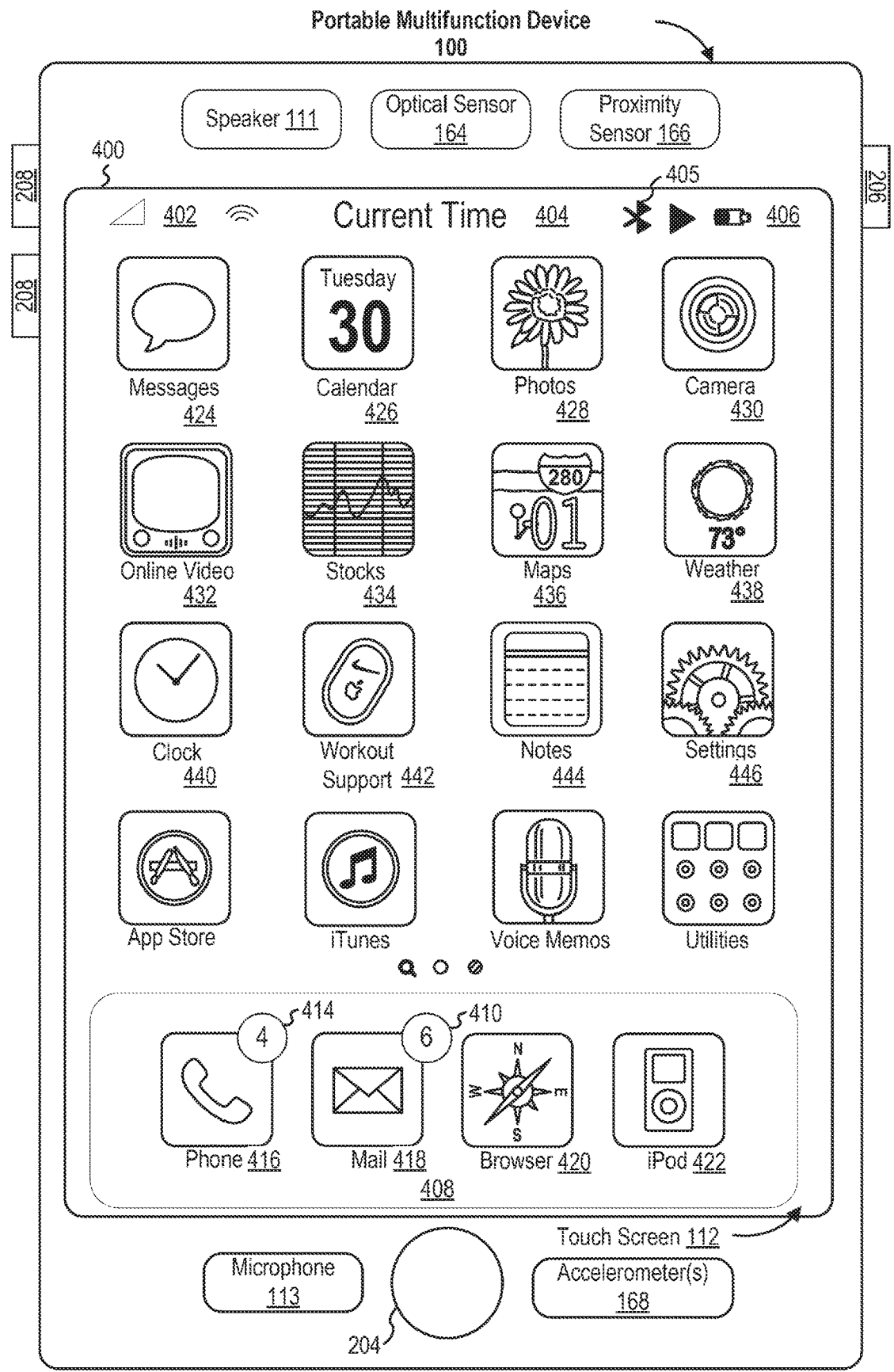
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
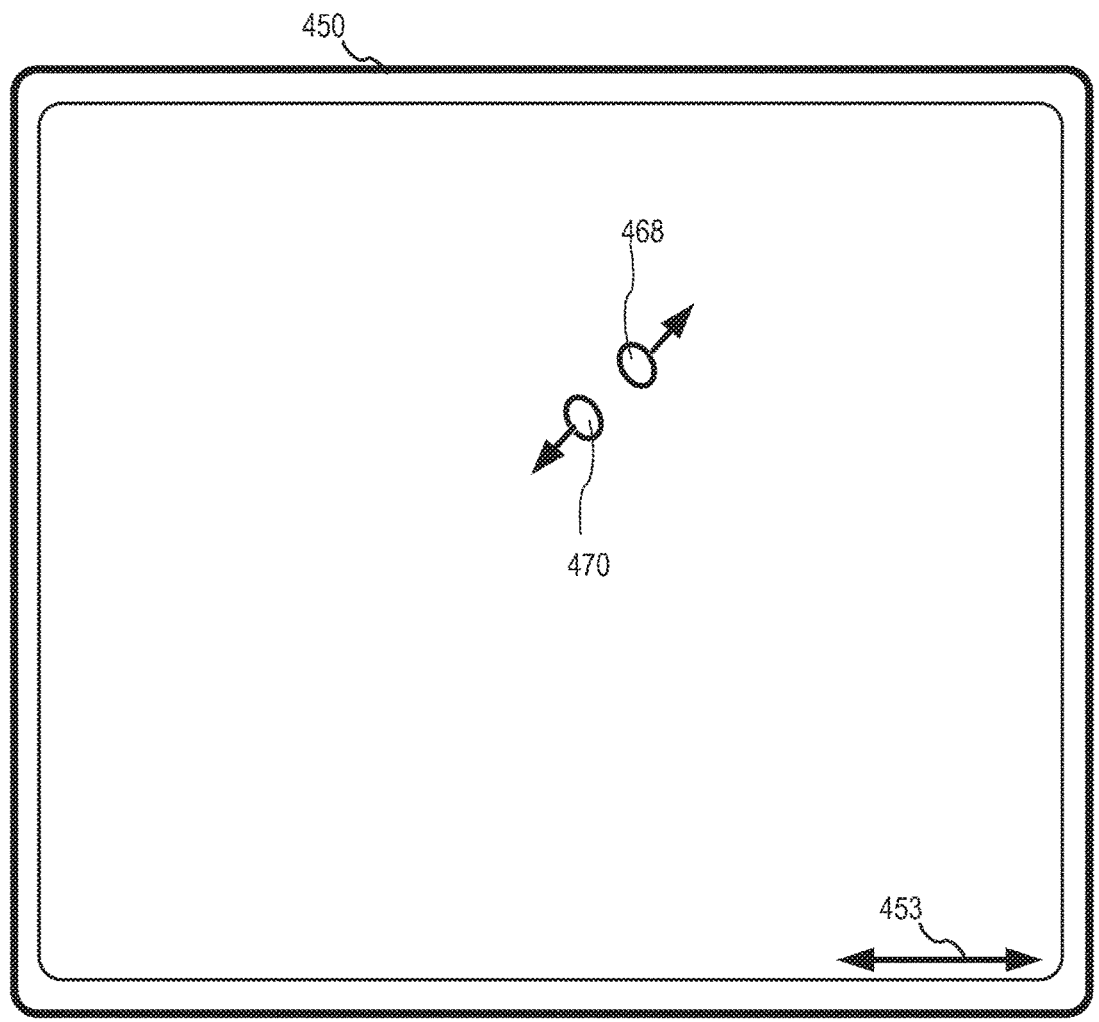
FIG. 4B illustrates an exemplary user interface for a multifunction device with a touch-sensitive surface that is separate from the display in accordance with some embodiments.
Figure 4B:
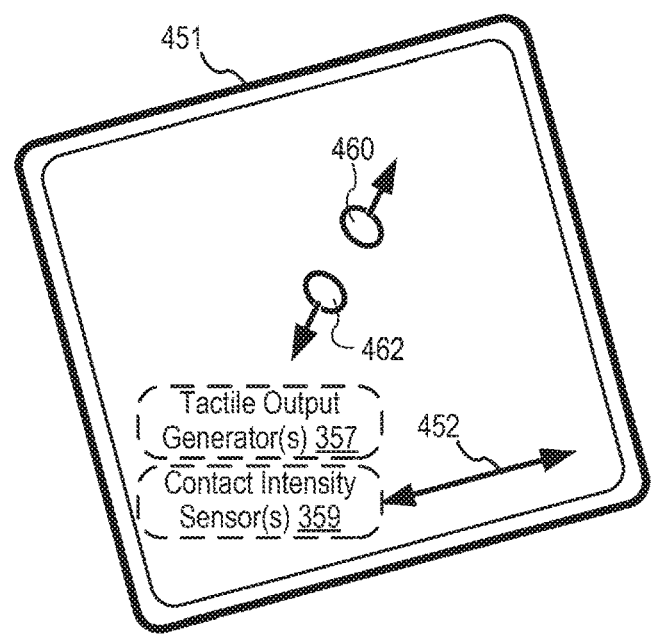

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
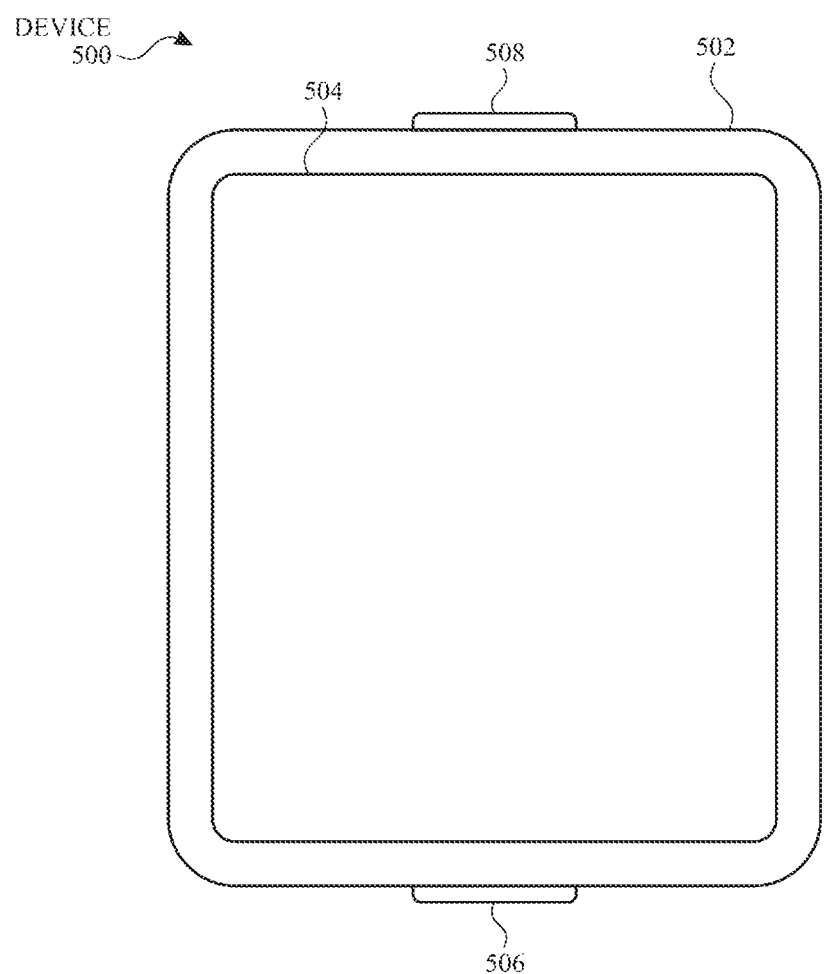
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
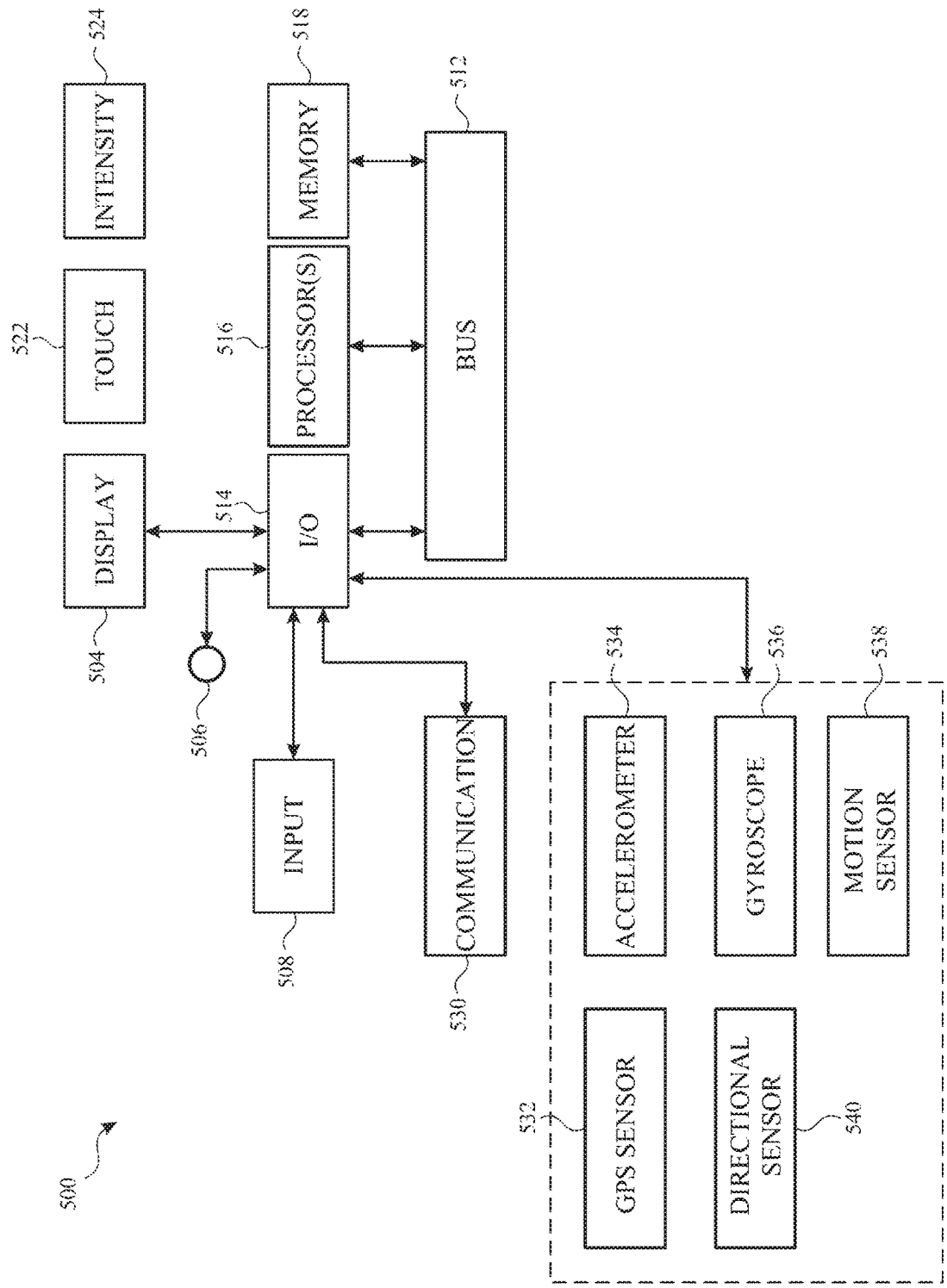
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700-1100 (FIGS. 7A-7B, 8A-8B, 9A-9B, 10A-10B, 11A-11C) and 1400 (FIGS. 14A-14B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5C:
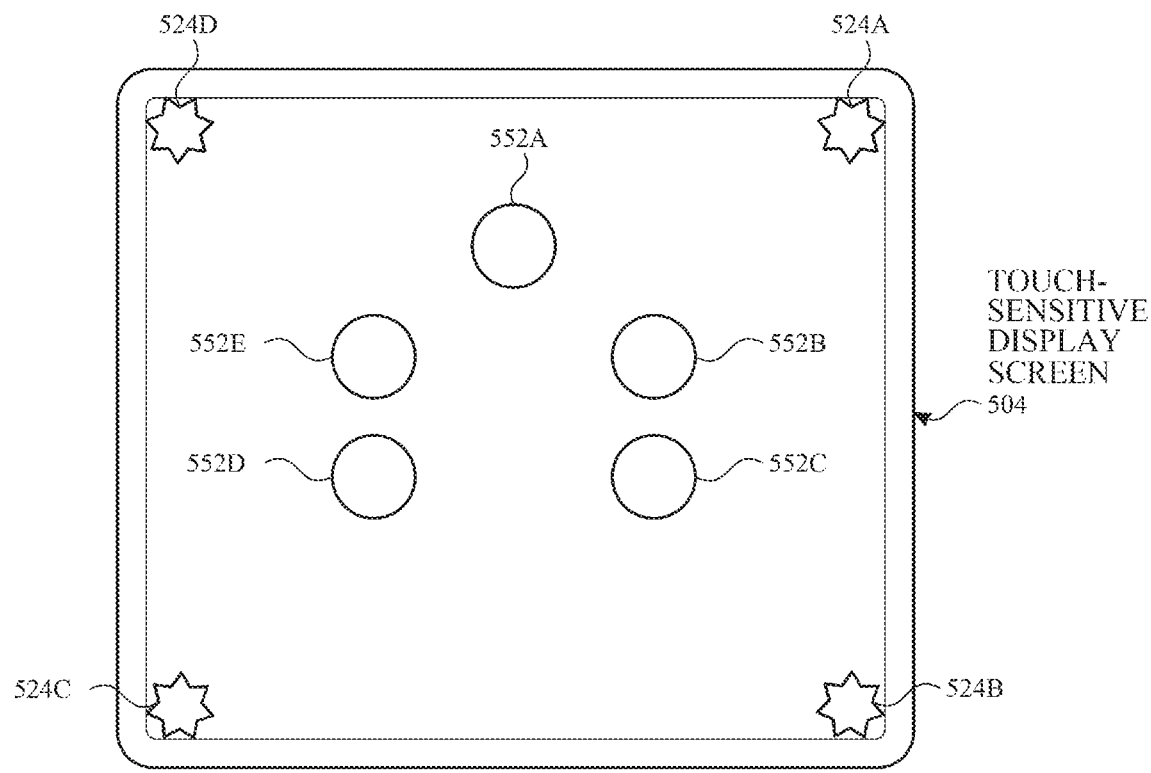
FIGS. 5C-5D illustrate exemplary components of a personal electronic device having a touch-sensitive display and intensity sensors in accordance with some embodiments.
Figure 5C:
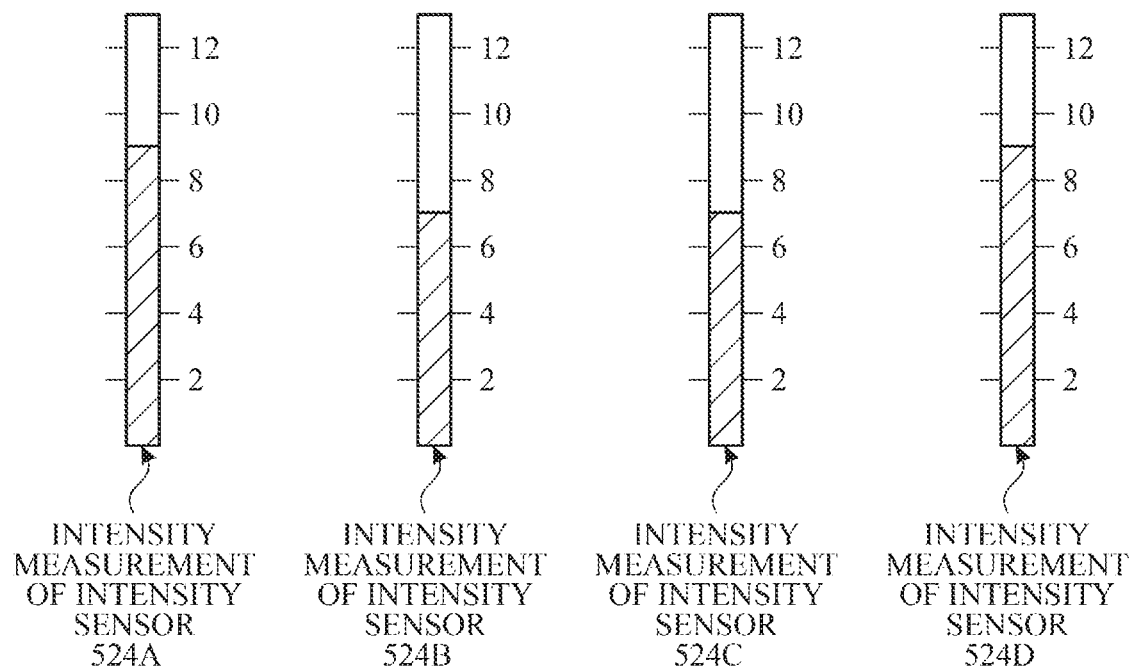
Figure 5D:
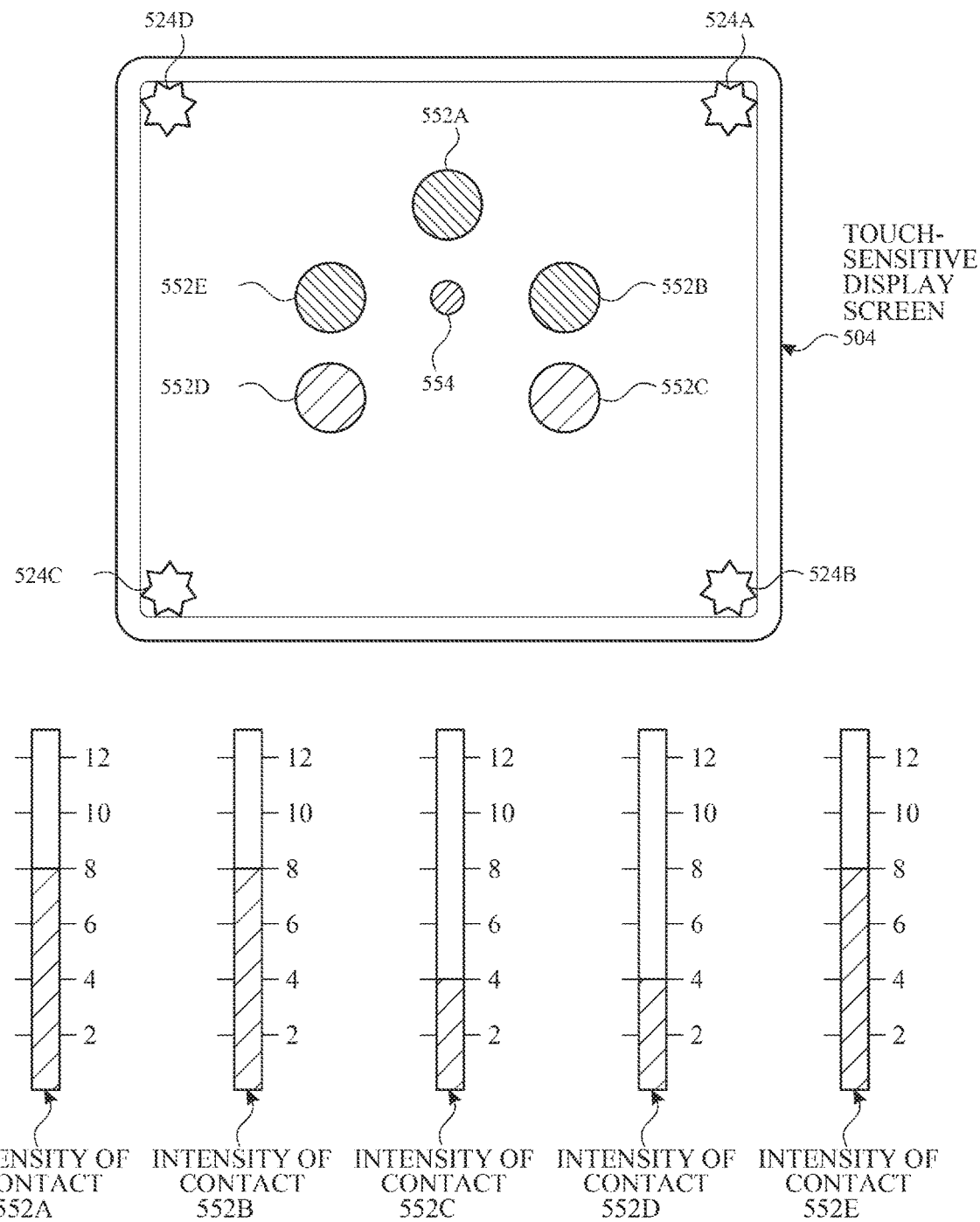

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, $Ij=A \cdot (Dj/\Sigma Di)$, where Dj is the distance of the respective contact j to the center of force, and $\Sigma Di$ is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

Figure 5E:
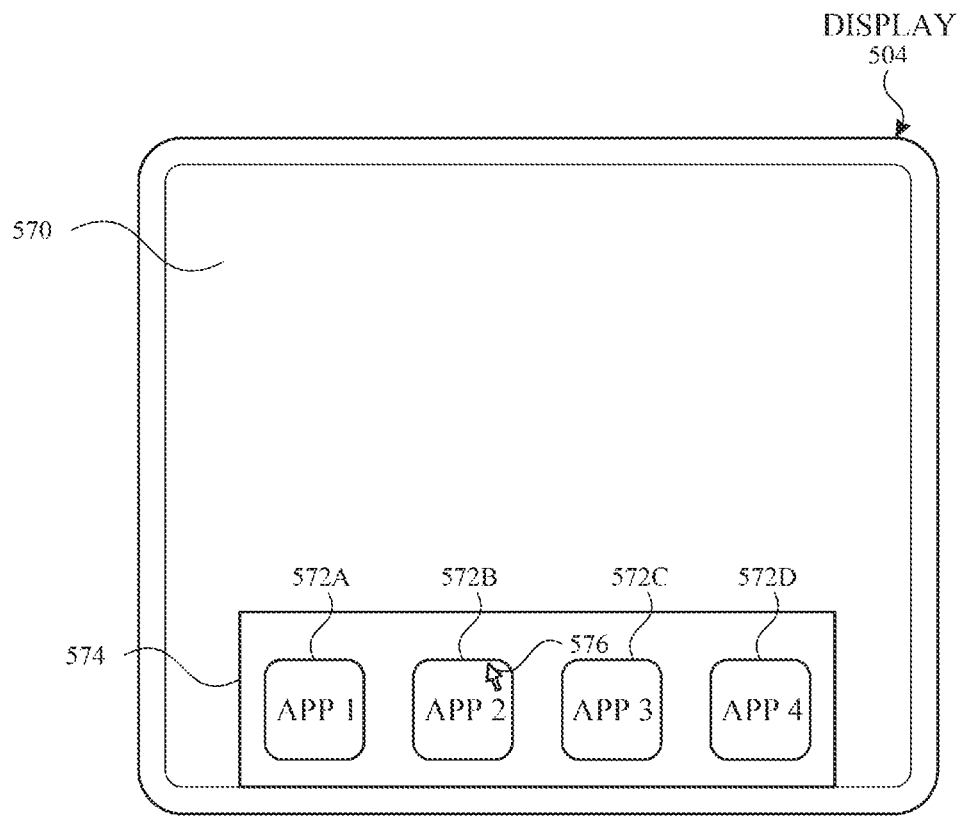
FIGS. 5E-5H illustrate exemplary components and user interfaces of a personal electronic device in accordance with some embodiments.
Figure 5E:
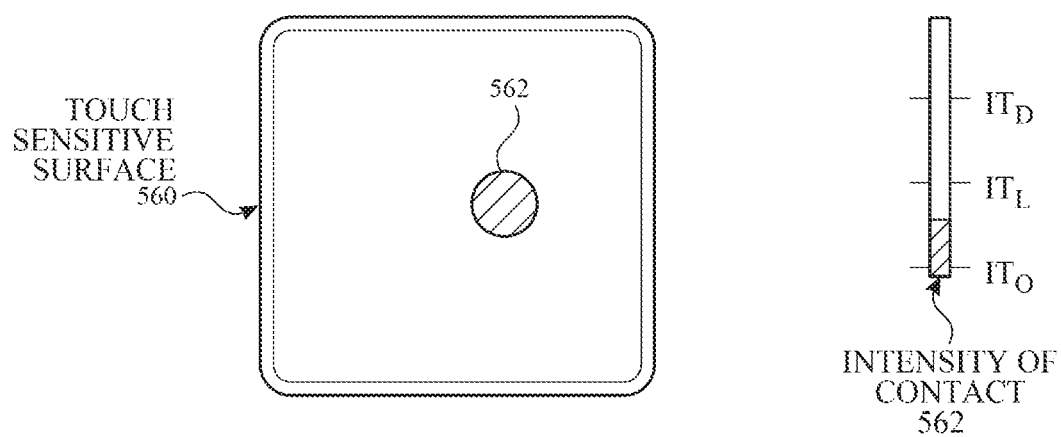
Figure 5F:
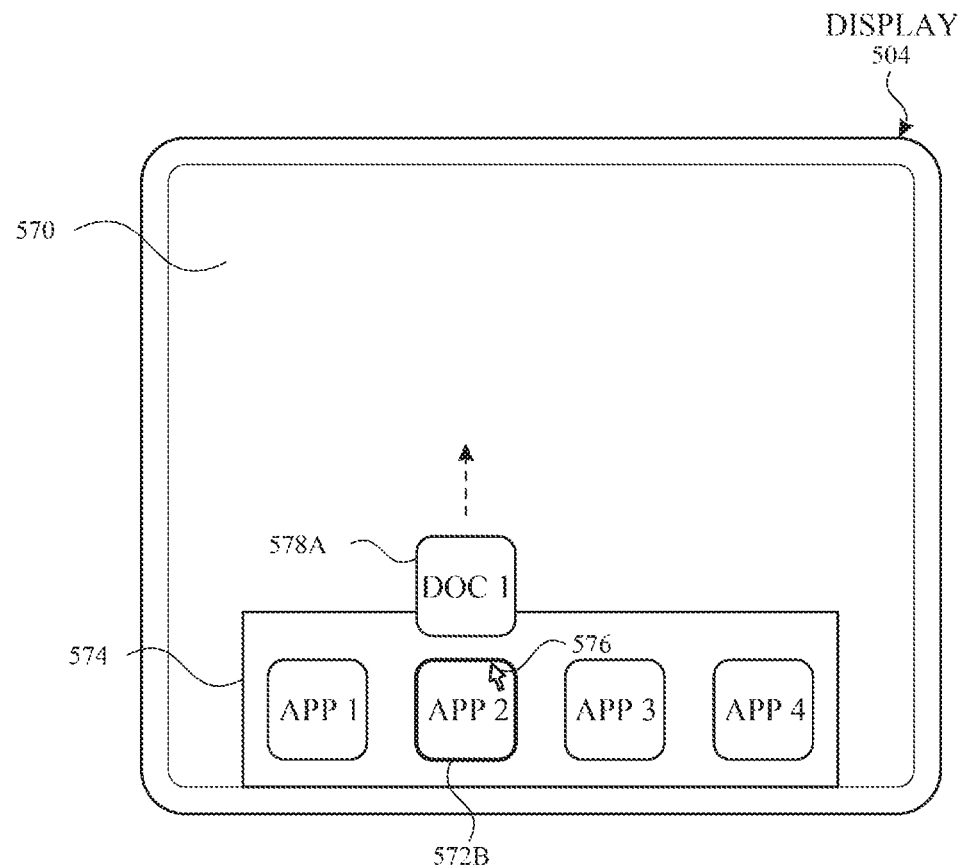
Figure 5F:
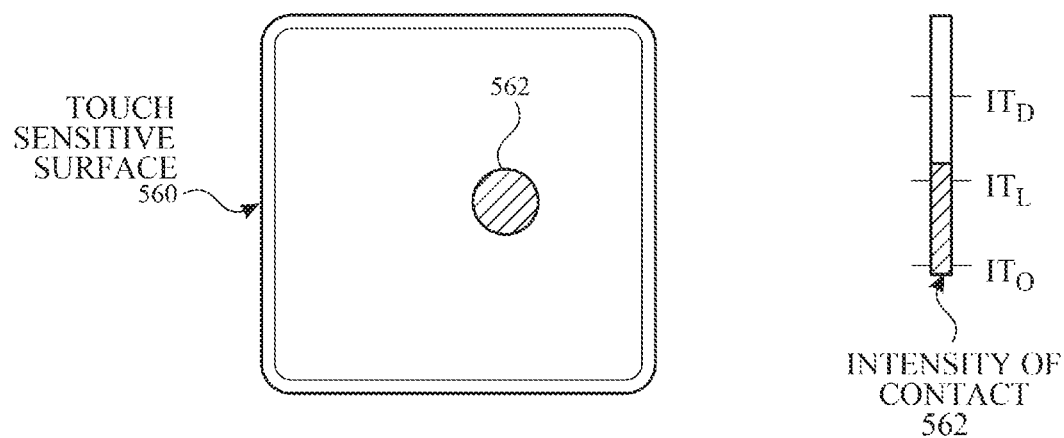
Figure 5G:
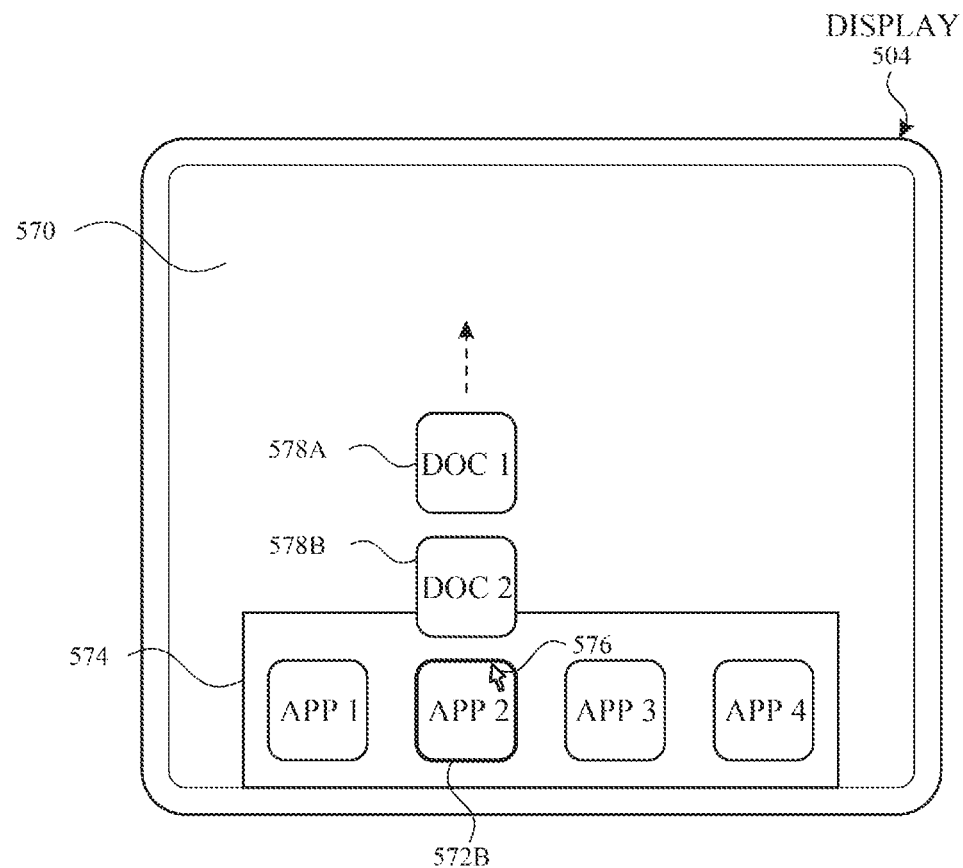
Figure 5G:
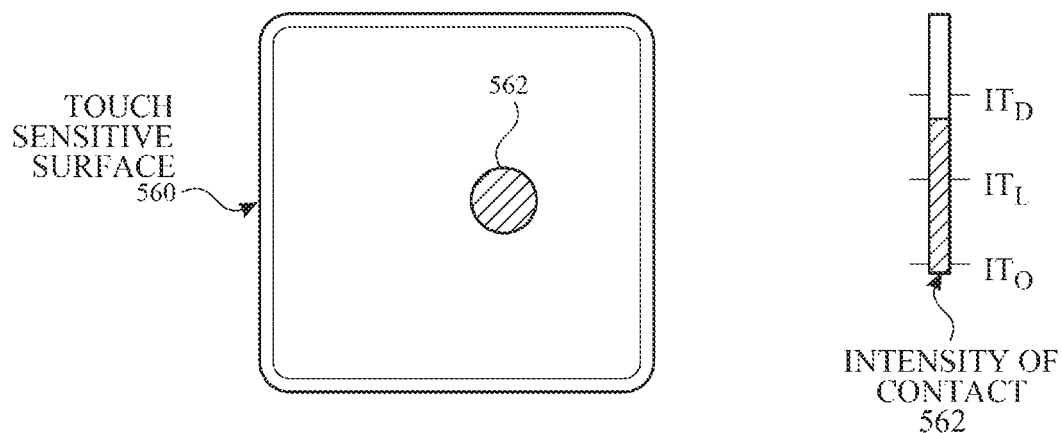
Figure 5H:
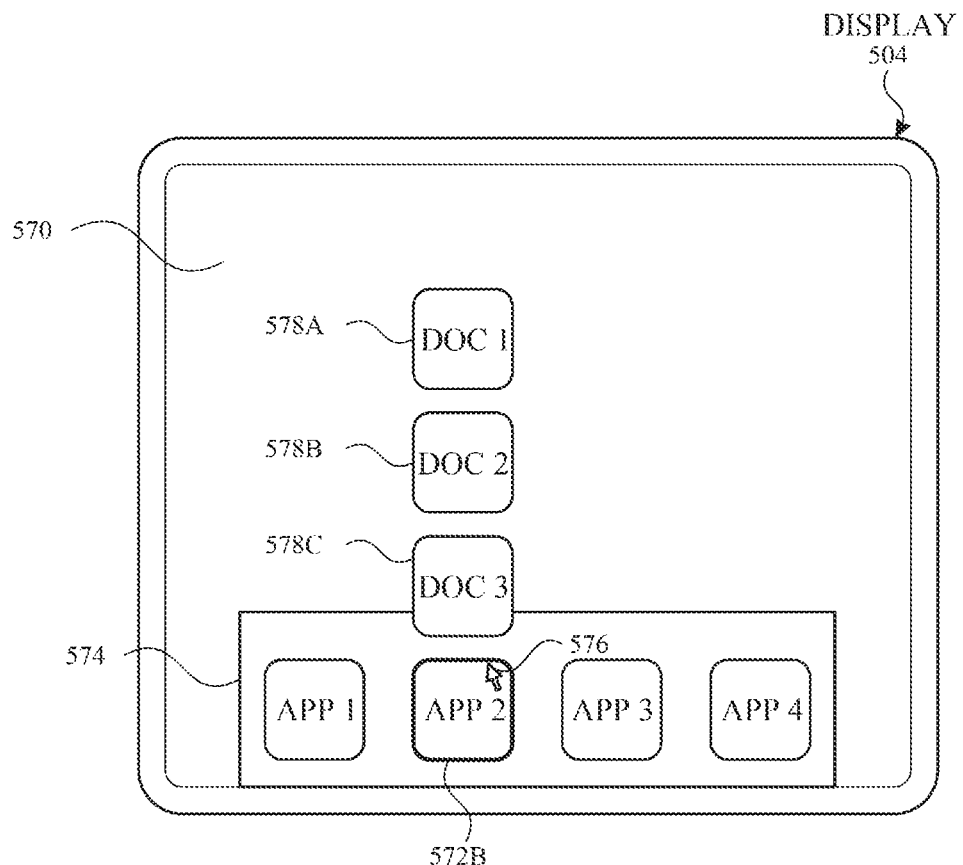
Figure 5H:
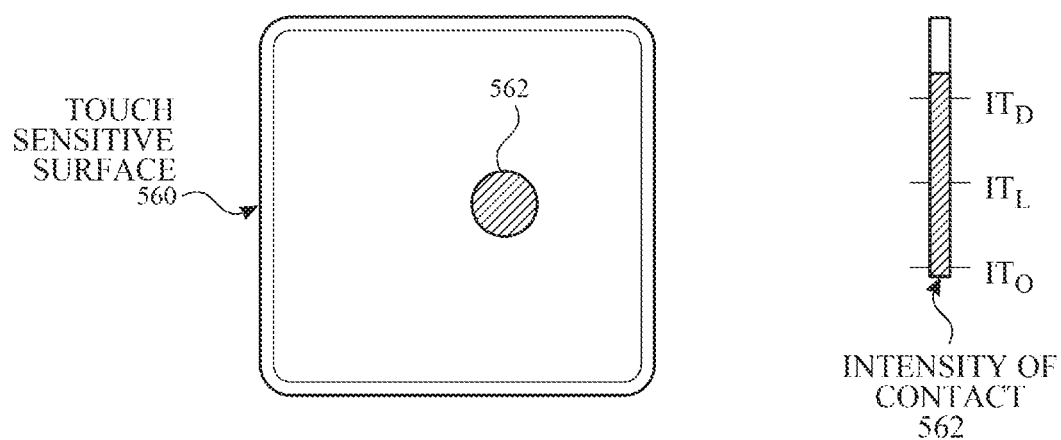

FIGS. 5E-5H illustrate detection of a gesture that includes a press input that corresponds to an increase in intensity of a contact 562 from an intensity below a light press intensity threshold (e.g., "IT$_L$") in FIG. 5E, to an intensity above a deep press intensity threshold (e.g., "IT$_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "IT$_D$"). Contact 562 is maintained on touch-sensitive surface 560. In response to the detection of the gesture, and in accordance with contact 562 having an intensity that goes above the deep press intensity threshold (e.g., "IT$_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "IT$_D$"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

- an active application, which is currently displayed on a display screen of the device that the application is being used on;
- a background application (or background processes), which is not currently displayed, but one or more processes for the application are being processed by one or more processors; and
- a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6Z illustrate exemplary user interfaces related to viewing health data, in accordance with some embodiments. The user interfaces in these figures are used to illustrate the processes described below, including the processes in FIGS. 7A-7B, 8A-8B, 9A-9B, 10A-10B, and 11A-11C.

FIG. 6A depicts first electronic device 600 (e.g., a phone) displaying lock user interface 604 via touch-sensitive display device 602 at a first time (e.g., 9:45). In some examples, first electronic device 600 includes one or more features of devices 100, 300, or 500.

In some examples, lock user interface 604 relates to a user interface displayed when first electronic device transitions out of an inactive mode. As depicted in FIG. 6A, lock user interface 604 includes multiple notifications (e.g., notification 604a and notification 604b) issued (e.g., caused to be displayed by first electronic device 600) by processes executing on first electronic device 600.

In some examples, notification 604a was issued by an activity process corresponding to an activity application (as indicated by icon 604aa). In some examples, user interface elements corresponding to the activity application will include icon 604aa (or some variant of icon 604aa, such as a smaller or larger version of icon 604aa). As depicted in FIG. 6A, notification 604a includes (1) a time that notification 604a was issued (e.g., time 604ad, which indicates "NOW," referring to 9:45) and (2) a description regarding why notification 604a was issued (e.g., 604ac).

In some examples, notification 604b was issued by a clinical health record (CHR) process corresponding to a CHR application (as indicated by icon 604ba). In some examples, user interface elements corresponding to the CHR application will include icon 604ba (or some variant of icon 604ba, such as a smaller or larger version of icon 604ba). As depicted in FIG. 6A, notification 604b includes (1) a time that notification 604b was issued (e.g., time 604bd, which indicates "8:00 AM") and (2) a description regarding why notification 604b was issued (e.g., 604bc).

FIG. 6B depicts second electronic device 606 (e.g., a watch) displaying notification 610 via touch-sensitive display device 608 at a second time (e.g., 10:24) after the first time. In some examples, second electronic device 606 includes one or more features of devices 100, 300, 500, or 600.

In some examples, notification 610 was issued (e.g., caused to be displayed by second electronic device 606) by a hearing process corresponding to a hearing application (as indicated by icon 610a) executing on second electronic device 606. In some examples, user interface elements corresponding to the hearing application will include icon 610a (or some variant of icon 610a, such as a smaller or larger version of icon 610a). As depicted in FIG. 6B, notification 610 includes a description regarding why notification 610 was issued (e.g., 610b).

Figure 6C:
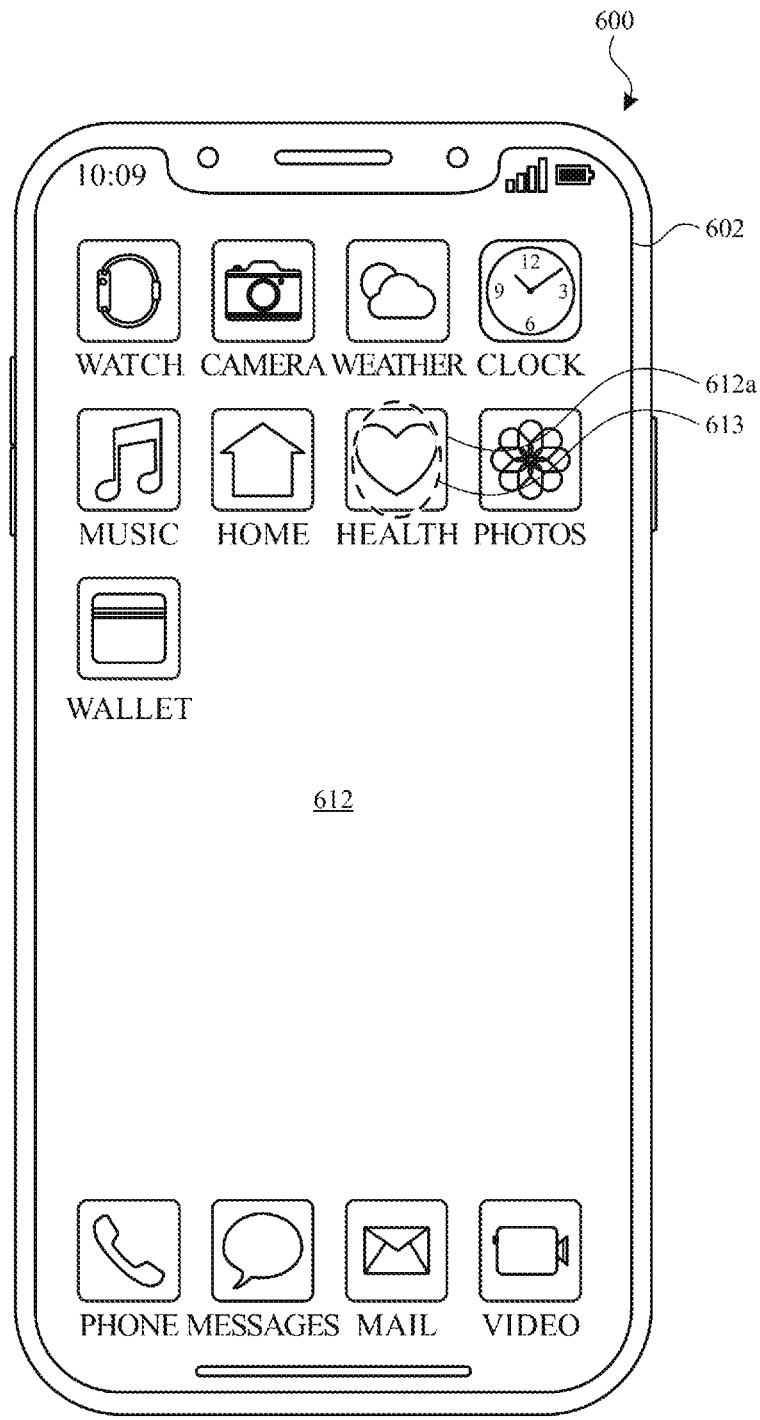

FIG. 6C depicts first electronic device 600 displaying home user interface 612 via touch-sensitive display device 602 at a third time after the second time. Home user interface 612 includes multiple icons, each icon corresponding to a different application. For example, home user interface 612 includes health icon 612a to initiate a health application and/or display a user interface of the health application.

FIG. 6C depicts first electronic device 600 receiving user input 613 corresponding to health icon 612a. In some examples, user input 613 is received via touch-sensitive display device 602 and corresponds to selection of health icon 612a (e.g., a tap gesture on health icon 612a). In other examples, other forms of an input can be used, such as a click via a mouse. In some examples, user input 613 causes a different user interface to be displayed via touch-sensitive display device 602, such as display of a user interface of the health application, as depicted in FIG. 6DA.

Figure 6D:
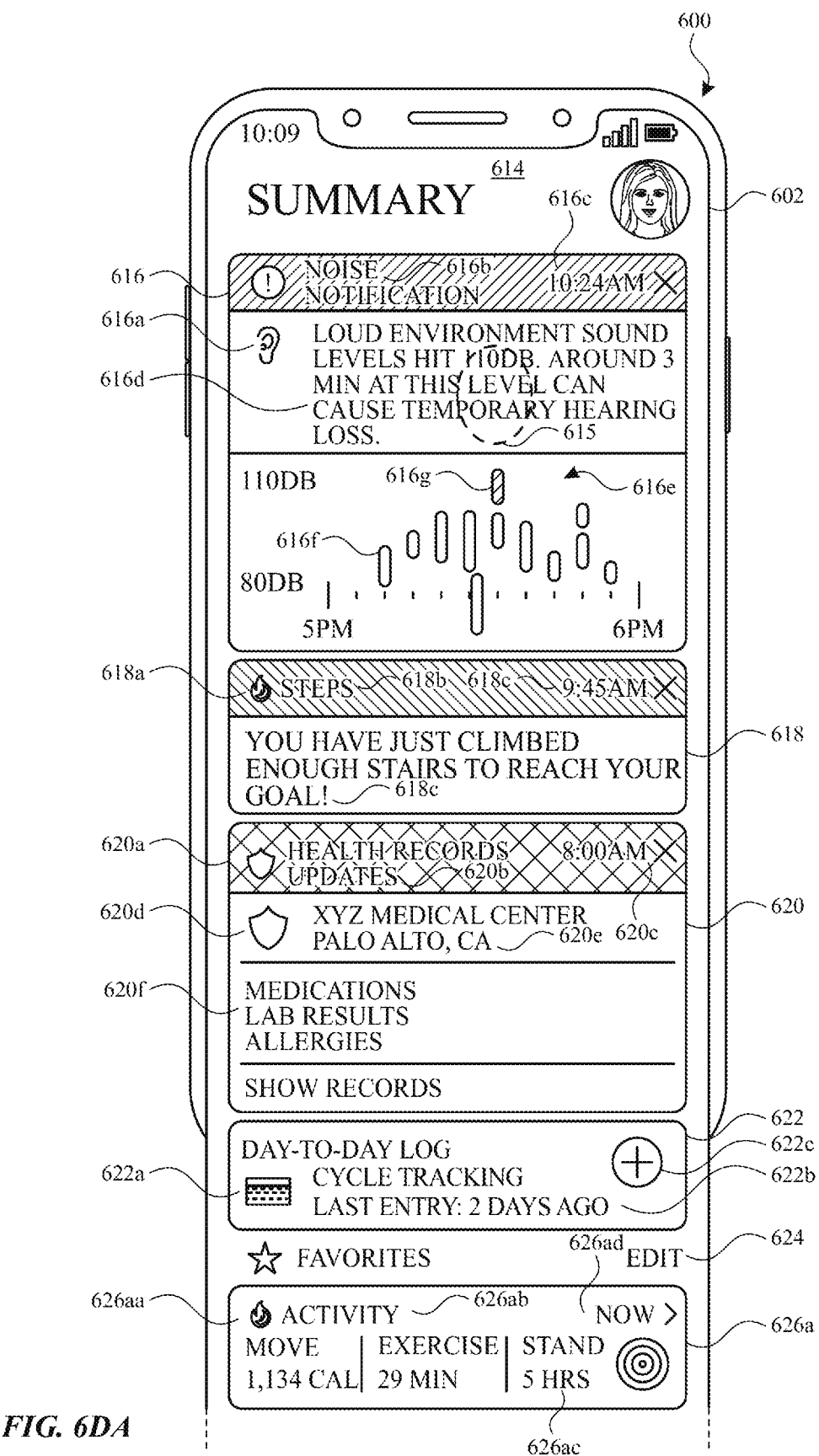
Figure 6D:
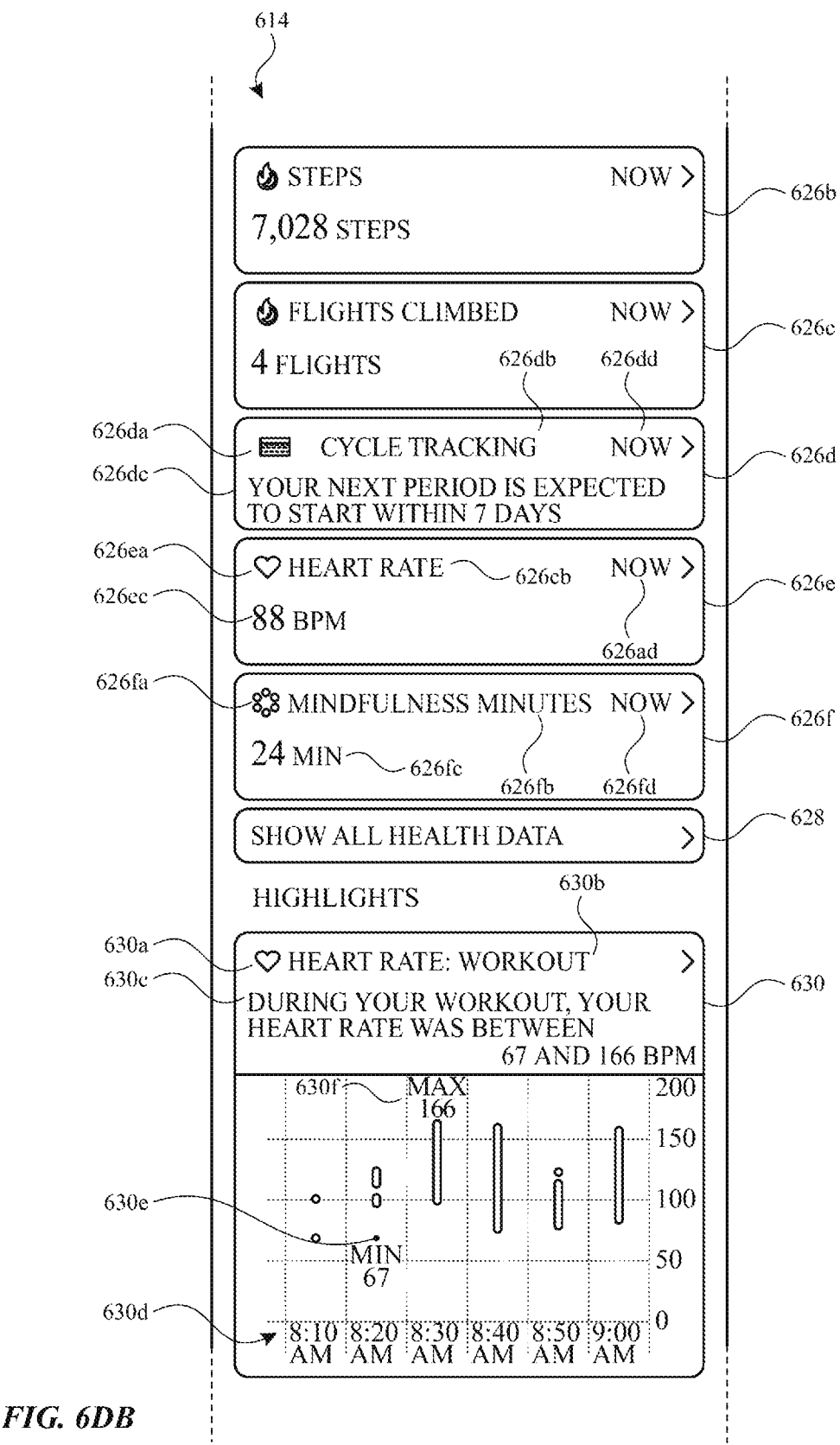
Figure 6D:
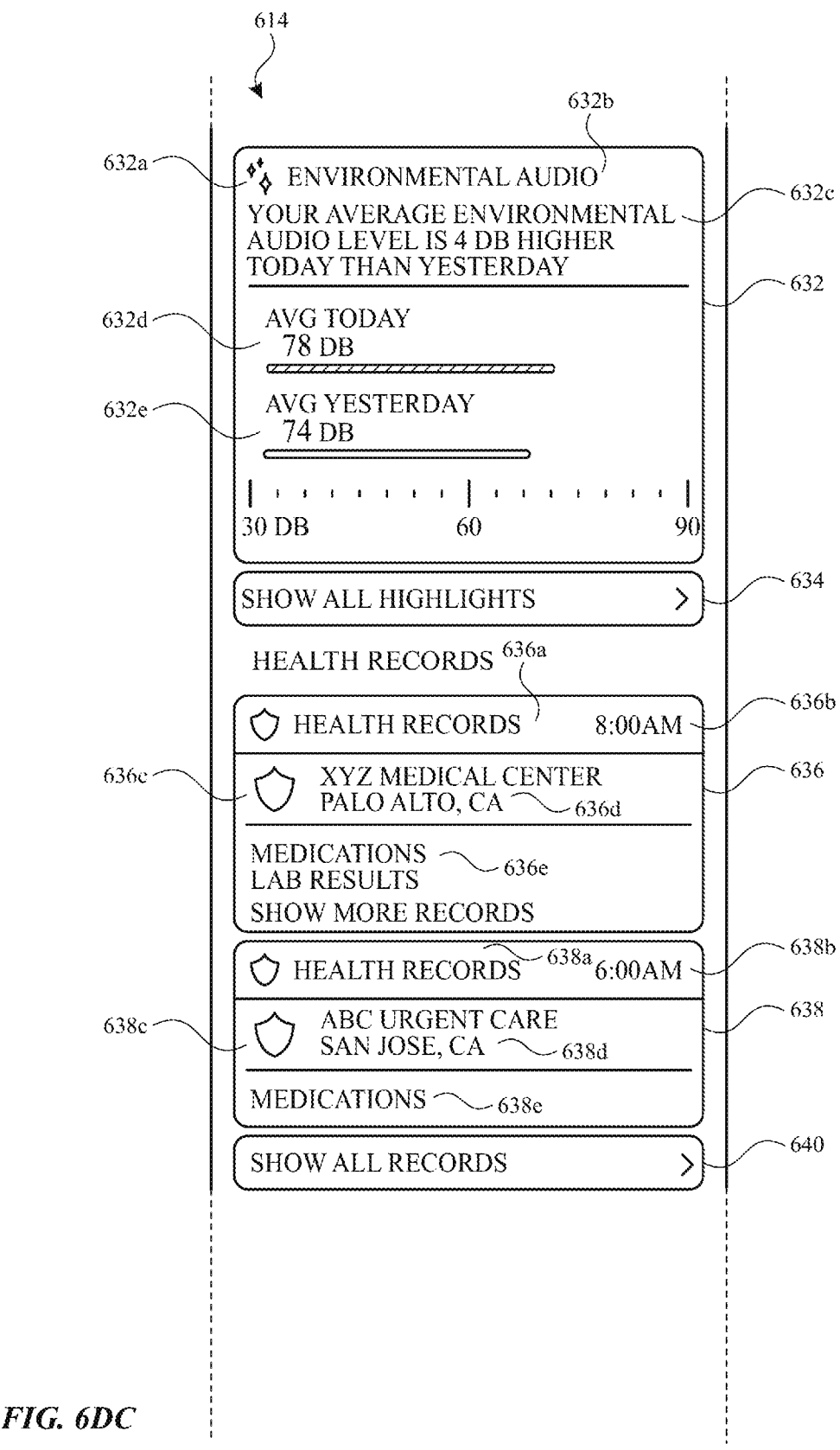
Figure 6D:
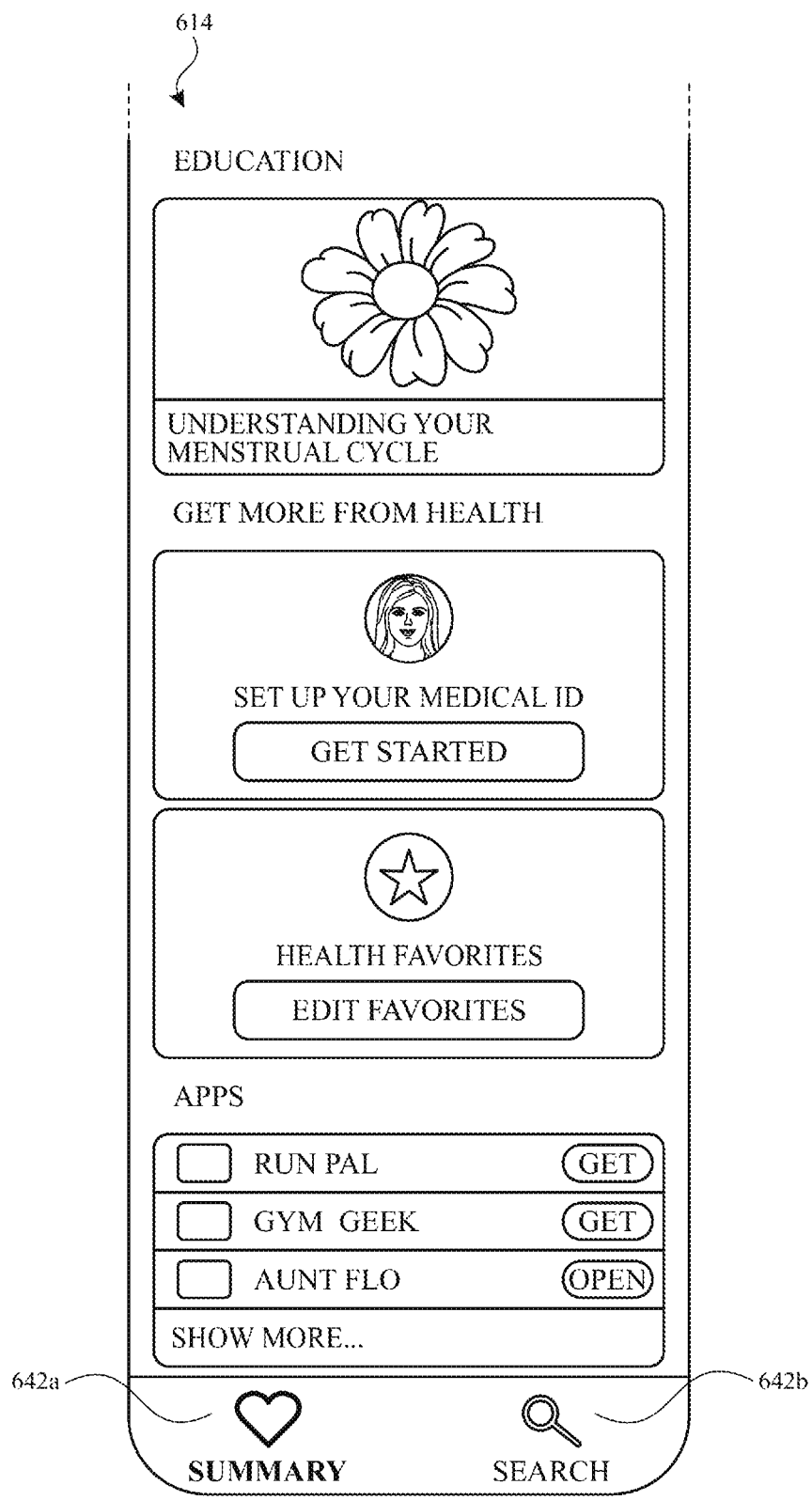

FIGS. 6DA-6DE depict first electronic device 600 displaying summary user interface 614 via touch-sensitive display device 602 at a fourth time after the third time. In some examples, summary user interface 614 is a user interface of the health application. As depicted in FIGS. 6DA-6DE, summary user interface 614 includes multiple regions that include different affordances, the regions including a notification region (e.g., the notification region including first notification affordance 616, second notification affordance 618, and third notification affordance 620), a logging region (e.g., the logging region including logging affordance 622), a favorites region (e.g., the favorites region including first favorite affordance 626a, second favorite affordance 626b, third favorite affordance 626c, fourth favorite affordance 626d, fifth favorite affordance 626e, sixth favorite affordance 626f, and show all health data affordance 628), a highlights region (e.g., the highlights region including first highlight affordance 630, second highlight affordance 632, and show all highlights affordance 634), a health records region (e.g., the health records region including first health records affordance 636, second health records affordance 638, and show all records affordance 640), an education region, a get more from health region, and an apps region.

In some examples, the notification region includes affordances for health-related notifications that have been issued/displayed by a device associated with an account logged into the health application. For example, the health-related notifications can be from first electronic device 600 (e.g., notification 604a and notification 604b, as depicted in FIG. 6A) or another electronic device (e.g., second electronic device 606) linked (e.g., both logged into a single account or paired, such as is performed with a smart phone and a corresponding smart watch) to either first electronic device 600 or the account (e.g., notification 610, as depicted in FIG. 6B). In such examples, the notification region is a location to display information associated with health-related notifications in one location that can be viewed after the health-related notifications are initially displayed.

As discussed above, the notification region includes first notification affordance 616, second notification affordance 618, and third notification affordance 620. In some examples, first notification affordance 616 corresponds to (e.g., includes information from) notification 610. In some examples, second notification affordance 618 corresponds to (e.g., includes information from) notification 604a. In some examples, third notification affordance 620 corresponds to (e.g., includes information from) notification 604b. As depicted in FIG. 6DA, notification affordances in the notification region are ordered by date that a corresponding notification was initially issued (e.g., a most recent notification is first, a next most recent notification is next, and so on).

In some examples, notification affordances are removed from the notification region after a particular amount of time has passed. In some examples, the particular amount of time varies based on an amount of user interaction associated with a respective notification affordance or the data related to the affordance. For example, a first notification affordance is removed quicker than a second notification affordance when the first notification affordance (or a notification corresponding to the first notification affordance) is interacted with by a user and the second notification affordance is not interacted with by a user. For another example, a first notification affordance is removed quicker than a second notification affordance when the first notification affordance (or a notification corresponding to the first notification affordance) is displayed for a longer amount of time than the second notification affordance (or a notification corresponding to the second notification affordance). For another example, a first notification affordance is removed quicker than a second notification affordance when the first notification affordance (or a notification corresponding to the first notification affordance) is associated with a type of health data that is viewed (or interacted with) by a user more often than a type of health data that is associated with the second notification affordance (or a notification corresponding to the second notification affordance). For another example, a first notification affordance is removed quicker than a second notification affordance when the first notification affordance (or a notification corresponding to the first notification affordance) has more information (e.g., more detailed information) or more important information (e.g., as defined by the health application) than the second notification affordance (or a notification corresponding to the second notification affordance). For another example, a first notification affordance is removed quicker than a second notification affordance when the data corresponding to the first notification affordance is viewed on another device (e.g., device 608) (e.g., even if the first notification affordance is not interacted with on device 600). Such removal criteria is discussed further with respect to FIG. 6F-6H.

First notification affordance 616 includes icon 616a, indicating that a notification (e.g., notification 610) corresponding to first notification affordance 616 was issued by an application (e.g., the hearing application) represented by icon 616a. First notification affordance 616 includes a header that is visually distinct from the rest of first notification affordance 616, the header including title 616b (indicating what first notification affordance 616 relates to) and time 616c (indicating a time that a notification corresponding to first notification affordance 616 was initially issued). In one example, the header is visually distinct from the rest of first notification affordance 616 by being a particular pattern or color that corresponds to the hearing application. In some examples, user interface elements related to the hearing application will include an element that is the particular pattern or color. As depicted in FIG. 6DA, first notification affordance 616 includes content 616d, which (in some examples) is at least a portion of content included in the notification corresponding to first notification affordance 616.

Second notification affordance 618 includes icon 618a, indicating that a notification (e.g., notification 604a) corresponding to second notification affordance 618 was issued by an application (e.g., the activity application) represented by icon 618a. Second notification affordance 618 includes a header that is visually distinct from the rest of second notification affordance 618 (and visually distinct from the headers of first notification affordance 616 and third notification affordance 620), the header including title 618b (indicating what second notification affordance 618 relates to) and time 618c (indicating a time that a notification corresponding to second notification affordance 618 was initially issued). In one example, the header is visually distinct from other elements by being a particular pattern or color that corresponds to the activity application. In some examples, user interface elements related to the activity application will include an element that is the particular pattern or color. As depicted in FIG. 6DA, second notification affordance 618 includes content 618d, which (in some examples) is at least a portion of content included in the notification corresponding to second notification affordance 618.

Third notification affordance 620 includes icon 620a, indicating that a notification (e.g., notification 604b) corresponding to third notification affordance 620 was issued by an application (e.g., the CHR application) represented by icon 620a. Third notification affordance 620 includes a header that is visually distinct from the rest of third notification affordance 620 (and visually distinct from the headers of first notification affordance 616 and second notification affordance 618), the header including title 620b (indicating what third notification affordance 620 relates to) and time 620c (indicating a time that a notification corresponding to third notification affordance 620 was initially issued). In one example, the header is visually distinct from other elements by being a particular pattern or color that corresponds to the CHR application. In some examples, user interface elements related to the CHR application will include an element that is the particular pattern or color. As depicted in FIG. 6DA, third notification affordance 620 includes icon 620d and content 620e, which (in some examples) is at least a portion of content included in the notification corresponding to third notification affordance 620. In some examples, icon 620d corresponds to a clinical institution that generated a notification associated with third notification affordance 620. In such examples, icon 620d is different from icon 620a.

Figure 6E:
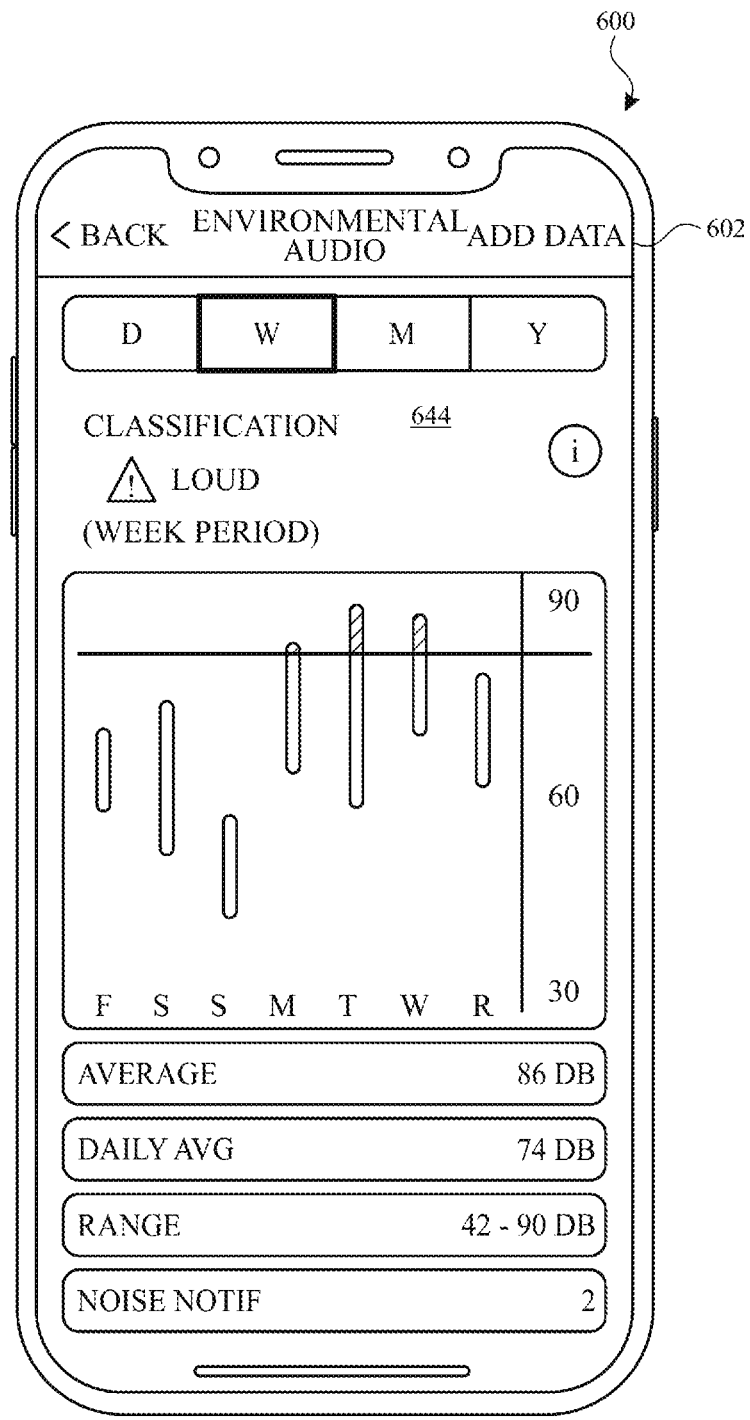
Figure 6F:
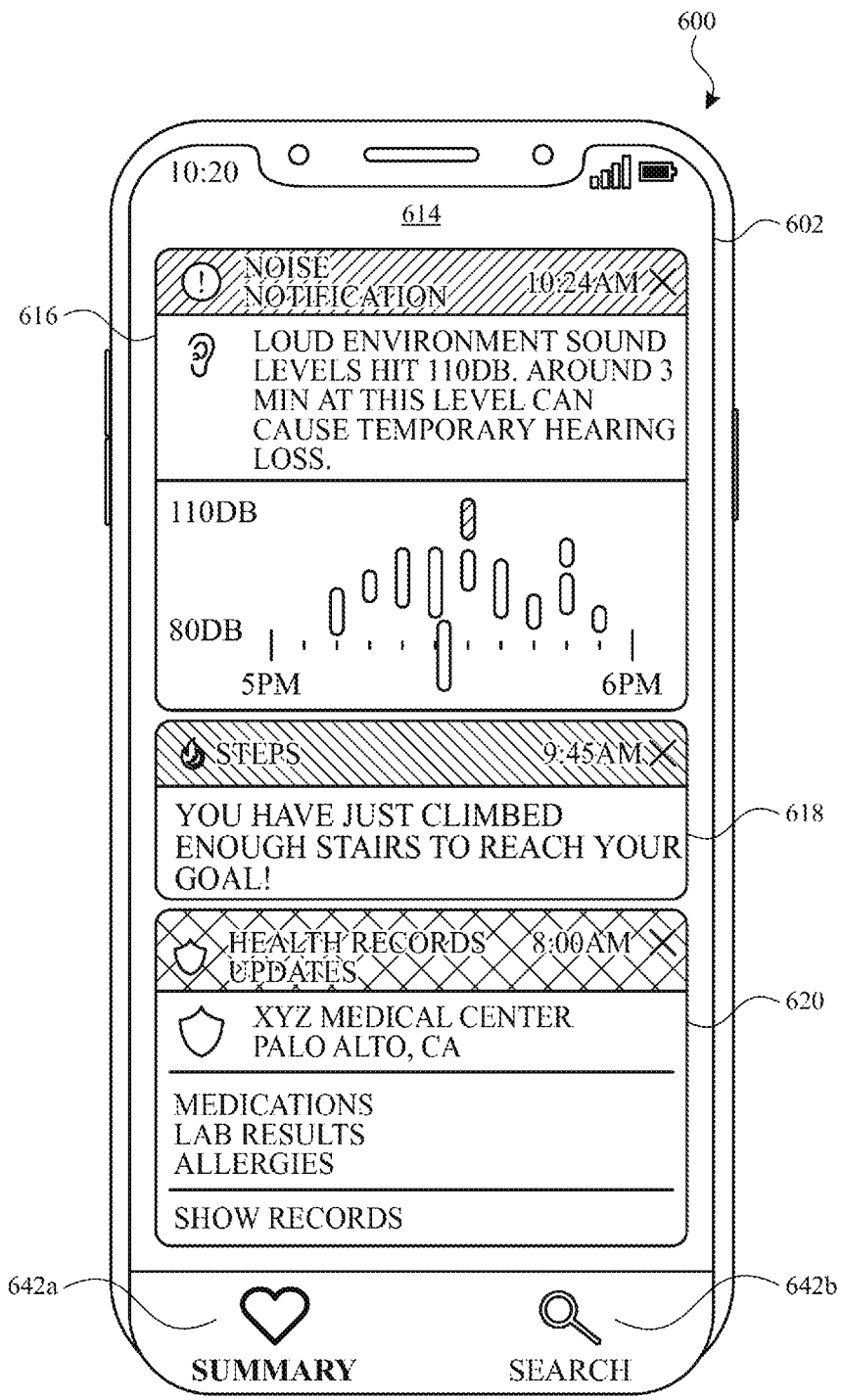
Figure 6G:
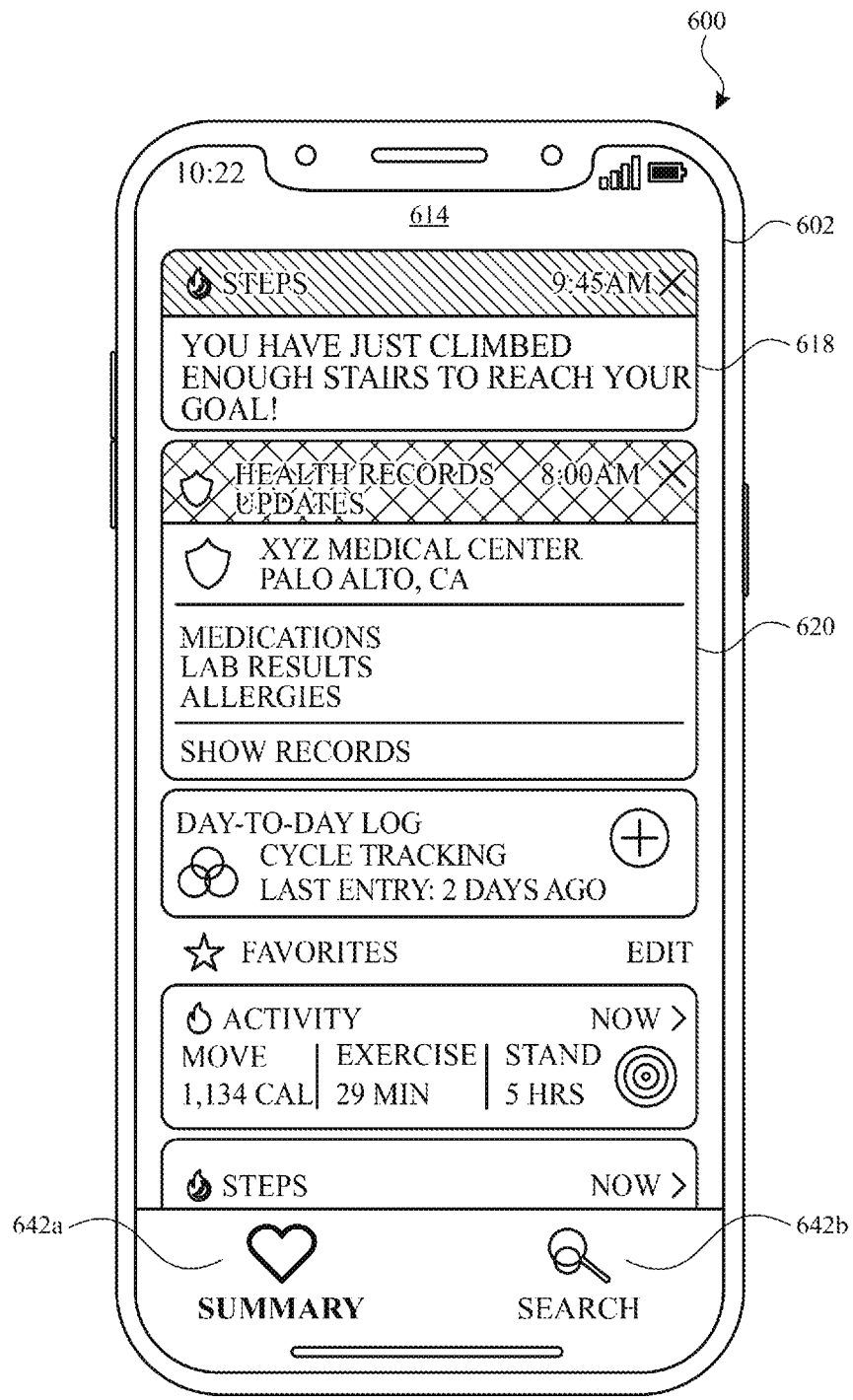
Figure 6H:
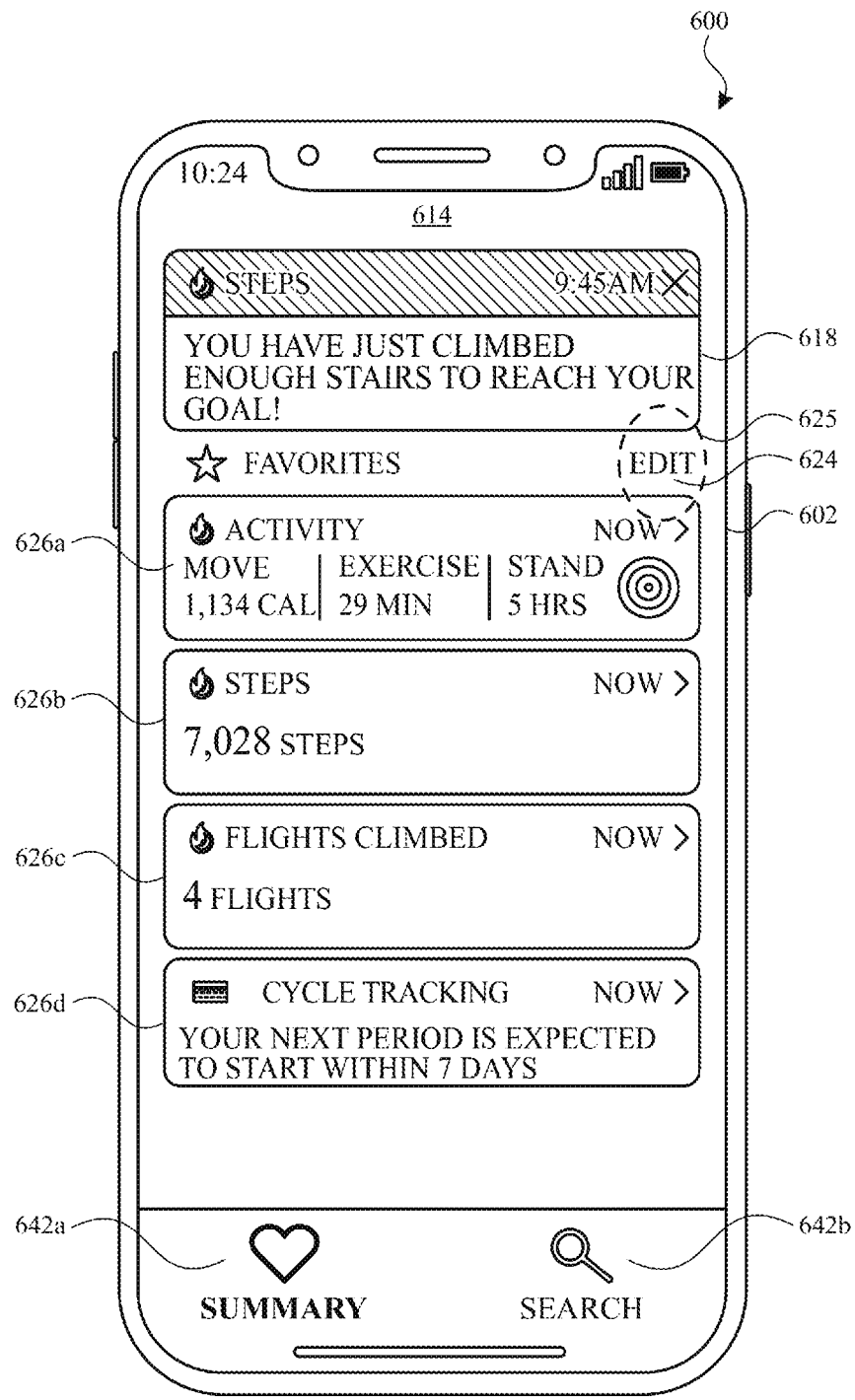

In some examples, selection of a notification affordance causes a user interface of the health application to be displayed, the user interface associated with a corresponding application. For example, selection of first notification affordance 616 causes a user interface of the health application to be displayed, the user interface including information from the hearing application (sometimes referred to as a hearing data room, as depicted in FIG. 6E and further discussed below).

In some examples, the logging region includes affordances for logging data. For example, logging affordance 622 relates to logging a cycle. Logging affordance 622 includes icon 622a, representative of a logging application corresponding to logging affordance 622 (e.g., a cycle tracking application). Logging affordance 622 also includes content 622b, describing logging affordance 622 and indicating a last time that a user has logged information associated with the logging application. Logging affordance 622 also includes graphic 622c, indicating whether logging criteria are met (e.g.: when logging criteria are not met, graphic 622c is a plus sign, indicating that a user has not logged a minimum number of times; when logging criteria are met, graphic 622c is a check mark, indicating that a user has logged a minimum number of times). In some examples, logging affordance 622 when selected, causes a user interface to be displayed that allows a user to log a cycle. In other examples, the act of selecting logging affordance 622 causes a cycle to be logged.

In some examples, a color or pattern associated with a portion of logging affordance 622 (e.g., a font color of the words "CYCLE TRACKING") are a particular color or pattern corresponding to the logging application. The particular color or pattern, in some examples, is used on at least a portion of user elements displayed in the health application that correspond to the logging application. In some examples, the particular color or pattern is visually distinct from colors/patterns used for other applications (e.g., the activity application, the hearing application, the CHR application, or other logging applications).

Figure 6I:
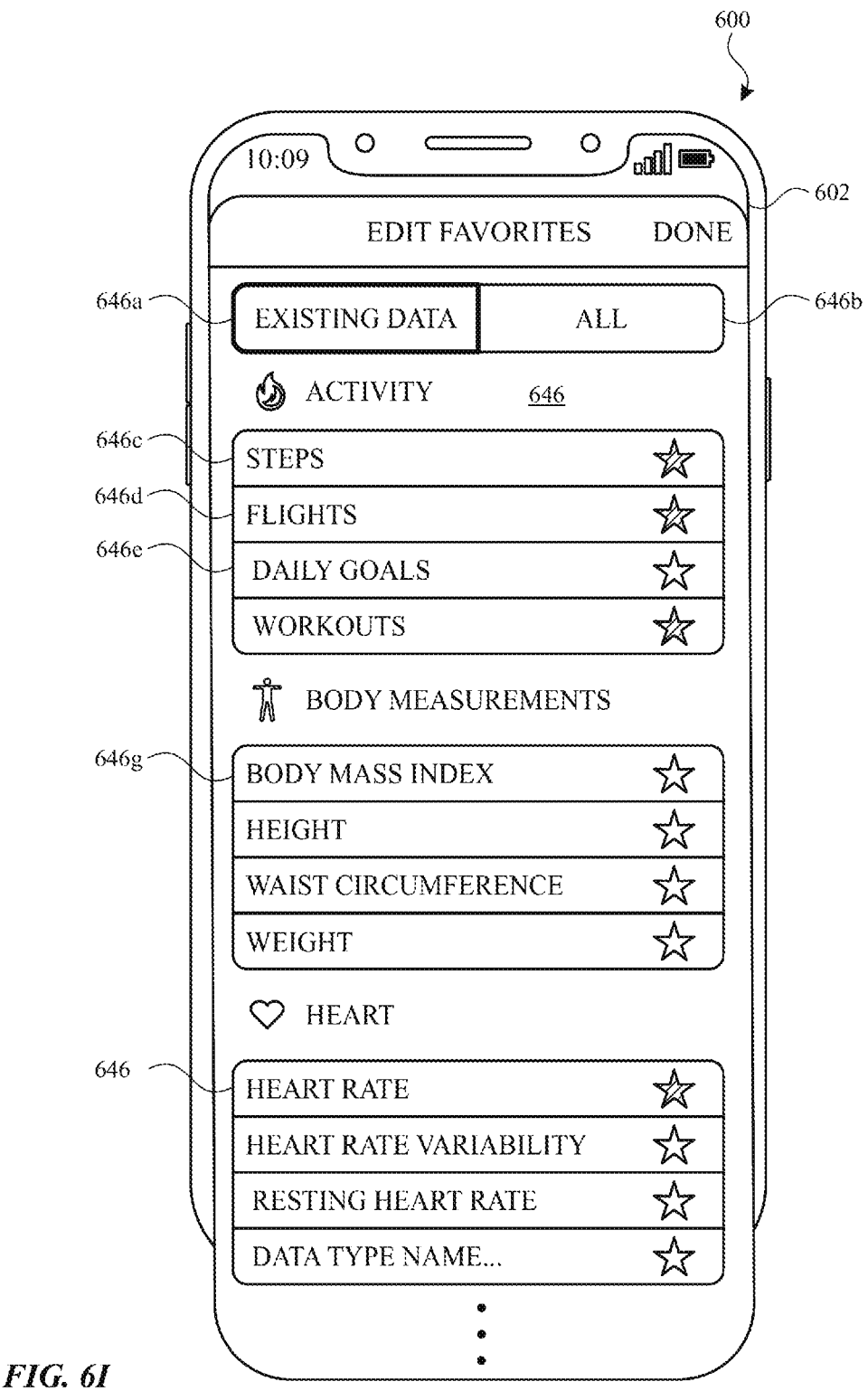

In some examples, the favorites region includes affordances for health-related data that a user has indicated as one of their favorites (as depicted in FIG. 6I and discussed below). In some examples, prior to the user indicating a favorite, the favorites region includes one or more predefined affordances corresponding to health-related data that a system has determined that the user would favorite (e.g., based on a device owned by the user, interactions of the user, the like, default favorites, or any combination thereof).

As discussed above, the favorites region includes first favorite affordance 626a, second favorite affordance 626b, third favorite affordance 626c, fourth favorite affordance 626d, fifth favorite affordance 626e, sixth favorite affordance 626f, and show all health data affordance 628. First favorite affordance 626a, second favorite affordance 626b, and third favorite affordance 626c correspond to health data from an activity application, as indicated by, for example, icon 626aa.

In some examples, at least a portion of each favorite affordance is visually distinct to represent a corresponding application (e.g., a font color of title 626ab, in some examples, corresponds to the activity application). In some examples, the element that makes each favorite affordance visually distinct is consistent across different user interface elements (e.g., if a color is the element that is visually distinct, other user interface elements corresponding to the activity application will include the same color (e.g., the header in second notification affordance 618, in some examples, is the same color as the font of "ACTIVITY" in first favorite affordance 626a).

As depicted in FIG. 6DA, first favorite affordance 626a includes a time stamp for the last time health data 626ac (e.g., move, exercise, and stand metrics) was updated.

As depicted in FIG. 6DB, fourth favorite affordance 626d includes icon 626da, which is a smaller version of icon 622a depicted in FIG. 6DA. Such correspondence illustrates that different user interface elements related to the same application, in some examples, include the same icon to represent the application. Icon 626ea and icon 626fa are further examples of icons corresponding to different applications. In addition, title 626db, in some examples, is colored similarly to "CYCLE TRACKING" in content 622b, to further indicate that both relate to the same application.

Figure 12A:
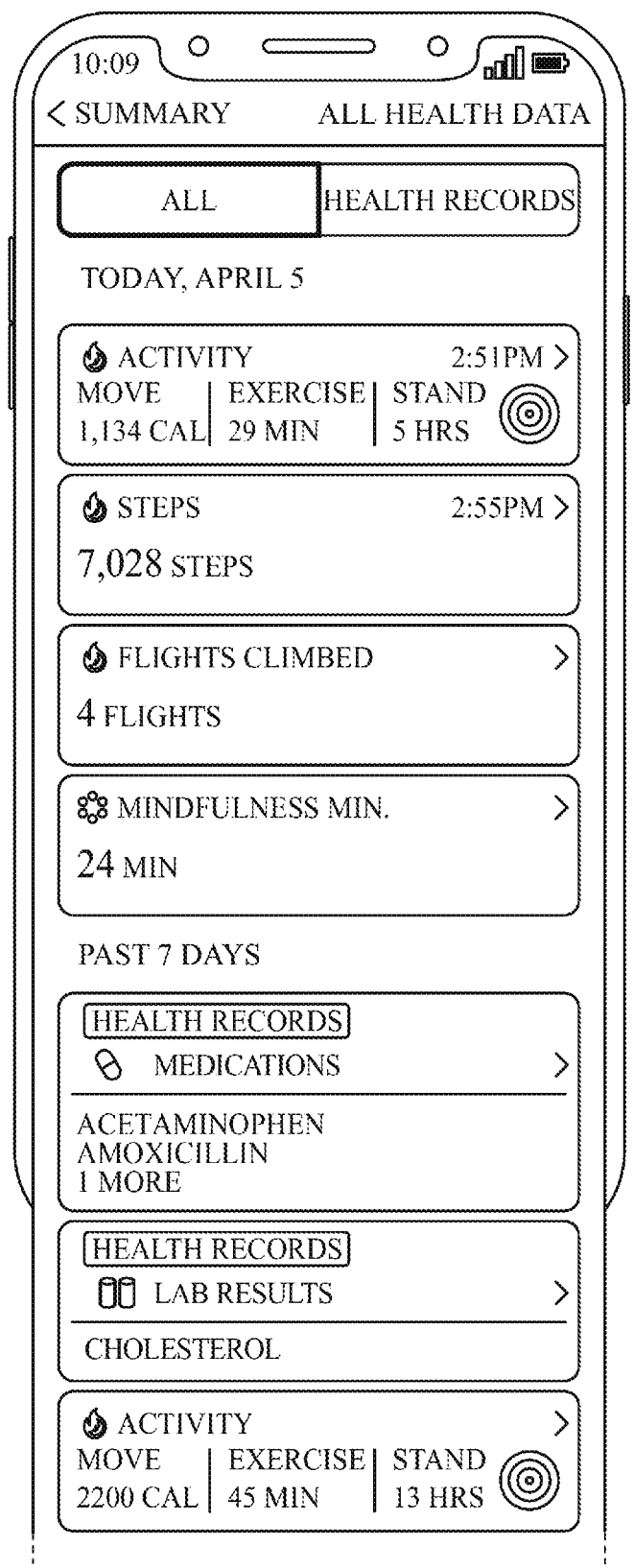
FIGS. 12A-12I illustrate exemplary user interfaces related to viewing health data using an electronic device, in accordance with some embodiments.
Figure 12A:
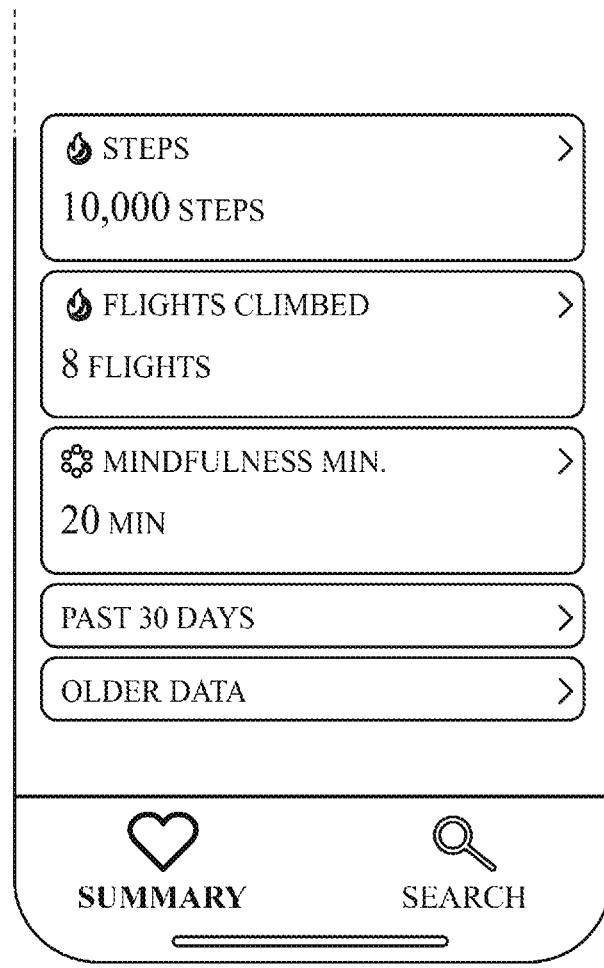

In some examples, show all health data affordance 628 causes a user interface to be displayed that includes representations of all health data corresponding to the account associated with the health application. An example of such a user interface is depicted in FIGS. 12AA-12AB.

In some examples, the highlights region includes graphical representations of health data over periods of time that are identified by the health application. For example, a particular graphical representation is displayed when it meets highlight criteria and is not displayed when it does not meet the highlight criteria. In some examples, the highlight criteria is based on differences between health data in time periods, time a user has spent viewing a particular graphic, interaction by a user with a particular graphic or element of interface 614, or any combination thereof.

FIG. 6DB depicts electronic device displaying first highlight affordance 630 in the highlight region of summary user interface 614 via touch-sensitive display device 602. First highlight affordance 630 includes icon 630a, indicating that first highlight affordance 630 primarily relates to a heart rate application (in some examples, first highlight affordance 630 secondarily relates to a second application (e.g., a workout application) such that first highlight affordance 630 is based on data from the second application). In some examples, a portion of first highlight affordance 630 is visually distinguished to identify that first highlight affordance 630 primarily relates to the heart rate application (e.g., a font color for title 630b, in some examples, is a particular color corresponding to the heart rate application). First highlight affordance 630 also includes description 630c to indicate information illustrated by first highlight affordance 630 (e.g., such as a range of values reached during a workout).

As depicted in FIG. 6DB, first highlight affordance 630 includes graph 630d with representations for heart rate during a workout. Graph 630d includes minimum indication 630e, indicating a minimum value for heart rate during the workout, and maximum indication 630f, indicating a maximum value for heart rate during the workout. Such indications are determined by comparing heart rates at different times during a time period corresponding to the workout to identify a minimum and maximum.

FIG. 6DC depicts electronic device displaying second highlight affordance 632 in the highlight region of summary user interface 614 via touch-sensitive display device 602. Second highlight affordance 632 includes icon 630a, indicating that second highlight affordance 632 relates to an environmental audio application. In some examples, a portion of second highlight affordance 632 is visually distinguished to identify that second highlight affordance 632 relates to the environmental audio application (e.g., a font color for title 632b, in some examples, is a particular color corresponding to the environmental audio application). Second highlight affordance 632 also includes description 632c to indicate information illustrated by second highlight affordance 632 (e.g., such as how the average environmental audio level for today is 4 dB higher than the average for yesterday).

As depicted in FIG. 6DC, second highlight affordance 632 includes a graph with an average representation for today (e.g., 632d) and an average representation for yesterday (e.g., 632e). As depicted in FIG. 6DC, each of the an average representation for today and the average representation for yesterday includes a graphical representation of the average and a textual representation of the average. In some examples, the graph represents an amount of a single health data metric compared between time periods of the same length.

As discussed above, the highlights region also includes show all highlights affordance 634. In some examples, selection of show all highlights affordance 634 causes a user interface corresponding to the health application to be displayed, such as show all highlights user interface as depicted in FIGS. 6MA-6MD.

In some examples, the health records region includes affordances (e.g., first health records affordance 636 and second health records affordance 638) corresponding to each clinical institution that has sent health record data regarding the account associated with the health application. For example, first health records affordance 636 indicates that it corresponds to XYZ Medical Center in Palo Alto, Calif. (see 636d). For another example, second health records affordance 638 indicates that it corresponds to ABC Urgent Care in San Jose, Calif. (see 638d).

In some examples, each affordance in the health records region includes a title indicating that the affordance corresponds to health records (e.g., title 636a and title 638a). As depicted in FIG. 6DC, each affordance in the health records region also includes an indication of when a most recent health record from the corresponding clinical institution was received (e.g., first health records affordance 636 includes time indication 636b of 8:00 AM and second health records affordance 638 includes time indication 638b of 6:00 AM). In some examples, the affordances in the health records region are ordered based on when a most recent health record from the corresponding clinical institution was received (e.g., first health records affordance 636 is above second health records affordance 638 based on a most recent health record corresponding to first health records affordance 636 being received after a most recent health record corresponding to second health records affordance 638). In other examples, the affordances in the health records region are ordered based on when health records updates were initially issued/generated for the account (e.g., first health records affordance 636 is above second health records affordance 638 based on a first health record corresponding to first health records affordance 636 being generated before a second health record corresponding to second health records affordance 638). In other examples, the affordances in the health records region are ordered based on a user-defined ordering, such as designating primary and secondary institutions (e.g., where primary institutions are above secondary institutions). In some examples, only primary institutions are represented in the health records region, where secondary institutions can be navigated to using show all health records affordance 640. In some examples, selection of show all health records affordance 640 causes a user interface of the health application to be displayed, the user interface including all health records received for the account associated with the health application (as depicted in FIGS. 6OA-6OB).

In some examples, each affordance in the health records region includes an indication of which records have been received from the corresponding institution. For example, first health records affordance 636 includes indication 636e, which indicates that health records corresponding to medications, lab results, and other records have been received from XYZ Medical Center. In some examples, indication 636e is ordered based on when health records were received (e.g., medications is before lab results because a health record with health data corresponding to medications was received more recent than a health record with health data corresponding to lab results was received). For another example, second health records affordance 638 includes indication 638e, which indicates that health records corresponding to medications have been received from ABC Urgent Care.

In some examples, the education region includes affordances that, when selected, cause a user interface to be displayed with educational content. In some examples, the get more from health region includes affordances that, when selected, cause a user interface to be displayed to configure the health application. In some examples, the apps region includes affordances corresponding to different applications that are determined to relate to the account of the health application.

As depicted in FIG. 6DD, summary user interface 614 includes a pair of affordances (e.g., summary affordance 642a and search affordance 642b) at the bottom of summary user interface 614 to indicate which section of the health application that a current user interface relates (e.g., the visually distinct affordance (e.g., bolded) indicates which section). In some examples, selection of a section of the health application that a current user interface does not relate (e.g., search affordance 642b in FIG. 6DD) causes a user interface corresponding to the selected section to be displayed (e.g., if search affordance 642b is selected, a user interface corresponding to the search section is displayed, as depicted in FIG. 6TA-6TB). In some examples, selection of an affordance corresponding to a section that relates to the current user interface causes a home interface of the selected section to be displayed (e.g., summary user interface 614 as depicted in FIG. 6DA for the summary section and search user interface 684 as depicted in FIGS. 6TA-6TB).

FIG. 6DA depicts first electronic device 600 receiving user input 615 corresponding to first notification affordance 616. In some examples, user input 615 is received via touch-sensitive display device 602 and corresponds to a selection gesture (e.g., tap) on first notification affordance 616. In other examples, other forms of selection can be used, such as a click using a mouse. In some examples, user input 615 causes a different user interface to be displayed via touch-sensitive display device 602, such as display of environmental audio data room user interface 644 of the health application as depicted in FIG. 6E.

FIG. 6E depicts first electronic device 600 displaying environmental audio data room user interface 644 via touch-sensitive display device 602 at a fifth time after the fourth time. In some examples, environmental audio data room user interface 644 is a user interface of the health application with information from the environmental audio application. As depicted in FIG. 6E, environmental audio data room user interface 644 includes a graph with data indicating noise levels detected by a device throughout a week. In some examples, the data is stored in a location associated with the environmental audio application and can be viewed within a user interface of the environmental audio application.

Environmental audio data room user interface 644 further includes time scale affordances at the top indicating different time scales (e.g., "D" indicating a day, "W" indicating a week, "M" indicating a month, and "Y" indicating a year). As depicted FIG. 6E, the time scale affordance indicating week is selected, causing the graph to indicate noise levels detected throughout a week. In some examples, selection of a different time scale affordance causes the graph to change to indicate noise levels detected throughout a selected time scale.

As depicted in FIG. 6E, environmental audio data room user interface 644 includes a number of affordances at the bottom textually indicating information depicted by the graph. For example, there is a first affordance indicating the average throughout the week, a second affordance indicating a daily average throughout the week, a third affordance indicating a range throughout the week, and a number of noise notifications that were issued by the environmental audio application throughout the week. In some examples, selection of one of the affordances causes the graph to be modified to highlight data in the graph that corresponds to the selected affordance. For example, selection of the average affordance can cause a line to be inserted in the graph that indicates the average. For another example, selection of the daily average affordance can cause points to be inserted in each bar for each day in the graph to indicate the average for the respective day. For another example, selection of the range affordance can cause a portion of the graph to be highlighted where the minimum and maximum of the range occurred throughout the week. For another example, selection of the noise notification affordance can cause a portion of the graph to be highlighted that caused the noise notifications to be issued.

FIG. 6F depicts first electronic device 600 displaying summary user interface 614 via touch-sensitive display device 602 at a sixth time after the fifth time. In some examples, summary user interface 614 is displayed in response to user input corresponding to selection of the back button at the top left of environmental audio data room user interface 644 (which is depicted in FIG. 6E without the user input).

Summary user interface 614 as depicted in FIG. 6F is scrolled down relative to summary user interface 614 as depicted in FIG. 6DA (e.g., the text "SUMMARY" at the top left and the icon of the account at the top right are no longer displayed). FIG. 6F depicts that first notification affordance 616 is still displayed in summary user interface 614 after first notification affordance 616 was interacted with (e.g., selected, as depicted in FIG. 6DA). FIG. 6F also depicts that second notification affordance 618 and third notification affordance 620 are also still displayed in summary user interface 614.

FIG. 6G depicts first electronic device 600 displaying summary user interface 614 via touch-sensitive display device 602 at a seventh time after the sixth time. In some examples, summary user interface 614 is displayed in response to user input corresponding to re-display of summary user interface 614.

FIG. 6G depicts that first notification affordance 616 is no longer displayed in summary user interface 614, even though second notification affordance 618 and third notification affordance 620 were received before first notification affordance 616. Such illustrates that notification affordances that are interacted with are, in some examples, removed in a shorter time than notification affordances that are not interacted with. FIG. 6G depicts that second notification affordance 618 and third notification affordance 620 are still displayed in summary user interface 614.

FIG. 6H depicts first electronic device 600 displaying summary user interface 614 via touch-sensitive display device 602 at an eighth time after the seventh time. In some examples, summary user interface 614 is re-displayed relative to touch-sensitive display device 602 at the seventh time (as depicted in FIG. 6G).

FIG. 6H depicts that third notification affordance 620 is no longer displayed in summary user interface 614, due at least partially to (1) a notification corresponding to third notification affordance 620 being issued before a notification corresponding to second notification affordance 618 and (2) neither the notification corresponding to third notification affordance 620, third notification affordance 620, the notification corresponding to second notification affordance 618, nor second notification affordance 618 has been interacted with by a user. Such illustrates that notification affordances that have not been interacted with are removed based on chronological order when issued (e.g., older notification affordances are removed first). FIG. 6H depicts that second notification affordance 618 is still displayed in summary user interface 614.

FIG. 6H depicts first electronic device 600 receiving user input 625 corresponding to edit affordance 624. In some examples, user input 625 is received via touch-sensitive display device 602 and corresponds to a selection gesture (e.g., tap) on edit affordance 624. In other examples, other forms of selection can be used, such as a click using a mouse. In some examples, user input 625 causes a different user interface to be displayed via touch-sensitive display device 602, such as display of edit user interface 646 as depicted in FIG. 6I.

FIG. 6I depicts first electronic device 600 displaying edit user interface 646 via touch-sensitive display device 602 at a ninth time after the eighth time. In some examples, edit user interface 646 is a user interface of the health application allowing a user to add and/or remove favorites to be displayed in the favorites region of summary user interface 614.

As depicted in FIG. 6I, edit user interface 646 includes existing data affordance 646a and all affordance 646b for switching between views of edit user interface 646. For example, user input corresponding to selection of existing data affordance 646a causes edit user interface 646 to display an existing data view, as depicted in FIG. 6I and discussed below. Similarly, user input corresponding to selection of all affordance 646b causes edit user interface 646 to display an all data view (not illustrated), which includes all possible health data types for adding and/or removing from the favorites region.

In the view corresponding to existing data affordance 646a (as depicted in FIG. 6I), edit user interface 646 includes representations for health data types that the account has at least some health data for (e.g., a representation of a health data type is displayed when the health application has access to health data of the health data type for the account (e.g., there has been at least some health data of the health data type stored for the account)). In such examples, edit user interface 646 in the view corresponding to existing data affordance 646a does not include any representations for health data types for which the account has no health data for (e.g., a representation for a health data type is not displayed when the health application does not have access to health data of the health data type for the account (e.g., there is no health data of the health data type stored for the account)).

In either view, selection of a representation of a health data type causes a favorite affordance for the health data type to be added to the favorites region of summary user interface 614, allowing a user to view stored data for the health data type from summary user interface 614. As depicted in FIG. 6I, a representation of a health data type is indicated as being selected by including an indication that is visually distinct from other indications within the representation. For example, representation 646c includes an indication indicating that a favorite affordance for the health data type corresponding to representation 646c is to be displayed in the favorites region of summary user interface 614. For another example, representation 646d includes an indication indicating that a favorite affordance for the health data type corresponding to representation 646c is not to be displayed in the favorites region of summary user interface 614. As depicted in FIG. 6I, groups of representations for health data types are displayed via edit user interface 646. For example, edit user interface 646 includes a group of representations corresponding to activity, body measurements, and heart, where each representation within a group of representations is related.

Figure 6J:
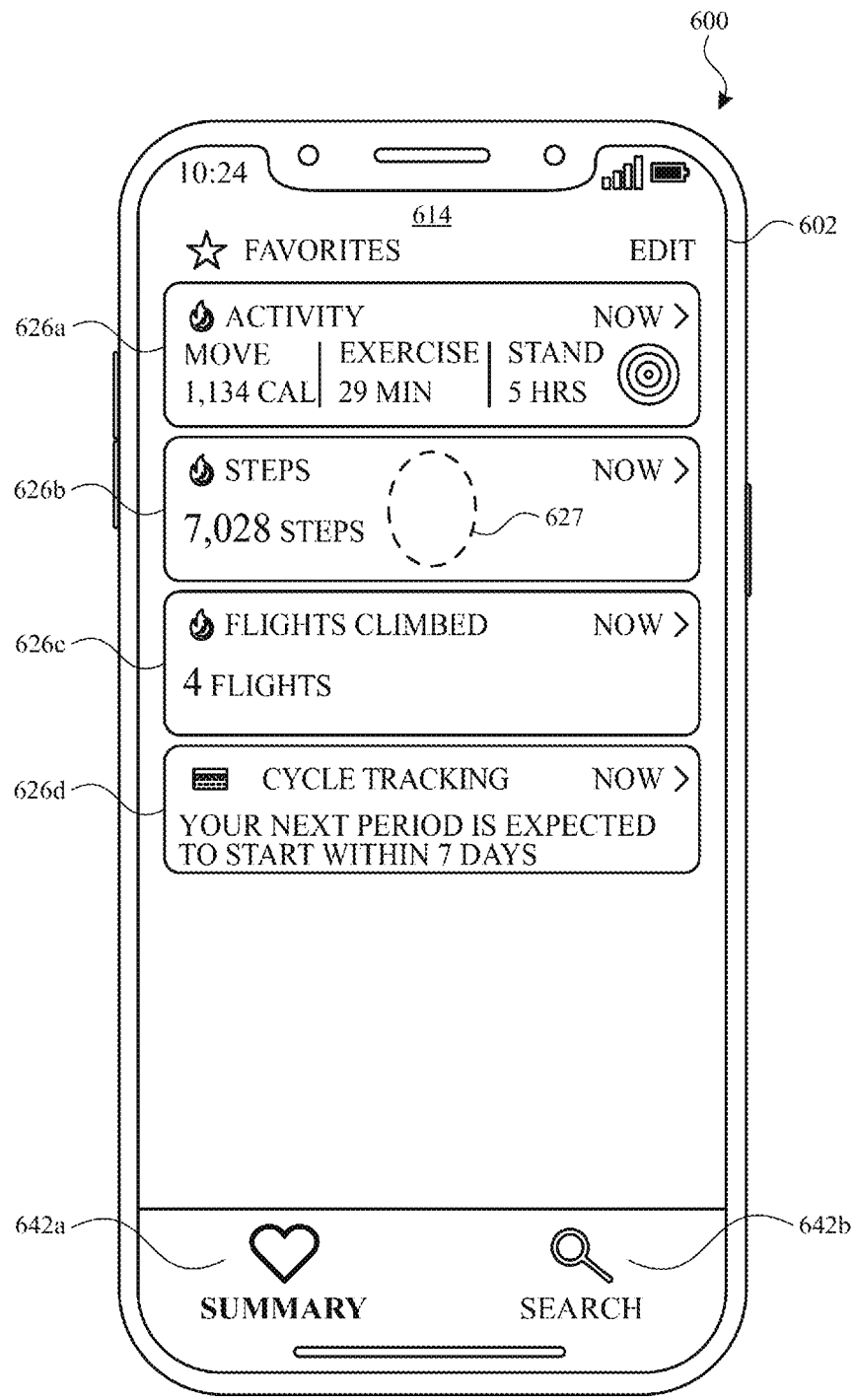

FIG. 6J depicts first electronic device 600 displaying summary user interface 614 via touch-sensitive display device 602 at a tenth time after the ninth time. In some examples, summary user interface 614 is displayed in response to user input corresponding to selection of the done button at the top right of edit user interface 646 (which is depicted in FIG. 6I without the user input). Summary user interface 614 as depicted in FIG. 6J is scrolled down relative to summary user interface 614 as depicted in FIG. 6H (e.g., logging affordance 622 is no longer displayed in FIG. 6J).

FIG. 6J depicts first electronic device 600 receiving user input 627 corresponding to second favorite affordance 626b. In some examples, user input 627 is received via touch-sensitive display device 602 and corresponds to a selection gesture (e.g., tap) on second favorite affordance 626b. In other examples, other forms of selection can be used, such as a click using a mouse. In some examples, user input 627 causes a different user interface to be displayed via touch-sensitive display device 602, such as display of steps data room user interface 648 as depicted in FIGS. 6KA-6KB.

Figure 6K:
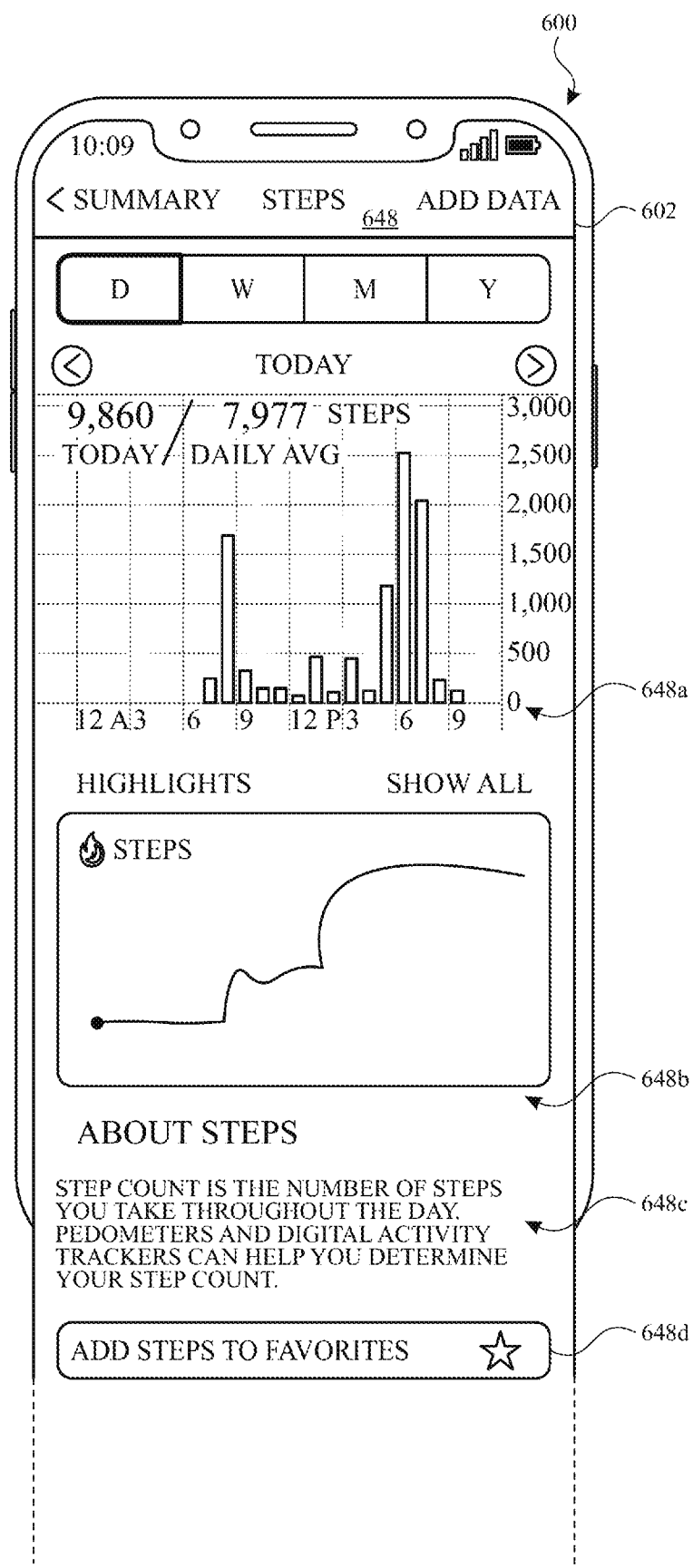
Figure 6K:
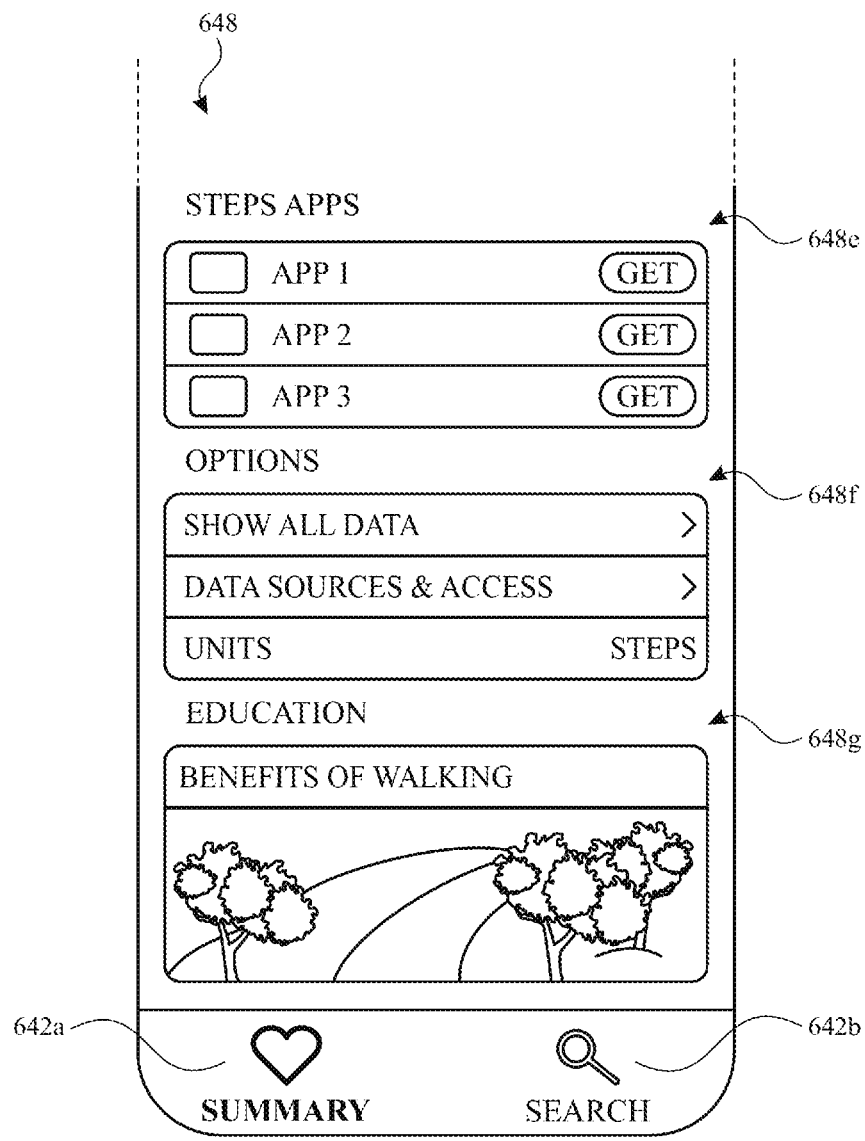

FIGS. 6KA-6KB depict first electronic device 600 displaying steps data room user interface 648 via touch-sensitive display device 602 at an eleventh time after the tenth time. In some examples, steps data room user interface 648 is displayed in response to user input corresponding to selection of second favorite affordance 626b in summary user interface 614, as depicted in FIG. 6J.

In some examples, steps data room user interface 648 is a user interface of the health application with information from the activity application. As depicted in FIG. 6KA, steps data room user interface 648 includes graph 648a with representations of health data associated with steps throughout a day. In some examples, the health data is stored in a location associated with the activity application and can be viewed within a user interface of the activity application.

Steps data room user interface 648 further includes time scale affordances at the top indicating different time scales (e.g., "D" indicating a day, "W" indicating a week, "M" indicating a month, and "Y" indicating a year). As depicted FIG. 6KA, the time scale affordance indicating day is selected, causing the graph to indicate number of steps detected throughout a day. In some examples, selection of a different time scale affordance causes the graph to change to indicate number of steps detected throughout a selected time scale.

Steps data room user interface 648 includes a highlight section including highlights associated with steps. As depicted in FIG. 6KA, steps data room user interface 648 includes a single highlight (e.g., 648b) depicting how the number of steps increased over a time period. It should be recognized that other highlights might be included in the highlight section. In some examples, identifying which highlights to display in steps data room user interface 648 includes a similar determination as discussed above for the highlights region. Steps data room user interface 648 further includes description 648c regarding what it means to be a step and add affordance 468 to cause steps to be added to the favorites region in summary user interface 614.

Referring to FIG. 6KB, steps data room user interface 648 includes (1) steps apps section 648e with links to suggested apps related to steps (e.g., a link to an app store or a link to an application installed on first electronic device 600), (2) options section 648f with various options related to steps, and (3) education section 648g with affordances, which, when selected, cause a user interface to be displayed with content pertaining to steps.

Figure 6L:
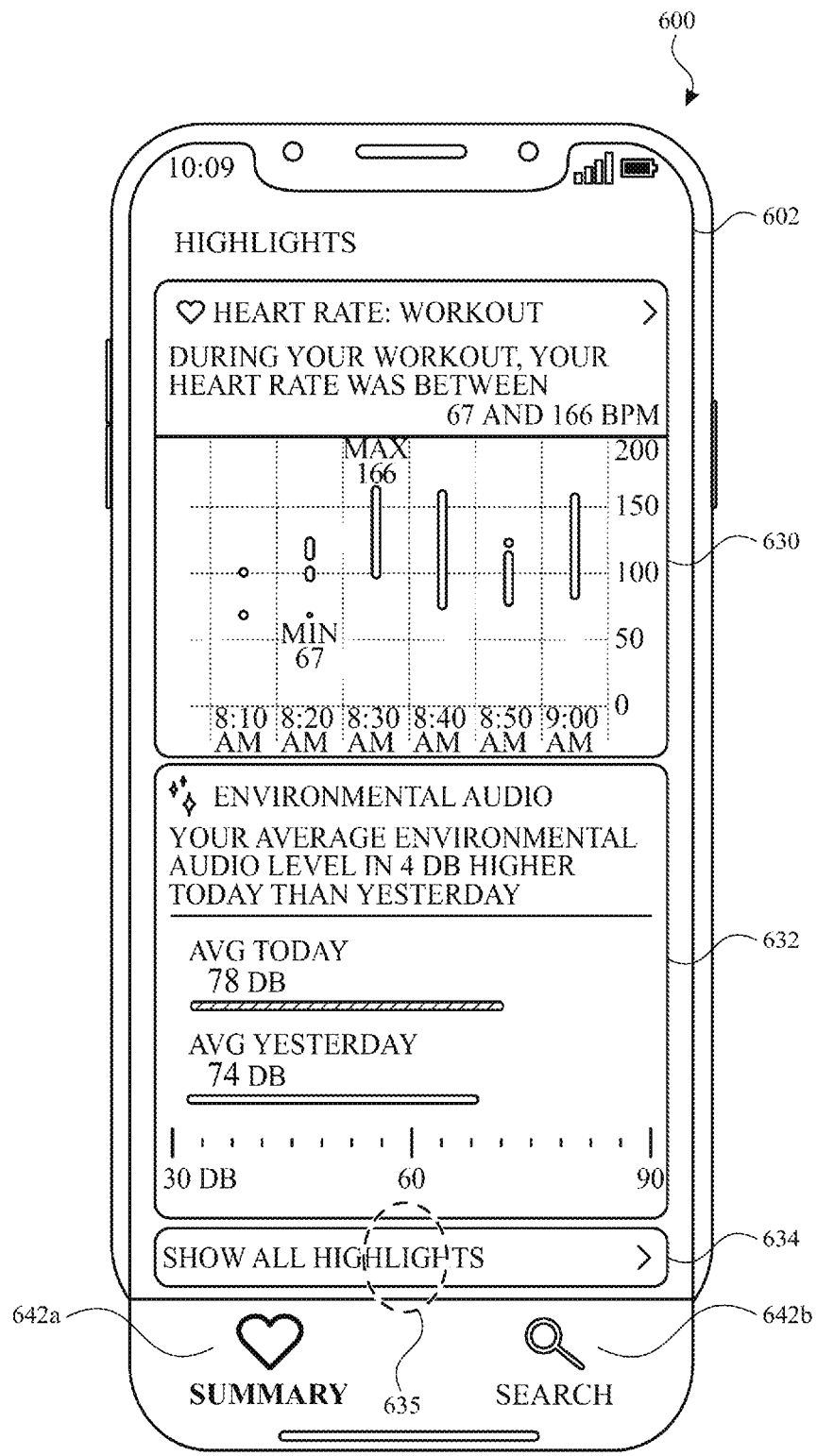
Figure 6M:
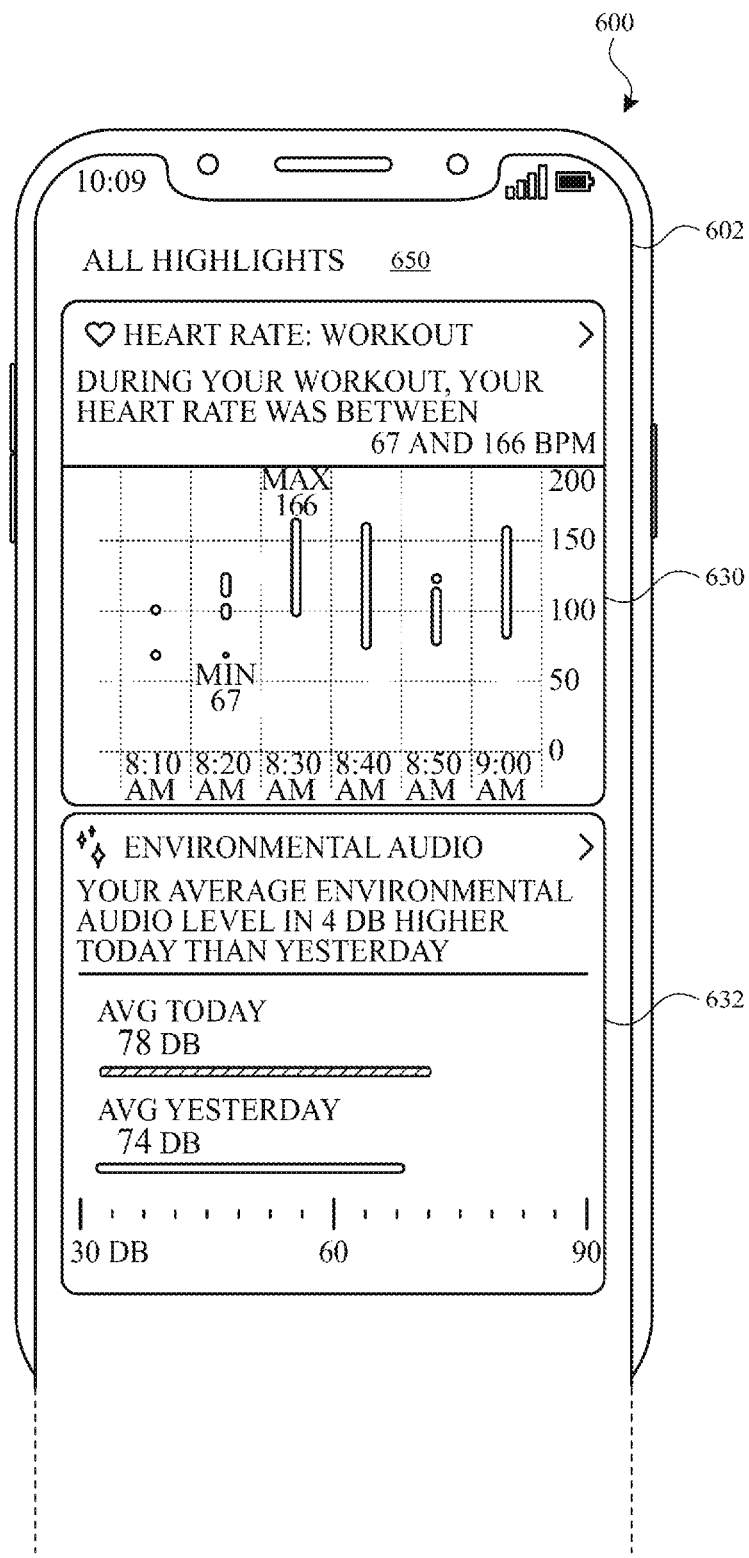
Figure 6M:
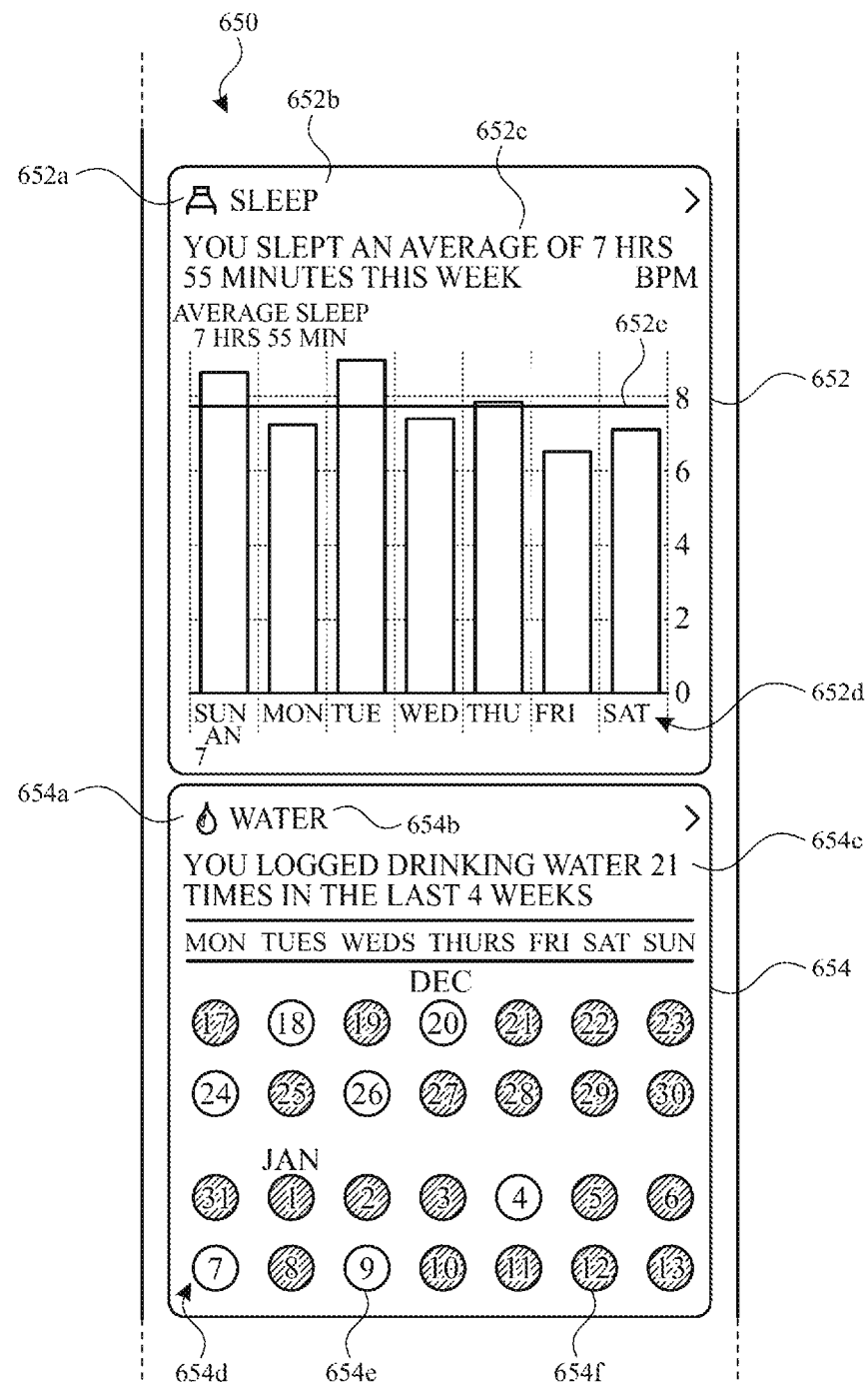
Figure 6M:
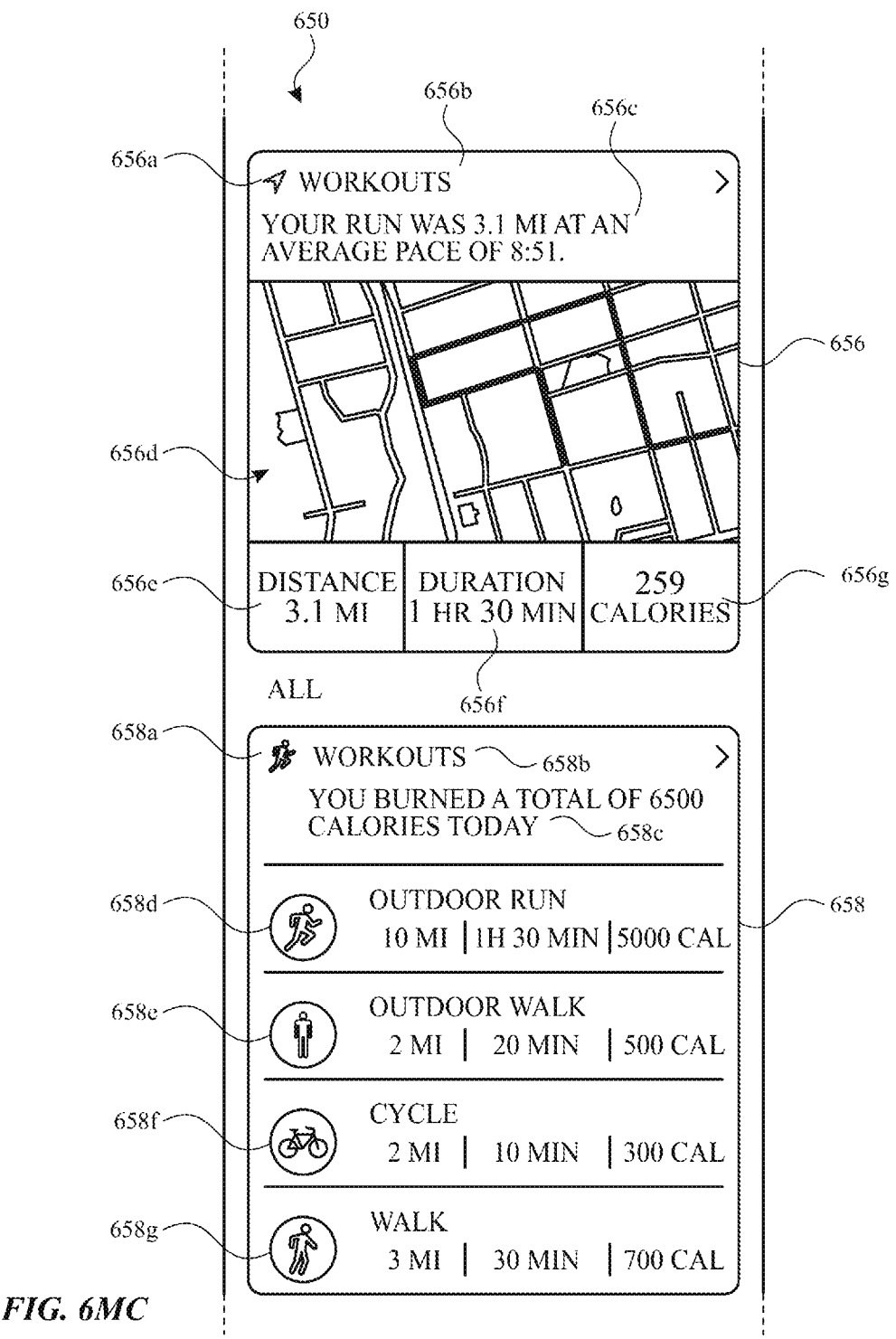
Figure 6M:
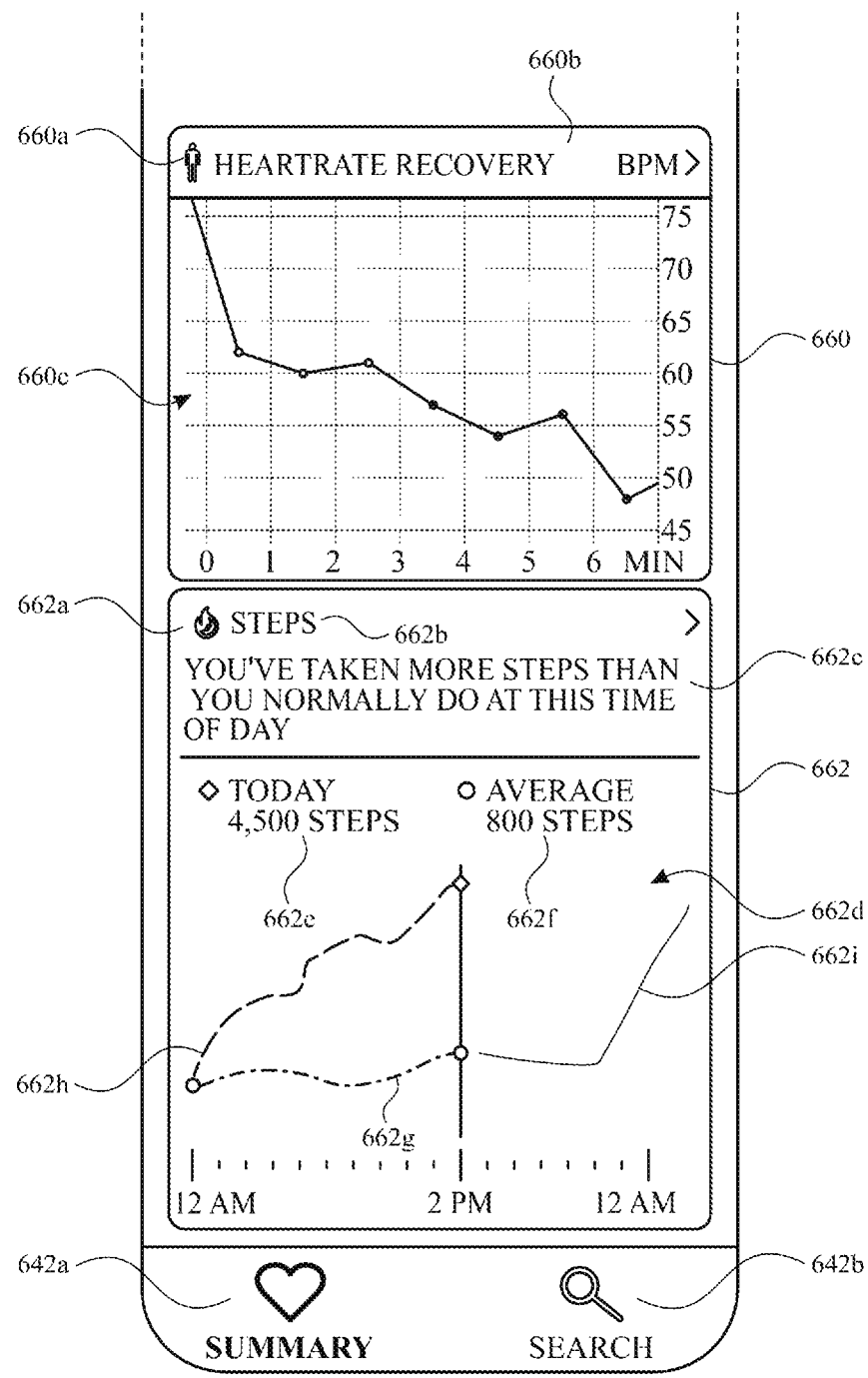

FIG. 6L depicts first electronic device 600 displaying summary user interface 614 via touch-sensitive display device 602 at a twelfth time after the eleventh time. In some examples, summary user interface 614 is displayed in response to user input corresponding to selection of the back to summary affordance at the top left of steps data room user interface 648 (which is depicted in FIG. 6KA without the user input). Summary user interface 614 as depicted in FIG. 6L is scrolled down relative to summary user interface 614 as depicted in FIG. 6J (e.g., the favorites region is no longer displayed and the highlights region is displayed in FIG. 6L).

FIG. 6L depicts first electronic device 600 receiving user input 635 corresponding to show all highlights affordance 634. In some examples, user input 635 is received via touch-sensitive display device 602 and corresponds to a selection gesture (e.g., tap) on show all highlights affordance 634. In other examples, other forms of selection can be used, such as a click using a mouse. In some examples, user input 635 causes a different user interface to be displayed via touch-sensitive display device 602, such as display of all highlights user interface 650 as depicted in FIGS. 6MA-6MD.

FIGS. 6MA-6MD depict first electronic device 600 displaying all highlights user interface 650 via touch-sensitive display device 602 at a thirteenth time after the twelfth time. In some examples, all highlights user interface 650 is displayed in response to user input corresponding to selection of show all highlights affordance 634 in summary user interface 614, as depicted in FIG. 6L.

In some examples, all highlights user interface 650 is a user interface of the health application with a list of highlights currently identified (e.g., identifying is based on the determination discussed above regarding the highlights region, such that not all highlights generated are included in all highlights user interface 650 (e.g., only highlights meeting a display criteria are displayed in all highlights user interface 650) by the health application for the account. FIG. 6MA depicts first electronic device 600 displaying first highlight affordance 630 and second highlight affordance 632, which were also displayed in the highlights region of summary user interface 614 and discussed above.

FIG. 6MB depicts first electronic device 600 displaying third highlight affordance 652 via touch-sensitive display device 602. Third highlight affordance 652 includes icon 652a, indicating that third highlight affordance 652 relates to a sleep application. In some examples, a portion of third highlight affordance 652 is visually distinguished to identify that third highlight affordance 652 relates to the sleep application (e.g., a font color for title 652b, in some examples, is a particular color corresponding to the sleep application). Second highlight affordance 632 also includes description 652c to indicate information illustrated by third highlight affordance 652 (e.g., such as how a user slept an average of 7 hours and 55 minutes this week).

As depicted in FIG. 6MB, third highlight affordance 652 includes a graph with representations of how much a user slept each day of the week. The graph also includes average line 652e to visually indicate an average over the week. In some examples, the graph represents an average over a time period (e.g., a week) that is broken into sub time periods (e.g., days).

FIG. 6MB depicts first electronic device 600 displaying fourth highlight affordance 654 via touch-sensitive display device 602. Fourth highlight affordance 654 includes icon 654a, indicating that fourth highlight affordance 654 primarily relates to a water application (in some examples, fourth highlight affordance 654 secondarily relates to a calendar application). In some examples, a portion of fourth highlight affordance 654 is visually distinguished to identify that fourth highlight affordance 654 relates to the water application (e.g., a font color for title 654b, in some examples, is a particular color corresponding to the water application). Fourth highlight affordance 654 also includes description 652c to indicate information illustrated by fourth highlight affordance 654 (e.g., such as how a user logged water 21 days in the last 4 weeks).

As depicted in FIG. 6MB, fourth highlight affordance 654 includes calendar 654d with representations for each day having an indication whether a user logged water for a respective day. As depicted in FIG. 6MB, representation 654f is visually distinguished from some other representations (e.g., representation 654e, indicating that a user logged water on a day corresponding to representation 654f and did not log water on a day corresponding to representation 654e). In some examples, calendar 654d represents frequency of a single health data metric compared between time periods of the same length.

FIG. 6MC depicts first electronic device 600 displaying fifth highlight affordance 656 via touch-sensitive display device 602. Fifth highlight affordance 656 includes icon 656a, indicating that fifth highlight affordance 656 primarily relates to a navigation application (in some examples, fifth highlight affordance 656 secondarily relates to a workout application). In some examples, a portion of fifth highlight affordance 656 is visually distinguished to identify that fifth highlight affordance 656 primarily relates to the navigation application (e.g., a font color for title 656b, in some examples, is a particular color corresponding to the navigation application). Fifth highlight affordance 656 also includes description 656c to indicate information illustrated by fifth highlight affordance 656 (e.g., such as that a user logged a run of 3.1 miles at an average pace of 8:51).

As depicted in FIG. 6MC, fifth highlight affordance 656 includes map 656d with an indication in map 656d of a route of the run. Fifth highlight affordance 656 also includes textual information regarding the run, including distance measurement 656e (which is in addition to and larger than the distance included in description 656c), duration 656f, and calories 656g.

FIG. 6MC depicts first electronic device 600 displaying sixth highlight affordance 658 via touch-sensitive display device 602. Sixth highlight affordance 658 includes icon 658a, indicating that sixth highlight affordance 658 relates to a workout application. In some examples, a portion of sixth highlight affordance 658 is visually distinguished to identify that sixth highlight affordance 658 relates to the workout application (e.g., a font color for title 658b, in some examples, is a particular color corresponding to the workout application). Sixth highlight affordance 658 also includes description 658c to indicate information illustrated by sixth highlight affordance 658 (e.g., such as that a user burned a total of 6500 calories today).

As depicted in FIG. 6MC, sixth highlight affordance 658 includes 4 different representations of different workouts recorded in a day. Each workout includes an icon corresponding to the type of workout, identification information (e.g., a name) of the type of workout, a length of time of the respective workout, and a number of calories burned during the respective workout. In some examples, sixth highlight affordance 658 represents multiple workouts for a single day in a single highlight with heath data for the single day.

FIG. 6MD depicts first electronic device 600 displaying seventh highlight affordance 660 via touch-sensitive display device 602. Seventh highlight affordance 660 includes icon 660a, indicating that seventh highlight affordance 660 primarily relates to a vitals application. In some examples, a portion of seventh highlight affordance 660 is visually distinguished to identify that seventh highlight affordance 660 relates to the vitals application (e.g., a font color for title 660b, in some examples, is a particular color corresponding to the vitals application). It should be noted that seventh highlight affordance 660 does not include a description to indicate information illustrated by seventh highlight affordance 660, showing that not all highlights have such a description. As depicted in FIG. 6MD, seventh highlight affordance 660 includes graph 660c depicting a beats per minute for a user over time, illustrating how the beats per minute reduced from a high point to a lower point.

FIG. 6MD depicts first electronic device 600 displaying eighth highlight affordance 662 via touch-sensitive display device 602. Eighth highlight affordance 662 includes icon 662a, indicating that eighth highlight affordance 662 relates to an activity application. In some examples, a portion of eighth highlight affordance 662 is visually distinguished to identify that eighth highlight affordance 662 relates to the activity application (e.g., a font color for title 662b, in some examples, is a particular color corresponding to the activity application). Eighth highlight affordance 662 also includes description 662c to indicate information illustrated by eighth highlight affordance 662 (e.g., such as that a user has taken more steps today than they normally do at this time of day).

As depicted in FIG. 6MD, eighth highlight affordance 662 includes graph 662d comparing an activity metric for a day (e.g., a current day) over a previous average. For example, graph 662d includes today line 662h and a previous average line (comprising first portion 662g and second portion 662i). Today line 662h depicts a number of steps for a user as time has progressed during a day up until the current time. The previous average line depicts a number of steps for a user as time has progressed on average during a number of days prior to the current day. First portion 662g represents time up until the current time and second portion 662i represents time after the current time. Graph 662d also includes a textual indication regarding a number of steps for today and a number of steps as of this time on average over the number of days prior to the current day. In some examples, sixth highlight affordance 658 represents average over a time period compared to today with instantaneous update of information.

Figure 6N:
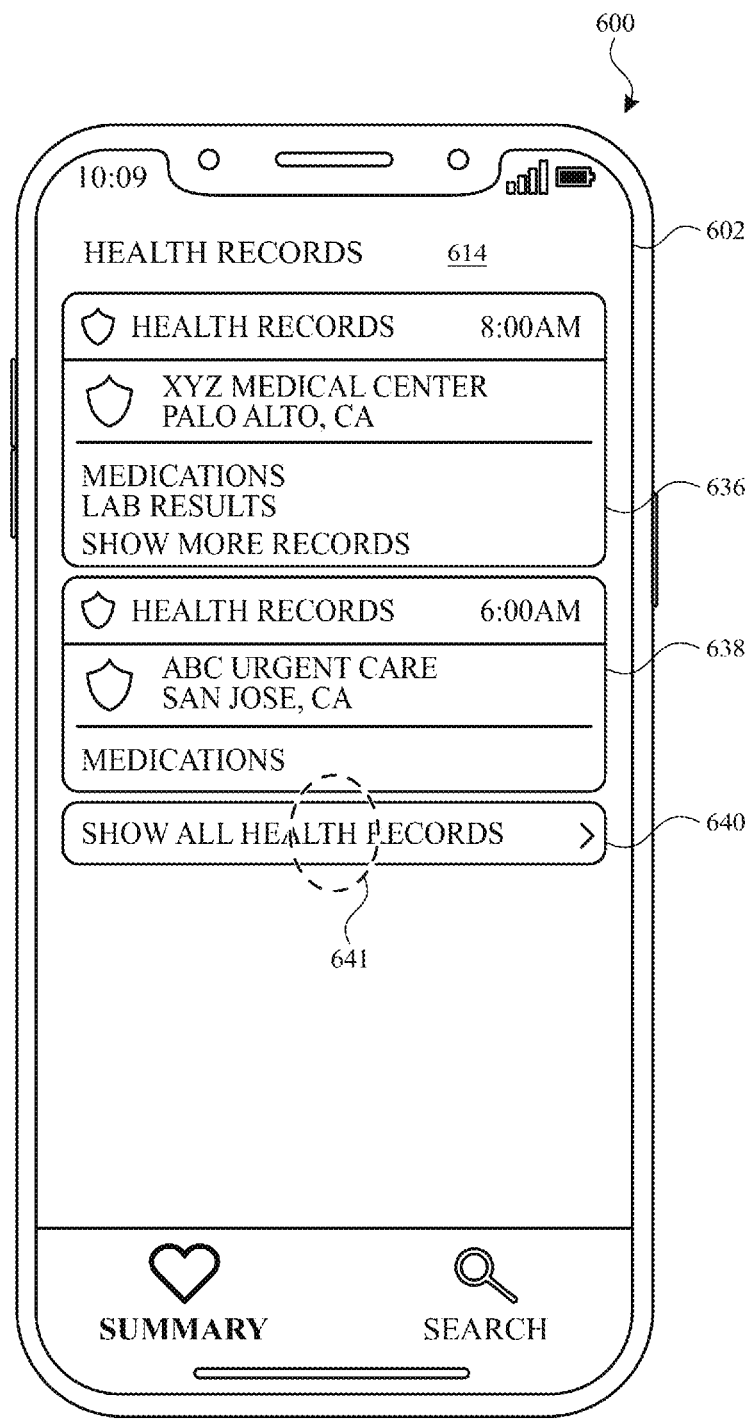
Figure 6O:
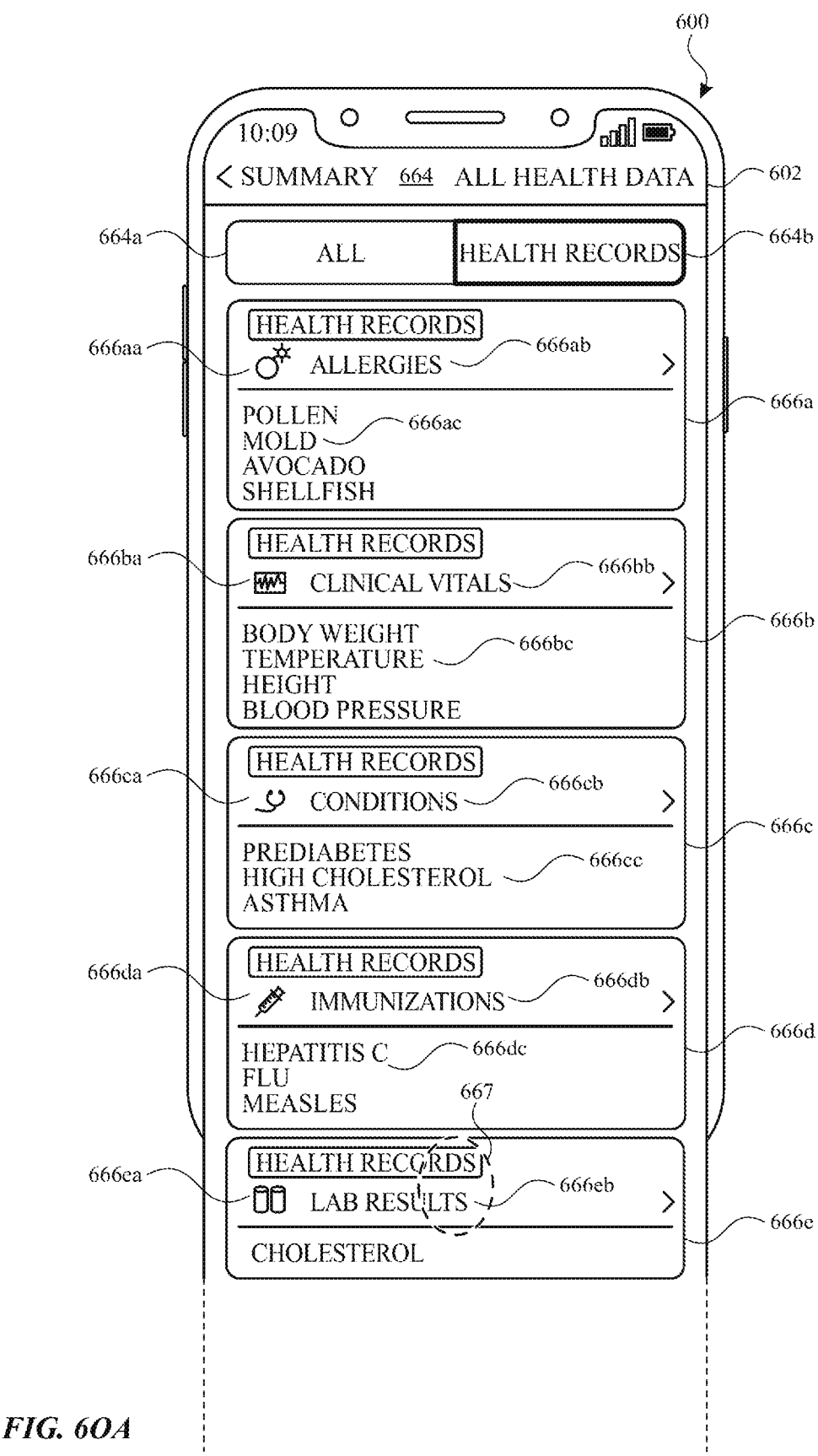
Figure 6O:
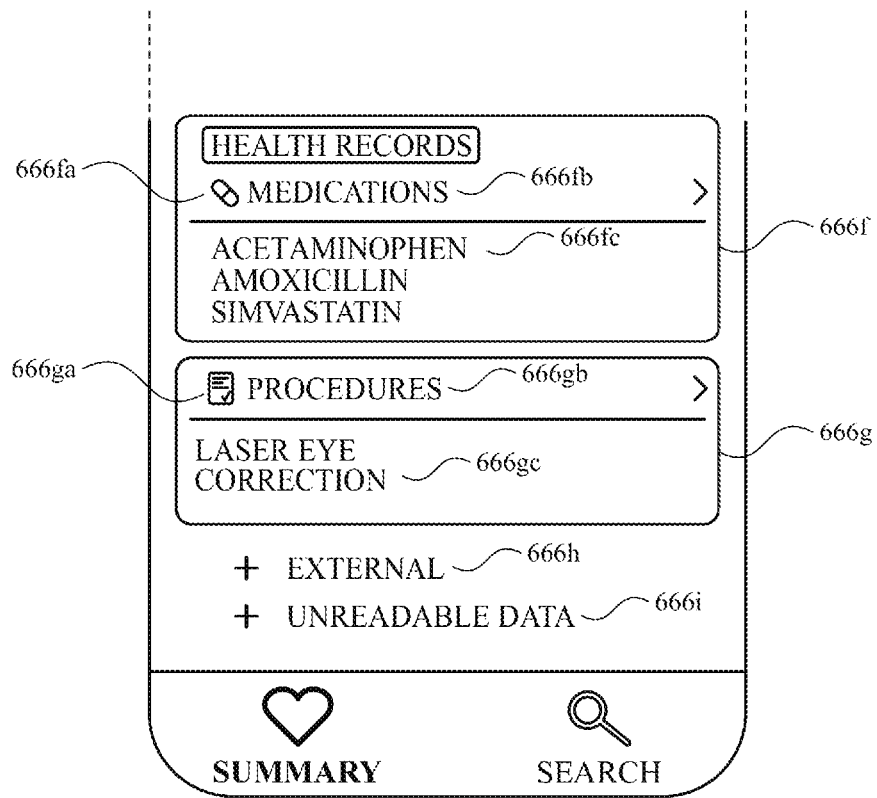

FIG. 6N depicts first electronic device 600 displaying summary user interface 614 via touch-sensitive display device 602 at a fourteenth time after the thirteenth time. In some examples, summary user interface 614 is displayed in response to user input corresponding to selection of summary affordance 642*a* in all highlights user interface 650 (which is depicted in FIG. 6MD without the user input). Summary user interface 614 as depicted in FIG. 6N is scrolled down relative to summary user interface 614 as depicted in FIG. 6L (e.g., the highlights region is no longer displayed and the health records region is displayed in FIG. 6N).

FIG. 6N depicts first electronic device 600 receiving user input 641 corresponding to show all health records affordance 640. In some examples, user input 641 is received via touch-sensitive display device 602 and corresponds to a selection gesture (e.g., tap) on show all health records affordance 640. In other examples, other forms of selection can be used, such as a click using a mouse. In some examples, user input 641 causes a different user interface to be displayed via touch-sensitive display device 602, such as display of all health data user interface 664 as depicted in FIGS. 6OA-6OB.

FIGS. 6OA-6OB depict first electronic device 600 displaying all health data user interface 664 via touch-sensitive display device 602 at a fifteenth time after the fourteenth time. In some examples, all health data user interface 664 is displayed in response to user input corresponding to selection of show all health records affordance 640 in summary user interface 614, as depicted in FIG. 6N.

In some examples, all health data user interface 664 is a user interface of the health application with a list of health data received for the account. As depicted in FIG. 6OA, all health data user interface 664 includes all data affordance 664*a* and health records affordance 664*b* for switching between views of all health data user interface 664. For example, user input corresponding to selection of all data affordance 664*a* causes all health data user interface 664 to display an all data view, as depicted in FIG. 12AA. Similarly, user input corresponding to selection of health records affordance 664*b* causes all health data user interface 664 to display a health record view (as depicted in FIGS. 6OA-6OB), which includes all health records received for the account. In some examples, in response to selection of show all health records affordance 640, the health record view is displayed instead of the all data view. In such examples, in response to selection of an all health data affordance (e.g., all health data affordance 628, as depicted in FIG. 6DB), the all data view is displayed instead of the health record view.

In the health record view, all health data user interface 664, in some examples, includes representations for health record types (e.g., representation 666 is for allergies, representation 666*b* is for clinical vitals, representation 666*c* is for conditions, representation 666*d* is for immunizations, representation 666*e* is for lab results, representation 666*f* is for medications, and representation 666*g* is for procedures). In such examples, the representations for health record types are ordered alphabetically (e.g., allergies before clinical vitals before conditions before immunizations before lab results before medications before procedures).

In some examples, each representation in the health record view includes an icon corresponding to the health record type (e.g., icon 666*aa* corresponds to allergies, icon 666*ba* corresponds to clinical vitals, icon 666*ca* corresponds to conditions, icon 666*da* corresponds to immunizations, icon 666*ea* corresponds to lab results, icon 666*fa* corresponds to medications, icon 666*ga* corresponds to procedures). In some examples, a user interface of the health application that includes a user interface element corresponding to the health record type will include a version of the corresponding icon.

In some examples, each representation in the health record view includes a list of information corresponding to the respective health record type. For example, representation 666*a*, which corresponds to allergies, includes a list of items for which health records have indicated that a user associated with the account is allergic to (e.g., pollen, mold, avocado, and shellfish). In some examples, the list of information is ordered based on recency (e.g., items that have been more recently identified for a health record type are ordered in front of (e.g., above) items that have less recently been identified for the health record type). In some examples, all health data user interface 664 in the health record view will include a representation for a health record type even when there is no health records for the health record type.

As depicted in FIG. 6OB, all health data user interface 664 includes external affordance 666*h*. Selection of external affordance 666*h* causes a user interface of the health application to be displayed, the user interface including information from one or more external sources (e.g., sources external to first electronic device 600). As depicted in FIG. 6OB, all health data user interface 664 includes unreadable data affordance 666*i*. Selection of unreadable data affordance 666*i* causes a user interface of the health application to be displayed, the user interface including representations of health records that could not be parsed by a process associated with the health application.

FIG. 6OA depicts first electronic device 600 receiving user input 667 corresponding to representation 666*e*. In some examples, user input 667 is received via touch-sensitive display device 602 and corresponds to a selection gesture (e.g., tap) on representation 666*e*. In other examples, other forms of selection can be used, such as a click using a mouse. In some examples, user input 667 causes a different user interface to be displayed via touch-sensitive display device 602, such as display of lab result data room user interface 668 as depicted in FIGS. 6PA-6PB.

Figure 6P:
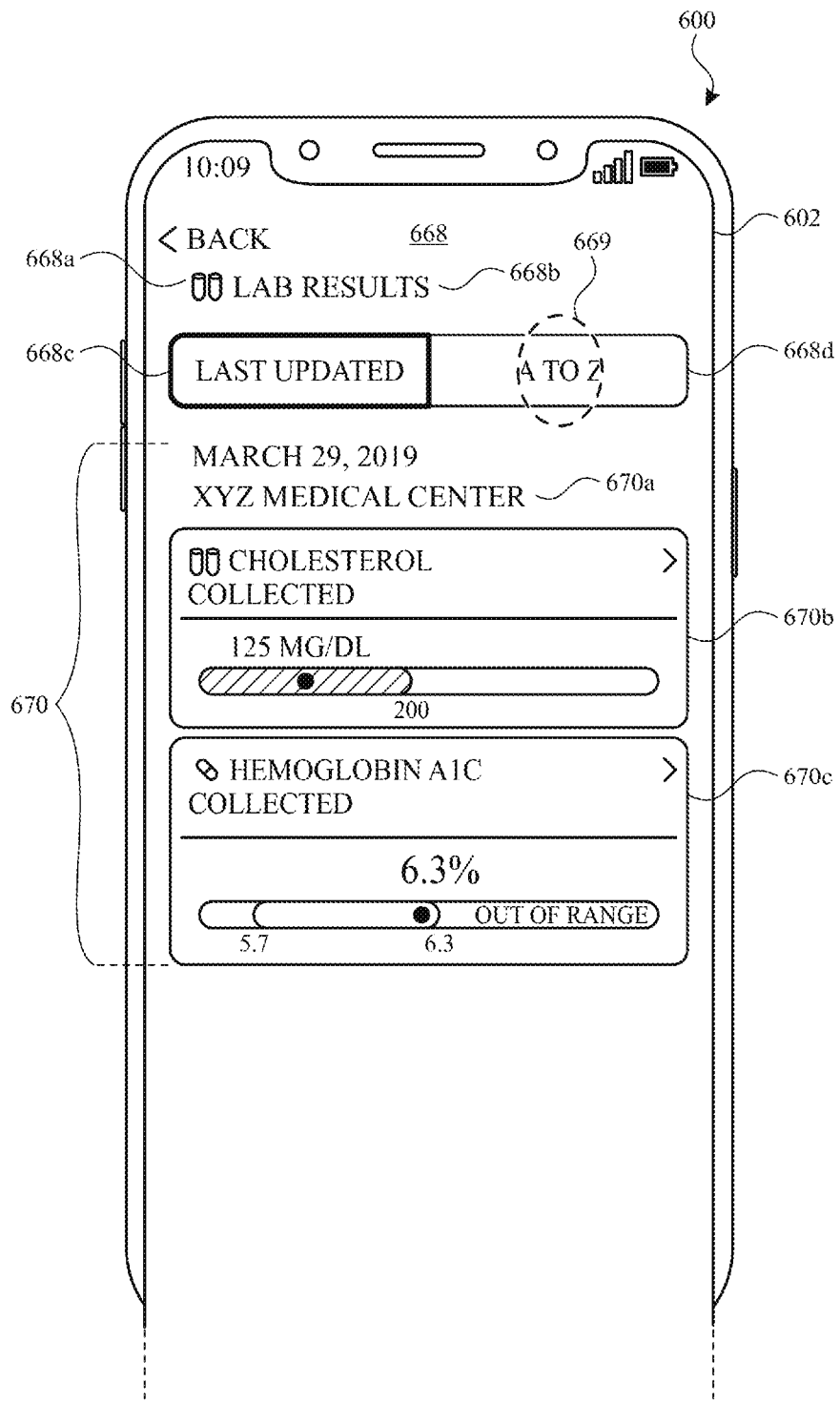
Figure 6P:
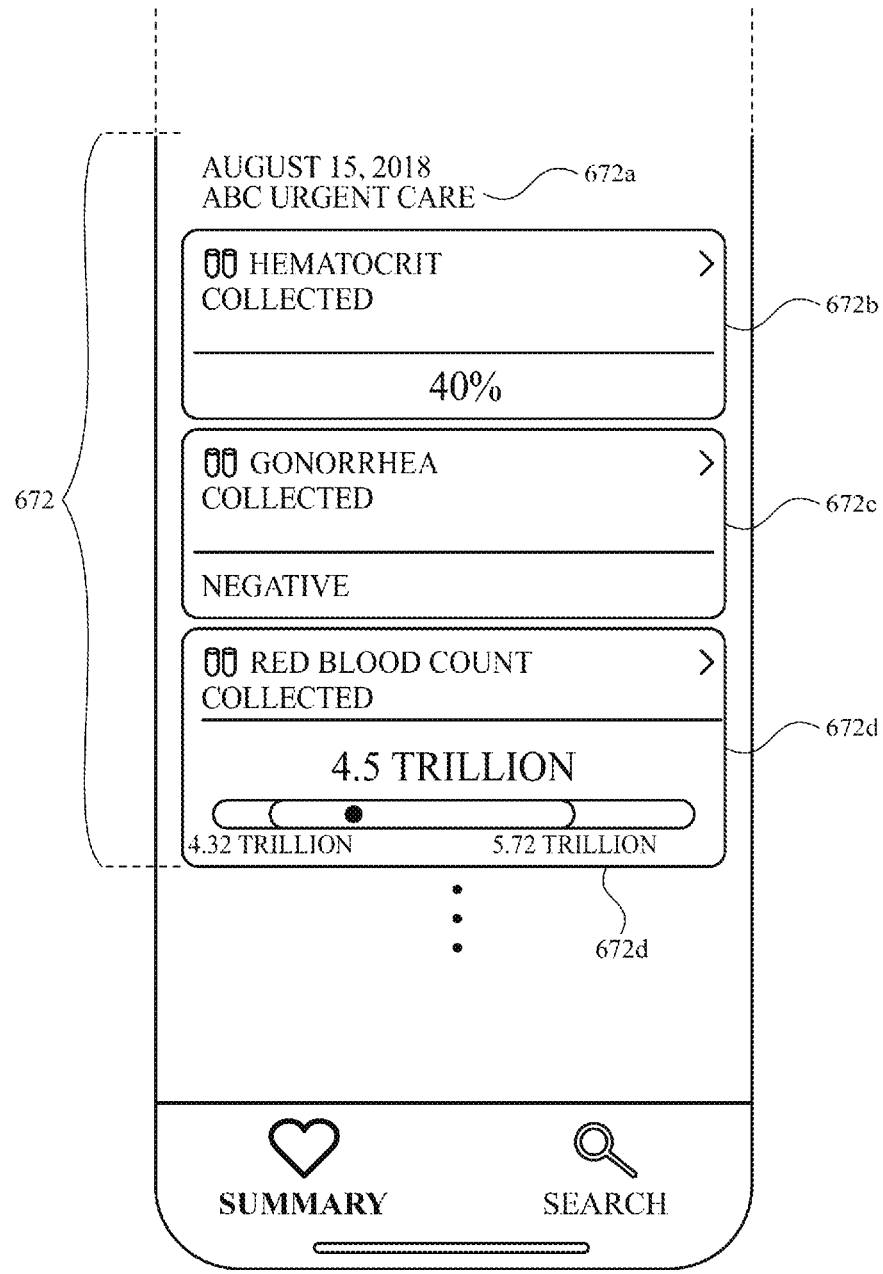
Figure 6Q:
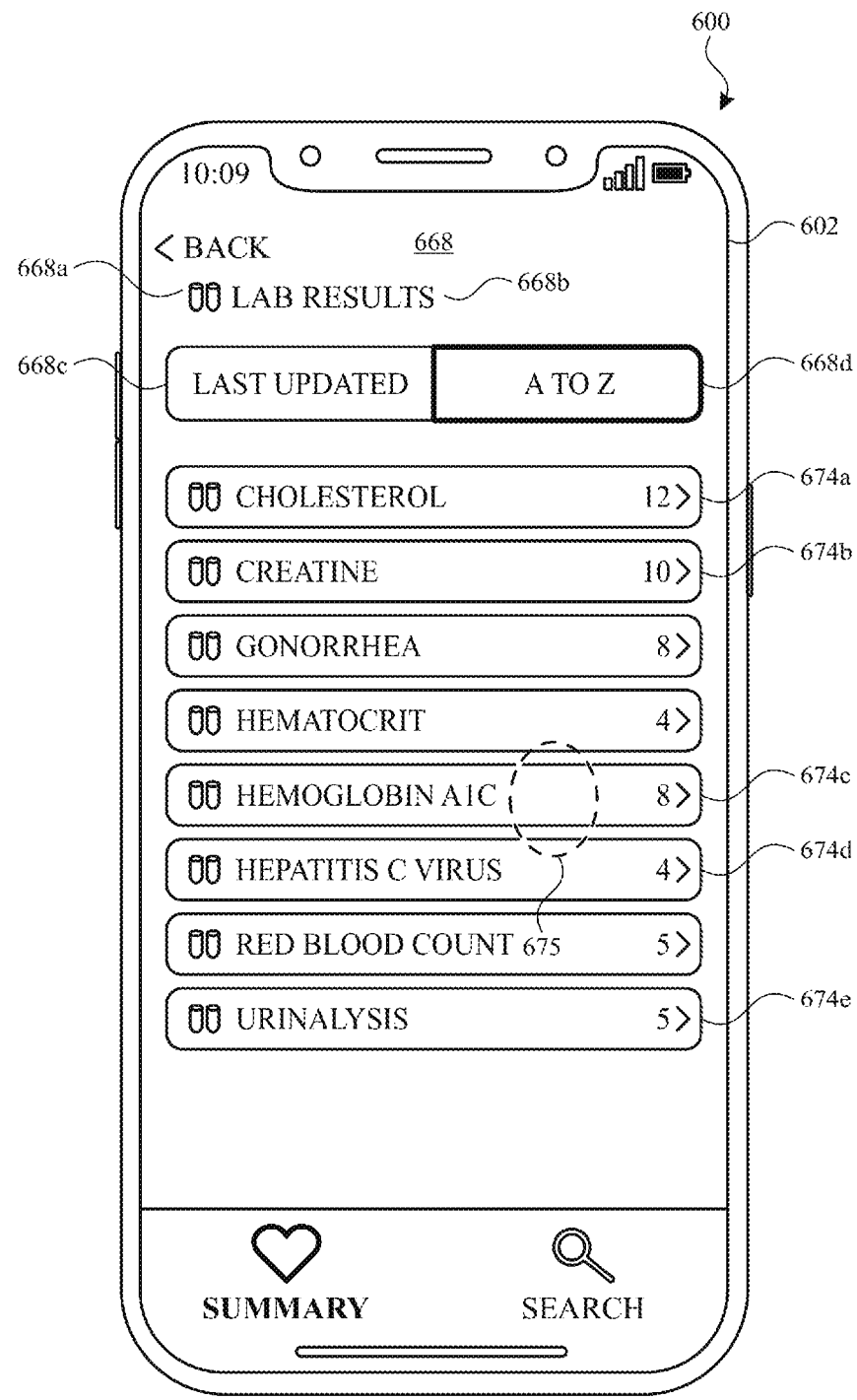

FIGS. 6PA-6PB depict first electronic device 600 displaying lab result data room user interface 668 via touch-sensitive display device 602 at a sixteenth time after the fifteenth time. In some examples, lab result data room user interface 668 is displayed in response to user input corresponding to selection of representation 666*e* in all health data user interface 664 as depicted in FIG. 6OA. In other examples, lab result data room user interface 668 is displayed in response to user input corresponding to a notification representation in summary user interface 614 indicating that lab results (e.g., and no other health record types) have been updated. In other examples, lab result data room user interface 668 is displayed in response to searching for lab results using search user interface 684 as depicted in FIG. 6TA and selecting an affordance corresponding to lab result data room user interface 668 in search results.

As depicted in FIG. 6PA, lab result data room user interface 668 includes icon 668*a* and title 668*b* corresponding to and indicating the health record type "lab result." In some examples, user interface elements corresponding to the health record type "lab result" include an icon similar to icon 668*a*.

As depicted in FIG. 6PA, lab result data room user interface 668 includes last updated affordance 668c and A-to-Z affordance 668d for switching between views of lab result data room user interface 668. For example, user input corresponding to selection of last updated affordance 668c causes lab result data room user interface 668 to display a first view, as depicted in FIGS. 6PA-6PB. Similarly, user input corresponding to selection of A-to-Z affordance 668d causes lab result data room user interface 668 to display a second view, as depicted in FIG. 6Q.

As depicted in FIGS. 6PA-6PB, lab result data room user interface 668 includes multiple regions (e.g., region 670 and region 672), each region corresponding to a different date that health records within the region were generated (e.g., collected, taken, or otherwise created by a clinical institution). In some examples, the multiple regions are ordered by date, such that regions corresponding to more recent dates are before regions corresponding to later dates. For example, lab result data room user interface 668 includes region 670 (which is indicated to correspond to Mar. 29, 2019) (as depicted in FIG. 6PA) higher in a list than (e.g., before) region 672 (which is indicated to correspond to Aug. 15, 2019) (as depicted in FIG. 6PB).

In some examples, each region included in lab result data room user interface 668 includes one or more representations of health records. For example, region 670 includes two representations of two separate health records: representation 670b and representation 670c. For another example, region 672 includes three representations: representation 672b, representation 672c, and representation 672d.

In some examples, representations within a region are included in a sub-region corresponding to a clinical institution associated with the health records. For example, representation 670b and representation 670c are included in a sub-region that corresponds to XYZ Medical Center, indicating that health records corresponding to representation 670b and representation 670c were received from (e.g., generated by) XYZ Medical Center. For another example, representation 672b, representation 672c, and representation 672d are included in a sub-region that corresponds to ABC Urgent Care, indicating that the health records corresponding to representation 672b, representation 672c, and representation 672d were received from (e.g., generated by) ABC Urgent Care. Such illustrates that lab result data room user interface 668 can includes representations from multiple clinical institutions.

In some examples, representations of health records in lab result data room user interface 668 include an icon indicating a corresponding health record type (as discussed above). In some examples, representations of health records in lab result data room user interface 668 include information corresponding to a respective health record. For example, information in 670b includes the word "collected," indicating that a corresponding health record was collected on the associated date (e.g., Mar. 29, 2019).

The information in representation 670b further includes a graph illustrating a corresponding health record. The graph in representation 670b includes multiple indications of a value (e.g., "125 MG/DL") included in the corresponding health record and a range defined for the value (e.g., 0 to 200, which is a minimum and maximum value). The multiple indications include a textual indication (e.g., the text) and a graphical representation (e.g., the dot in the visual representation of the range). In some examples, the value is considered to meet particular criteria (e.g., criteria related to whether the value is acceptable, such as criteria set by a governing body) when the value is within the range. In some examples, the range is included in the corresponding health record. In other examples, the range is known by the health application, such as from being provided by a remote source (such as a clinical institution).

FIG. 6PA depicts representation 670c including a graph illustrating a corresponding health record. The graph in representation 670c includes multiple indications of a value (e.g., "6.3%") included in the corresponding health record and a range defined for the value (e.g., 5.7 to 6.3, which is a minimum and maximum value). The multiple indications include a textual indication (e.g., the text) and a graphical representation (e.g., the dot in the visual representation of the range). In some examples, the value is considered to meet particular criteria (e.g., criteria related to whether the value is acceptable, such as criteria set by a governing body) when the value is within the range. In some examples, the range is included in the corresponding health record. In other examples, the range is known by the health application, such as from being provided by a remote source (such as a clinical institution).

FIG. 6PB depicts representation 672b including information from a corresponding health record. The information in representation 672b includes a single indication (e.g., a textual indication) of a value (e.g., "40%") included in the corresponding health record and no indication of a range defined for the value. In some examples, the information in representation 672b does not include a graph (and/or an indication of a range) because the health application is unable to identify a range for the value (e.g., the corresponding health record did not include the range and/or an institution has not provided the range).

FIG. 6PB depicts representation 672c including information from a corresponding health record. The information in representation 672c includes a single indication (e.g., a textual indication) of a value (e.g., "NEGATIVE") included in the corresponding health record. In some examples, the information in representation 672b does not include a graph (and/or an indication of a range) because the value is less than a minimum number of possible values for the corresponding health record (in some examples, the minimum number of possible values is three (e.g., binary values will not be graphed).

FIG. 6PB depicts representation 672d including a graph illustrating a corresponding health record. The graph in representation 672d includes multiple indications of a value (e.g., "4.5 trillion") included in the corresponding health record and a range defined for the value (e.g., 5.32 to 5.72 trillion, which is a minimum and maximum value). The multiple indications include a textual indication (e.g., the text) and a graphical representation (e.g., the dot in the visual representation of the range). In some examples, the value is considered to meet particular criteria (e.g., criteria related to whether the value is acceptable, such as criteria set by a governing body) when the value is within the range. In some examples, the range is included in the corresponding health record. In other examples, the range is known by the health application, such as from being provided by a remote source (such as a clinical institution). FIG. 6PB illustrates that some representations can include graphs while other representations do not include a graph, even representations corresponding to the same health record type. Such a result, in some examples, is due to some health records not including ranges and/or being binary values.

FIG. 6PA depicts first electronic device 600 receiving user input 669 corresponding to A-to-Z affordance 668d. In some examples, user input 669 is received via touch-sensitive display device 602 and corresponds to a selection gesture (e.g., tap) on A-to-Z affordance 668d. In other examples, other forms of selection can be used, such as a click using a mouse. In some examples, user input 669 causes a different view of lab result data room user interface 668 to be displayed via touch-sensitive display device 602, such as the A-to-Z view depicted in FIG. 6Q.

FIG. 6Q depicts first electronic device 600 displaying an A-to-Z view of lab result data room user interface 668 via touch-sensitive display device 602 at a seventeenth time after the sixteenth time. In some examples, the A-to-Z view is displayed in response to user input corresponding to selection of A-to-Z affordance 668d in lab result data room user interface 668 as depicted in FIG. 6PA.

As depicted in FIG. 6Q, the A-to-Z view includes last updated affordance 668c and A-to-Z affordance 668d for switching between views of lab result data room user interface 668. For example, user input corresponding to selection of last updated affordance 668c causes lab result data room user interface 668 to display a first view, as depicted in FIGS. 6PA-6PB. Similarly, user input corresponding to selection of A-to-Z affordance 668d causes lab result data room user interface 668 to display a second view, as depicted in FIG. 6Q.

As depicted in FIG. 6Q, the A-to-Z view includes a list of affordances for different lab results, each affordance corresponding to a different type of lab result. In some examples, the list of affordances are alphabetically ordered by each affordance's corresponding type of lab result (e.g., a cholesterol affordance (e.g., affordance 674a) is before a creatine affordance (e.g., affordance 674b)). In some examples, each affordance in the list of affordances includes an indication regarding a number of health records associated with a corresponding type of lab result. For example, the "12" in affordance 674a indicates that the health system has received 12 health records corresponding to cholesterol.

FIG. 6Q depicts first electronic device 600 receiving user input 675 corresponding to affordance 674c. In some examples, user input 675 is received via touch-sensitive display device 602 and corresponds to a selection gesture (e.g., tap) on affordance 674c. In other examples, other forms of selection can be used, such as a click using a mouse. In some examples, user input 675 causes a different user interface to be displayed via touch-sensitive display device 602, such as hemoglobin user interface 676 depicted in FIGS. 6RA-6RB.

Figure 6R:
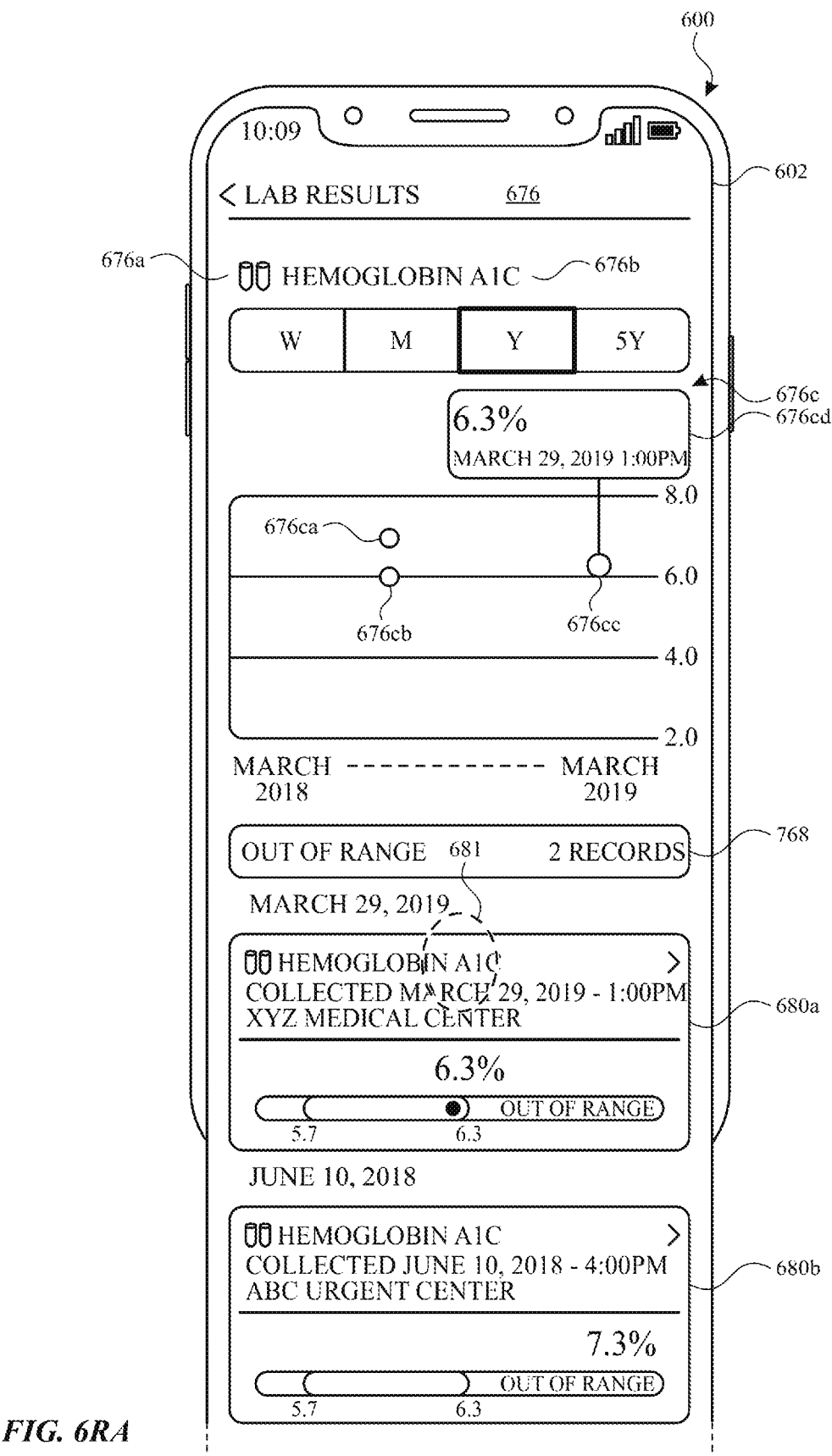
Figure 6R:
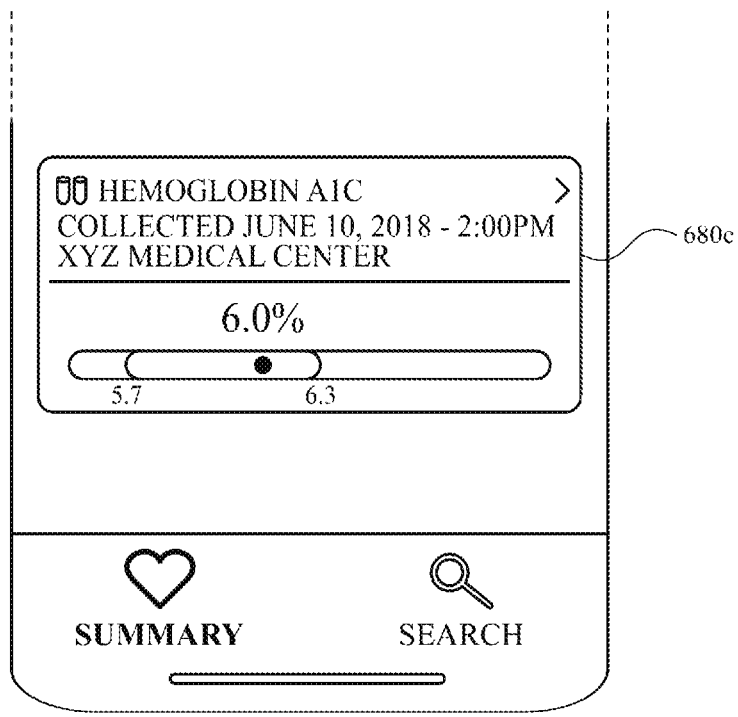

FIGS. 6RA-6RB depict first electronic device 600 displaying hemoglobin user interface 676 via touch-sensitive display device 602 at an eighteenth time after the seventeenth time. In some examples, hemoglobin user interface 676 is displayed in response to user input corresponding to selection of affordance 674c in lab result data room user interface 668 as depicted in FIG. 6Q. In some examples, hemoglobin user interface 676 is displayed in response to user input corresponding to selection of affordance 670c in lab result data room user interface 668 as depicted in FIG. 6PA. In some examples, hemoglobin user interface 676 is a user interface of the health application with information based on health records corresponding to Hemoglobin A1C.

As depicted in FIG. 6RA, hemoglobin user interface 676 includes a graph with data indicating values obtained from health records corresponding to Hemoglobin A1C throughout a year. For example, a first health record can indicate that results for a first Hemoglobin A1C test were 6.3% (e.g., the first health record corresponds to affordance 680a), a second health record can indicate that results for a second Hemoglobin A1C test were 7.3% (e.g., the second health record corresponds to affordance 680b), and a third health record can indicate that results for a third Hemoglobin A1C test were 6% (e.g., the third health record corresponds to affordance 680c). With such health records, the graph includes an indication for the first health record (e.g., 676cc), the second health record (e.g., 676ca), and the third health record (e.g., 676cb). In some examples, the graph also includes representation 676cd, providing additional information regarding one of the health records in the graph. As depicted in FIG. 6RA, representation 676cd relates to the first health record. In some examples, representation 676cd relates to the first health record in response to user input on indication 676cc and/or selection of an affordance on a different user inter to cause hemoglobin user interface 676 to be displayed, the affordance corresponding to a health record associated with indication 676cc (e.g., affordance 670c as depicted in FIG. 6PA).

As depicted in FIG. 6RA, hemoglobin user interface 676 includes time scale affordances at the top indicating different time scales (e.g., "W" indicating a week, "M" indicating a month, "Y" indicating a year, and "5Y" indicating 5 years). As depicted FIG. 6RA, the time scale affordance indicating year is selected, causing the graph to indicate health records throughout a year. In some examples, selection of a different time scale affordance causes the graph to change to indicate health records detected throughout a selected time scale.

As depicted in FIG. 6RA, hemoglobin user interface 676 includes out of range affordance 678. Selection of out of range affordance 678 causes indications in the graph to be visually distinguished (e.g., highlighted) that correspond to a value that is out of a defined range, as discussed above.

FIG. 6RA depicts first electronic device 600 receiving user input 681 corresponding to affordance 680a. In some examples, user input 681 is received via touch-sensitive display device 602 and corresponds to a selection gesture (e.g., tap) on affordance 680a. In other examples, other forms of selection can be used, such as a click using a mouse. In some examples, user input 681 causes a different user interface to be displayed via touch-sensitive display device 602, such as lab result record user interface 682 depicted in FIG. 6SA.

Figure 6S:
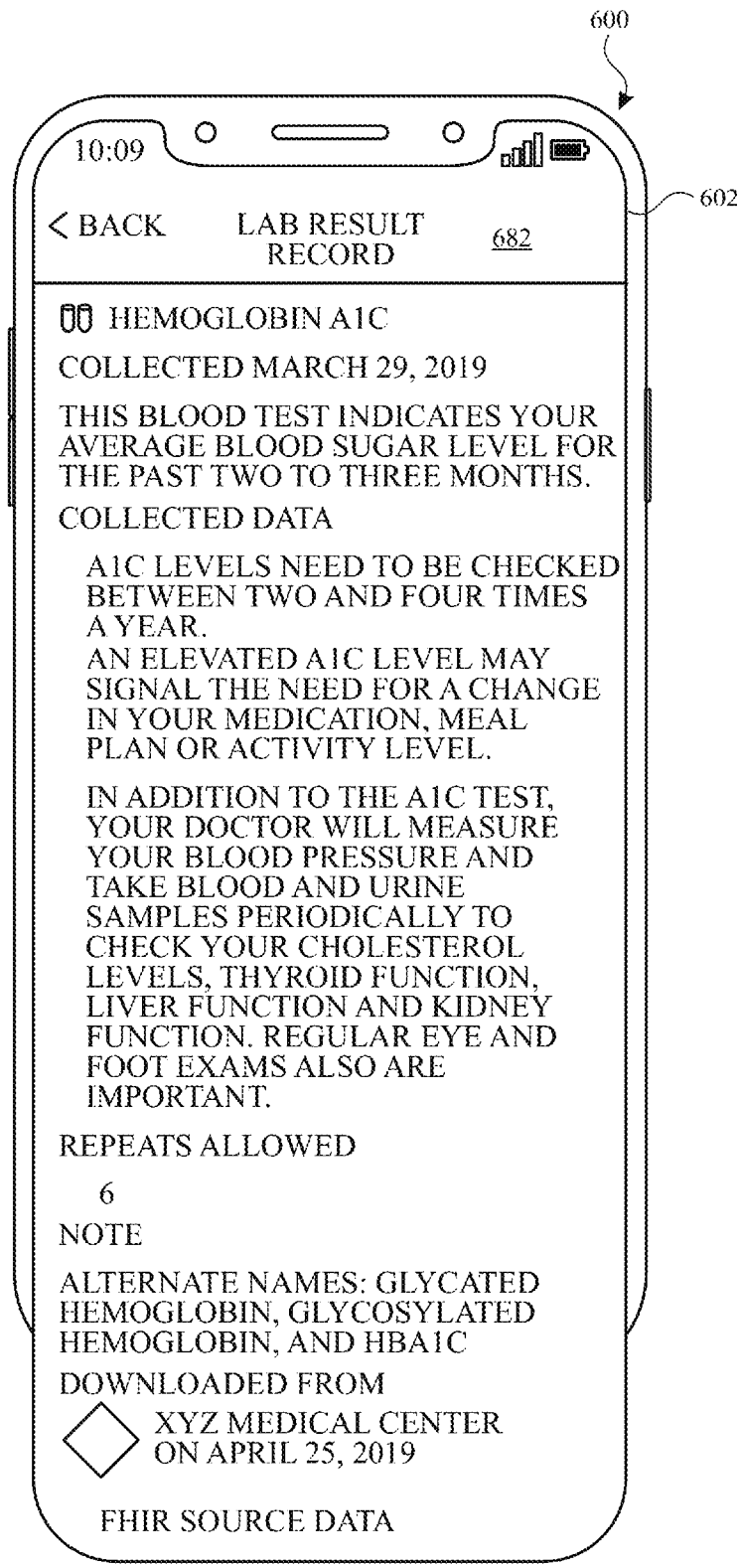
Figure 6S:
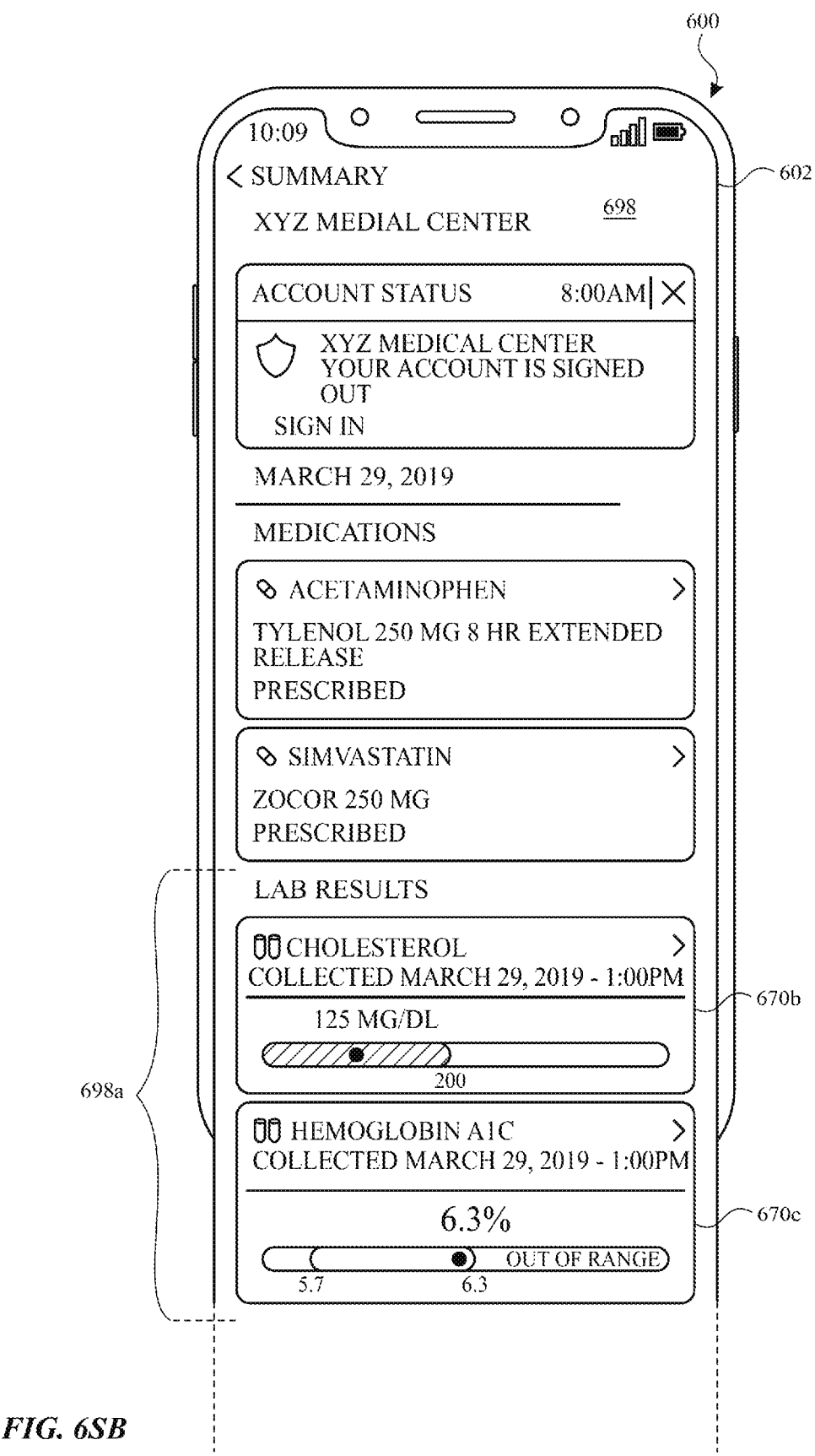
Figure 6S:
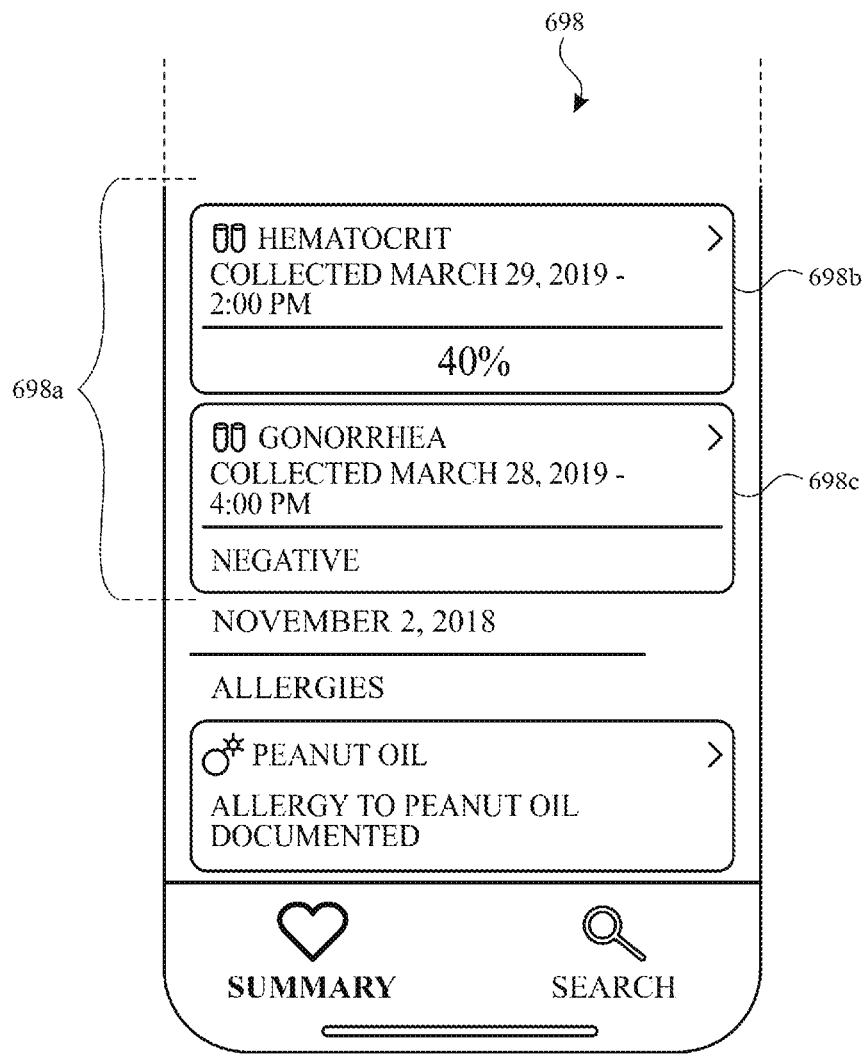
Figure 6T:
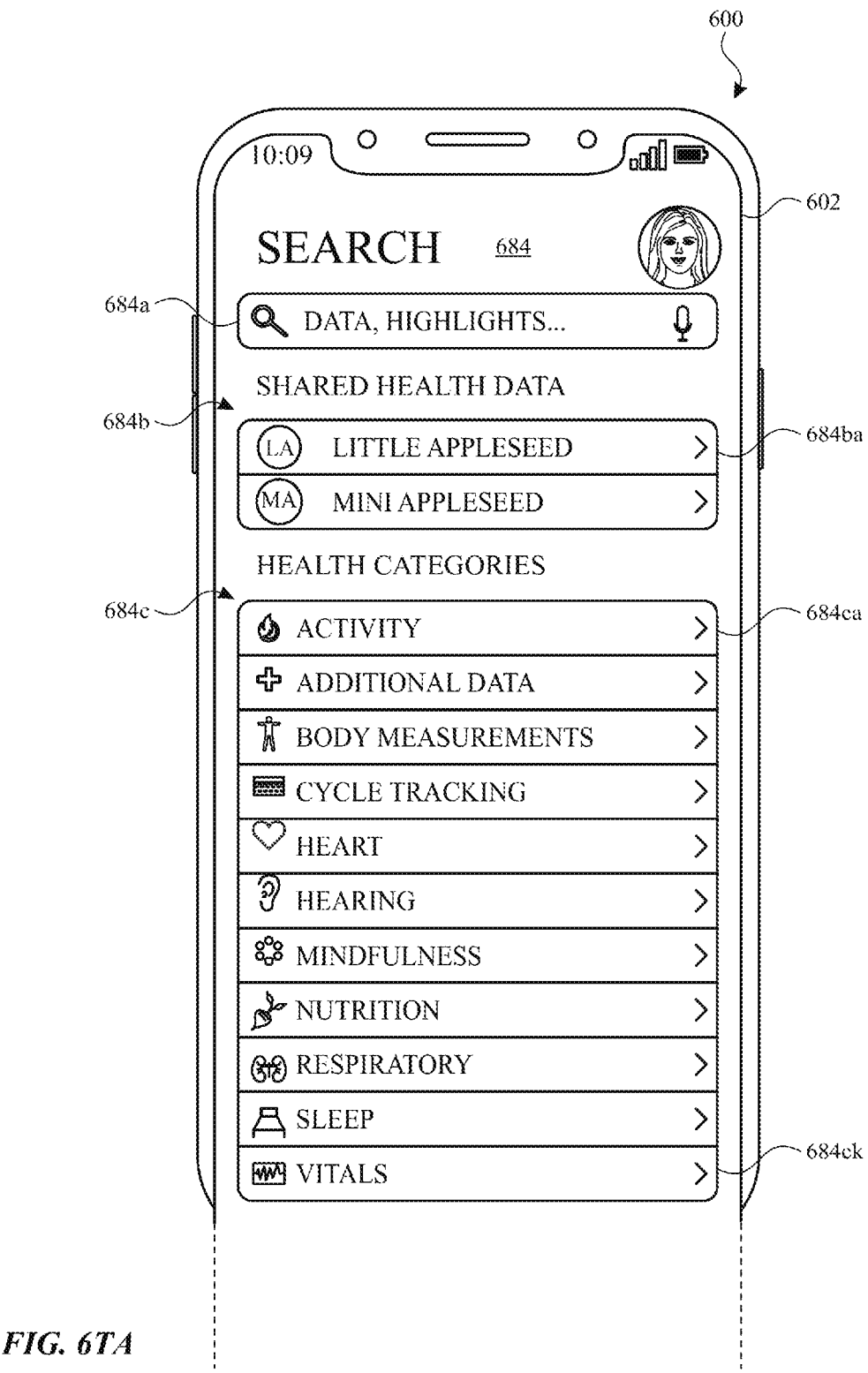
Figure 6T:
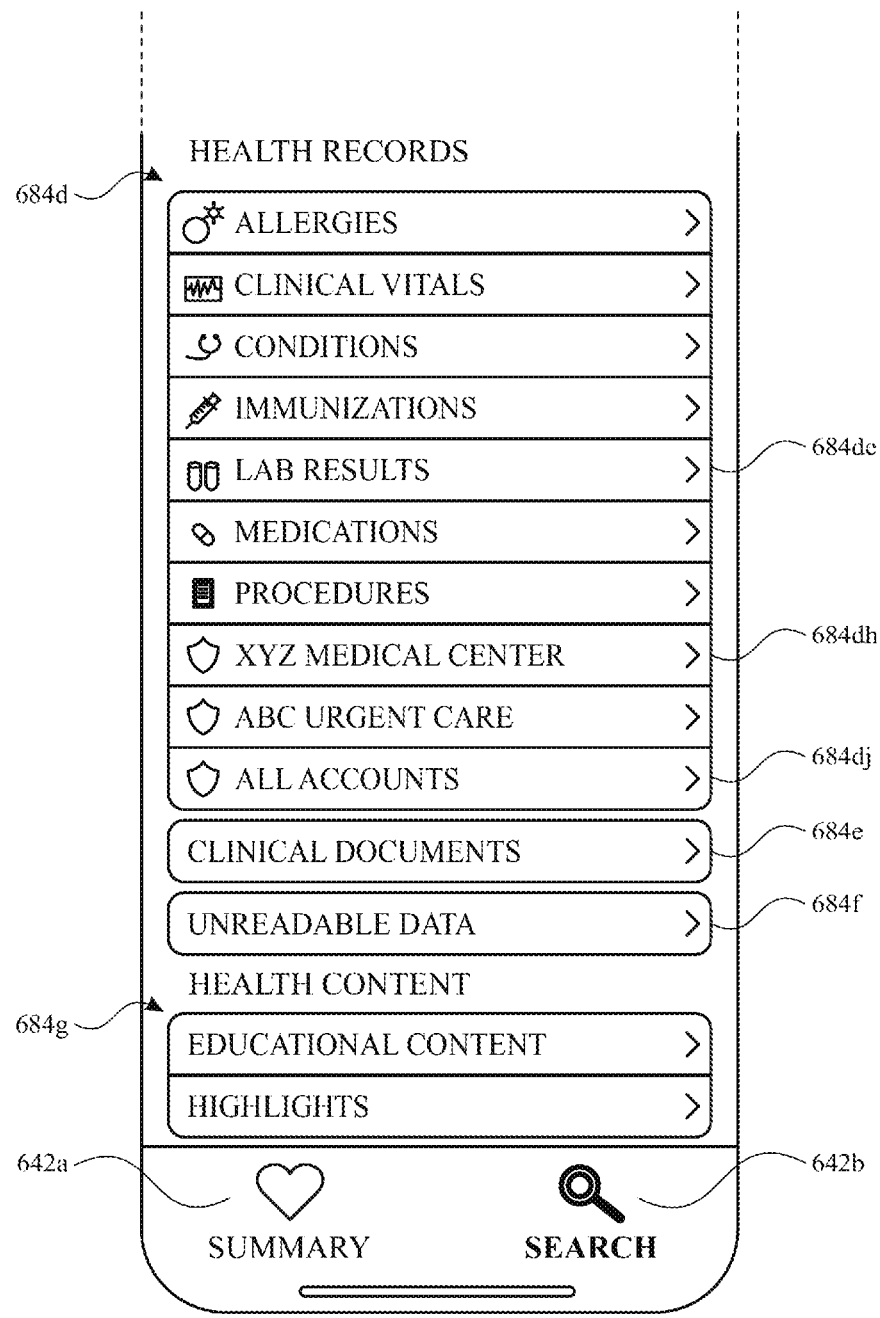

FIG. 6SA depicts first electronic device 600 displaying lab result record user interface 682 via touch-sensitive display device 602 at a nineteenth time after the eighteenth time. In some examples, lab result record user interface 682 is displayed in response to user input corresponding to selection of affordance 680a in hemoglobin user interface 676 as depicted in FIG. 6RA. In some examples, lab result record user interface 682 includes detailed information regarding a particular health record. In some examples, the detailed information includes a date when the particular health record was collected, a date when the particular health record was received by the health application, alternate names for the particular health record (e.g., as identified from either a remote source or other health records associated with the account of the health application), a clinical institution associated with the particular health record, and other information included in the particular health record.

FIGS. 6SB-6SC depict first electronic device 600 displaying XYZ medical center user interface 698 via touch-sensitive display device 602. In some examples, XYZ medical center user interface 698 is displayed in response to user input corresponding to selection of first health records affordance 636 in the health records region of summary user interface 614 as depicted in FIG. 6DC.

As depicted in FIGS. 6SB-6SC, XYZ medical center user interface 698 includes multiple regions (e.g., regions for different days), each region corresponding to a different date that health records within the region were generated (e.g., collected, taken, or otherwise created by a clinical institution). In some examples, the multiple regions are ordered by date, such that regions corresponding to more recent dates are before regions corresponding to later dates. For example, XYZ medical center user interface 698 includes a region corresponding to Mar. 29, 2019, (as depicted in FIG. 6SB) higher in a list than (e.g., before) a region corresponding to Nov. 2, 2018 (as depicted in FIG. 6SC).

In some examples, each region included in XYZ medical center user interface 698 includes one or more sub-regions, each sub-region corresponding to a different health records type (e.g., allergies, medications, etc.) within the sub-region. In some examples, multiple sub-regions are ordered alphabetically (e.g., allergies before medications) (not illustrated).

In some examples, each sub-region included in XYZ medical center user interface 698 includes one or more representations of health records. For example, sub-region 698a includes four representations of four separate health records, such as representation 670b (as also depicted and described in FIG. 6PA), representation 670c (as also depicted and described in FIG. 6PA), representation 698b (similar to 672b as depicted and described in FIG. 6PB, but from XYZ Medical Center instead of ABC Urgent Care), and representation 698c (similar to 672c as depicted and described in FIG. 6PB, but from XYZ Medical Center instead of ABC Urgent Care). FIGS. 6SB-6SC illustrate that some representations can include graphs while other representations do not include a graph, even representations corresponding to the same health record type. Such a result, in some examples, is due to some health records not including ranges and/or being binary values. While FIGS. 6SB-6SC depict a user interface for a single clinical institution, it should be recognized that similar techniques can be used for a user interface with representations for health records from multiple clinical institutions.

FIG. 6TA depicts first electronic device 600 displaying search user interface 684 via touch-sensitive display device 602 at a twentieth time after the nineteenth time. In some examples, search user interface 684 is displayed in response to user input corresponding to selection of search affordance 642b in any user interface of health application, such as summary user interface 614.

Figure 6U:
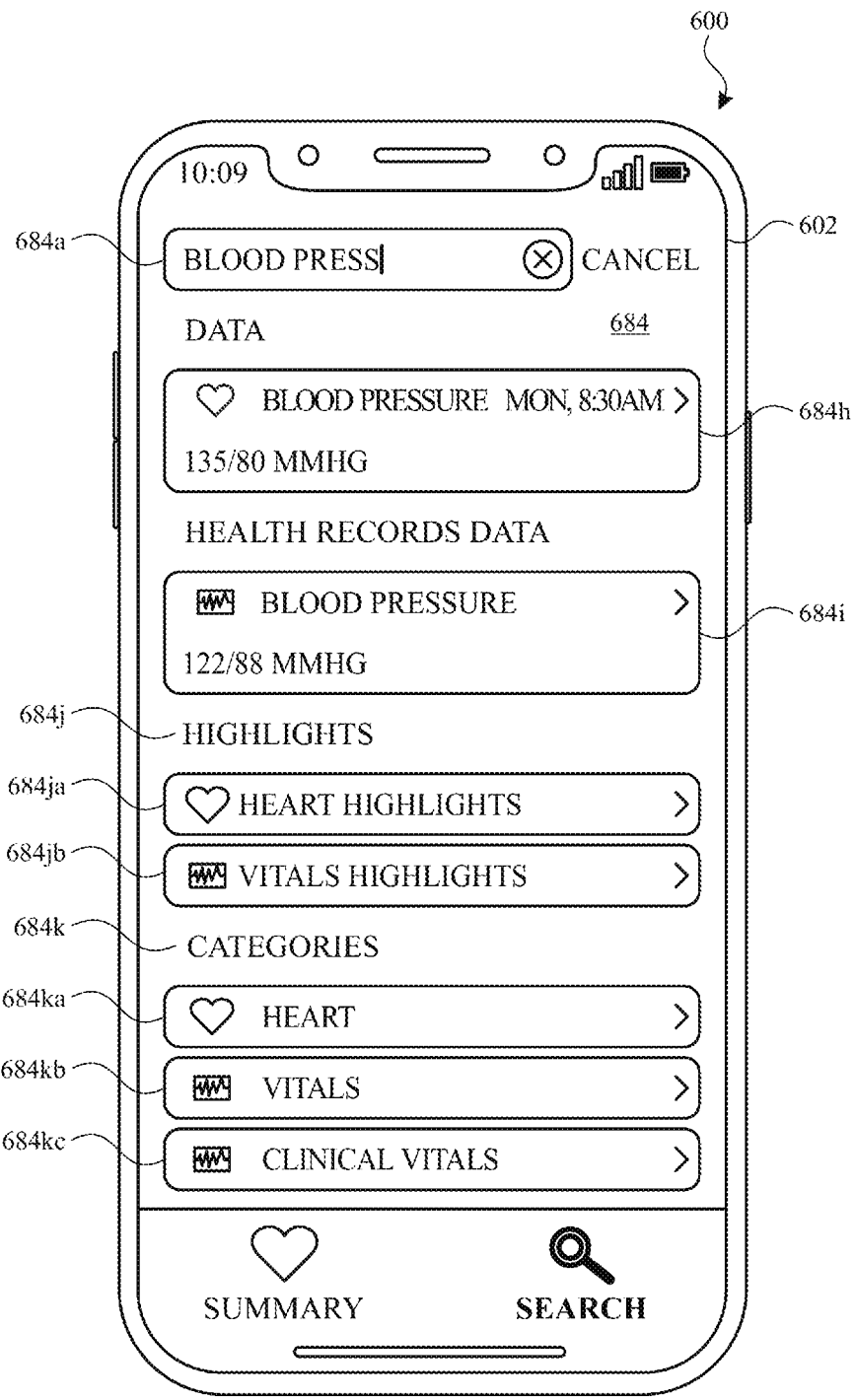

As depicted in FIG. 6TA, search user interface 684 includes search area 684a for inserting a search query to use to search the health application. For example, when first electronic device 600 receives user input corresponding to a string (e.g., a user types in a string using a keyboard) while focusing on search area 684a (e.g., an insertion marker is located within search area 684a) and a request to perform a search, first electronic device 600 searches data associated with the health application based on the string, as depicted in FIG. 6U and further discussed below.

As depicted in FIG. 6TA, search user interface 684 includes four groups of affordances: shared health data affordances 684b, health categories affordances 684c, health records affordances 684d, and health content affordances 684g. In some examples, search user interface 684 includes less groups of affordances, such as not including shared health data affordances 684b when first electronic device 600 is not receiving shared health data from another device.

In some examples, affordances of shared health data affordances 684b relate to other accounts for which are linked with the account associated with the health application. In one example, linking includes a connection between the two accounts such that health data recorded for one account is sent to the other account. For example, FIG. 6TA depicts that shared health data affordances 684b includes affordance 684ba. In some examples, affordance 684ba relates to an account associated with "Little Appleseed" such that selection of affordance 684ba causes display of a user interface for the account associated with "Little Appleseed" (e.g., a user interface allowing a user to view health data associated with the account associated with "Little Appleseed"), as depicted in FIG. 6XA and discussed below.

In some examples, affordances of health categories affordances 684c relate to categories of health data types. In particular, health categories affordances 684c represents a hierarchy of health data, allowing a user to navigate to particular health data through one or more user inputs. For example, health categories affordances 684c includes affordance 684ca corresponding to activity health data type (e.g., a type of health data corresponding to activity). In some examples, the activity health data type corresponds to health data stored by an activity application. For another example, health categories affordances 684c includes affordance 684ck corresponding to vitals health data type (e.g., a type of health data corresponding to vitals). In some examples, the vitals health data type corresponds to health data stored by a vitals application.

Figure 6V:
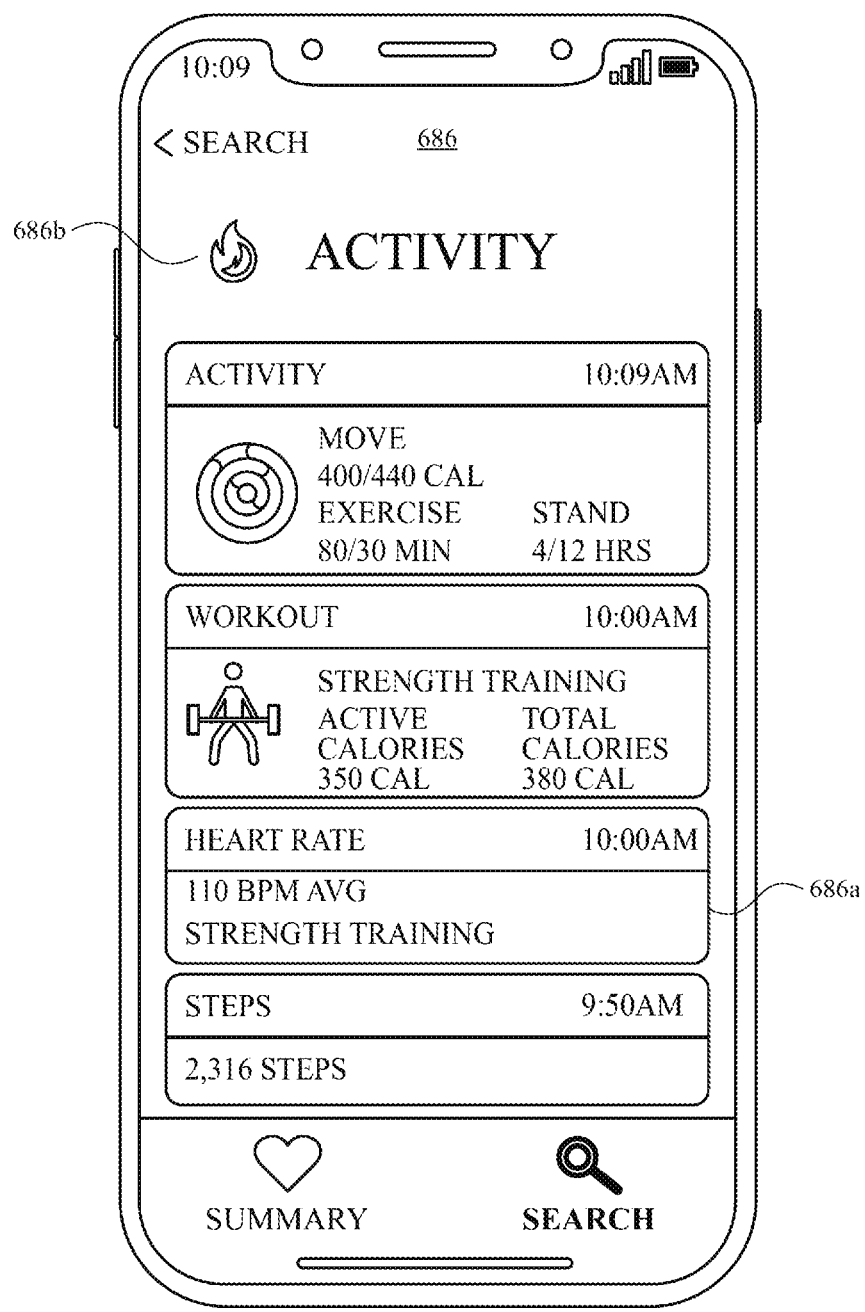
Figure 6W:
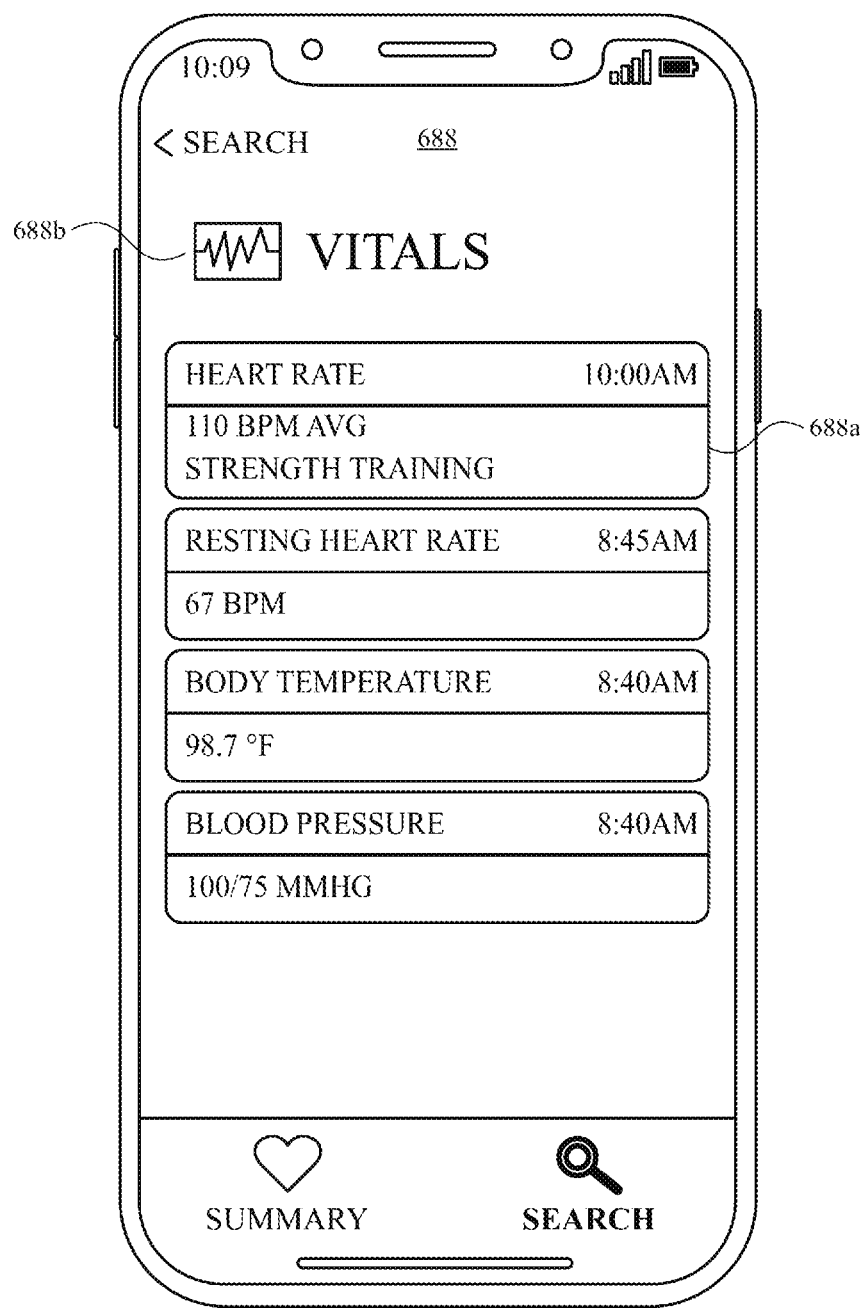
Figure 6X:
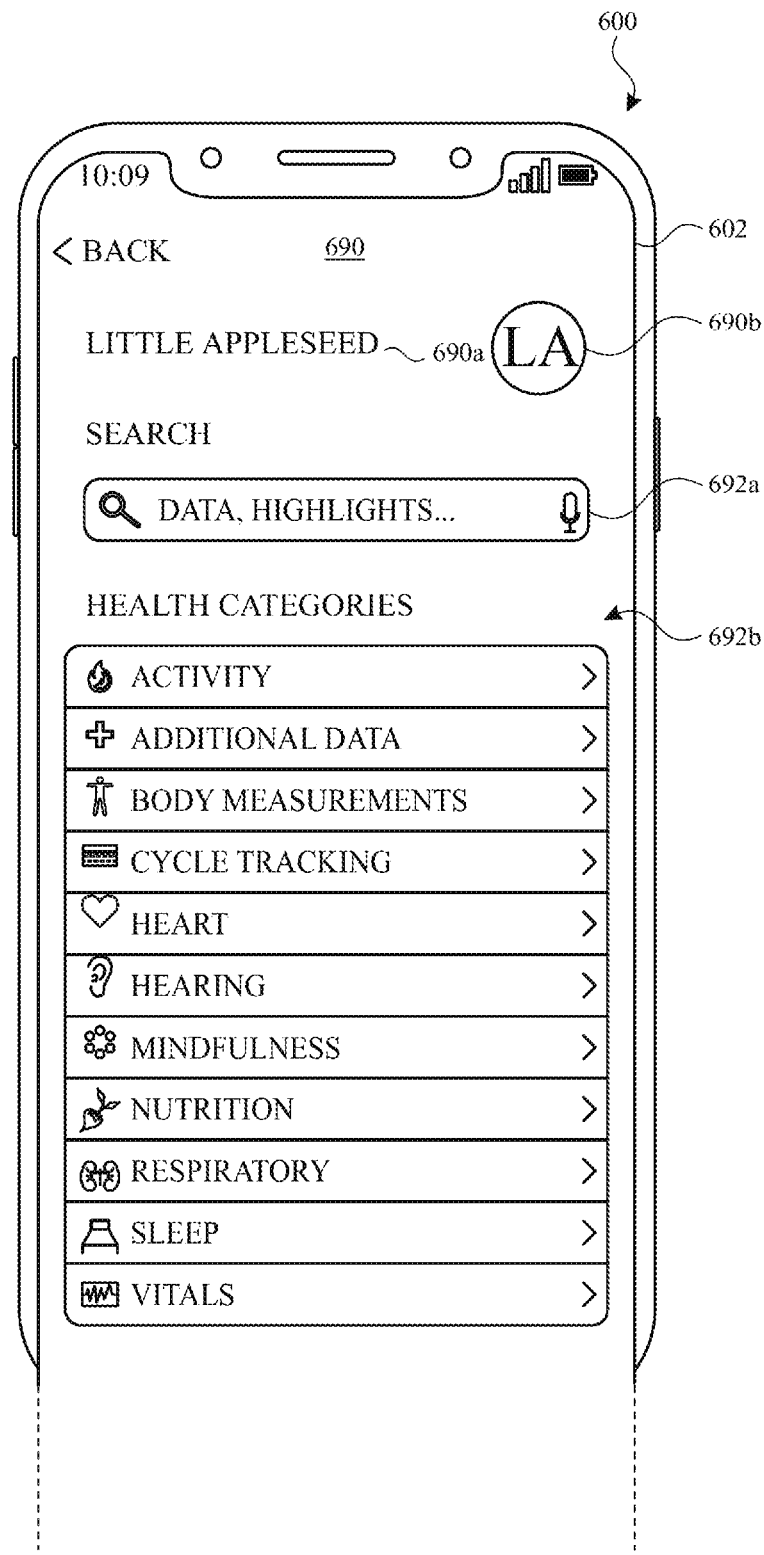
Figure 6X:
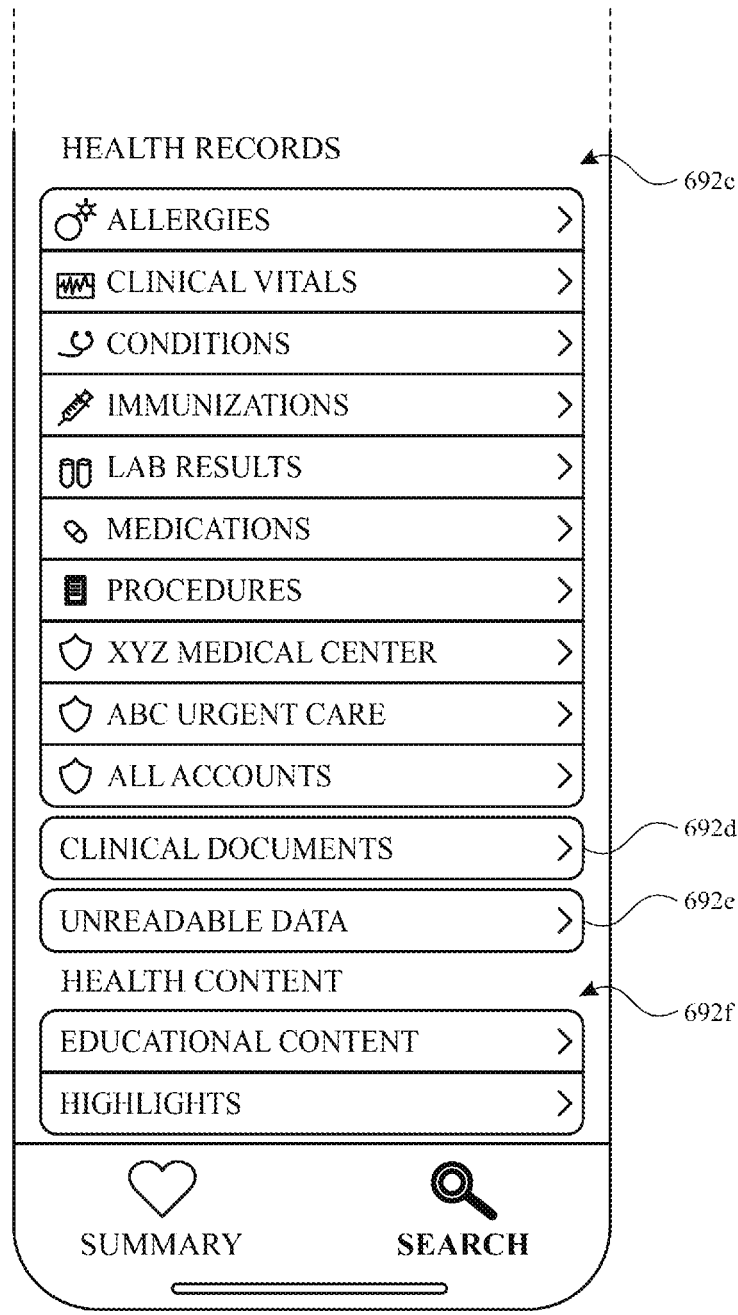

In some examples, selection of an affordance of health categories affordances 684c causes a user interface of the health application to be displayed, the user interface including health data associated with a respective health data type, as depicted in FIGS. 6V-6W and discussed below.

In some examples, affordances of health records affordances 684d relate to categories of health records, as discussed above. For example, health records affordances 684d represents a hierarchy of health records, allowing a user to navigate to a particular health record through one or more user inputs. For example, health records affordances 684d includes affordance 684de corresponding to lab results (e.g., a type of health record). In some examples, selection of affordance 684de causes a user interface to be displayed, the user interface including lab results health records. Health records affordances 684d also include affordances related to clinical institutions (e.g., affordance 684h). Selection of an affordance related to a clinical institution causes a user interface of the health application to be displayed, the user interface including heath records gathered by the clinical institution. Selection of an affordance related to all accounts (e.g., affordance 684dj) causes a user interface of the health application to be displayed, the user interface including all heath records.

As depicted in FIG. 6TB, search user interface 684 includes affordance 684e for viewing clinical documents. Selection of affordance 684e causes a user interface of the health application to be displayed, the user interface including clinical documents. As depicted in FIG. 6TB, search user interface 684 includes affordance 684f for viewing unreadable data (e.g., data that the health application (or a process related to the health application) is unable to parse (e.g., interpret or read). Selection of affordance 684f causes a user interface of the health application to be displayed, the user interface including representations of health records that were unable to be parsed by the health application (or a process related to the health application).

In some examples, affordances of health content affordances 684g relate to links to other health content. For example, health content affordances 684g includes an affordance to view educational content. Selection of such an affordance causes a user interface of the health application to be displayed, the user interface including educational content. For another example, health content affordances 684g includes an affordance to view highlights, which were discussed above. Selection of such an affordance causes a user interface of the health application to be displayed, the user interface including one or more highlight representations.

FIG. 6U depicts first electronic device 600 displaying search user interface 684 via touch-sensitive display device 602 at a twenty-first time after the twentieth time. In some examples, search user interface 684 (as depicted in FIG. 6U) is displayed in response to a user requesting to search for a string entered into search area 684a. For example, FIG. 6U depicts that a user has entered "BLOOD PRESS" into search area 684a, causing search results to be displayed corresponding to a search for "BLOOD PRESS" using the health application. In some examples, the user requesting to search for the string causes the search results to replace (e.g., cease to display) the four groups of affordances in search user interface 684 depicted in FIGS. 6TA-6TB.

In some examples, the search results include data from different sources. For example, first search result 684h includes health data (e.g., health data detected by first electronic device 600 or another device linked to either first electronic device 600 or the account associated with the health application). As depicted in FIG. 6U, first search result 684h includes a representation of blood pressure detected for a user associated with the account. For another example, second search result 684i includes health record data (e.g., health records received by first electronic device 600 from, for example, a clinical institution). As depicted in FIG. 6U, second search result 685i includes blood pressure that was included in a health record.

In some examples, the search results include categories of highlights determined to be related to the string. For example, FIG. 6U depicts that the search results include heart highlights affordance 685ja (e.g., an affordance related to highlights associated with the heart) and vitals highlights affordance 685jb (e.g., an affordance related to highlights associated with vitals). In some examples, selection of a highlight affordances causes a user interface of the health application to be displayed, the user interface including one or more highlight representations related to the respective category of highlights.

In some examples, the search results include categories of health data determined to be related to the string (684k). Such categories correspond to health categories affordances 684c discussed above. For example, FIG. 6U depicts that the search results include heart category affordance 684ka, vitals affordance 684kb, and clinical vitals affordance 684kc. The categories of health data represents a hierarchy of health records, allowing a user to navigate to a particular health record through one or more user inputs. For example, selection of an affordance corresponding to a category of health data causes a user interface to be displayed, the user interface including health records corresponding to the category.

FIG. 6V depicts first electronic device 600 displaying activity user interface 686 via touch-sensitive display device 602 at a twenty-second time after the twenty-first time. In some examples, activity user interface 686 is displayed in response to user input corresponding to selection of affordance 684ca in search user interface 684.

As depicted in FIG. 6V, activity user interface 686 includes representations of health data related to activity for the account associated with the health application. For example, activity user interface 686 includes representation 686a with heart rate data during strength training.

FIG. 6W depicts first electronic device 600 displaying vitals user interface 688 via touch-sensitive display device 602 at a twenty-third time after the twenty-second time. In some examples, vitals user interface 688 is displayed in response to user input corresponding to selection of affordance 684ck in search user interface 684.

As depicted in FIG. 6W, vitals user interface 688 includes representations of health data related to vitals for the account associated with the health application. For example, activity user interface 686 includes representation 688a with heart rate data during strength training. Representation 688a is an example that health data included in one category (e.g., vitals) can be included in another category (e.g., activity). Such a result is due to health data having multiple categories for which they are associated. For example, heart rate data during strength training, as depicted in FIGS. 6V-6W, is associated with both activity and vitals. In some examples, health data has a primary and a secondary health category.

FIGS. 6XA-6XB depict first electronic device 600 displaying child search user interface 690 via touch-sensitive display device 602 at a twenty-fourth time after the twenty-third time. In some examples, child search user interface 690 and user interfaces navigated from affordances included in child search user interface 690 are read-only (as compared to search user interface 684, which, in some examples, allows a user to add/remove/edit data when navigating to data associated with the account of the health application). In some examples, child search user interface 690 is displayed in response to user input corresponding to selection of affordance 684ba in search user interface 684.

In some examples, child search user interface 690 is a version of search user interface 684 for an account linked to the account associated with the health application. As depicted in FIGS. 6XA-6XB, child search user interface 690 includes search area 692a (similar to search area 684a in search user interface 684, except that search area 692a searches data corresponding to Little Appleseed instead of the account associated with the health application), health categories affordances 692b (similar to health categories affordances 684c in search user interface 684, except that health categories affordances 692b is associated with data corresponding to Little Appleseed instead of the account associated with the health application), health records affordances 692c (similar to health records affordances 684d in search user interface 684, except that health records affordances 692c is associated with data corresponding to Little Appleseed instead of the account associated with the health application), and health content affordances 692e (similar to health content affordances 684g in search user interface 684). In some examples, child search user interface 690 does not include shared health data affordances (e.g., shared health data affordances 684ba). In other examples, child search user interface 690 includes shared health data affordances for devices that are linked to Little Appleseed's account.

Figure 6Y:
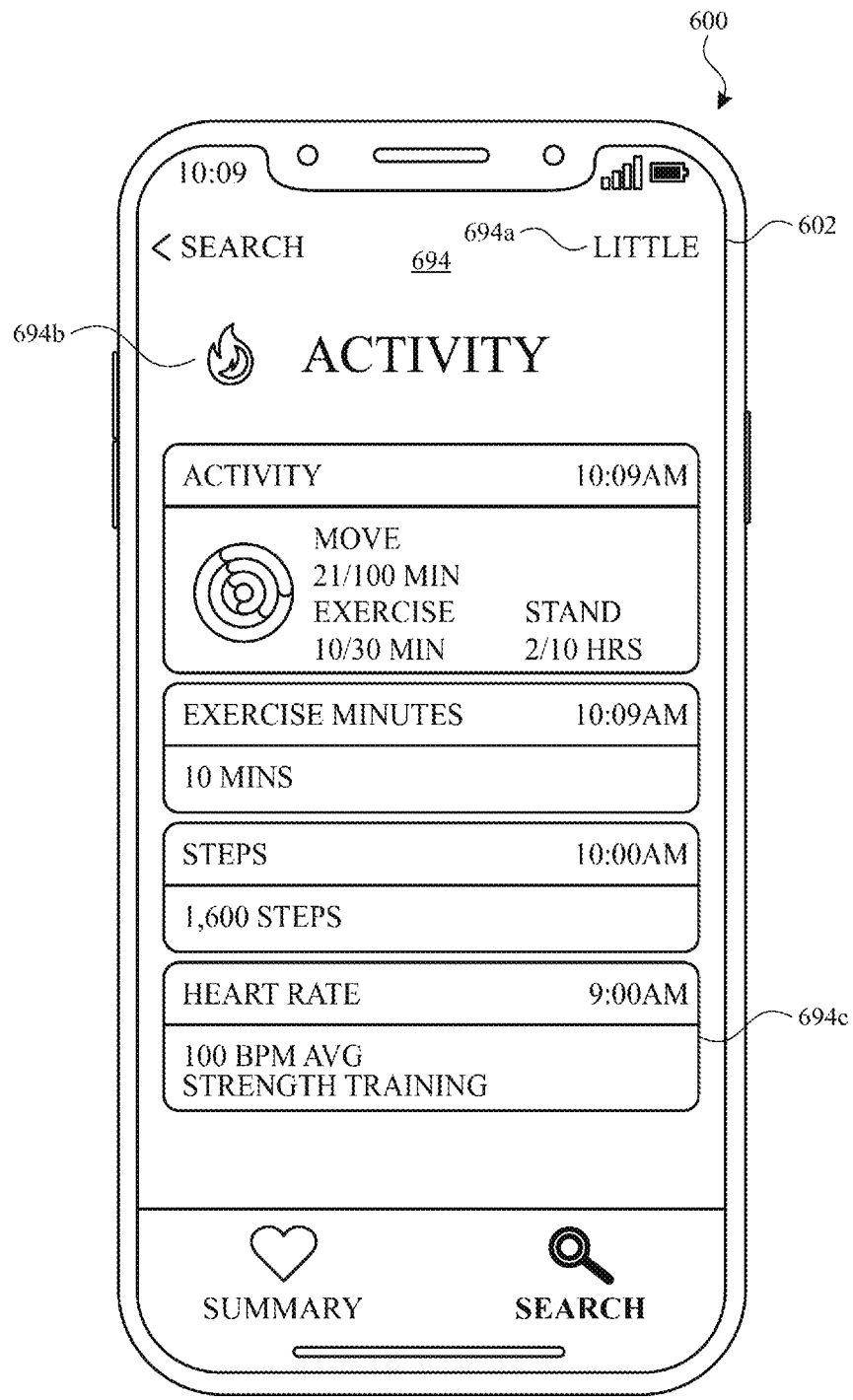

FIG. 6Y depicts first electronic device 600 displaying activity user interface 694 via touch-sensitive display device 602 at a twenty-fifth time after the twenty-fourth time. In some examples, activity user interface 694 is displayed in response to user input corresponding to selection of activity affordance in child search user interface 690.

As depicted in FIG. 6Y, activity user interface 694 includes representations of health data related to activity for Little Appleseed's account (e.g., as indicated by indication 694a). For example, activity user interface 694 includes representation 694c with heart rate data during strength training for Little Appleseed.

FIG. 6Z depicts first electronic device 600 displaying vitals user interface 696 via touch-sensitive display device 602 at a twenty-sixth time after the twenty-fifth time. In some examples, vitals user interface 696 is displayed in response to user input corresponding to selection of vitals affordance in child search user interface 690.

As depicted in FIG. 6Z, vitals user interface 696 includes representations of health data related to vitals for Little Appleseed's account (e.g., as indicated by indication 696a). For example, vitals user interface 696 includes representation 696c with heart rate data during strength training for Little Appleseed. Representation 696c is an example that health data included in one category (e.g., vitals) can be included in another category (e.g., activity). Such a result is due to health data having multiple categories for which they are associated. For example, heart rate data during strength training, as depicted in FIGS. 6Y-6Z, is associated with both activity and vitals. In some examples, health data has a primary and a secondary health category.

FIGS. 7A-7B are a flow diagram illustrating a method for managing notifications using an electronic device in accordance with some embodiments. Method 700 is performed at a device (e.g., 100, 300, 500, 600, 606) with a display device. Some operations in method 700 are, optionally, combined, the orders of some operations are, optionally, changed, and some operations are, optionally, omitted.

As described below, method 700 provides an intuitive way for managing notifications. The method reduces the cognitive burden on a user for viewing and acting on notifications, thereby creating a more efficient human-machine interface. For battery-operated computing devices, enabling a user to view and act on notifications faster and more efficiently conserves power and increases the time between battery charges.

The electronic device displays (702), via the display device, a first instance (e.g., 614, as depicted in FIG. 6DA) of a first user interface including a first notification (e.g., 616, 618, 620) (e.g., a notification affordance) that, when selected, causes display of a first set of data (e.g., 644) (e.g., notification data, data generated or received (e.g., from an external device) at a first time; health data; sensor data; biometric data; physical activity data; clinical data).

In some embodiments, the first notification includes a first visual property (704) (e.g., a color (e.g., depicted as pattern in header of 616, which includes 616b and 616c, pattern in header of 618, which includes 618a, 618b and 618c, and pattern in header of 620, which includes 620a, 620b, and 620c) (e.g., a foreground color, a background color, inclusion (or exclusion) of a respective icon). In some embodiments, in accordance with (706) a determination that the first set of data corresponds to (e.g., was generated by) a first application, the first visual property has a first value (e.g., blue). In some embodiments, in accordance with (708) a determination that the first set of data corresponds to a second application, the first visual property has a second value (e.g., red) different from the first value.

Specifying a visual quality (e.g., color) of a notification based on the corresponding application provides the user with feedback that helps identify the application. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

After displaying the first instance of the first user interface, the electronic device displays (710) (e.g., in response to an input corresponding to a request to display the first user interface) a second instance (e.g., 614, as depicted in FIG. 6G) of the first user interface.

In accordance with (712) a determination that a set of interaction criteria (a set of criteria relating to whether the first set of data has been interacted with (e.g., via selection of the first notification)) are met, the set of interaction criteria including a criterion that is met when the first set of data has been displayed (e.g., displayed in the first instance of the first user interface, displayed in a subsequent instance of the first user interface, displayed on the electronic device, displayed on a second electronic device that receives the same notifications as the electronic device (e.g., because both are associated with the same user account)), and in accordance with a determination that a first set of removal criteria (e.g., a set of criteria that govern display of a notification that corresponds to data that has been interacted with) are not met, the first set of removal criteria including a first criterion that is based on a first period of time (e.g., a period time that must be exceeded to meet the first criterion; a period of time determined from when the first set of data was received or generated; a period of time determined from when a notification corresponding to the first set of data was first displayed; a non-zero period of time), the second instance of the first user interface includes the first notification (FIG. 6G-6H).

In accordance with (714) a determination that the set of interaction criteria are met and in accordance with a determination that the first set of removal criteria are met, the second instance of the first user interface does not include the first notification (FIG. 6G-6H).

In accordance with (716) a determination that the set of interaction criteria are not met and in accordance with a determination that a second set of removal criteria (e.g., a set of criteria that govern display of a notification that corresponds to data that has not been interacted with) are not met, the second set of removal criteria including a second criterion that is based on a second period of time (e.g., a period time that must be exceeded to meet the second criterion; a period of time determined from when the first set of data was received or generated; a period of time determined from when a notification corresponding to the first set of data was first displayed) that is greater than the first period of time, the second instance of the first user interface includes the first notification (FIG. 6G-6H). In some embodiments, the second period of time is less than the first period of time.

In accordance with (718) a determination that the set of interaction criteria are not met and in accordance with a determination that the second set of removal criteria are met, the second instance of the first user interface does not include the first notification (FIG. 6G-6H). In some embodiments, a notification is displayed (or redisplayed) in a first user interface for a period of time that varies based on whether the notification has been interacted with. In some embodiments, a notification that has not been interacted with is displayed for a period of time that is greater than for a notification that has been interacted with.

Displaying the first notification based on whether the set of interaction criteria and the sets of removal criteria are met enables the user to view relevant notifications without providing unwanted notifications. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, prior to displaying the first instance of the first user interface, the electronic device receives, from an external device (e.g., a smart watch that includes one or more sensors (e.g., biometric sensors)), a second set of data, wherein the first set of data corresponds to the second set of data (e.g., 610). In some embodiments, the external device is in a paired relationship with the electronic device (e.g., both devices are associated with the same user account and have a persistent relationship). In some embodiments, the second set of data is the first set of data. In some embodiments, the second set of data is included in the first set of data. In some embodiments, the first set of data is derived from (e.g., calculated based on) the second set of data. In some embodiments, the second set of data is sensor data from one or more sensors of the external device. In some embodiments, the second set of data includes clinical health data (e.g., 604*b*) (e.g., medical records from a health institution; test results from a clinical testing lab).

In some embodiments, the electronic device includes a set of one or more sensors (e.g., biometric sensors). In some embodiments, prior to displaying the first instance of the first user interface, the electronic device receives (e.g., detecting), via the set of one or more sensors, a third set of data (e.g., 604*a*). In some embodiments, the first set of data corresponds to the third set of data. In some embodiments, the third set of data is the first set of data. In some embodiments, the third set of data is included in the first set of data. In some embodiments, the first set of data is derived from (e.g., calculated based on) the third set of data. In some embodiments, prior to displaying the first instance of the first user interface, the electronic device displays a second user interface (e.g., any user interface other than the summary tab of the health application, such as a lock screen) including a second notification corresponding to the third set of data. In some embodiments, the second user interface is different from the first user interface. In some embodiments, the second notification includes the same content as the first notification.

In some embodiments, the first notification is included in a first list of notifications. In some embodiments, the first list of notifications is ordered based on chronological or reverse chronological order (e.g., based on an initial notification issuance time; based on a time when data that is displayed when a respective notification is selected was generated or received) (e.g., FIG. 6DA).

Ordering the first list based on chronological or reverse chronological order structures provides the user with feedback about the sequence in which the notifications were generated. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the first notification (e.g., in the first instance or the second instance of the first user interface), the electronic device receives a first input (e.g., 615) corresponding to selection of the first notification. In some embodiments, in response to receiving the first input, the electronic device displays, via the first display device, a second user interface (e.g., 644) (e.g., that includes the first set of data. In some embodiments, the first set of data corresponds to a first application and the second user interface includes additional data and/or information from the first application.

In some embodiments, the first set of data corresponds to a first data type (e.g., biometric data, sensor data). In some embodiments, the second user interface includes: a first affordance that, when selected, causes display of a first value (e.g., a first average) of the first data type; and a second affordance that, when selected, causes display of a second value (e.g., a second average that based on a different filter (e.g., a time filter, a source filter) than the first average) of the first data type that is different from the first value (e.g., average and daily average affordances in 644).

Note that details of the processes described above with respect to method 700 (e.g., FIGS. 7A-7B) are also applicable in an analogous manner to the methods described below/above. For example, methods 800, 900, 1000, 1100, and 1400 optionally include one or more of the characteristics of the various methods described above with reference to method 700. For brevity, these details are not repeated below.

FIGS. 8A-8B are a flow diagram illustrating a method for managing display of health-related information using an electronic device in accordance with some embodiments. Method 800 is performed at a device (e.g., 100, 300, 500, 600) with a display device. Some operations in method 800 are, optionally, combined, the orders of some operations are, optionally, changed, and some operations are, optionally, omitted.

As described below, method 800 provides an intuitive way for managing display of health-related information. The method reduces the cognitive burden on a user for viewing health-related information, thereby creating a more efficient human-machine interface. For battery-operated computing devices, enabling a user to view health-related information faster and more efficiently conserves power and increases the time between battery charges.

The electronic device receives (802) first health data (e.g., physical activity performed by a user; data detected via one or more biometric sensors) (e.g., see 626*b*). In some embodiments, the first health data is received over a period of time. In some embodiments, the first health data is received together, as a set.

The electronic device receives (804) a request (e.g., 613) (e.g., a request to view a summary tab of a health application, such as a user tapping on an icon for the health application or a user tapping on an affordance for the summary tab) to display a first user interface (e.g., 614).

In response to receiving the request, the electronic device displays (806), via the display device, the first user interface (e.g., 614) including a first region (e.g., the favorites region in 614) (808) (e.g., favorites section). The first user region, in accordance with (812) a determination that a type of data (e.g., activity, environmental noise, etc.) corresponding to the first health data has been identified by user input (e.g., a user has favorited the type of data), includes a first representation (e.g., 626*a*) of the first health data (e.g., a number of steps made during a current day). The first user region, in accordance with (814) a determination that the type of data corresponding to the first health data has not been identified by user input (e.g., the user has not favorited the type of data), does not include the representation of the first health data.

In response to receiving the request, the electronic device displays (806), via the display device, the first user interface including a second region (e.g., the highlights region in 614) (810) (e.g., highlights section). The second region, in accordance with (816) a determination that a first set of highlight criteria are met (e.g., a system determines that the representation corresponding to the health data should be displayed to a user), includes a second representation (e.g., 630, 632 652, 654, 656, 658, 660, 662) of the first health data different from the first representation (e.g., a graphical representation comparing health data for a first health metric over a first time period with health data for the first health metric over a second time period different from the first time period). In some embodiments, representations that are displayed in the second region are not user-customizable/user-selectable. In some embodiments, representations that are displayed in the second region include a comparison of the health data to health data that corresponds to a different period of time than the period time of the health data. The second region, in accordance with (818) a determination that the first set of highlight criteria are not met (e.g., a system determines that the representation corresponding to the health data should not be displayed to a user), does not include the second representation of the first health data.

Including the second representation of the first health data based on the first set of highlight criteria being met enables the device to display relevant information and to avoid using display space when the information is not relevant. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the health data includes health data for a first plurality of time periods (e.g., days, weeks, months). In some embodiments, the first representation of the health data includes: a first indication (e.g., a text indication, a graphical indication; an indication of a first metric (e.g., steps, miles, calories)) of the health data corresponding to a first time period (e.g., today) of the first plurality of time periods; and a second indication (e.g., a text indication, a graphical indication) of the health data corresponding to a second time period (e.g., yesterday) of the first plurality of time periods that is different from the first time period. In some embodiments, the first representation includes a bar graph having values for today compared to values for yesterday (e.g., 632).

Providing different indications for different time periods provides the user with feedback about the stored data that corresponds to the respective time periods. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first time period of the first plurality of time periods corresponds to a specific instance of a recurring time interval (e.g., specific hours of a day, specific day in a week or a month). In some embodiments, the second time period of the first plurality of time periods is a plurality of instances. In some embodiments, all of the instances of the recurring time interval available in the health data) of the recurring time interval (e.g., multiple Mondays of weeks; multiple mornings of days). In some embodiments, the first indication is a value of a health metric for the Mondays of a week and the second indication is an average value of the health metric for all Mondays (e.g., 662).

In some embodiments, the health data includes health data for a second plurality of time periods (e.g., days, weeks, months). In some embodiments, the first representation of the health data includes a third indication of the health data corresponding to the frequency (e.g., as a ratio, as a percentage, as a fraction (e.g., 4 days out of the last week)) of the occurrence of a first health event (e.g., a health-related event) within the second plurality of time periods (e.g., a day, a week, a year) (e.g., 654).

In some embodiments, the health data includes health data for a third plurality of time periods (e.g., days, weeks, months). In some embodiments, the first representation of the health data includes: a fourth indication of an average value of the health data for the third plurality of time periods (e.g., an average for the week); a fifth indication corresponding to the value of the health data for a first time period of the third plurality of time periods (e.g., a day within the week); and a sixth indication corresponding to the value of the health data for a second time period of the third plurality of time periods (e.g., a day within the week) that is different from the first time period of the plurality of time periods (e.g., 652).

In some embodiments, the first representation includes a seventh indication corresponding to a first physical activity tracking session (e.g., a first workout). In some embodiments, the first representation includes an eighth indication corresponding to a second physical activity tracking session. In some embodiments, the first and second physical activity tracking sessions are different types of workouts (e.g., running and swimming). In some embodiments, the first physical activity tracking session and the second physical activity tracking session correspond to the same time period (e.g., same day, same week, same month). In some embodiments, a ninth indication of the health data (e.g., total calories burned, an average pace) that is based on the first physical activity tracking session and the second physical activity tracking session (e.g., 658).

Displaying an indication of the health data that is based on the first and second physical activity tracking sessions provides the user with feedback, using the indication, about both the sessions. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first set of highlight criteria includes a criterion that is based on a factor selected from the group consisting of: a relationship (e.g., a mathematical relationship (e.g., a difference)) between a first portion (e.g., a portion corresponding to a first time period (e.g., a day)) of the health data and a second portion (e.g., a portion corresponding to a second time period (e.g., a week)) of the health data, a degree of user interaction with the health data, and a duration of time in which a representation (e.g., any representation) of the health data has been displayed (e.g., on the electronic device).

In some embodiments, the first representation is included in a first list of representation. In some embodiments, the first list of representations is ordered based on the types of data of the health data (e.g., physical activity data is grouped together; heart-related data is grouped together) (e.g., 660).

Note that details of the processes described above with respect to method 800 (e.g., FIGS. 8A-8B) are also applicable in an analogous manner to the methods described below/above. For example, methods 700, 900, 1000, 1100, and 1400 optionally include one or more of the characteristics of the various methods described above with reference to method 800. For brevity, these details are not repeated below.

FIGS. 9A-9B is a flow diagram illustrating a method for managing display of clinical health record representations using an electronic device in accordance with some embodiments. Method 900 is performed at a device (e.g., 100, 300, 500, 600, 606) with a display device. Some operations in method 900 are, optionally, combined, the orders of some operations are, optionally, changed, and some operations are, optionally, omitted.

As described below, method 900 provides an intuitive way for managing display of clinical health record representations. The method reduces the cognitive burden on a user for accessing clinical health records, thereby creating a more efficient human-machine interface. For battery-operated computing devices, enabling a user to access clinical health records faster and more efficiently conserves power and increases the time between battery charges.

The electronic device receives (902) clinical health record data corresponding to a particular health institution (e.g., 672*a*, XYZ Medical Center in 698). The electronic device receives (904) a request (e.g., 667, tap first health records affordance 636 in summary user interface 614) (e.g., a request to view all clinical health records for XYZ Medical Center) to display a first user interface (e.g., 668, 698).

In response to receiving the request, the electronic device displays (906), via the display device, the first user interface (e.g., 668, 698). The first user interface includes a first region (e.g., 672, 698*a*) (908) corresponding to a first type of clinical health record (e.g., 668*b*, 698*a*, a lab results region). The first region includes, in accordance with (912) a determination that a first clinical health record of the first type of clinical health record fails to meet a first set of graphing criteria (e.g., the first clinical health record either (1) does not include a range for the first clinical health record or (2) includes binary information (which, in some examples, does not achieve benefit from graphing)), a first textual representation (e.g., 672*b*, 672*c*, 698*b*, 698*c*) for the first clinical health record based on the clinical health record data, wherein the first user interface does not include a graphical representation (e.g., a non-textual graphical representation) for the first clinical health record. The first region includes, in accordance with (914) a determination that the first clinical health meets the first set of graphing criteria (e.g., the first clinical health record includes a range for the first clinical health record and includes non-binary information (which, in some examples, achieves benefit from graphing)), a first graphical representation (e.g., 672*d* in 668) (e.g., 670*b* and 670*c* in 698) for the first clinical health record based on the clinical health record data.

In response to receiving the request, the electronic device displays (906), via the display device, the first user interface including a second region (e.g., a different date range in 668, the medications region in 698) (910) corresponding to a second type of clinical health record (e.g., medications region). The second region includes, in accordance with (916) a determination that a second clinical health record of the second type of clinical health record fails to meet the first set of graphing criteria (e.g., the second clinical health record either (1) does not include a range for the second clinical health record or (2) includes binary information (which, in some examples, does not achieve benefit from graphing)), a second textual representation for the second clinical health record based on the clinical health record data, wherein the user interface does not include a graphical representation for the second clinical health record. The second reason includes, in accordance with (918) a determination that the second clinical health record meets the first set of graphing criteria (e.g., the second clinical health record includes a range for the second clinical health record and includes non-binary information (which, in some examples, achieves benefit from graphing)), a second graphical representation for the second clinical health record based on the clinical health record data.

Displaying textual representations or graphical representations for health records provides the user with feedback about whether the health record meets the graphing criteria and enables the user to more quickly and efficient access information related to the record. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first set of graphing criteria are met (e.g., the first set of graphing criteria includes a criterion that is met when the clinic health record includes a range for the clinical health record) for a respective clinical health record when the respective clinical health record (e.g., the first clinical health record) corresponds to health data that includes a range of data (e.g., a minimum and maximum value that defines a range, where a data value corresponding to the respective clinical health record is considered to meet particular criteria (e.g., criteria related to whether the data value is acceptable, such as criteria set by a governing body)) (e.g., 670*b*, 670*c*).

In some embodiments, the first set of graphing criteria are not met (e.g., the first set of graphing criteria includes a criterion that is met when the clinic health record includes non-binary numeric data) for a respective clinical health record when the respective clinical health record (e.g., the first clinical health record) corresponds to health data that is binary (e.g., having binary states (positive or negative; up or down; prescribed or not prescribed)) (e.g., 698*c*).

In some embodiments, the first region includes a plurality of representations (e.g., textual representations) of clinical health records. In some embodiments, the plurality of representations is ordered primarily by a date (e.g., chronological by the date, reverse chronologically by the date) and secondarily by a health record type associated with each clinical health record of each representation of the plurality of representations. In some embodiments, record types include medications, lab results, symptoms, ailments, treatments.

Ordering the representations by date first, then by health record type provides the user with feedback about the corresponding date order of the records and the type of record. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first region includes a second plurality of representations (e.g., textual representations) of clinical health records. In some embodiments, the second plurality of representations is ordered primarily by a health record type and secondarily by a date (e.g., chronological by the date, reverse chronologically by the date) associated with each clinical health record of each representation of the second plurality of representations. In some embodiments, health record types include medications, lab results, symptoms, ailments, treatments.

Ordering the representations by health record type first, then by date provides the user with feedback about the corresponding type of record and the date order of the records. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first region includes a third plurality of representations (e.g., textual representations) of clinical health records that each correspond to a clinical health record that is associated with a first date (e.g., a date of when the record was received (e.g., received by the electronic device)) and a second date (e.g., a date corresponding to a health event (e.g., when a test was performed, when a prescription was written) of the clinical health record) different from the first date. In some embodiments, the third plurality of representations is ordered by, in accordance with a determination that the first user interface is a user interface of a first interface type (e.g., a summary user interface), the first date. In some embodiments, the third plurality of representations is ordered by, in accordance with a determination that the first user interface is a user interface of a second interface type (e.g., a user interface for a specific type of health data) different from the first interface type, the second date.

Note that details of the processes described above with respect to method 900 (e.g., FIGS. 9A-9B) are also applicable in an analogous manner to the methods described below/above. For example, methods 700, 800, 1000, 1100, and 1400 optionally include one or more of the characteristics of the various methods described above with reference to method 900. For brevity, these details are not repeated below.

FIGS. 10A-10B is a flow diagram illustrating a method for managing display of clinical health record representations using an electronic device in accordance with some embodiments. Method 1000 is performed at a device (e.g., 100, 300, 500, 600) with a display device. Some operations in method 1000 are, optionally, combined, the orders of some operations are, optionally, changed, and some operations are, optionally, omitted.

As described below, method 1000 provides an intuitive way for managing display of clinical health record representations. The method reduces the cognitive burden on a user for accessing clinical health record, thereby creating a more efficient human-machine interface. For battery-operated computing devices, enabling a user to access clinical health record faster and more efficiently conserves power and increases the time between battery charges.

The electronic device receives (1002) clinical health record data, including: first clinical health record data corresponding to a first type of clinical health record (e.g., medication); and second clinical health record data corresponding to a second type of clinical health record (e.g., lab results) (e.g., 668). The electronic device receives (1004) a request (e.g., a request (e.g., 667, to view all clinical health records for a health record type) to display a first user interface (e.g., 668).

In response to receiving the request, the electronic device displays (1006), via the display device, the first user interface (e.g., 668), including a first representation (e.g., 674c), based on the first clinical health record data, for a first clinical health record of the first type of clinical health record (e.g., an Acetaminophen health record (where the type of clinical health record is a medicine)).

While displaying the first user interface, the electronic device receives (1008) first user input (e.g., 675) corresponding to selection of the first representation.

In response to receiving the first user input, the electronic device displays (1010), via the display device, a second user interface (e.g., 676) (e.g., an Acetaminophen user interface with representations for different health records corresponding to Acetaminophen). The second user interface includes a second representation (e.g., 680a) (1012), based on the first clinical health record data, for the first clinical health record of the first type of clinical health record, wherein the second representation is different from the first representation (e.g., a more-detailed representation for the Acetaminophen health record). The second user interface includes a third representation (e.g., 680b) (1014), based on the first clinical health record data, for a second clinical health record of the first type of clinical health record, wherein the third representation is different from the second representation and the second clinical health record of the first type is different from the first clinical health record (e.g., a more-detailed representation of another Acetaminophen health record) of the first type.

While displaying the second user interface, the electronic device receives (1016) second user input (e.g., 681) corresponding to selection of the third representation.

In response to receiving the second user input, the electronic device displays (1018), via the display device, a third user interface (e.g., 682) (e.g., an Acetaminophen user interface with a detailed representation for a particular Acetaminophen record), including a fourth representation, based on the first clinical health record data, for the first clinical health record of the first type of clinical health record (e.g., a most-detailed representation for the Acetaminophen health record), wherein the fourth representation is different from the first representation, and wherein the fourth representation is different from the second representation.

In some embodiments, the request to display the first user interface is received while displaying, via the display device, a fourth user interface (e.g., FIG. 12AA) that includes a fifth representation, based on the second clinical health record data, for a second clinical health record of the second type of clinical health record (e.g., a Cholesterol health record (where the type of clinical health record is a lab result)).

In some embodiments, the fourth user interface includes a plurality of representations (e.g., representations of clinical health records of the first type and/or second type) of clinical health records. In some embodiments, the plurality of representations is ordered primarily by a date (e.g., chronological by the date, reverse chronologically by the date) and secondarily by a health record type associated with each clinical health record of each representation of the plurality of representations. In some embodiments, health record types include medications, lab results, symptoms, ailments, treatments.

Ordering the representations by date first, then by health record type provides the user with feedback about the corresponding date order of the records and the type of record. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second user interface includes a second plurality of representations (e.g., representations of clinical health records of the first type and/or second type) of clinical health records. In some embodiments, the second plurality of representations ordered by a date (e.g., chronological by the date, reverse chronologically by the date).

Ordering the representations by health record type first, then by date provides the user with feedback about the corresponding type of record and the date order of the records. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a first set of graphic criteria is met, the first representation includes a graphical indication of the first clinical health record (e.g., a graph of the health data in the clinical health record). In some embodiments, the first set of graphic criteria are met when the clinical health record includes non-binary numeric data (e.g., data sufficient to provide a multi-point graph). In some embodiments, in accordance with the first set of graphic criteria not being met, the first representation does not include the graphical indication of the first clinical health record (e.g., a graph of the health data in the clinical health record). In some embodiments, the first set of graphic criteria are met when the clinical health record includes non-binary numeric data (e.g., data sufficient to provide a multi-point graph).

In some embodiments, the first representation includes a first detail (e.g., first information, first piece of data, within the record) of the first clinical health record. In some embodiments, the second representation includes the first detail and a second detail, different from the first detail, of the first clinical health record. In some embodiments, the fourth representation includes the first detail, the second detail, and a third detail, different from the first and second details, of the first clinical health record. In some embodiments, the representation of the first clinical health record becomes progressive more detailed, as the hierarchy of the user interface is traversed.

In some embodiments, the second user interface includes a graphical representation (e.g., a graph) of a first portion (e.g., a portion corresponding to a first time period) of the first clinical health record data. In some embodiments, the graphical representation includes an indication of a relationship (e.g., a comparison) between a first sub-portion of the first clinical health record data and a second sub-portion of the first clinical health record data.

In some embodiments, the second user interface includes a first affordance. In some embodiments, the electronic device receives an input corresponding to selection of the first affordance. In some embodiments, in response to receiving the input corresponding to selection of the first affordance, the electronic device visually distinguishes (e.g., emphasizing, highlighting, deemphasizing) a portion of the graphical representation that corresponds to a first sub-portion of the first portion of the first clinical health record data that matches a first filter condition (e.g., a filter that identifies data that falls outside of a clinical range (e.g., a healthy range) for the first clinical health record data).

Visually distinguishing a portion of the graphical representation that corresponds to an aspect that matches a first filter condition provides the user with feedback that the first filter condition has been matched. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first clinical health record of the first type of clinical health record was received from (e.g., was sourced from, was generated by) a first data source (e.g., data supplier; a clinical health data source (e.g., a clinician)). In some embodiments, the second clinical health record of the first type of clinical health record was received from a second data source that is different from the first data source.

In some embodiments, the fourth representation includes an indication of a data source (e.g., data provider) of the first clinical health record. In some embodiments, the fourth representation includes an indication of a primary identifier (e.g., a primary name, such as Hemoglobin A1c) of the first type of clinical health record and a secondary identifier (e.g., secondary or alternative name, such as Gylcated Hemoglobin, Glycosylated Hemoglobin, and HbA1c) of the first type of clinical health record. In some embodiments, the fourth representation includes an indication of a first date corresponding to when the first clinical health record was received by the electronic device and an indication of a second date corresponding to when the first clinical health record was created (e.g., created by the electronic device or externally).

Note that details of the processes described above with respect to method 1000 (e.g., FIGS. 10A-10B) are also applicable in an analogous manner to the methods described below/above. For example, methods 700, 800, 900, 1100, and 1400 optionally include one or more of the characteristics of the various methods described above with reference to method 1000. For brevity, these details are not repeated below.

FIGS. 11A-11C is a flow diagram illustrating a method for display of health-related information using an electronic device in accordance with some embodiments. Method 1100 is performed at a device (e.g., 100, 300, 500, 600) with a display device. Some operations in method 1100 are, optionally, combined, the orders of some operations are, optionally, changed, and some operations are, optionally, omitted.

As described below, method 1100 provides an intuitive way for display of health-related information. The method reduces the cognitive burden on a user for viewing health-related information, thereby creating a more efficient human-machine interface. For battery-operated computing devices, enabling a user to view health-related information faster and more efficiently conserves power and increases the time between battery charges.

The electronic device receives (1102) request (e.g., request to view search user interface 684) to display a first user interface (e.g., search user interface 684) (e.g., a request to view a search tab of a health application, such as a user tapping on an icon for the health application or a user tapping on an affordance for the search tab).

In response to receiving the first request, the electronic device displays (1104), via the display device, the first user interface (e.g., search user interface 684) (e.g., the search tab of the health application). The first user interface includes a first portion (e.g., 684c) (1106) (e.g., a health category section), including a first category affordance (e.g., 684ca) (e.g., activity affordance) (e.g., a category of health data; a category of biometric sensor data; an activity category). The first user interface includes a second portion (e.g., 684b) (1108) (e.g., a shared health data section) including a first shared affordance (e.g., 684ba) (e.g., Little Appleseed affordance) corresponding to a second user account (e.g., Little Appleseed account). In some embodiments, the second portion is included in the first user interface in accordance with a determination that the first user account is associated with a second user account (e.g., a child account) different from the first user account.

While (1110) displaying the first user interface, the electronic device receives (1112) first user input corresponding to selection of the first category affordance. While (1110) displaying the first user interface, the electronic device receives (1114) second user input corresponding to selection of the first shared affordance.

In response to receiving the first user input, the electronic device displays (1116), via the display device, a second user interface (e.g., 686) (e.g., a user interface with health data for the selected health category, such as activity, for a user's account associated with the electronic device), including a representation (e.g., 686a) of first health data (e.g., a first discrete health record) associated with the first user account for the first category (e.g., activity).

In response to receiving the second user input, the electronic device displays (1118), via the display device, a third user interface (e.g., 690) (e.g., a user interface with health categories for Little Appleseed). The third user interface includes a first portion (e.g., 692b). The first portion includes a second category affordance (e.g., an activity affordance) corresponding to health data associated with the second user account for the first category (e.g., activity).

While displaying the third user interface, the electronic device receives (1120) third user input corresponding to selection of the second category affordance. In response to receiving the third user input, the electronic device displays (1122), via the display device, a fourth user interface (e.g., 694) (e.g., a user interface with health data for the selected health category, such as activity, for Little Appleseed), including a representation (e.g., 694c) of health data associated with the second user account for the first category.

In some embodiments, the first health data associated with the first user account for the first category is also associated with the first user account for a second category (e.g., the first health data is represented in multiple categories accessible from the first user interface). In some embodiments, the first user interface includes a second category affordance corresponding to health data associated with the first user account for a second category different from the first category and, in response to a user input corresponding to the second category affordance, an additional (e.g., a fourth) user interface is displayed that includes the first health data (e.g., 688).

In some embodiments, the fourth user interface does not include an option (e.g., an editing affordance; any options) for modifying the representation of health data associated with the second user account for the first category (or, in some embodiments, for modifying the health data associated with the second user account for the first category).

In some embodiments, while displaying the first user interface, the electronic device receives a first set of inputs corresponding to a request to search health data accessible to the electronic device (e.g., health data stored on the electronic device, health data stored on a remote device (e.g., a server) that is accessible to the electronic device), including one or more inputs corresponding to entry of a search string (e.g., a text string of one or more characters). In some embodiments, the first user interface includes a search field and the one or more inputs correspond to entry of the search string are provided in the search field (e.g., FIG. 6U).

In some embodiments, in response to receiving the set of inputs, the electronic device displays a plurality of search results including: a first set of one or more search results including a representation of second health data associated with the first user account, wherein the second health data associated with the first user account is associated with a first source (e.g., one or more sensors of the electronic device, one or more sensors of an external device that is associated with the first user account, an external device that is not associated with the first user account (e.g., a clinical source)); and a second set of one or more search results including a representation of third health data associated with the first user account, wherein the third health data associated with the first user account is associated with a second source different from the first source (e.g., FIG. 6U).

Displaying search results including representations of health data from different sources provides the user with feedback about health data from varying sources on a single user interface. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, as a part of displaying the plurality of search results, the electronic device ceases to display the first portion and the second portion of the first user interface (e.g., FIG. 6U).

Ceasing to display the first portion and the second portion of the first user interface enables the device to display other content at those same locations. Increasing the availability of display space for content enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first user interface includes a third portion (e.g., 684d) including a first health record affordance that, when selected, displays a representation of health data associated with the first user account that was received from a first external source (e.g., clinical health records; health records provided by a medical professional).

In some embodiments, the representation of health data associated with the first user account for the first category corresponds to health data that satisfied a set of formatting criteria (e.g., a set of criteria that governs whether data is displayable in the second user interface). In some embodiments, health data (e.g., clinical health data) that is accessible to the first electronic device is sorted based on whether the data is in a format that can be parsed by one or more parsing processes. In some embodiments, the third portion includes a first affordance. In some embodiments, the electronic device receives a fourth user input corresponding to selection of the first affordance. In some embodiments, in response to receiving the fourth user input, the electronic device displays a set of health data that did not satisfy the set of formatting criteria (e.g., 684*f*).

Note that details of the processes described above with respect to method 1100 (e.g., FIGS. 11A-11C) are also applicable in an analogous manner to the methods described below/above. For example, methods 700, 800, 900, 1000, and 1400 optionally include one or more of the characteristics of the various methods described above with reference to method 1100. For brevity, these details are not repeated below.

Figure 12B:
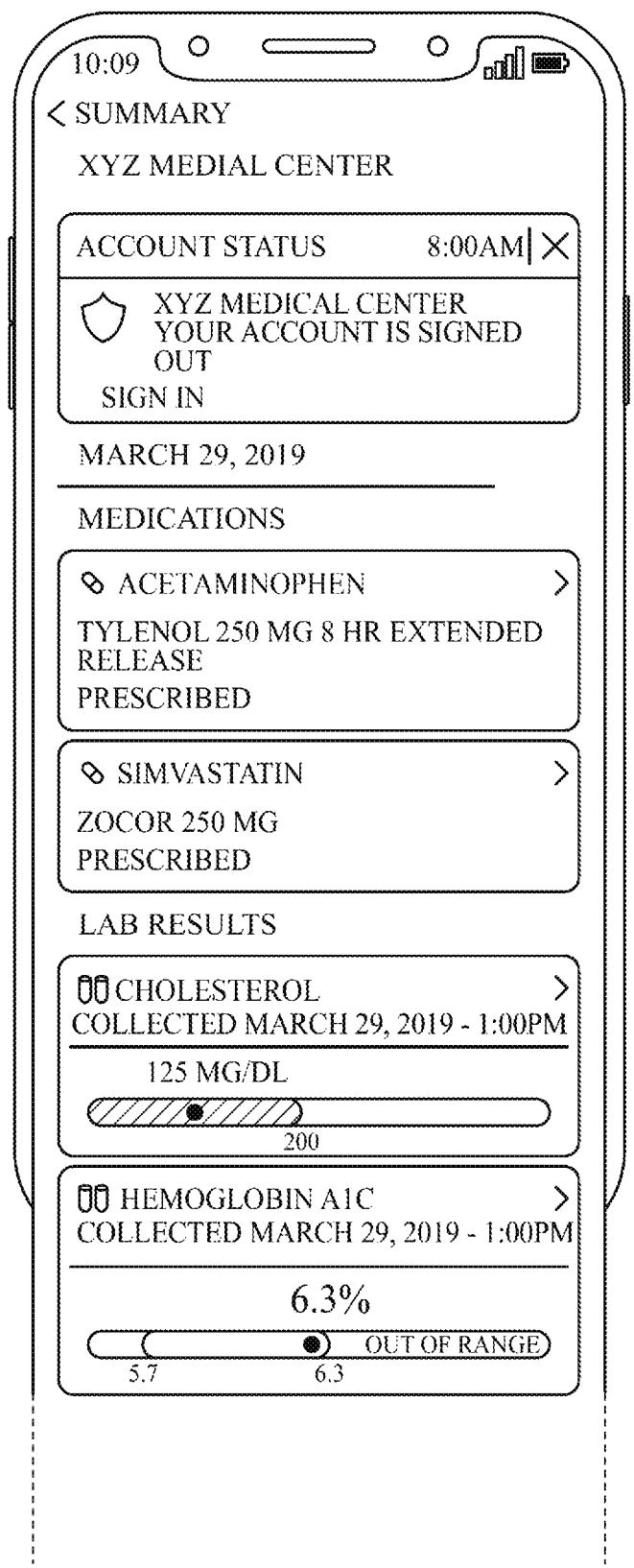
Figure 12B:
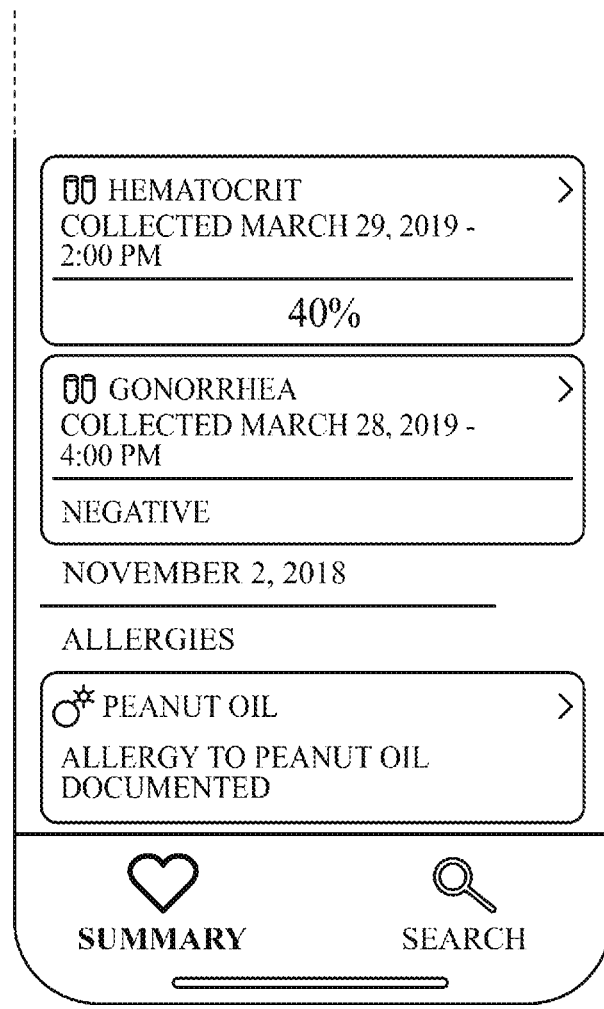
Figure 12C:
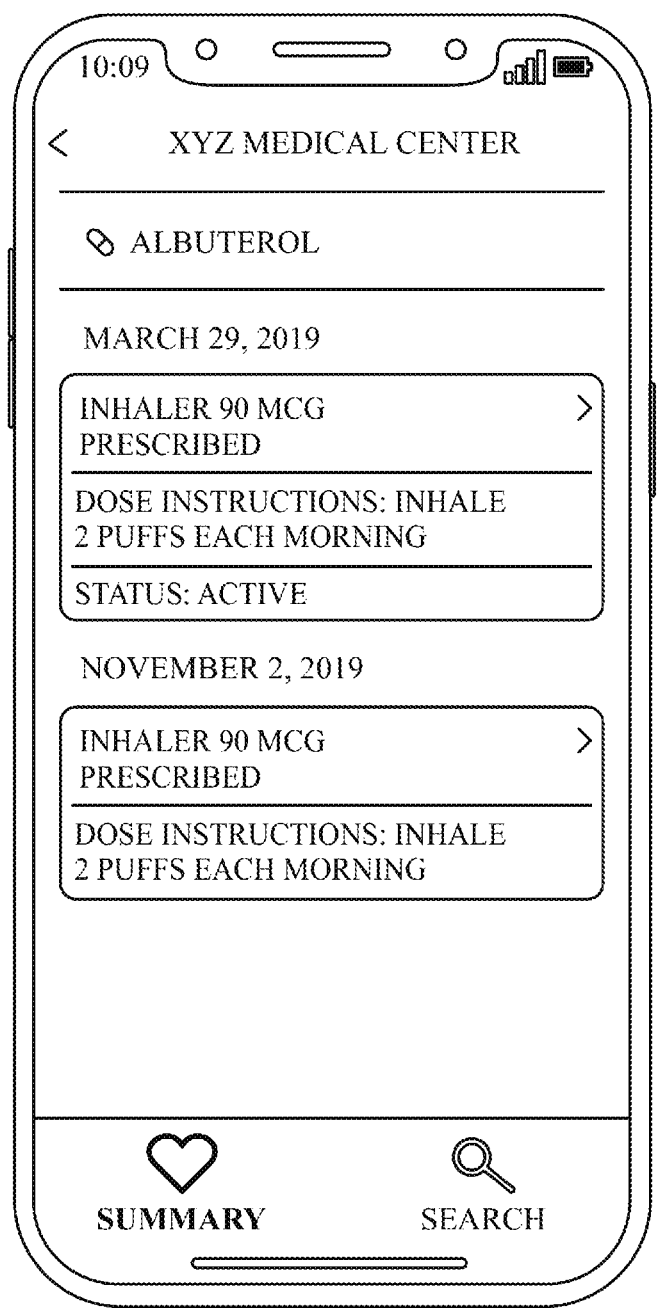
Figure 12D:
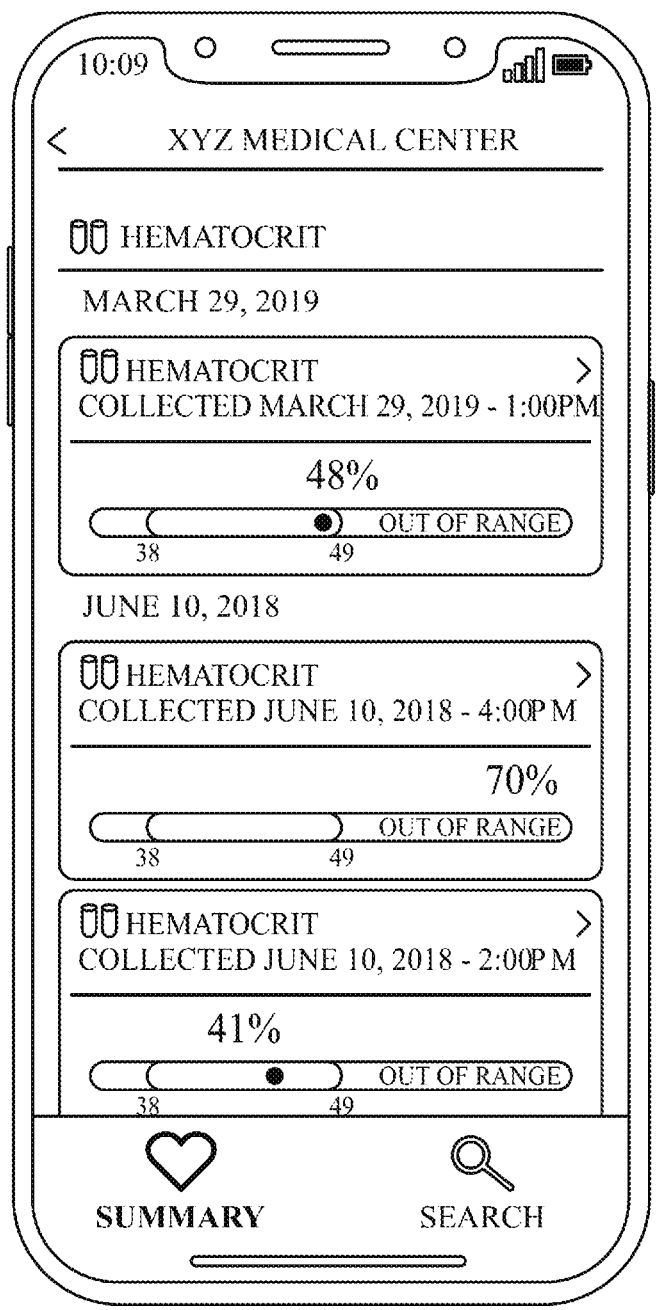
Figure 12E:
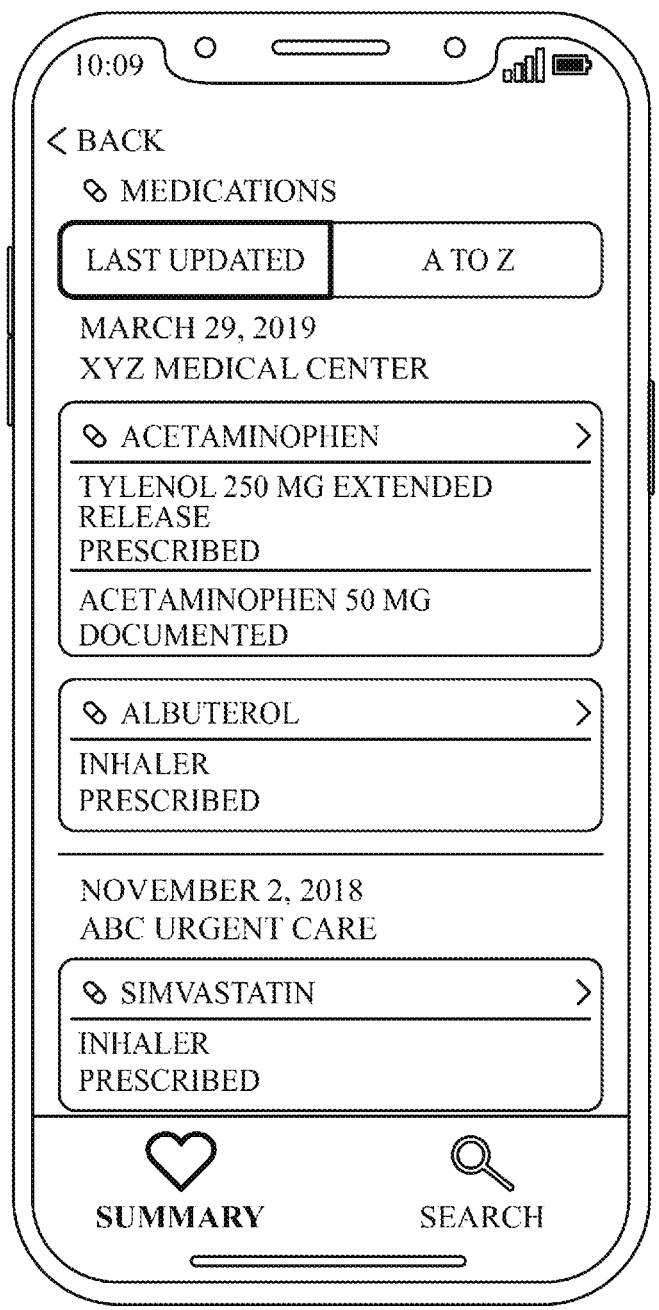
Figure 12F:
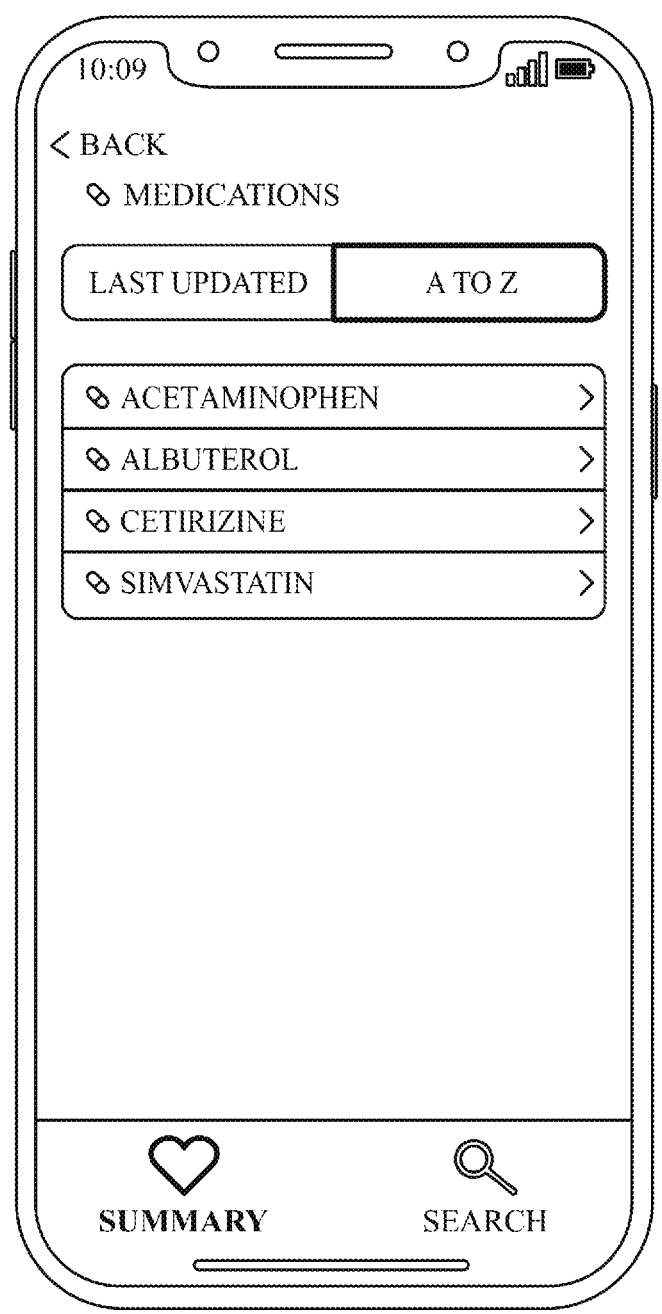
Figure 12G:
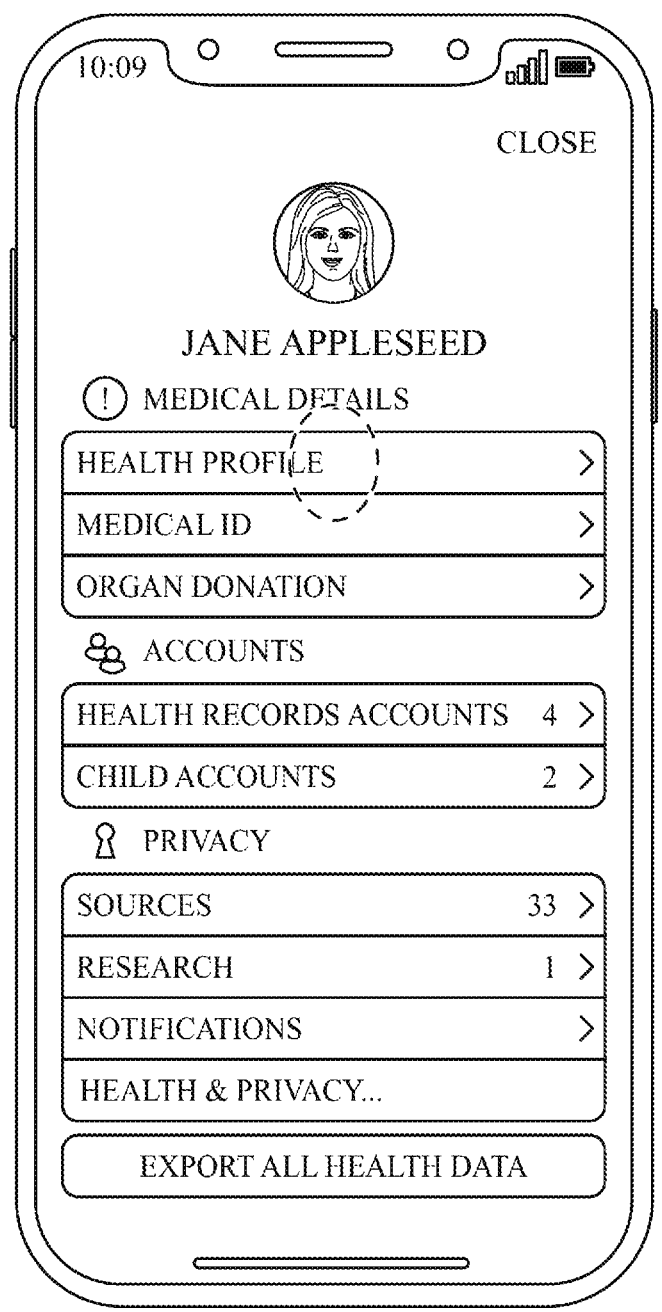
Figure 12H:
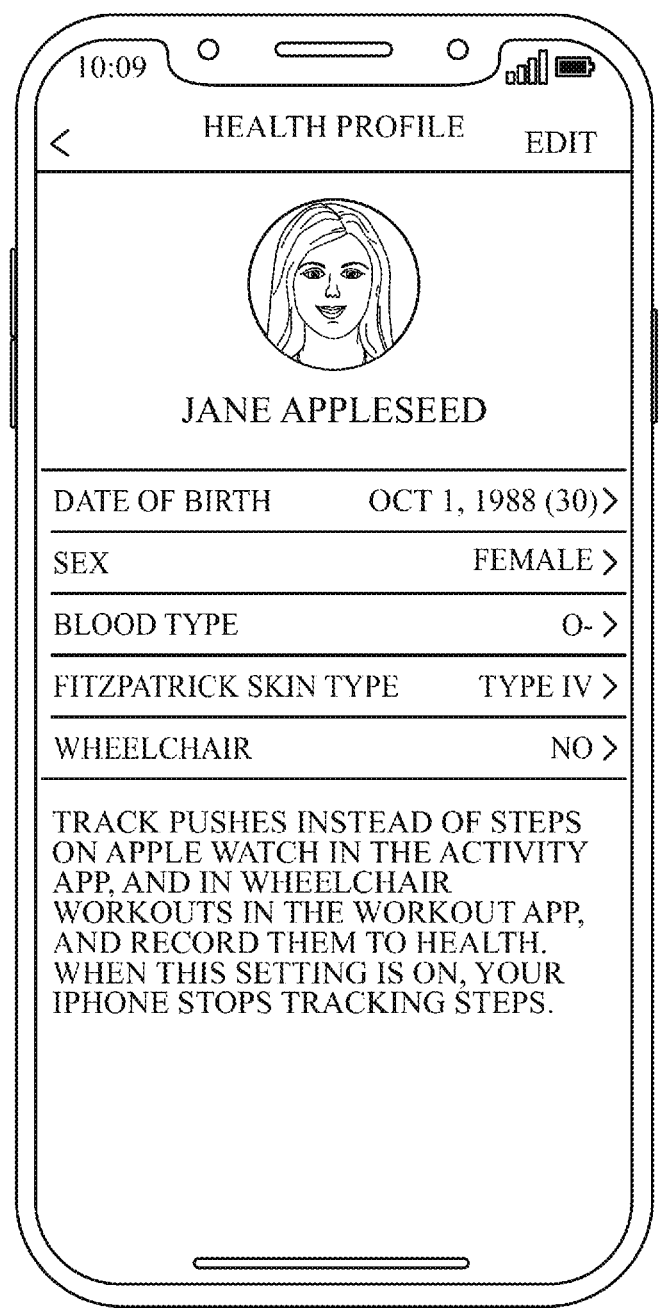
Figure 12I:
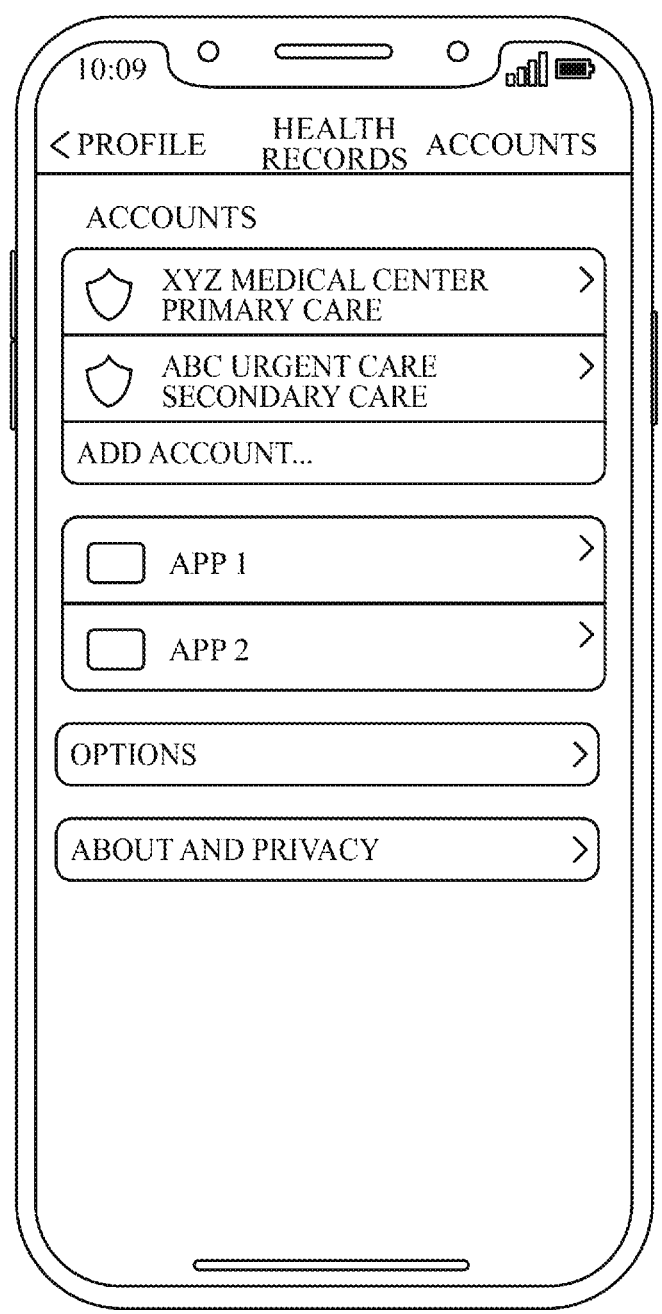

FIGS. 12AA-12AB depict an all health data user interface. In some examples, the all health data user interface is displayed in response to selection of all health data affordance 628 depicted in FIG. 6DA. FIGS. 12BA-12BB depict an XYZ Medical Center user interface. In some examples, the XYZ Medical Center user interface is displayed in response to selection of third notification affordance 620 depicted in FIG. 6DA, first health records affordance 636 depicts in FIG. 6DC, or title 670*a* depicted in FIG. 6PA. FIG. 12C depicts an albuterol user interface. In some examples, the albuterol user interface is displayed in response to selection of albuterol affordance in FIG. 12BA. FIG. 12D depicts a hematocrit user interface. In some examples, the hematocrit user interface is displayed in response to selection of hematocrit affordance in FIG. 6PB, hematocrit affordance in FIG. 6Q, or hematocrit affordance in FIG. 12BB. FIGS. 12E-12F depicts a medications user interface. In some examples, the medications user interface is displayed in response to selection of affordance 666F in FIG. 60B, medications affordance in FIG. 12AA, or medications affordance in FIG. 12BA. FIGS. 12G-12I depicts user interfaces related to a profile. In some examples, the user interface are navigated to by selecting a picture on a user interface matching the picture at the top of FIG. 12G.

FIGS. 13A-13G illustrate exemplary user interfaces related to sharing health data, in accordance with some embodiments. The user interfaces in these figures are used to illustrate the processes described below, including the processes in FIGS. 14A-14B.

Figure 13A:
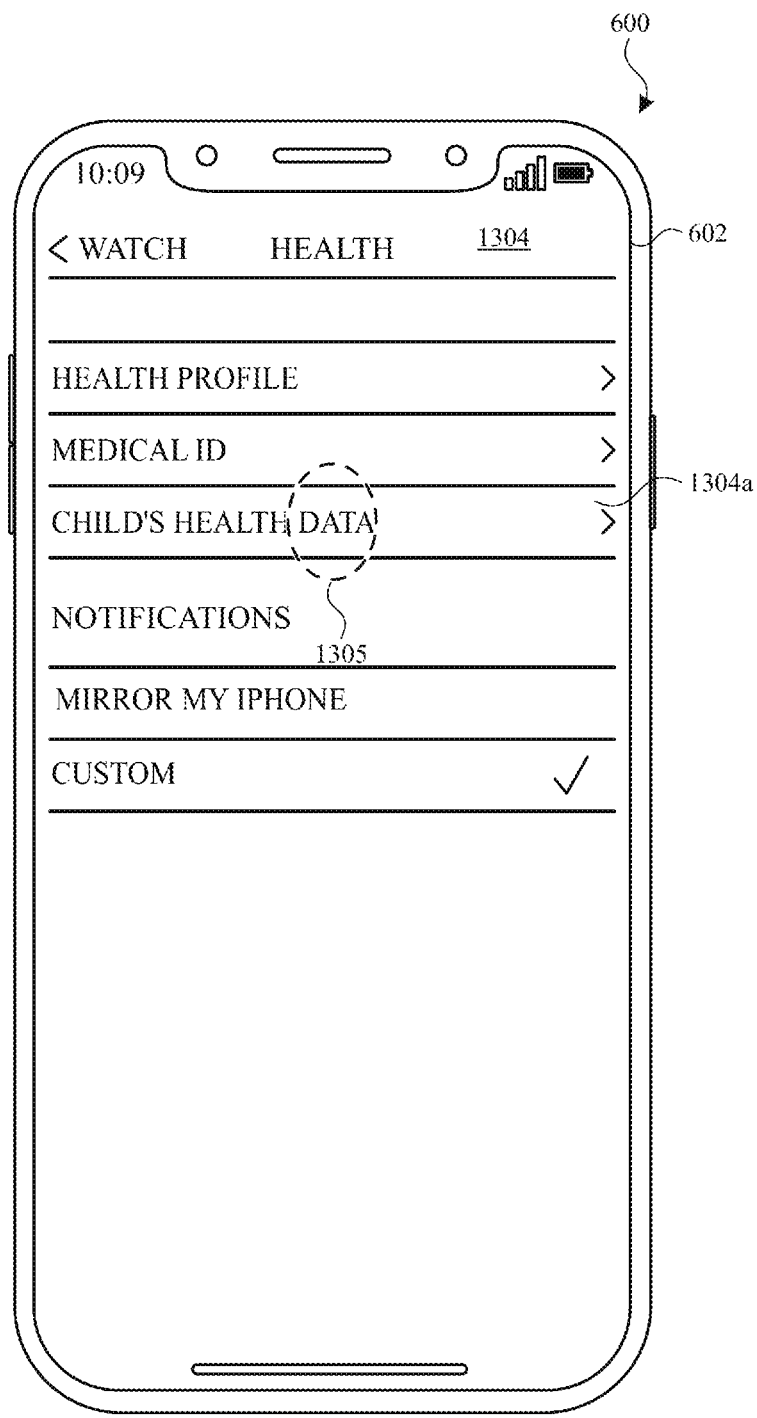
FIGS. 13A-13G illustrate exemplary user interfaces related to sharing health data using an electronic device, in accordance with some embodiments.
Figure 14A:
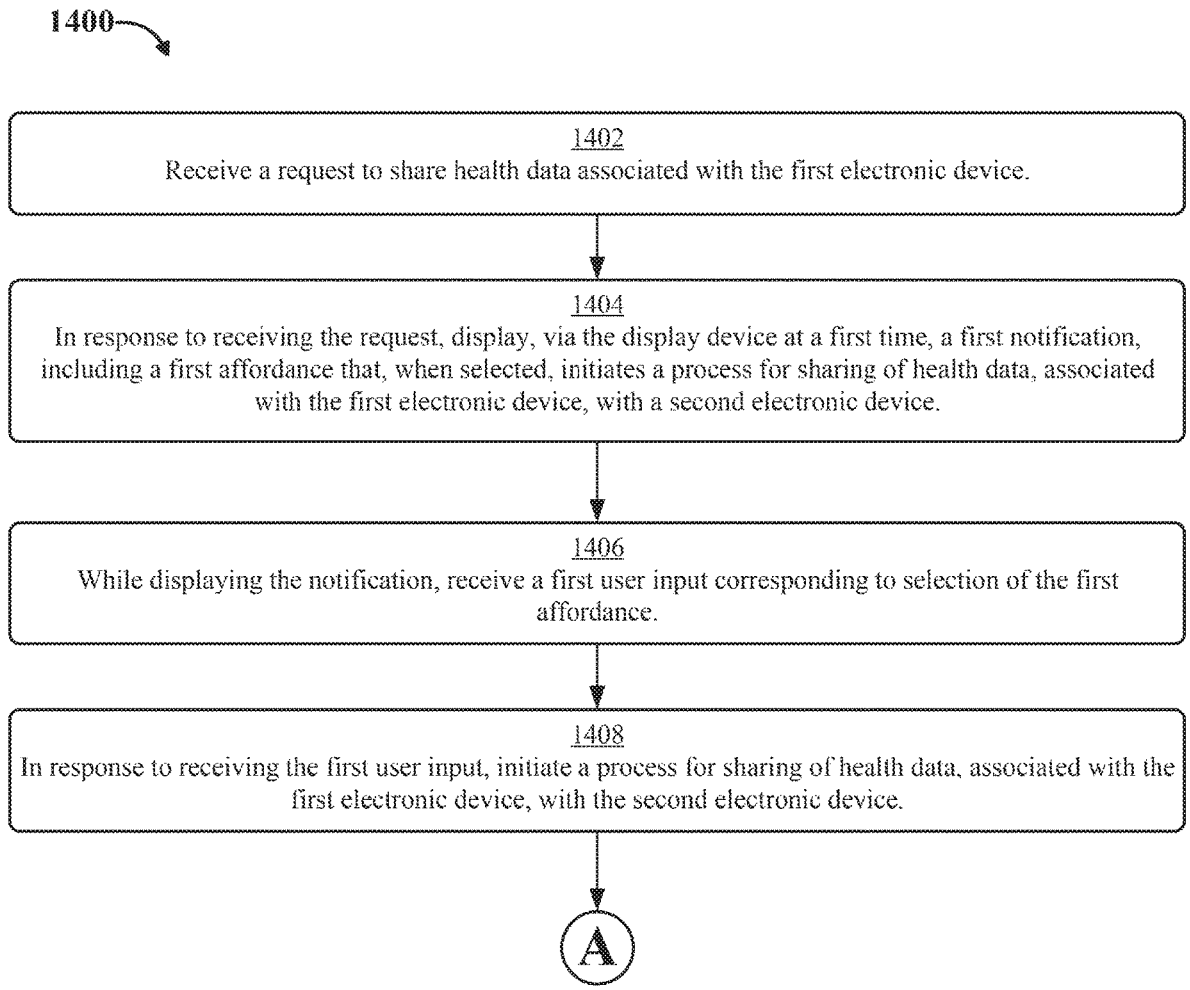
FIGS. 14A-14B are a flow diagram illustrating methods related to sharing health data, in accordance with some embodiments.
Figure 14B:
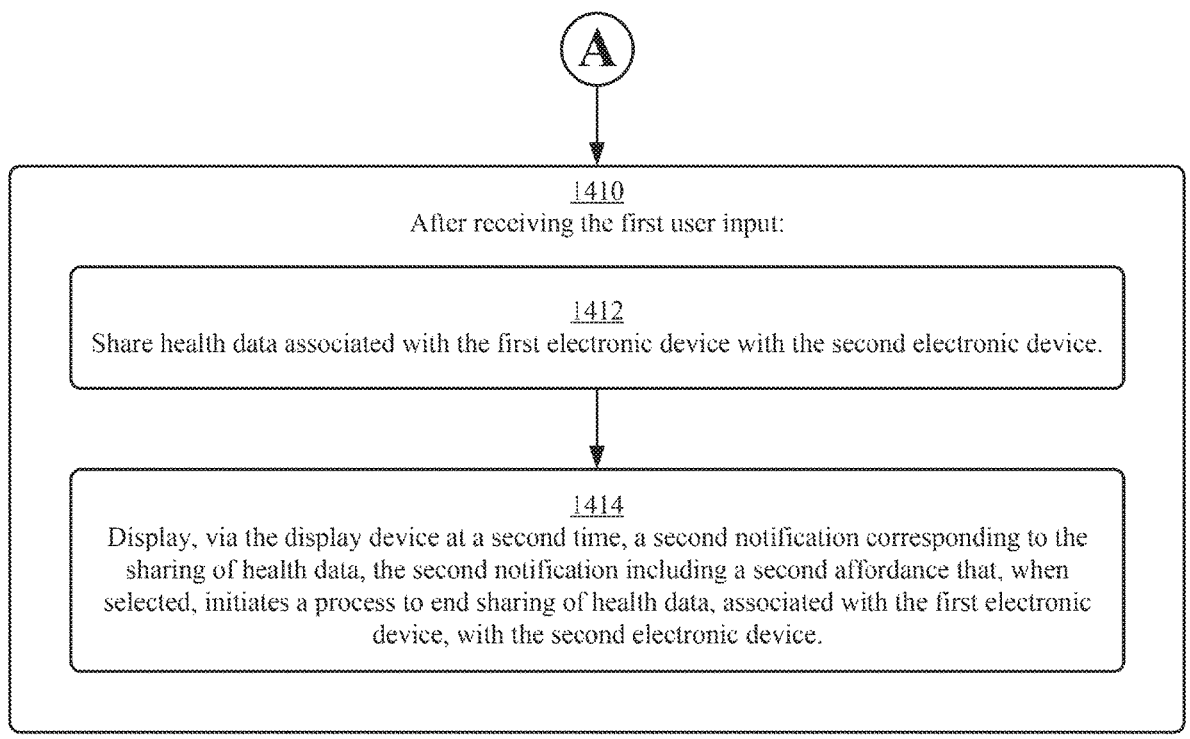

FIG. 13A depicts first electronic device 600 displaying health user interface 1304 via touch-sensitive display device 602 at a first time. In some examples, first electronic device 600 includes one or more features of devices 100, 300, 500, 606.

Health user interface 1304 relates to health data for a user associated with first electronic device 600 (e.g., the user logged into a first account via first electronic device 600). Health user interface 1304 includes a number of affordances, including child's health data affordance 1304*a*. In some examples, selection of child's health data affordance 1304*a* causes a user interface (e.g., share user interface 1306 as depicted in FIG. 13B) to be displayed, as further discussed below.

FIG. 13A depicts first electronic device 600 receiving user input 1305 corresponding to child's health data affordance 1304*a*. In some examples, user input 1305 is received via touch-sensitive display device 602 and corresponds to a selection gesture (e.g., tap) on child's health data affordance 1304*a*. In other examples, other forms of selection can be used, such as a click using a mouse. In some examples, user input 1305 causes a different user interface to be displayed via touch-sensitive display device 602, such as display of share user interface 1306 as depicted in FIG. 13B. In other examples, user input 1305 causes a request to be sent to a second electronic device requesting for the second electronic device to share health data with first electronic device 600. In such examples, the second electronic device is associated with a second account different from but linked to the first account (e.g., the second account corresponds to a child account of the first account).

Figure 13B:
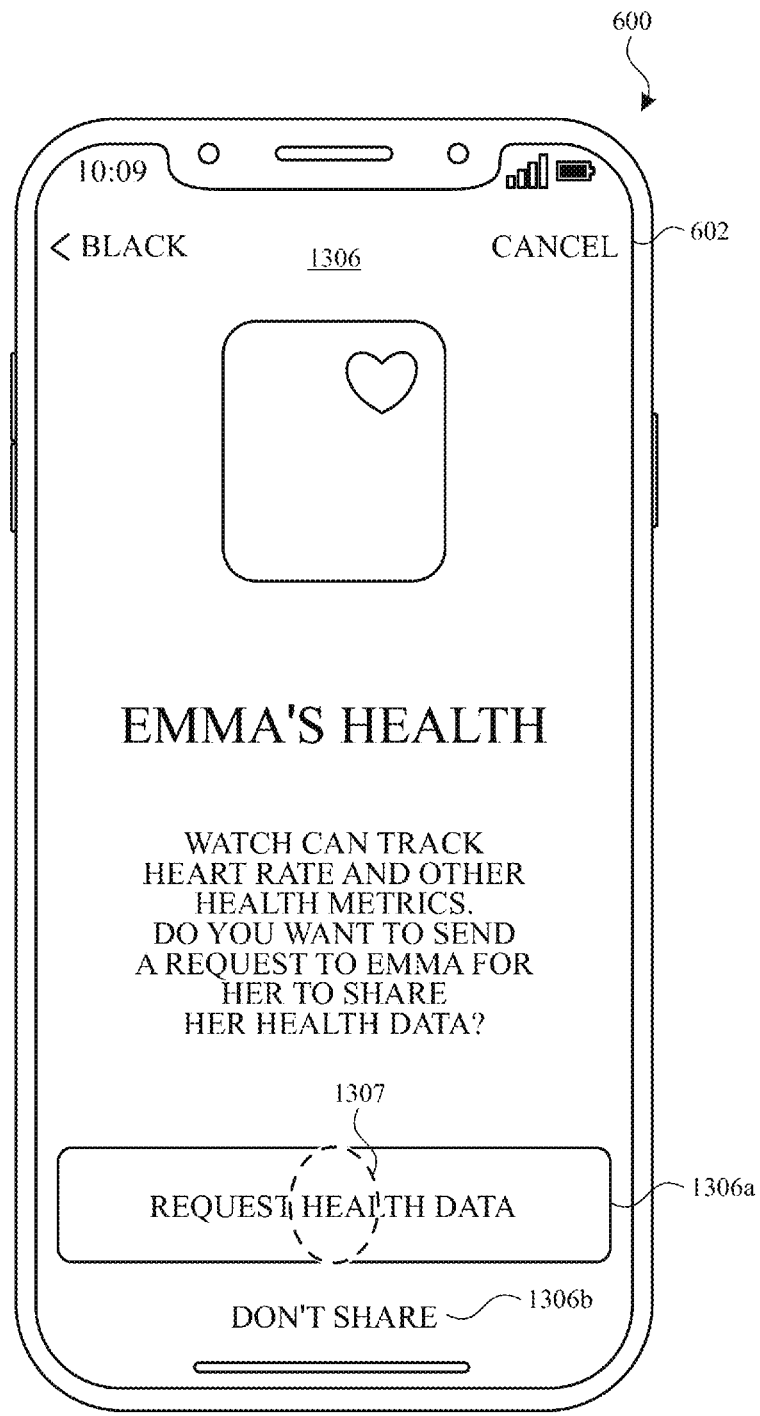

FIG. 13B depicts first electronic device 600 displaying share user interface 1306 via touch-sensitive display device 602 at a second time after the first time. In some examples, share user interface 1306 is displayed in response to (e.g., without any additional user input) selection of child's health data affordance 1304*a* on health user interface 1304, as depicted in 13A.

Share user interface 1306 includes request affordance 1304*a*. Selection of request affordance 1304*a* causes a request to be sent to a second electronic device (e.g., second electronic device 1308) for the second electronic device to share health data with first electronic device 600. In some examples, before displaying share user interface 1306, a user interface to identify an account for which to request to share is displayed (e.g., to identify Emma's account) (not illustrated).

Figure 13C:
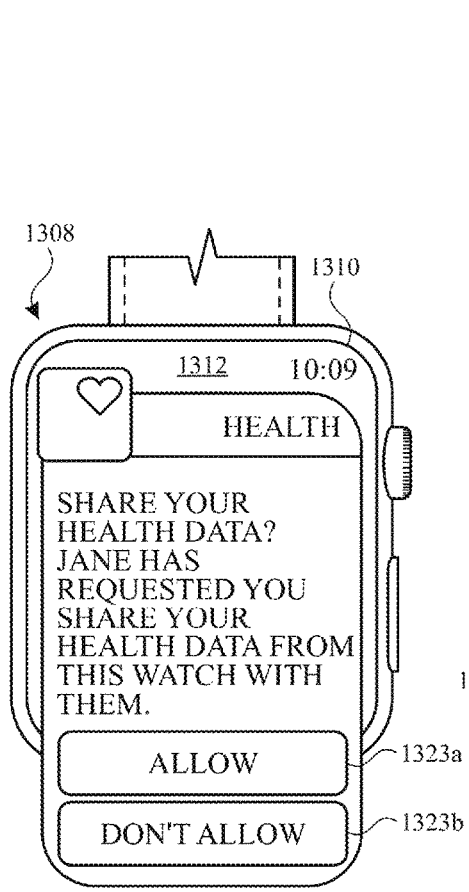

FIG. 13C depicts second electronic device 1308 displaying notification 1312 via touch-sensitive display device 1310 at a third time after the second time. In some examples, notification 1312 is a notification that was issued (e.g., caused to be displayed by second electronic device 1308) from a process executing on second electronic device 1308. For example, the process can be a health process associated with a health application. In some examples, notification 1312 is issued in response to a determination that a user associated with first electronic device 600 has requested for second electronic device 1308 to share health data with first electronic device 600, as depicted in FIG. 13B.

As depicted in FIG. 13C, notification 1312 includes allow affordance 1323*a* and don't allow affordance 1323*b*. Selection of allow affordance 1323*a* causes second electronic device 1308 to initiate a process for sending health data to first electronic device 600. For example, second electronic device 1308 transitions into a mode where new health data that is associated with second electronic device 1308 is sent to first electronic device 600 for display via first electronic device 600. In some examples, selection of allow affordance 1323*a* also causes second electronic device 1308 to initiate a process for sending old health data to first electronic device 600 (e.g., health data associated with second electronic device 1308 that was obtained before selection of allow affordance 1323*a*).

In some examples, selection of don't allow affordance 1323*b* causes second electronic device 1308 to not share health data with first electronic device 600. In some examples, selection of don't allow affordance 1323*b* also causes health data from second electronic device 1308 to not be backed up to another device (e.g., a backup server) due to the selection causing there to not be memory allocated for second electronic device 1308 on a backup server (e.g., health cloud space is not created for the second account when second electronic device 1308 selects don't allow affordance 1323*b*). In other examples, selection of don't allow affordance 1323*b* causes health data from second electronic device 1308 to still be backed up to another device (e.g., a backup server) (e.g., health cloud space is created for the second account when second electronic device 1308 selects don't allow affordance 1323*b*). In some examples, backup data associated with second electronic device 1308 is separate from backup data associated with first electronic device 600 (e.g., first electronic device 600 stores its health data in a separate location from second electronic device 1308).

Figure 13D:
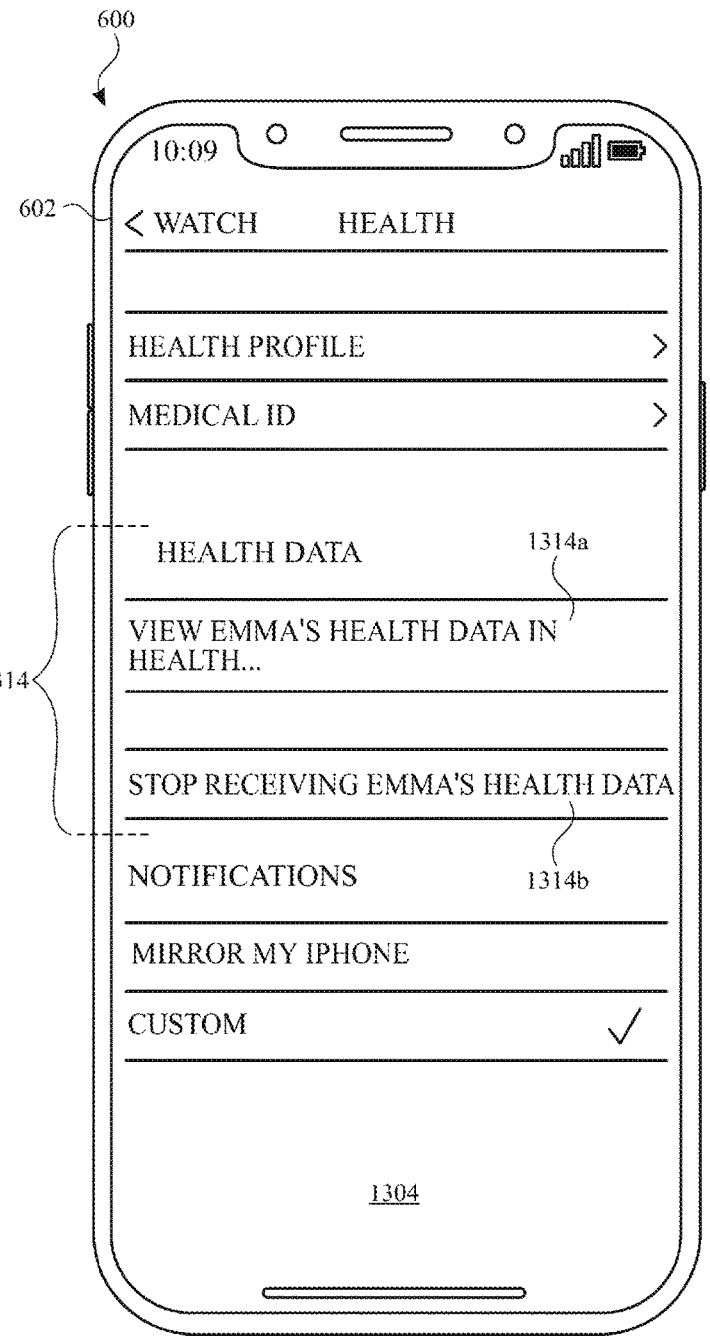

FIG. 13D depicts first electronic device 600 displaying health user interface 1304 via touch-sensitive display device 602 at a fourth time after the third time. Health user interface 1304 depicted in FIG. 13D is the same user interface depicted in FIG. 13A. The difference with health user interface 1304 as depicted in FIG. 13D is that it includes health data section 1314 with multiple affordances associated with second electronic device 1308. In some examples, health data section 1314 is included in health user interface 1304 in response to selection of allow affordance 1323*a* on second electronic device 1308 (as depicted in FIG. 13C).

Health data section 1314 includes health data affordance 1314*a* and stop affordance 1314*b*. In some examples, health data affordance 1314*a*, when selected, causes first electronic device 600 to display a user interface (e.g., a user interface corresponding to the health application) with health data corresponding to Emma (e.g., the user associated with second electronic device 1308). An example of such a user interface is depicted in FIGS. 6XA-6XB.

In some examples, stop affordance 1314*b*, when selected, causes first electronic device 600 to (1) stop receiving health data corresponding to second electronic device 1308 and (2) delete any health data corresponding to second electronic device 1308 that is stored in memory associated with first electronic device 600 (e.g., health data corresponding to second electronic device 1308 is not deleted from second electronic device 1308 or another device used to backup health data corresponding to second electronic device 1308 (e.g., a backup server)).

Figure 13E:
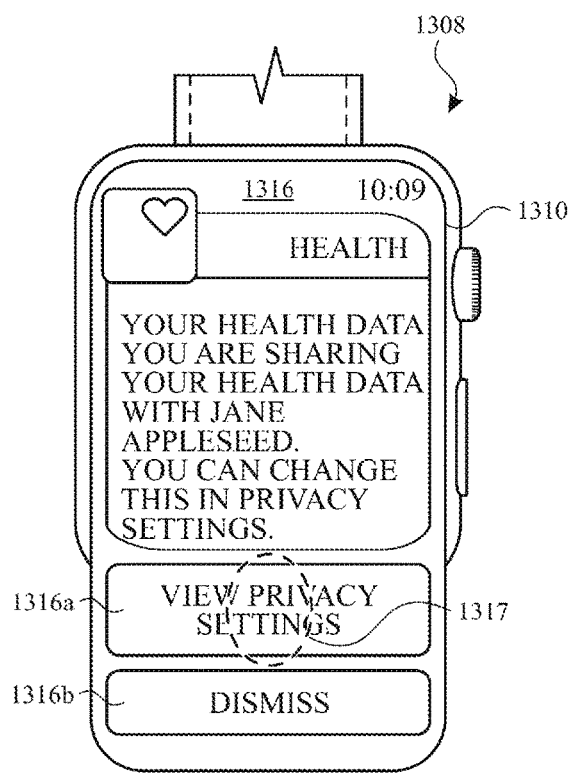

FIG. 13E depicts second electronic device 1308 displaying notification 1316 via touch-sensitive display device 1310 at a fifth time after the fourth time. In some examples, notification 1316 is a notification that was issued (e.g., caused to be displayed by second electronic device 1308) from a process executing on second electronic device 1308. For example, the process can be a health process associated with a health application. In some examples, notification 1316 is issued in response to a determination that second electronic device 1308 is sharing health data with first electronic device 600 and a predefined, non-zero amount of time (e.g., a few days, a few weeks, a few months, or the like) has passed since second electronic device 1308 has begun sharing health data with first electronic device 600. In some examples, multiple such notifications are issued at different times.

Figure 13F:
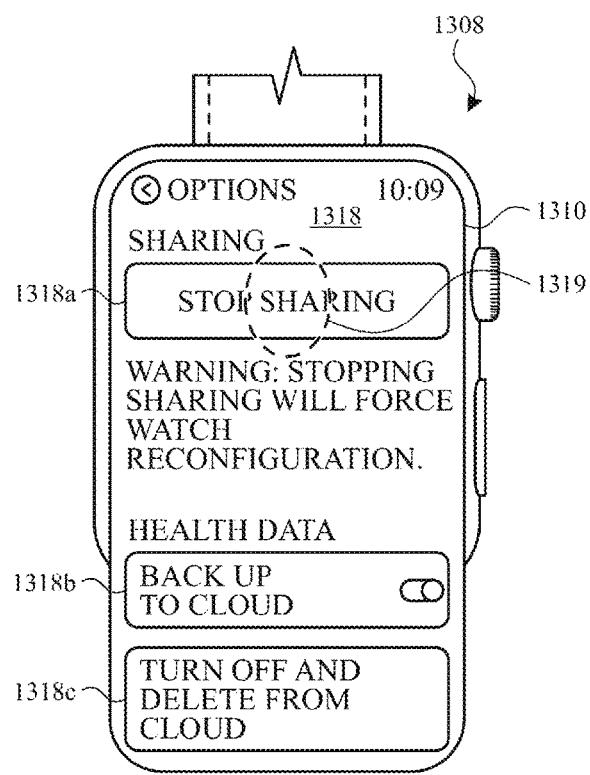

As depicted in FIG. 13E, notification 1318 includes view affordance 1316*a* and dismiss affordance 1316*b*. Selection of view affordance 1316*a* causes second electronic device 1308 to display a different user interface via touch-sensitive display device 602, such as sharing options user interface 1318 as depicted in FIG. 13F. In other examples, selection of view affordance 1316*a* causes first electronic device 600 to (1) stop receiving health data corresponding to second electronic device 1308 and (2) delete any health data corresponding to second electronic device 1308 that is stored in memory associated with first electronic device 600 (e.g., health data corresponding to second electronic device 1308 is not deleted from second electronic device 1308 or another device used to backup health data corresponding to second electronic device 1308 (e.g., a backup server)). Selection of dismiss affordance 1316*b* causes second electronic device 1308 to forgo display of notification 1316.

FIG. 13E depicts second electronic device 1308 receiving user input 1317 corresponding to view affordance 1316*a*. In some examples, user input 1317 is received via touch-sensitive display device 1310 and corresponds to a selection gesture (e.g., tap) on view affordance 1316*a*. In other examples, other forms of selection can be used, such as a click using a mouse. As discussed above, in some examples, user input 1317 causes a different user interface to be displayed (e.g., sharing options user interface 1318, as depicted in FIG. 13F).

FIG. 13F depicts second electronic device 1308 displaying sharing options user interface 1318 via touch-sensitive display device 1310 at a sixth time after the fifth time. In some examples, sharing options user interface 1318 is displayed in response to (e.g., without any additional user input) selection of view affordance 1316*a* on notification 1316, as depicted in 13E.

Sharing options user interface 1318 includes stop affordance 1318*a*, backup affordance 1318*b*, and off affordance 1318*c*. Selection of stop affordance 1318*a* causes second electronic device 1308 to initiate a process to stop sharing health data with first electronic device 600. The process causes first electronic device 600 to (1) stop receiving health data corresponding to second electronic device 1308 and (2) delete any health data corresponding to second electronic device 1308 that is stored in memory associated with first electronic device 600 (e.g., health data corresponding to second electronic device 1308 is not deleted from second electronic device 1308 or another device used to backup health data corresponding to second electronic device 1308 (e.g., a backup server)). In some examples, selection of stop affordance 1318*a* causes multiple devices (in addition to first electronic device 600) (e.g., all devices for which second electronic device 1308 is sharing health data with) to (1) stop receiving health data corresponding to second electronic device 1308 and (2) delete any health data corresponding to second electronic device 1308 that is stored in memory associated with the respective device 600 (e.g., health data corresponding to second electronic device 1308 is not deleted from second electronic device 1308 or another device used to backup health data corresponding to second electronic device 1308 (e.g., a backup server)).

In some examples, selection of stop affordance 1318*a* does not stop second electronic device 1308 from sharing health data with another device used to backup health data corresponding to second electronic device 1308 (e.g., a backup server) (e.g., second electronic device 1308 continues to backup health data to the backup server). In some examples, selection of stop affordance 1318*a* also causes health data section 1314 to be removed from health user interface 1304 on first electronic device 600. In some examples, when first electronic device 600 is receiving health data from at least one other device according to techniques described herein, selection of stop affordance 1318*a* causes user interface elements related to second electronic device 1308 to be removed from health data section 1314 but health data section 1314 will still be included in health user interface 1304 on first electronic device 600 for the other device.

Selection of backup affordance 1318*b* causes second electronic device 1308 to stop sending health data to another device used to backup health data corresponding to second electronic device 1308 (e.g., a backup server). In some examples, selection of backup affordance 1318*b* also causes the other device to delete health data corresponding to second electronic device 1308 such that the health data corresponding to second electronic device 130 is only stored on second electronic device 1308.

Selection of off affordance 1318*c* causes second electronic device 1308 to (1) turn off (e.g., stop) collection of health data corresponding to second electronic device 1308, (2) stop sending health data to another device used to backup health data corresponding to second electronic device 1308 (e.g., a backup server), (3) cause other devices to delete health data corresponding to second electronic device 1308 such that the health data corresponding to second electronic device 1308 is not stored on other devices, or (4) any combination thereof.

FIG. 13F depicts second electronic device 1308 receiving user input 1319 corresponding to stop affordance 1318*a*. In some examples, user input 1319 is received via touch-sensitive display device 1310 and corresponds to a selection gesture (e.g., tap) on stop affordance 1318*a*. In other examples, other forms of selection can be used, such as a click using a mouse. As discussed above, in some examples, user input 1318*a* causes second electronic device 1308 to initiate a process to stop sharing health data with first electronic device 600. The process causes first electronic device 600 to (1) stop receiving health data corresponding to second electronic device 1308, (2) delete any health data corresponding to second electronic device 1308 that is stored in memory associated with first electronic device 600 (e.g., health data corresponding to second electronic device 1308 is not deleted from second electronic device 1308 or another device used to backup health data corresponding to second electronic device 1308 (e.g., a backup server)), and (3) health data section 1314 to be removed from health user interface 1304 on first electronic device 600, as depicted in 13G.

Figure 13G:
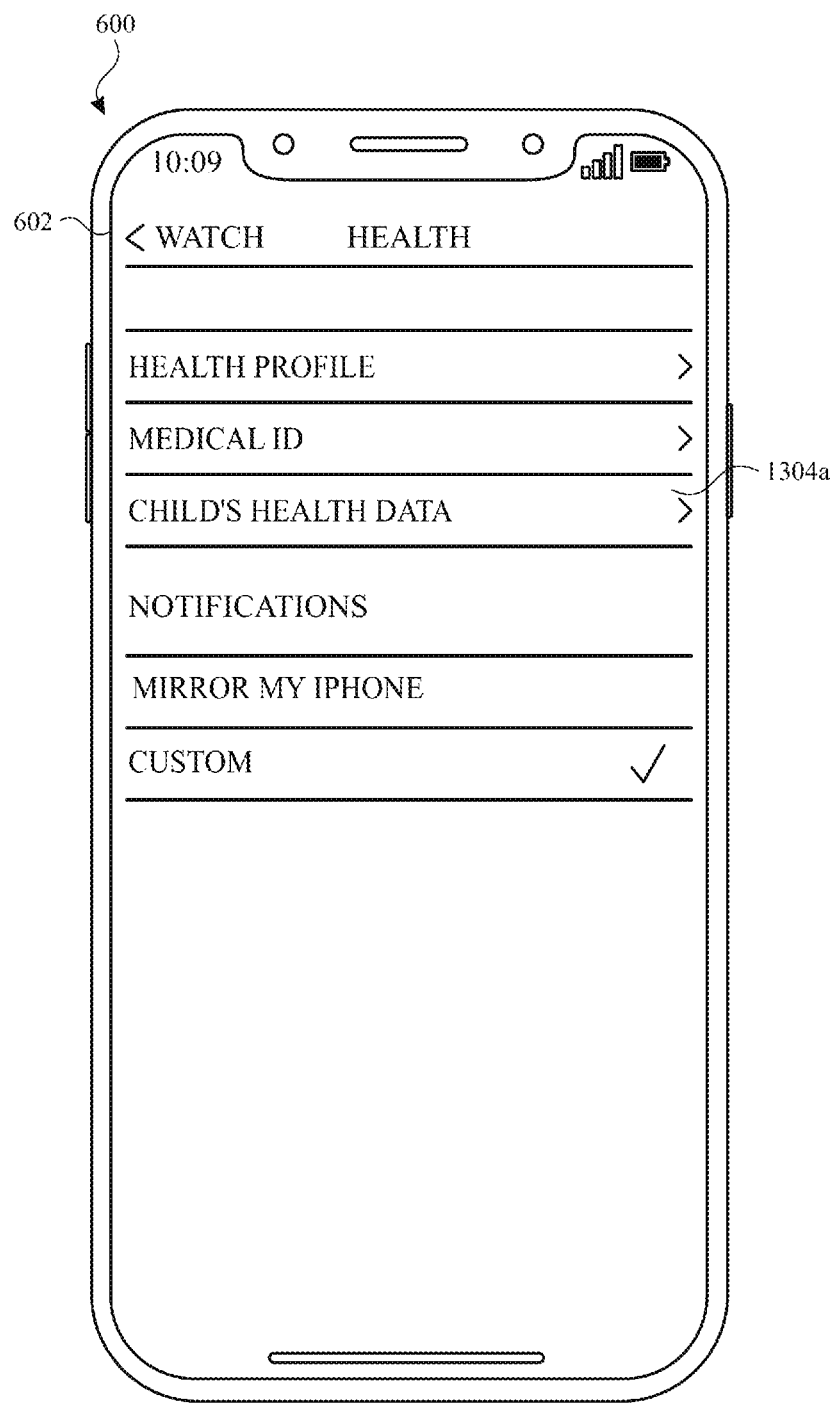

FIG. 13G depicts first electronic device 600 displaying health user interface 1304 via touch-sensitive display device 602 at a seventh time after the sixth time. As depicted in FIG. 13G, health user interface 1304 no longer includes health data section 1314 (as depicted in FIG. 13D).

FIGS. 14A-14B is a flow diagram illustrating a method for managing shared health data using an electronic device in accordance with some embodiments. Method 1400 is performed at a device (e.g., 100, 300, 500, 600, 606, 1308) with a display device. Some operations in method 1400 are, optionally, combined, the orders of some operations are, optionally, changed, and some operations are, optionally, omitted.

As described below, method 1400 provides an intuitive way for related to sharing health data. The method reduces the cognitive burden on a user for managing shared health data, thereby creating a more efficient human-machine interface. For battery-operated computing devices, enabling a user to manage shared health data faster and more efficiently conserves power and increases the time between battery charges.

The first electronic device receives (1402) a request (e.g., 1307) to share health data associated with (e.g., detected by) the first electronic device. In some embodiments, the request to share is sent to the first electronic device in response to a second electronic device requesting that the first electronic device share health data.

In response to receiving the request, the first electronic device displays (1404), via the display device at a first time, a first notification (e.g., 1312) (e.g., a notification indicating that the second electronic device is requesting that the first electronic device share health data with the first electronic device), including a first affordance (e.g., 1323*a*) (e.g., an allow affordance) that, when selected, initiates a process for sharing of health data, associated with the first electronic device, with a second electronic device.

While displaying the notification, the first electronic device receives (1406) a first user input corresponding to selection of the first affordance.

In response to receiving the first user input, the first electronic device initiates (1408) a process for sharing of health data, associated with the first electronic device, with the second electronic device.

After (1410) receiving the first user input, the first electronic device shares (1412) health data associated with the first electronic device with the second electronic device. In some embodiments, the sending is performed in response to receiving the first user input. After (1410) receiving the first user input, the first electronic device displays (1414), via the display device at a second time, a second notification (e.g., 1316) (e.g., a notification to confirm that a user associated with the first electronic device wishes to share health data with the second electronic device) corresponding to the sharing of health data, the second notification including a second affordance (e.g., 1316*a*) that, when selected, initiates a process to end sharing of health data, associated with the first electronic device, with the second electronic device. In some embodiments, the second notification is displayed at a different time than the sending, such as a few days after receiving the first user input. In some embodiments, the second notification is displayed after the sending. In some embodiments, while displaying the second notification, receiving a set of one or more inputs that includes an input corresponding to selection of a third affordance (e.g., 1318*a*); and in response to receiving the set of one or more inputs (e.g., 1319), ceasing to share health data, associated with the first electronic device, with the second electronic device.

Displaying a notification that enables a user to end sharing of health data provides the user with feedback that the health data is being shared and enables the user to more efficiently access the interface for ending the sharing of the health data. Providing improved visual feedback to the user and reducing the number of inputs needed to perform an operation enhance the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the second notification, the first electronic device receives a set of one or more inputs that includes an input corresponding to selection of the second affordance (e.g., 1317). In some embodiments, in response to receiving the set of one or more inputs, the first electronic device ceases to share health data, associated with the first electronic device, with the second electronic device.

In some embodiments, after receiving the first user input, the first electronic device shares health data associated with the first electronic device with a third electronic device (e.g., a server storing health related data associated with the first electronic device). In some embodiments, after receiving the set of one or more inputs, the first electronic device continues to share health data associated with the first electronic device with the third electronic device (e.g., selection of the second affordance does not cause the device to stop sharing health data with the third electronic device).

In some embodiments, the first notification includes a third affordance (e.g., 1323b) (e.g., a "do not allow sharing" affordance) that, when selected: causes the first electronic device to forgo initiating a process for sharing of health data, associated with the first electronic device, with the second electronic device (and, in some embodiments, transmitting information to the second electronic device indicating that the request to share health data was not granted); and causes the first electronic device to transmit a request to a fourth electronic device (e.g., a server storing health related data associated with the first electronic device) to accept health data (e.g., to allocate storage resources to accept health data) associated with the first electronic device.

In some embodiments, the first notification includes a fourth affordance (e.g., 1323b) (e.g., a "do not allow sharing" affordance) that, when selected: causes the first electronic device to forgo initiating a process for sharing of health data, associated with the first electronic device, with the second electronic device (and, in some embodiments, transmitting information to the second electronic device indicating that the request to share health data was not granted); and causes the first electronic device to transmit a request to a fifth electronic device (e.g., a server storing health related data associated with the first electronic device) to accept health data (e.g., to allocate storage resources to accept health data) associated with the first electronic device.

In some embodiments, the first electronic device is associated with a first user account (e.g., a primary user account; a health-related user account) and second electronic device is associated with a second user account that is different from the first user account.

Note that details of the processes described above with respect to method 1400 (e.g., FIGS. 14A-14B) are also applicable in an analogous manner to the methods described below/above. For example, methods 700, 800, 900, 1000, and 1100 optionally include one or more of the characteristics of the various methods described above with reference to method 1400. For brevity, these details are not repeated below.

Figure 15A:
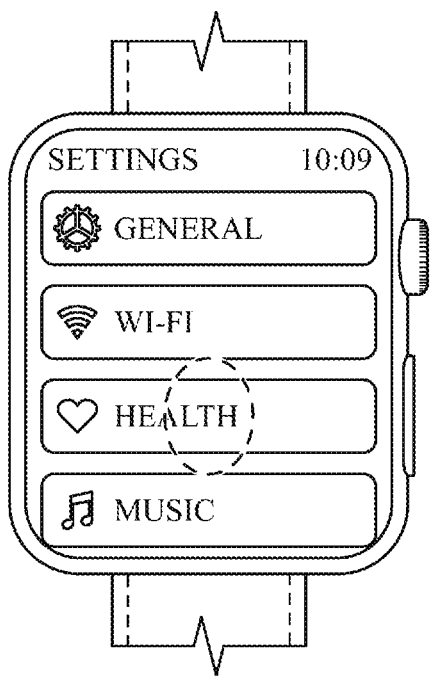
Figure 15B:
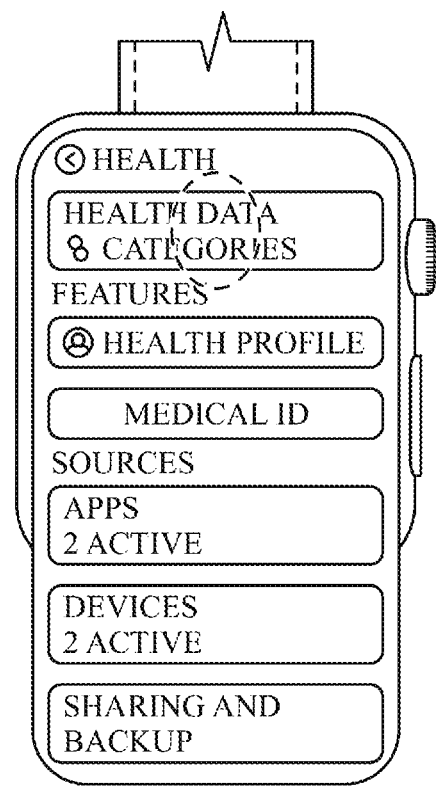

FIGS. 15A-5F depict a flow through a heath user interface within a settings user interface on second electronic device 1308.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the management and delivery of health information to users. The present disclosure contemplates that in some instances, this gathered data can include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver appropriate notifications and health summaries to the user. Accordingly, use of such personal information data enables users to manage their health information more efficiently. Further, other uses for personal information data that benefit the user are also contemplated by the present disclosure. For instance, health and fitness data can be used to provide insights into a user's general wellness, or can be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of accessing or storing health information, the present technology can be configured to allow users to select to "opt in" or "opt out" of participation in the collection of personal information data during registration for services or anytime thereafter. In another example, users can select not to provide certain types of health-related information. In yet another example, users can select to limit the length of time health-related information is maintained or entirely prohibit the storage of health-related information. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. An electronic device, comprising:
a display device;
one or more processors; and
memory storing one or more programs configured to be executed by the one or more processors, the one or more programs including instructions for:
receiving first health data;
receiving a selection of a health data type;
after receiving the selection of the health data type, receiving a request to display a first user interface;
in response to receiving the request, displaying, via the display device, the first user interface including:
a first region of the first user interface:
in accordance with a determination that a type of data corresponding to the first health data has been identified by the selection of the health data type, including a first representation of the first health data in the first region of the first user interface; and
in accordance with a determination that the type of data corresponding to the first health data has not been identified by the selection of the health data type, not including the first representation of the first health data in the first region of the first user interface; and
a second region of the first user interface:
in accordance with a determination that a first set of highlight criteria are met, including a second representation of the first health data different from the first representation in the second region of the first user interface; and
in accordance with a determination that the first set of highlight criteria are not met, not including the second representation of the first health data in the second region of the first user interface.

2. The electronic device of claim 1, wherein:
the first health data includes health data for a first plurality of time periods; and
the first representation of the first health data includes:
a first indication of the first health data corresponding to a first time period of the first plurality of time periods; and
a second indication of the first health data corresponding to a second time period of the first plurality of time periods that is different from the first time period.

3. The electronic device of claim 2, wherein:
the first time period of the first plurality of time periods corresponds to a specific instance of a recurring time interval; and
the second time period of the first plurality of time periods is a plurality of instances of the recurring time interval.

4. The electronic device of claim 1, wherein:
the first health data includes health data for a second plurality of time periods; and
the first representation of the first health data includes a third indication of the first health data corresponding to a frequency of an occurrence of a first health event within the second plurality of time periods.

5. The electronic device of claim 1, wherein:
the first health data includes health data for a third plurality of time periods; and
the first representation of the first health data includes:
a fourth indication of an average value of the first health data for the third plurality of time periods;
a fifth indication corresponding to the value of the first health data for a first time period of the third plurality of time periods; and
a sixth indication corresponding to the value of the first health data for a second time period of the third plurality of time periods that is different from the first time period of the plurality of time periods.

6. The electronic device of claim 1, wherein the first representation includes:
a seventh indication corresponding to a first physical activity tracking session;
an eighth indication corresponding to a second physical activity tracking session; and
a ninth indication of the first health data that is based on the first physical activity tracking session and the second physical activity tracking session.

7. The electronic device of claim 1, wherein the first set of highlight criteria includes a criterion that is based on a factor selected from the group consisting of: a relationship between a first portion of the first health data and a second portion of the first health data, a degree of user interaction with the first health data, and a duration of time in which a representation of the first health data has been displayed.

8. The electronic device of claim 1, wherein:
the first representation is included in a first list of representation; and
the first list of representations is ordered based on types of data of the first health data.

9. The electronic device of claim 1, wherein the first user interface is associated with a health application, and wherein the one or more programs further include instructions for:

while displaying the first user interface including the first representation of the first health data in the first region of the first user interface, receiving second user input corresponding to the first representation of the first health data; and in response to receiving the second user input corresponding to the first representation of the first health data, displaying a second user interface, different from the first user interface, including information from an activity application different from the health application.

10. The electronic device of claim 1, wherein the second region includes a show all highlights affordance, and wherein the one or more programs further include instructions for:

while displaying the show all highlights affordance, receiving third user input corresponding to the show all highlights affordance; and in response to receiving the third user input corresponding to the show all highlights affordance, displaying a third user interface including a list of highlights affordances corresponding to the first health data.

11. A non-transitory computer-readable storage medium storing one or more programs configured to be executed by one or more processors of an electronic device with a display device, the one or more programs including instructions for:

receiving first health data;

receiving a selection of a health data type;

after receiving the selection of the health data type, receiving a request to display a first user interface;

in response to receiving the request, displaying, via the display device, the first user interface including:

a first region of the first user interface:

in accordance with a determination that a type of data corresponding to the first health data has been identified by the selection of the health data type, including a first representation of the first health data in the first region of the first user interface; and in accordance with a determination that the type of data corresponding to the first health data has not been identified by the selection of the health data type, not including the first representation of the first health data in the first region of the first user interface; and a second region of the first user interface:

in accordance with a determination that a first set of highlight criteria are met, including a second representation of the first health data different from the first representation in the second region of the first user interface; and in accordance with a determination that the first set of highlight criteria are not met, not including the second representation of the first health data in the second region of the first user interface.

12. The non-transitory computer-readable storage medium of claim 11, wherein:

the first health data includes health data for a first plurality of time periods; and the first representation of the first health data includes:

a first indication of the first health data corresponding to a first time period of the first plurality of time periods; and a second indication of the first health data corresponding to a second time period of the first plurality of time periods that is different from the first time period.

13. The non-transitory computer-readable storage medium of claim 12, wherein:

the first time period of the first plurality of time periods corresponds to a specific instance of a recurring time interval; and the second time period of the first plurality of time periods is a plurality of instances of the recurring time interval.

14. The non-transitory computer-readable storage medium of claim 11, wherein:

the first health data includes health data for a second plurality of time periods; and the first representation of the first health data includes a third indication of the first health data corresponding to the frequency of the occurrence of a first health event within the second plurality of time periods.

15. The non-transitory computer-readable storage medium of claim 11, wherein:

the first health data includes health data for a third plurality of time periods; and the first representation of the first health data includes:

a fourth indication of an average value of the first health data for the third plurality of time periods;

a fifth indication corresponding to the value of the first health data for a first time period of the third plurality of time periods; and a sixth indication corresponding to the value of the first health data for a second time period of the third plurality of time periods that is different from the first time period of the plurality of time periods.

16. The non-transitory computer-readable storage medium of claim 11, wherein the first representation includes:

a seventh indication corresponding to a first physical activity tracking session;

an eighth indication corresponding to a second physical activity tracking session; and a ninth indication of the first health data that is based on the first physical activity tracking session and the second physical activity tracking session.

17. The non-transitory computer-readable storage medium of claim 11, wherein the first set of highlight criteria includes a criterion that is based on a factor selected from the group consisting of: a relationship between a first portion of the first health data and a second portion of the first health data, a degree of user interaction with the first health data, and a duration of time in which a representation of the first health data has been displayed.

18. The non-transitory computer-readable storage medium of claim 11, wherein:

the first representation is included in a first list of representation; and the first list of representations is ordered based on the types of data of the first health data.

19. The non-transitory computer-readable storage medium of claim 11, wherein the first user interface is associated with a health application, and wherein the one or more programs further include instructions for:

while displaying the first user interface including the first representation of the first health data in the first region of the first user interface, receiving second user input corresponding to the first representation of the first health data; and in response to receiving the second user input corresponding to the first representation of the first health data, displaying a second user interface, different from the first user interface, including information from an activity application different from the health application.

20. The non-transitory computer-readable storage medium of claim 11, wherein the second region includes a show all highlights affordance, and wherein the one or more programs further include instructions for:
    while displaying the show all highlights affordance, receiving third user input corresponding to the show all highlights affordance; and
    in response to receiving the third user input corresponding to the show all highlights affordance, displaying a third user interface including a list of highlights affordances corresponding to the first health data.

21. A method, comprising:
    at an electronic device with a display device:
        receiving first health data;
        receiving a selection of a health data type;
        after receiving the selection of the health data type, receiving a request to display a first user interface; and
        in response to receiving the request, displaying, via the display device, the first user interface including:
            a first region of the first user interface:
                in accordance with a determination that a type of data corresponding to the first health data has been identified by the selection of the health data type, including a first representation of the first health data in the first region of the first user interface; and
                in accordance with a determination that the type of data corresponding to the first health data has not been identified by the selection of the health data type, not including the first representation of the first health data in the first region of the first user interface; and
            a second region of the first user interface:
                in accordance with a determination that a first set of highlight criteria are met, including a second representation of the first health data different from the first representation in the second region of the first user interface; and
                in accordance with a determination that the first set of highlight criteria are not met, not including the second representation of the first health data in the second region of the first user interface.

22. The method of claim 21, wherein:
    the first health data includes health data for a first plurality of time periods; and
    the first representation of the first health data includes:
        a first indication of the first health data corresponding to a first time period of the first plurality of time periods; and
        a second indication of the first health data corresponding to a second time period of the first plurality of time periods that is different from the first time period.

23. The method of claim 22, wherein:
    the first time period of the first plurality of time periods corresponds to a specific instance of a recurring time interval; and
    the second time period of the first plurality of time periods is a plurality of instances of the recurring time interval.

24. The method of claim 21, wherein:
    the first health data includes health data for a second plurality of time periods; and
    the first representation of the first health data includes a third indication of the first health data corresponding to the frequency of the occurrence of a first health event within the second plurality of time periods.

25. The method of claim 21, wherein:
    the first health data includes health data for a third plurality of time periods; and
    the first representation of the first health data includes:
        a fourth indication of an average value of the first health data for the third plurality of time periods;
        a fifth indication corresponding to the value of the first health data for a first time period of the third plurality of time periods; and
        a sixth indication corresponding to the value of the first health data for a second time period of the third plurality of time periods that is different from the first time period of the plurality of time periods.

26. The method of claim 21, wherein the first representation includes:
    a seventh indication corresponding to a first physical activity tracking session;
    an eighth indication corresponding to a second physical activity tracking session; and
    a ninth indication of the first health data that is based on the first physical activity tracking session and the second physical activity tracking session.

27. The method of claim 21, wherein the first set of highlight criteria includes a criterion that is based on a factor selected from the group consisting of: a relationship between a first portion of the first health data and a second portion of the first health data, a degree of user interaction with the first health data, and a duration of time in which a representation of the first health data has been displayed.

28. The method of claim 21, wherein:
    the first representation is included in a first list of representation; and
    the first list of representations is ordered based on the types of data of the first health data.

29. The method of claim 21, wherein the first user interface is associated with a health application, and wherein the method further comprises:
    while displaying the first user interface including the first representation of the first health data in the first region of the first user interface, receiving second user input corresponding to the first representation of the first health data; and
    in response to receiving the second user input corresponding to the first representation of the first health data, displaying a second user interface, different from the first user interface, including information from an activity application different from the health application.

30. The method of claim 21, wherein the second region includes a show all highlights affordance, and wherein the method further comprises:
    while displaying the show all highlights affordance, receiving third user input corresponding to the show all highlights affordance; and
    in response to receiving the third user input corresponding to the show all highlights affordance, displaying a third user interface including a list of highlights affordances corresponding to the first health data.

* * * * *